(12) United States Patent
Uno

(10) Patent No.: US 12,295,257 B2
(45) Date of Patent: May 6, 2025

(54) ORGANIC ELECTROLUMINESCENCE DEVICE AND POLYCYCLIC COMPOUND FOR SAME

(71) Applicant: Samsung Display Co., Ltd., Yongin-Si (KR)

(72) Inventor: Takuya Uno, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 855 days.

(21) Appl. No.: 17/010,424

(22) Filed: Sep. 2, 2020

(65) Prior Publication Data

US 2021/0126199 A1 Apr. 29, 2021

(30) Foreign Application Priority Data

Oct. 24, 2019 (KR) .................. 10-2019-0133147

(51) Int. Cl.
*H10K 85/60* (2023.01)
*C07D 498/06* (2006.01)
(Continued)

(52) U.S. Cl.
CPC ......... *H10K 85/636* (2023.02); *C07D 498/06* (2013.01); *C07F 7/0812* (2013.01);
(Continued)

(58) Field of Classification Search
CPC ........ H10K 50/11; H10K 50/15; H10K 50/17; H10K 85/40; H10K 85/615; H10K 85/624;
(Continued)

(56) References Cited

U.S. PATENT DOCUMENTS 9,012,599 B2 4/2015 Stoessel et al.
9,093,650 B2 7/2015 Kim et al.
(Continued)

FOREIGN PATENT DOCUMENTS

CN 111704624 A 9/2020
JP 5782836 9/2015
(Continued)

OTHER PUBLICATIONS

English translation of JP 2012/248663A, and the original JP 2012/248663A, Mayuka Hikime, Dec. 13, 2012 (Year: 2012).*
(Continued)

*Primary Examiner* — Seokmin Jeon
(74) *Attorney, Agent, or Firm* — Womble Bond Dickinson (US) LLP

(57) ABSTRACT

An organic electroluminescence device includes a first electrode; a hole transport region disposed on the first electrode; an emission layer disposed on the hole transport region; an electron transport region disposed on the emission layer; and
(Continued)

a second electrode disposed on the electron transport region, wherein the hole transport region includes a polycyclic compound of Formula 1:

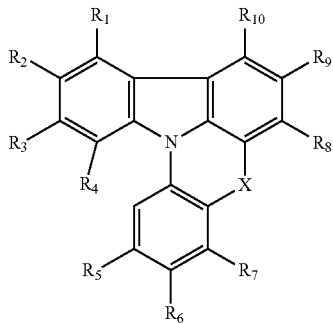

Formula 1 wherein, in Formula 1, the variables are defined herein.

20 Claims, 2 Drawing Sheets

(51) Int. Cl.

| | | |
|---|---|---|
| *C07F 7/08* | (2006.01) | |
| *C09K 11/06* | (2006.01) | |
| *H10K 50/11* | (2023.01) | |
| *H10K 50/15* | (2023.01) | |
| *H10K 50/17* | (2023.01) | |
| *H10K 85/40* | (2023.01) | |
| *H10K 101/10* | (2023.01) | |

(52) U.S. Cl.
CPC .............. *C09K 11/06* (2013.01); *H10K 85/40* (2023.02); *H10K 85/633* (2023.02); *C09K 2211/1018* (2013.01); *H10K 50/11* (2023.02); *H10K 50/15* (2023.02); *H10K 50/17* (2023.02); *H10K 85/615* (2023.02); *H10K 85/624* (2023.02); *H10K 85/626* (2023.02); *H10K 85/657* (2023.02); *H10K 85/6574* (2023.02); *H10K 85/6576* (2023.02); *H10K 2101/10* (2023.02)

(58) Field of Classification Search
CPC .. H10K 85/626; H10K 85/633; H10K 85/636; H10K 85/657; H10K 85/6574; H10K 85/6576; C07B 59/001; C07D 491/06; C07D 498/06; C07D 513/06; C07F 7/0812; C09K 11/06; C09K 2211/1018
See application file for complete search history.

(56) References Cited

U.S. PATENT DOCUMENTS

| | | | |
|---|---|---|---|
| 9,133,119 | B2 | 9/2015 | Parham et al. |
| 9,515,270 | B2 | 12/2016 | Kosuge et al. |
| 9,708,262 | B2 | 7/2017 | Parham et al. |
| 10,283,718 | B2 | 5/2019 | Watanabe et al. |
| 10,326,111 | B2 | 6/2019 | Yoo et al. |
| 10,336,772 | B2 | 7/2019 | Ishii et al. |
| 10,797,246 | B2 | 10/2020 | Lee |
| 2012/0292576 | A1* | 11/2012 | Parham .................. 252/500 |
| 2013/0228770 | A1* | 9/2013 | Kosuge ............... H01L 51/0071 257/40 |
| 2014/0027747 | A1* | 1/2014 | Mun ..................... H01L 51/006 257/40 |
| 2016/0079542 | A1* | 3/2016 | Itoi ..................... H01L 51/0061 |
| 2017/0018600 | A1 | 1/2017 | Ito et al. |
| 2017/0054083 | A1 | 2/2017 | Lee |
| 2017/0077416 | A1 | 3/2017 | Kim et al. |
| 2017/0183360 | A1* | 6/2017 | Ishii ..................... C07D 498/06 |
| 2017/0200899 | A1 | 7/2017 | Kim et al. |
| 2020/0199154 | A1 | 6/2020 | Parham et al. |
| 2022/0199912 | A1* | 6/2022 | Uno ..................... H01L 51/0071 |

FOREIGN PATENT DOCUMENTS

| | | |
|---|---|---|
| JP | 5782836 B2 | 9/2015 |
| JP | 6009816 | 10/2016 |
| KR | 10-1546215 | 8/2015 |
| KR | 10-2015-0130797 | 11/2015 |
| KR | 10-2016-0006472 | 1/2016 |
| KR | 10-1781235 B1 | 9/2017 |
| KR | 10-2017-0116974 | 10/2017 |
| KR | 10-1796227 B1 | 11/2017 |
| KR | 10-2017-0139350 | 12/2017 |
| KR | 10-1936221 B1 | 1/2019 |
| KR | 10-1962420 | 3/2019 |
| KR | 10-2019-0141220 A | 12/2019 |
| KR | 10-2020-0136713 A | 12/2020 |
| WO | 2010-050778 | 5/2010 |
| WO | WO 2010/050778 A1 | 5/2010 |
| WO | 2011-088877 | 7/2011 |
| WO | WO 2011/088877 A1 | 7/2011 |
| WO | 2012-077582 | 6/2012 |
| WO | 2017-099326 | 6/2017 |
| WO | WO 2018/197447 A1 | 11/2018 |

OTHER PUBLICATIONS

English translation of WO 2013/183851 A1, and the original WO 2013/183851 A1, Seo-Yong Hyun, Dec. 12, 2013 (Year: 2013).*
U.S. Office Action dated Aug. 28, 2024, issued in U.S. Appl. No. 17/486,049 (12 pages).
Google_Translation_of_CN_111704624 (Year: 2024).

* cited by examiner

ORGANIC ELECTROLUMINESCENCE DEVICE AND POLYCYCLIC COMPOUND FOR SAME

CROSS-REFERENCE TO RELATED APPLICATION

This application claims priority from and the benefit of Korean Patent Application No. 10-2019-0133147, filed on Oct. 24, 2019, which is hereby incorporated by reference for all purposes as if fully set forth herein.

BACKGROUND

Field

Exemplary embodiments of the invention relate generally to an organic electroluminescence device, and more particularly, to a polycyclic compound for the organic electroluminescence device.

Discussion of the Background

Recently, the development of organic electroluminescence displays as an image display is being actively conducted. Unlike liquid crystal display devices and the like, organic electroluminescence displays are so-called self-luminescent display devices in which holes and electrons injected from a first electrode and a second electrode recombine in an emission layer, and thus a luminescent material including an organic compound in the emission layer emits light to implement a display.

For a display having an organic electroluminescence device, there is a demand for an organic electroluminescence device having a low driving voltage, high luminous efficiency, and long life, and development of materials of stably attaining such characteristics for an organic electroluminescence device is continuously being required.

The above information disclosed in this Background section is only for understanding of the background of the inventive concepts, and, therefore, it may contain information that does not constitute prior art.

SUMMARY

Applicant discovered that by combining a hole transport region having a polycyclic compound in an organic electroluminescence device with one or more other regions and/or layers with different attributes unexpected synergistic improvements in organic electroluminescence devices can be obtained, including low driving voltage, high luminous efficiency, and/or long life.

Organic electroluminescence devices constructed according to the principles and exemplary implementations of the invention have low driving voltage, high luminous efficiency, and/or long life. For example, the hole transport region having the polycyclic compound may optionally be combined with an emission layer to obtain improved low driving voltage, high luminous efficiency, and long life in organic electroluminescence devices.

Additional features of the inventive concepts will be set forth in the description which follows, and in part will be apparent from the description, or may be learned by practice of the inventive concepts.

According to one aspect of the invention, an organic electroluminescence device includes a first electrode; a hole transport region disposed on the first electrode; an emission layer disposed on the hole transport region; an electron transport region disposed on the emission layer; and a second electrode disposed on the electron transport region, wherein the hole transport region includes a polycyclic compound of Formula 1:

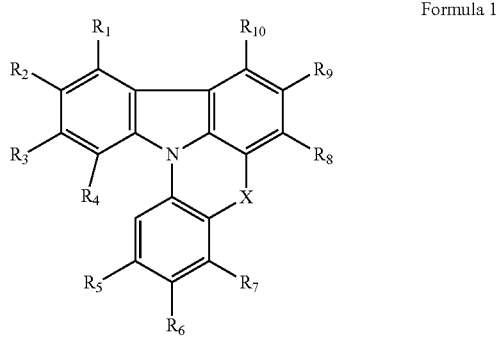

Formula 1 wherein, in Formula 1

X is O or S;

R1 to R10 are each, independently from one another, a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms; and at least one of R1, R3 to R5, R7, R8, and R10 is a group of Formula 2:

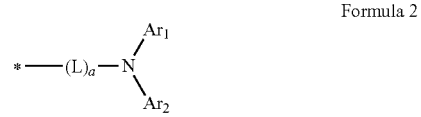

Formula 2 wherein, in Formula 2,

L is a direct linkage, a substituted or unsubstituted arylene group having 6 to 30 ring-forming carbon atoms, or a substituted or unsubstituted heteroarylene group having 2 to 30 ring-forming carbon atoms;

Ar1 and Ar2 are each, independently from one another, a substituted or unsubstituted aryl group having 6 to 30 ring-forming carbon atoms or a substituted or unsubstituted heteroaryl group having 2 to 30 ring-forming carbon atoms; and a is 0, 1, 2, 3, or 4.

The variables R1, R3 to R5, R7, R8, and R10 may each, independently from one another, be a hydrogen atom, a deuterium atom, a halogen atom, a substituted or unsubstituted alkyl group having 1 to 20 carbon atoms, or a substituted or unsubstituted aryl group having 6 to 30 ring-forming carbon atoms, and at least one of R1, R3 to R5, R7, R8, and R10 is a group of Formula 2.

The compound of Formula 1 may be a compound of Formula 3 to Formula 5:

Formula 3

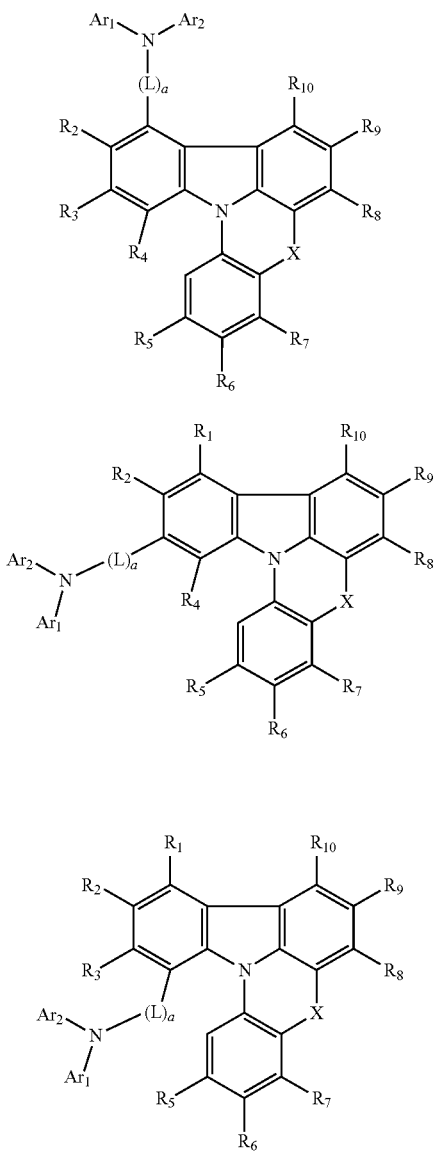

Formula 4

Formula 5 wherein, the variables are defined herein.

The compound Formula 1 may be a compound of Formula 6 or Formula 7:

Formula 6

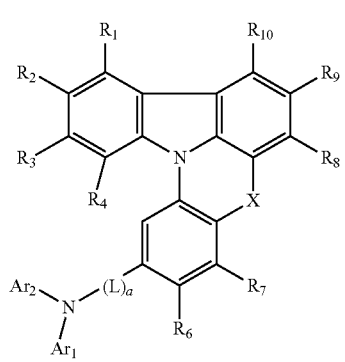

Formula 7

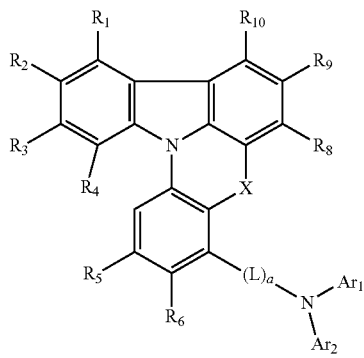

wherein, the variables are defined herein.

The compound of Formula 1 may be a compound of Formula 8 or Formula 9:

Formula 8

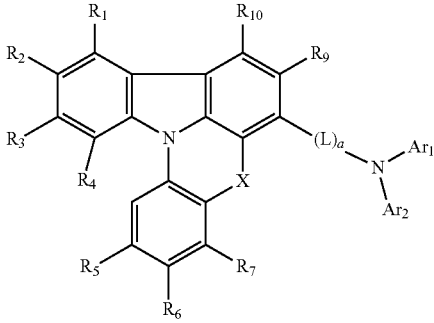

Formula 9

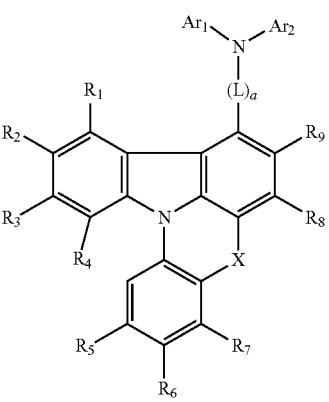

wherein, the variables are defined herein.

The variables R2, R6, and R9 may each, independently from one another, be a hydrogen atom, a deuterium atom, a halogen atom, or a substituted or unsubstituted alkyl group having 1 to 20 carbon atoms.

The variable X may be O.

The variable L may be a direct linkage, a substituted or unsubstituted phenylene group, a substituted or unsubstituted biphenylene group, a substituted or unsubstituted fluorenylene group, or a substituted or unsubstituted naphthylene group.

The variables Ar1 and Ar2 may each, independently from one another, be a substituted or unsubstituted phenyl group, a substituted or unsubstituted biphenyl group, a substituted or unsubstituted triphenyl group, a substituted or unsubstituted fluorenyl group, a substituted or unsubstituted dibenzofuran group, or a substituted or unsubstituted dibenzothiophene group.

The hole transport region may include a hole injection layer disposed on the first electrode; and a hole transport layer including a polycyclic compound of Formula 1 disposed on the hole injection layer.

The polycyclic compound of Formula 1 may be at least one compound of Compound Group 1, as defined herein.

The polycyclic compound of Formula 1 may be at least one compound of Compound Group 2, as defined herein.

The polycyclic compound of Formula 1 may be at least one compound of Compound Group 3, as defined herein:

According to another aspect of the invention, a polycyclic compound for an organic electroluminescence device is of Formula 1:

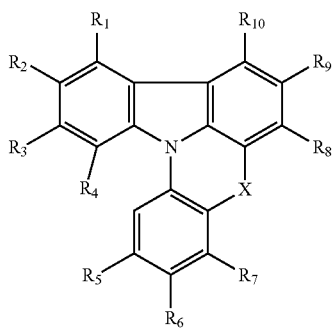

Formula 1 wherein, in Formula 1,

X is O or S;

R1 to R10 are each, independently from one another, a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms; and at least one among R1, R3 to R5, R7, R8, and R10 is a group of Formula 2:

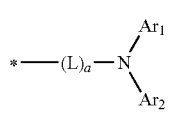

Formula 2 wherein, in Formula 2,

L is a direct linkage, a substituted or unsubstituted arylene group having 6 to 30 ring-forming carbon atoms, or a substituted or unsubstituted heteroarylene group having 2 to 30 ring-forming carbon atoms;

Ar1 and Ar2 are each, independently from one another, a substituted or unsubstituted aryl group having 6 to 30 ring-forming carbon atoms, or a substituted or unsubstituted heteroaryl group having 2 to 30 ring-forming carbon atoms, and a is 0, 1, 2, 3, or 4.

The compound of Formula 1 may be a compound of Formula 3 to Formula 5:

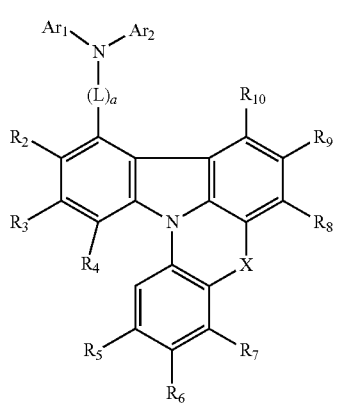

Formula 3

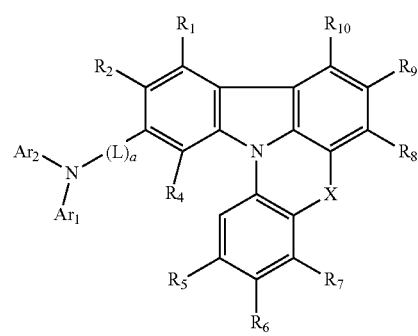

Formula 4

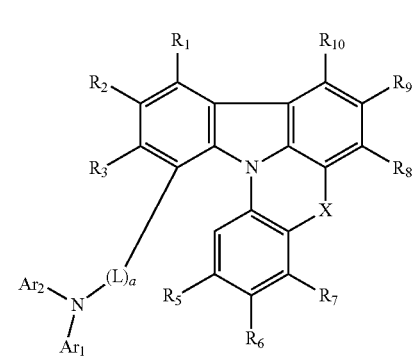

Formula 5 wherein, in Formula 3 to Formula 5, the variables are defined herein.

The compound of Formula 1 may be a compound of Formula 6 or Formula 7:

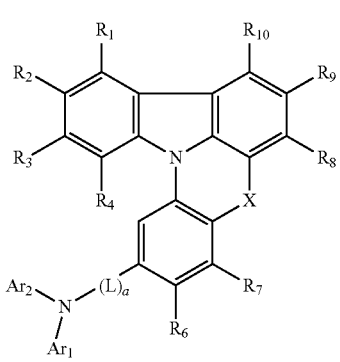

Formula 6

-continued

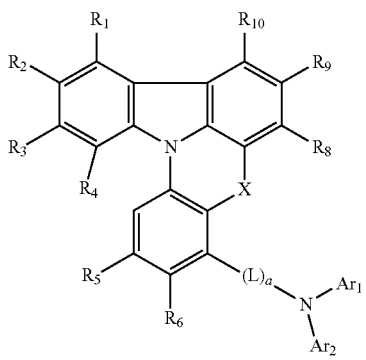

Formula 7 wherein, in Formula 6 and Formula 7, the variables are defined herein.

The compound of Formula 1 may be a compound of Formula 8 or Formula 9:

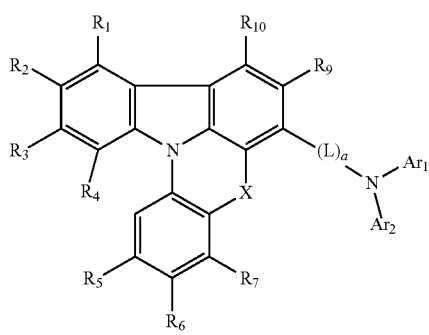

Formula 8

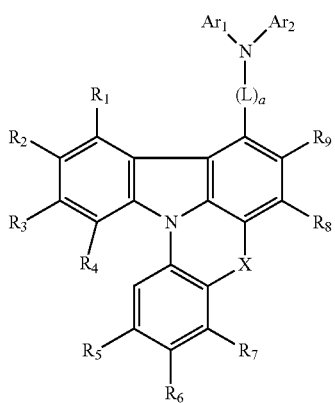

Formula 9 wherein, in Formula 8 and Formula 9, the variables are defined herein.

The polycyclic compound of Formula 1 may be a compound of Compound Group 1, as defined herein.

The polycyclic compound of Formula 1 may be a compound of Compound Group 2, as defined herein.

The polycyclic compound of Formula 1 may be a compound of Compound Group 3, as defined herein.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
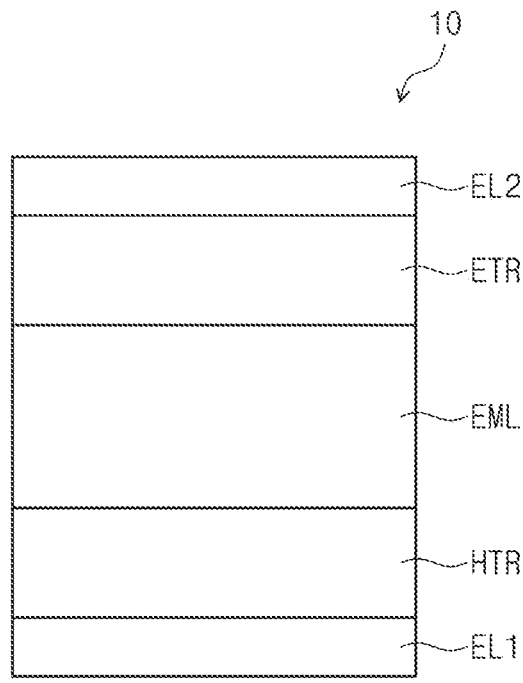
FIG. 1 is a schematic cross-sectional diagram of an exemplary embodiment of an organic electroluminescence device constructed according to principles of the invention.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

As used herein, the term "substituted" means at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents may be substituted or unsubstituted. For example, a biphenyl group may be interpreted as an aryl group or a phenyl group substituted with a phenyl group. If a compound or a group unsubstituted, then the compound or group lacks a substituent.

As used herein, examples of the halogen atom may include a fluorine atom, a chlorine atom, a bromine atom, and an iodine atom, or a corresponding radical.

As used herein, the term "atom" may mean an element or its corresponding radical bonded to one or more other atoms As used herein, the term "alkyl" may mean a paraffinic hydrocarbon group optionally derived from an alkane by dropping one hydrogen from the formula, and be linear, branched or cyclic. The number of carbon atoms in the alkyl group may be 1 to 50, 1 to 30, 1 to 20, 1 to 10, or 1 to 6. Examples of the alkyl group may include, but are not limited to, methyl group, ethyl group, n-propyl group, isopropyl group, n-butyl group, s-butyl group, t-butyl group, i-butyl group, 2-ethylbutyl group, 3,3-dimethylbutyl group, n-pentyl group, i-pentyl group, neopentyl group, t-pentyl group, cyclopentyl group, 1-methylpentyl group, 3-methylpentyl group, 2-ethylpentyl group, 4-methyl-2-pentyl group, n-hexyl group, 1-methylhexyl group, 2-ethylhexyl group, 2-butylhexyl group, cyclohexyl group, 4-methylcyclohexyl group, 4-t-butylcyclohexyl group, n-heptyl group, 1-methylheptyl group, 2,2-dimethylheptyl group, 2-ethylheptyl group, 2-butylheptyl group, n-octyl group, t-octyl group, 2-ethyloctyl group, 2-butyloctyl group, 2-hexyloctyl group, 3,7-dimethyloctyl group, cyclooctyl group, n-nonyl group, n-decyl group, adamantyl group, 2-ethyldecyl group, 2-butyldecyl group, 2-hexyldecyl group, 2-octyldecyl group, n-undecyl group, n-dodecyl group, 2-ethyldodecyl group, 2-butyldodecyl group, 2-hexyldocecyl group, 2-octyldodecyl group, n-tridecyl group, n-tetradecyl group, n-pentadecyl group, n-hexadecyl group, 2-ethylhexadecyl group, 2-butylhexadecyl group, 2-hexylhexadecyl group, 2-octylhexadecyl group, n-heptadecyl group, n-octadecyl group, n-nonadecyl group, n-eicosyl group, 2-ethyleicosyl group, 2-butyleicosyl group, 2-hexyleicosyl group, 2-octyleicosyl group, n-henicosyl group, n-docosyl group, n-tricosyl group, n-tetracosyl group, n-pentacosyl group, n-hexacosyl group, n-heptacosyl group, n-octacosyl group, n-nonacosyl group, n-triacontyl group, etc., without limitation.

As used herein, alkenyl means an unsaturated aliphatic hydrocarbon group including at least one carbon double bond at the middle or end of a carbon chain having two or more carbon atoms. The alkenyl group may be a linear or branched chain. The number of carbon atoms may be 2 to 30, 2 to 20 or 2 to 10, but is not limited thereto. Examples of the alkenyl group include, but are not limited to, a vinyl group, 1-butenyl group, 1-pentenyl group, 1,3-butadienyl aryl group, styrenyl group, styryl vinyl group, etc., without limitation.

As used herein, alkynyl means an unsaturated aliphatic hydrocarbon group including at least one carbon triple bond at the middle or end of a carbon chain having two or more carbon atoms. The alkynyl group may be a linear or branched chain. The number of carbon atoms may be 2 to 30, 2 to 20 or 2 to 10, but is not limited thereto. Specific examples of the alkynyl group may include, but are not limited to, ethynyl, propynyl, etc.

As used herein, the hydrocarbon ring group may be an optional functional group or substituent derived from an aliphatic hydrocarbon ring, or any functional group or substituent derived from an aromatic hydrocarbon ring. The number of carbon atoms for forming a ring of the hydrocarbon ring group may be 5 to 60, 5 to 30, or 5 to 20.

As used herein, aryl means an optional functional group or substituent whose ring structure may have the characteristics of benzene, naphthalene, phenanthrene, anthracene, etc. The aryl group may be a monocyclic aryl group or a polycyclic aryl group. The number of carbon atoms for forming a ring in the aryl group may be 6 to 30, 6 to 20, or 6 to 15. Examples of the aryl group may include, but are not limited to, phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc.

As used herein, fluorenyl is a polycyclic aromatic group that may be substituted, and two substituents may be combined with each other to form a spiro structure. Examples of the substituted fluorenyl group are as follows, however, the exemplary embodiments are not limited thereto.

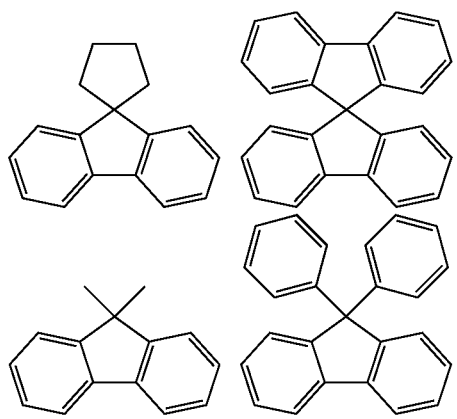

As used herein, the heterocyclic group may be a closed-ring structure usually of five or six members that one or more of the atoms in the ring is an element other than carbon and may include one or more of B, O, N, P, Si, and S as a heteroatom. The heterocyclic ring includes an aliphatic heterocyclic ring and an aromatic heterocyclic ring. The aromatic heterocyclic group may be a heteroaryl group. The aliphatic heterocyclic ring and the aromatic heterocyclic ring may be monocyclic or polycyclic. If the heterocyclic group includes two or more heteroatoms, two or more heteroatoms may be the same as or different from each other. The heterocyclic group may be a monocyclic heterocyclic group or a polycyclic heterocyclic group, and include a heteroaryl group. The number of carbon atoms for forming a ring of the heterocyclic group may be 2 to 30, 2 to 20, or 2 to 10.

As used herein, the aliphatic heterocyclic group may include one or more of B, O, N, P, Si, and S as a heteroatom. The number of carbon atoms for forming a ring of the aliphatic heterocyclic group may be 2 to 30, 2 to 20, or 2 to 10. Examples of the aliphatic heterocyclic group may include, but are not limited to, oxirane, thiirane, pyrrolidine, piperidine, tetrahydrofuran, tetrahydrothiophene, thiane, tetrahydropyran, 1,4-dioxane, etc.

As used herein, heteroaryl may include one or more among B, O, N, P, Si, and S as a heteroatom in a group. If the heteroaryl group includes two or more heteroatoms, two or more heteroatoms may be the same as or different from each other. The heteroaryl group may be a monocyclic heterocyclic group or a polycyclic heterocyclic group. The number of carbon atoms for forming a ring of the heteroaryl group may be 2 to 30, 2 to 20, or 2 to 10. Examples of the heteroaryl group may include, but are not limited to, thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxazole, oxadiazole, thiadiazole, phenothiazine, dibenzosilole, dibenzofuran, etc.

As used herein, the number of carbon atoms of the amine group may be 1 to 30, but is not particularly limited thereto. The amine group may include an alkyl amine group, aryl amine group, or a heteroaryl amine group. Examples of the amine group includes, but are not limited to, methylamine group, dimethylamine group, phenylamine group, diphenylamine group, naphthylamine group, 9-methyl-anthracenylamine group, triphenylamine group, etc.

As used herein, the definition of the aryl group may be applied to an arylene group except that the arylene group is a divalent group.

As used herein, the definition of the heteroaryl group may be applied to a heteroarylene group except that the heteroarylene group is a divalent group.

As used herein, the abbreviation "SiPh$_3$" represents a group having three phenyl moieties, each typically connected the silicon serving as a linker, which in turn may be connected to an aryl ring.

As used herein, a substituent for a monovalent group, e.g., alkyl, may also be, independently, a substituent for a corresponding divalent group, e.g., alkylene.

As used herein, "——*" means the position to be linked.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Figure 2:
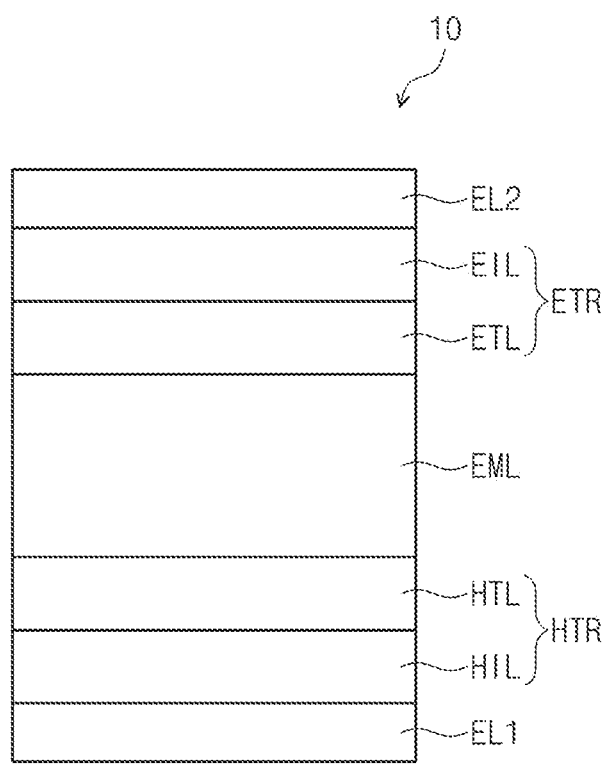
FIG. 2 is a schematic cross-sectional diagram of another exemplary embodiment of an organic electroluminescence device constructed according to principles of the invention.
Figure 3:
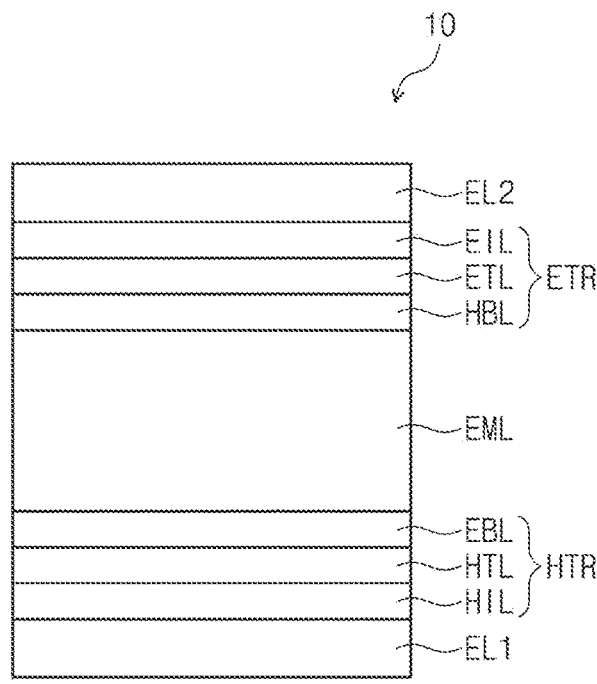
FIG. 3 is a schematic cross-sectional diagram of yet another exemplary embodiment of an organic electroluminescence device constructed according to principles of the invention.
Figure 4:
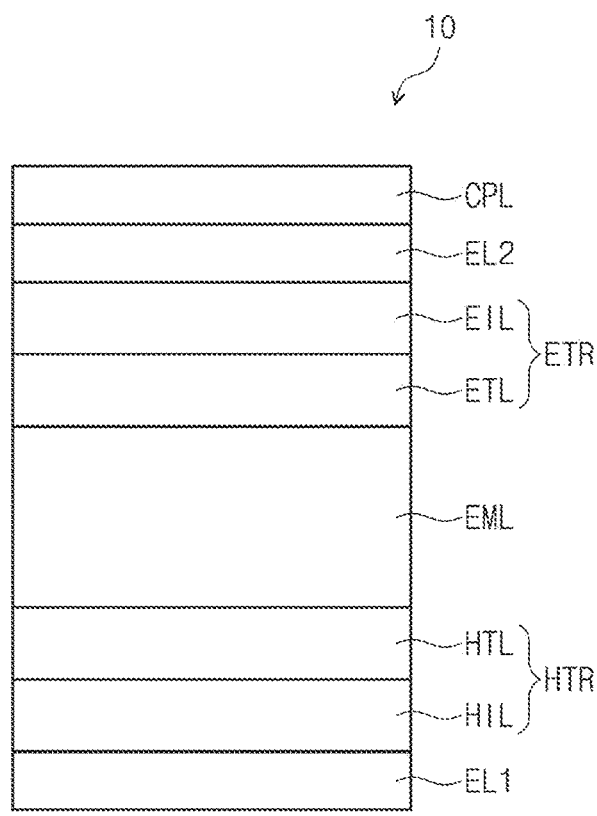
FIG. 4 is a schematic cross-sectional diagram of a further exemplary embodiment of an organic electroluminescence device constructed according to principles of the invention.

FIG. 1 is a schematic cross-sectional diagram of an exemplary embodiment of an organic electroluminescence device constructed according to principles of the invention. FIG. 2 is a schematic cross-sectional diagram of another exemplary embodiment of an organic electroluminescence device constructed according to principles of the invention. FIG. 3 is a schematic cross-sectional diagram of yet another exemplary embodiment of an organic electroluminescence device constructed according to principles of the invention. FIG. 4 is a schematic cross-sectional diagram of a further exemplary embodiment of an organic electroluminescence device constructed according to principles of the invention.

Referring to FIGS. 1 to 4, an organic electroluminescence device 10 includes a first electrode EL1 and a second electrode EL2 disposed opposite each other, and an emission layer EML disposed between the first electrode EL1 and the second electrode EL2. Furthermore, the organic electroluminescence device 10 further includes a plurality of functional layers disposed between the first electrode EL1 and the second electrode EL2, as well as the emission layer EML. The plurality of functional layers may include a hole transport region HTR, and an electron transport region ETR. That is, the organic electroluminescence device 10 according to some exemplary embodiments may include a first electrode EL1, a hole transport region HTR, an emission layer EML, an electron transport region ETR, and a second electrode EL2 laminated sequentially. In addition, the organic electroluminescence device 10 of some exemplary embodiments may include a capping layer CPL disposed on the second electrode EL2, as depicted in FIG. 4.

The organic electroluminescence device 10 includes a polycyclic compound described below in the emission layer EML disposed between the first electrode EL1 and the second electrode EL2. However, the exemplary embodiments are not limited thereto, and the organic electroluminescence device 10 may include a compound described below in the hole transport region HTR or the electron transport region ETR, which is one of the plurality of functional layers disposed between the first electrode EL1 and the second electrode EL2, or may include a compound described below in the capping layer CPL disposed on the second electrode EL2, as well as in the emission layer EML.

In comparison to FIG. 1, FIG. 2 shows a cross-sectional view of an organic electroluminescence device 10, where the hole transport region HTR includes a hole injection layer HIL and a hole transport layer HTL, and the electron transport region ETR includes an electron injection layer EIL and an electron transport layer ETL. Furthermore, FIG. 3 shows a cross-sectional view of an organic electroluminescence device 10, where the hole transport region HTR includes a hole injection layer HIL, a hole transport layer HTL, and an electron blocking layer EBL, the electron transport region ETR includes an electron injection layer EIL, an electron transport layer ETL, and a hole blocking layer HBL. In comparison with FIG. 2, FIG. 4 shows a cross-sectional view of an organic electroluminescence device 10 including the capping layer CPL disposed on the second electrode EL2.

The first electrode EL1 has conductivity. The first electrode EL1 may be formed of a metal alloy or a conductive compound. The first electrode EL1 may be a pixel electrode or positive electrode. The first electrode EL1 may be a transmissive electrode, a transflective electrode, or a reflective electrode. When the first electrode EL1 is the transmissive electrode, the first electrode EL1 may include a transparent metal oxide, for example, an indium tin oxide (ITO), an indium zinc oxide (IZO), a zinc oxide (ZnO), or an indium tin zinc oxide (ITZO). When the first electrode EL1 is the transflective electrode or the reflective electrode, the first electrode EL1 may include Ag, Mg Cu, Al, Pt, Pd, Au, Ni, Nd, Ir, Cr, Li, Ca, LiF/Ca, LiF/Al, Mo, Ti, or a compound or mixture (e.g., a mixture of Ag and Mg) thereof. Alternatively, the first electrode EL1 may have a multi-layered structure including a reflective layer or transflective layer and a transparent conductive layer formed of an indium tin oxide (ITO), an indium zinc oxide (IZO), a zinc oxide (ZnO), and/or an indium tin zinc oxide (ITZO). For example, the first electrode EL1 may have, but is not limited to, a three-layer structure of ITO/Ag/ITO. The first electrode EL1 may have a thickness from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, or the electron blocking layer EBL.

The hole transport region HTR may have a multilayer structure having a single layer formed of a single material, a single layer formed of materials different from each other, or a plurality of layers formed of materials different from each other.

For example, the hole transport region HTR may have a single layer structure of the hole injection layer HIL or the hole transport layer HTL, or a single layer structure formed of a hole injection material and a hole transport material. Furthermore, the hole transport region HTR may have a single layer structure formed of a plurality of different materials, or a structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL which are sequentially laminated from the first electrode EL1, but the exemplary embodiments are not limited thereto.

The hole transport region HTR in the organic electroluminescence device 10 includes a polycyclic compound.

The polycyclic compound according to some exemplary embodiments may be represented by Formula 1 below:

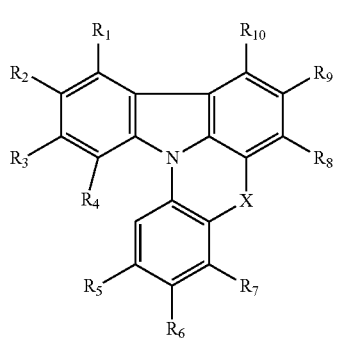

Formula 1

In Formula 1, X is O or S.

In Formula 1, R1 to R10 are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and at least one among R1, R3 to R5, R7, R8, and R10 is represented by Formula 2 below:

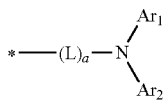

Formula 2

In Formula 2, L is a direct linkage, a substituted or unsubstituted arylene group having 6 to 30 ring-forming carbon atoms, or a substituted or unsubstituted heteroarylene group having 2 to 30 ring-forming carbon atoms.

In Formula 2, Ar1 and Ar2 are each independently a substituted or unsubstituted aryl group having 6 to 30 ring-forming carbon atoms, or a substituted or unsubstituted heteroaryl group having 2 to 30 ring-forming carbon atoms.

In Formula 2, the variable "a" is an integer of 0 to 4. When the variable "a" is 2 or more, a plurality of L's are the same as or different from each other.

In an exemplary embodiment, any one among R1, R3 to R5, R7, R8, and R10 in Formula 1 may be represented by Formula 2 below.

In some exemplary embodiments, any one among R1, R3 to R4 in Formula 1 may be represented by Formula 2.

In some exemplary embodiments, R1 in Formula 1 may be represented by Formula 2. In this case, Formula 1 may be represented by Formula 3 below:

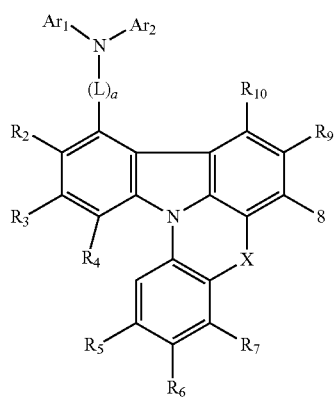

Formula 3

In Formula 3, R2 to R10 may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 3, the variables X, Ar1, Ar2, L, and a are the same as defined in Formula 1 and Formula 2.

In some exemplary embodiments, R3 in Formula 1 may be represented by Formula 2. In this case, Formula 1 may be represented by Formula 4 below:

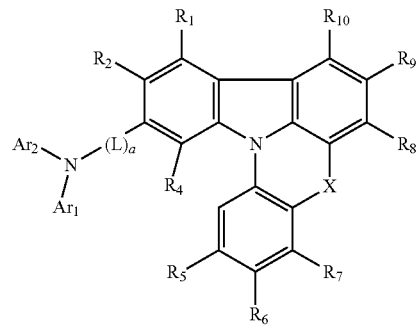

Formula 4

In Formula 4, R1, R2, and R4 to R10 may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 4, the variables X, Ar1, Ar2, L, and a are the same as defined in Formula 1 and Formula 2.

In some exemplary embodiments, R4 in Formula 1 may be represented by Formula 2. In this case, Formula 1 may be represented by Formula 5 below:

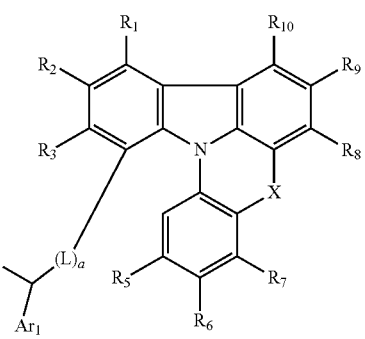

Formula 5

In Formula 5, R1 to R3 and R5 to R10 may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 5, the variables X, Ar1, Ar2, L, and a are the same as defined in Formula 1 and Formula 2.

In some exemplary embodiments, R5 or R7 in Formula 1 may be represented by Formula 2.

In an exemplary embodiment, R5 in Formula 1 may be represented by Formula 2. In this case, Formula 1 may be represented by Formula 6 below:

Formula 6

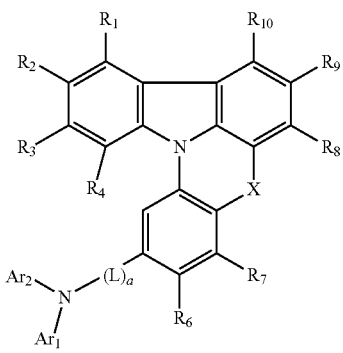

In Formula 6, R1 to R4 and R6 to R10 may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 6, the variables X, Ar1, Ar2, L, and a are the same as defined in Formula 1 and Formula 2.

In some exemplary embodiments, R7 in Formula 1 may be represented by Formula 2. In this case, Formula 1 may be represented by Formula 7 below:

Formula 7

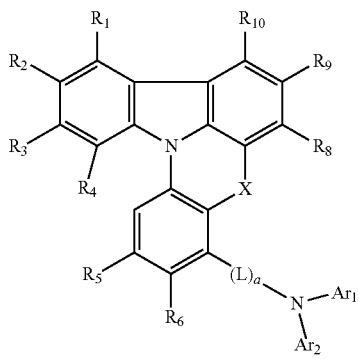

In Formula 7, R1 to R6 and R8 to R10 may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 7, the variables X, Ar1, Ar2, L, and a are the same as defined in Formula 1 and Formula 2.

In some exemplary embodiments, R8 or R10 in Formula 1 may be represented by Formula 2.

In some exemplary embodiments, R8 in Formula 1 may be represented by Formula 2. In this case, Formula 1 may be represented by Formula 8 below:

Formula 8

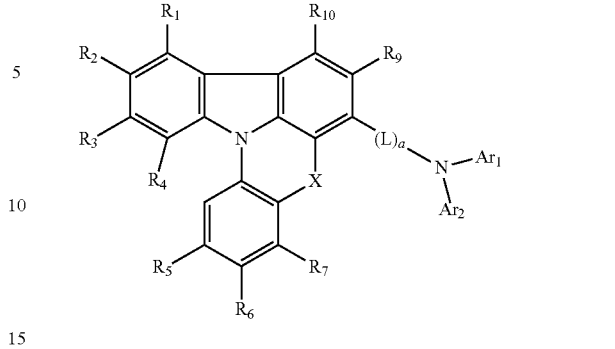

In Formula 8, R1 to R7, R9 and R10 may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 8, the variables X, Ar1, Ar2, L, and a are the same as defined in Formula 1 and Formula 2.

In some exemplary embodiments, R10 in Formula 1 may be represented by Formula 2. In this case, Formula 1 may be represented by Formula 9 below:

Formula 9


In Formula 9, R1 to R9 may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 9, the variables X, Ar1, Ar2, L, and a are the same as defined in Formula 1 and Formula 2.

In some exemplary embodiments, R1, R3 to R5, R7, R8, and R10 in Formula 1 and Formula 3 to Formula 9 may be each independently a hydrogen atom, a deuterium atom, a halogen atom, a substituted or unsubstituted alkyl group having 1 to 20 carbon atoms, or a substituted or unsubstituted aryl group having 6 to 30 ring-forming carbon atoms.

In some exemplary embodiments, R2, R6, and R9 in Formula 1 and Formula 3 to Formula 9 may be each independently a hydrogen atom, a deuterium atom, a halogen atom, a substituted or unsubstituted alkyl group having 1 to 20 carbon atoms.

In some exemplary embodiments, X in Formula 1 and Formula 3 to Formula 9 may be O.

In some exemplary embodiments, L in Formula 1 and Formula 3 to Formula 9 may be a direct linkage, a substituted or unsubstituted phenylene group, a substituted or unsubstituted biphenylene group, a substituted or unsubstituted fluorenylene group, or a substituted or unsubstituted naphthylene group.

The polycyclic compound represented by Formula 1 according to some exemplary embodiments may be any one selected from among compounds represented by Compound Groups 1 to 3 below: However, the exemplary embodiments are not limited thereto.

Compound Group 1

A1

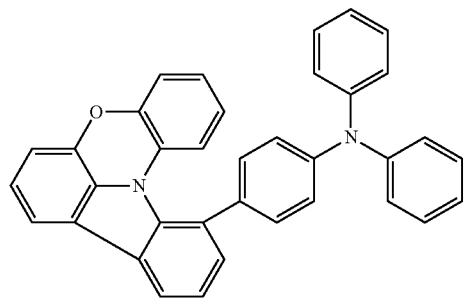

A2

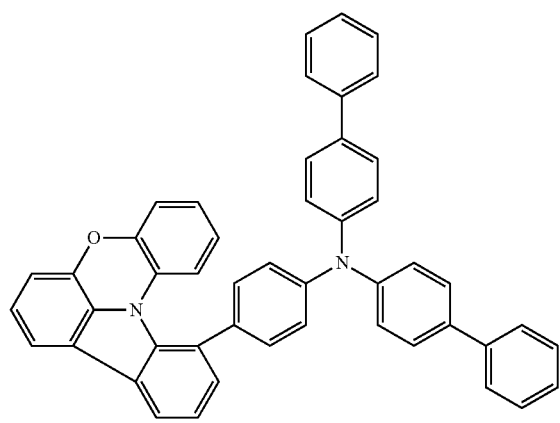

A3

-continued

A4

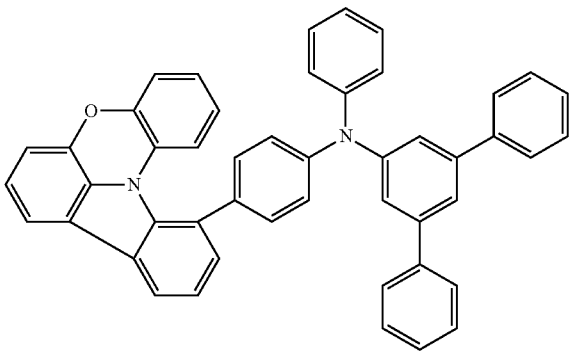

A5

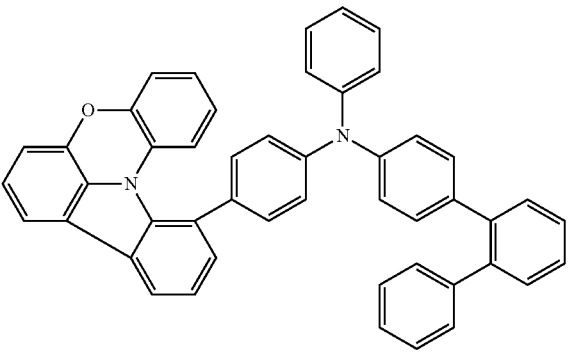

A6

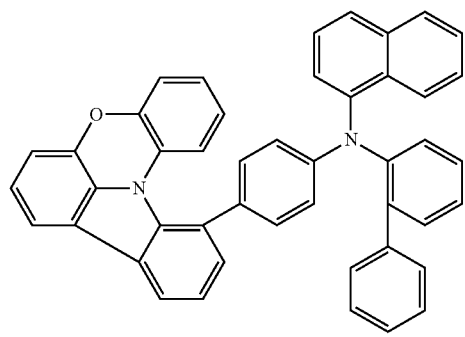

A7

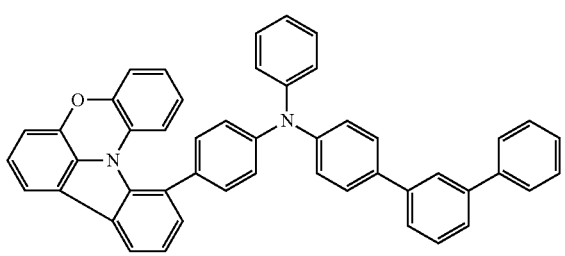

A8
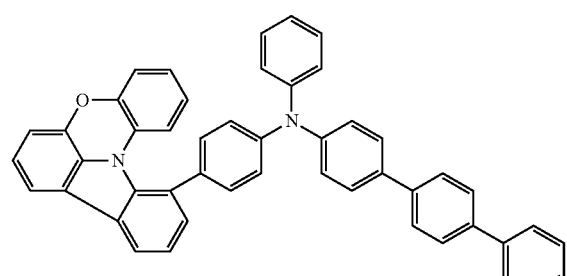
A12
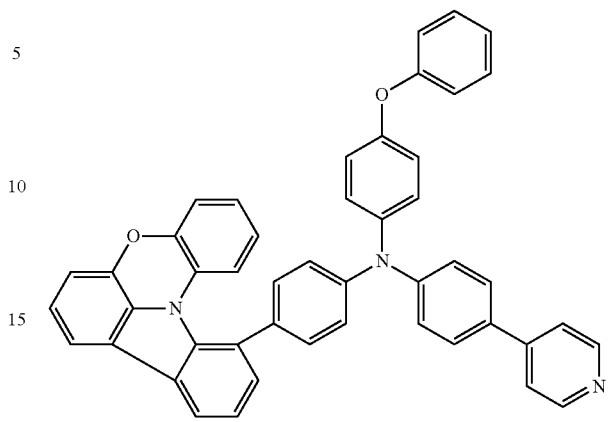
A9
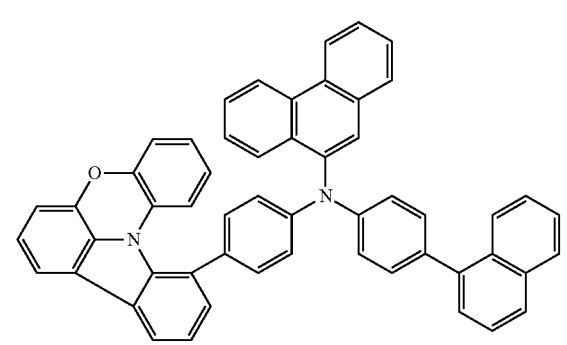
A13
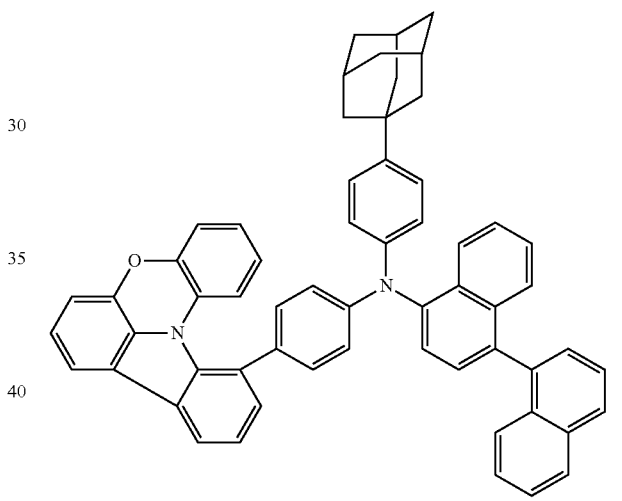
A10
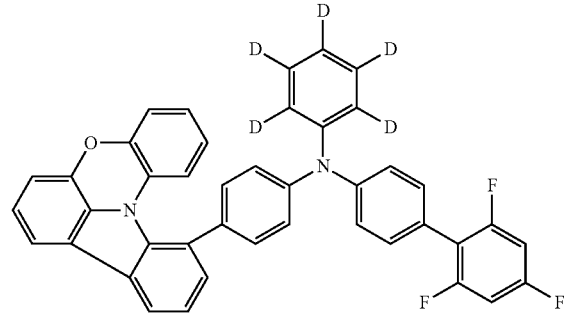
A11
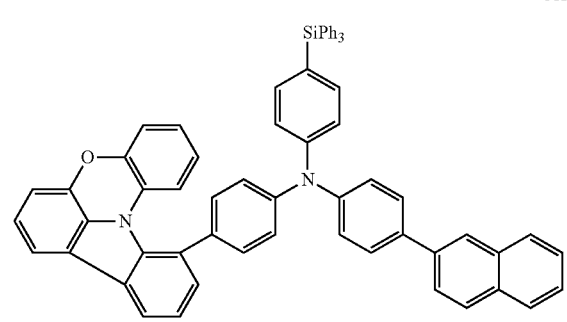
A14
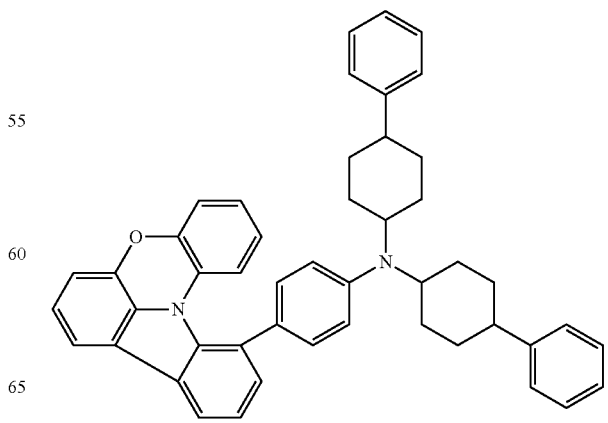

A15
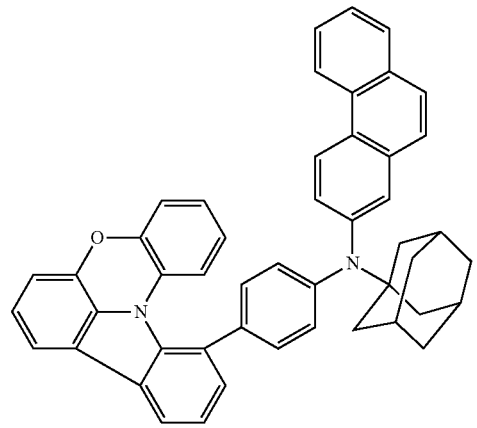
A16
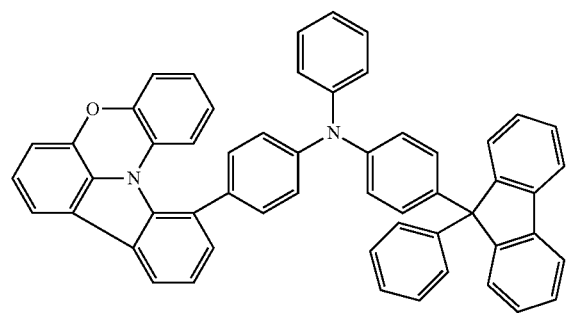
A17
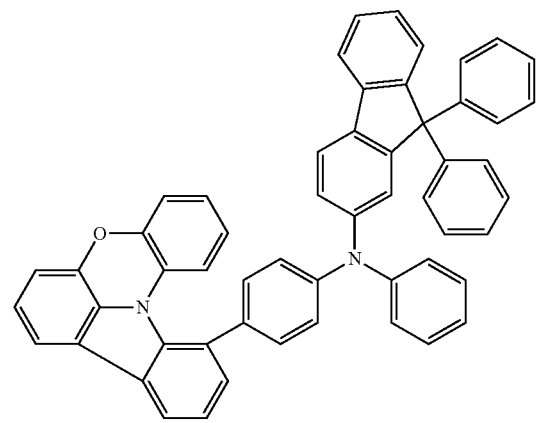
A18
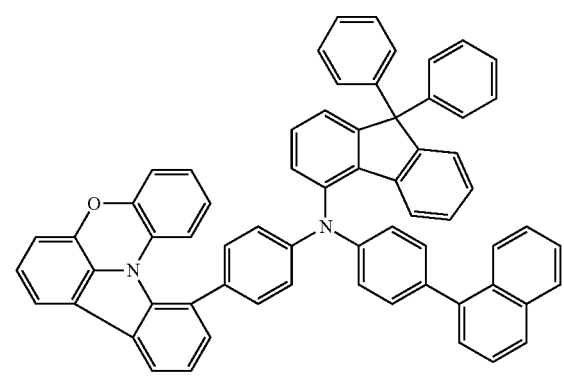
A19
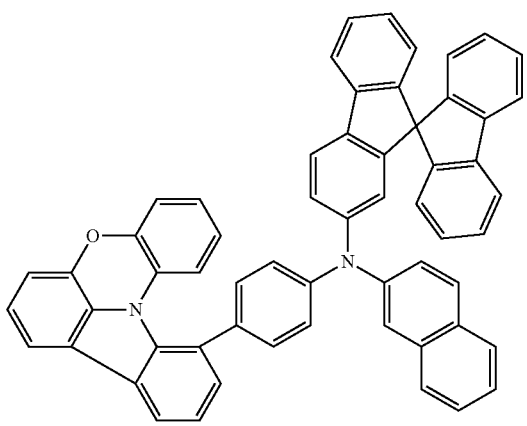
A20
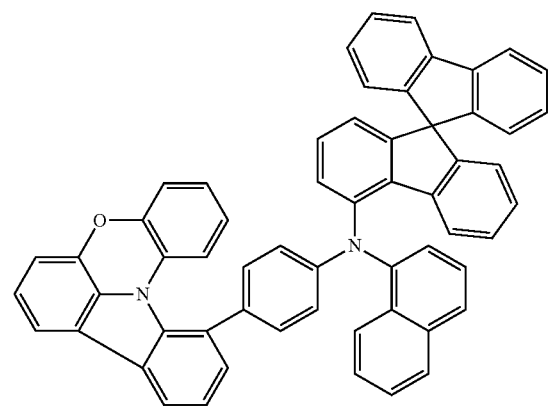
A21
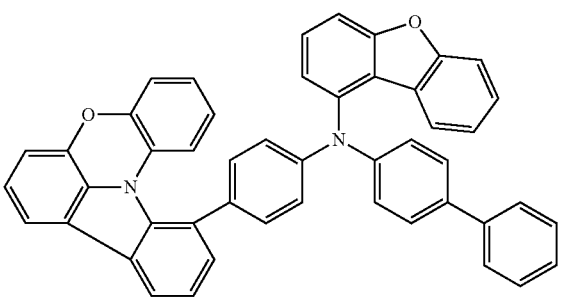
A22
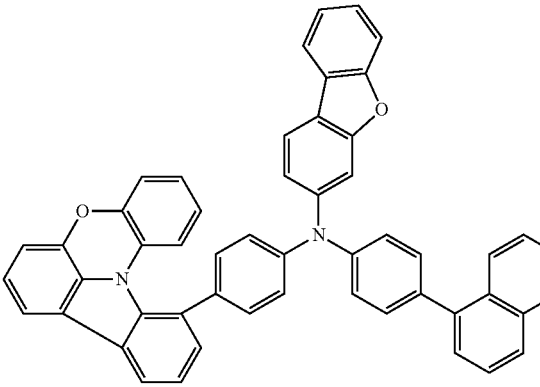

A23
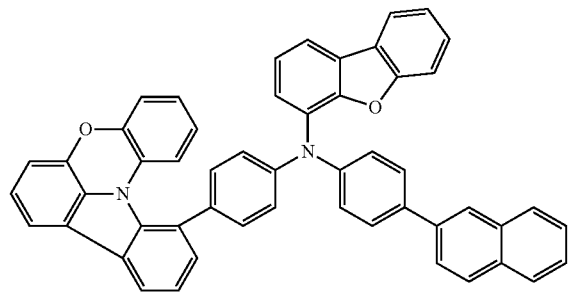
A24
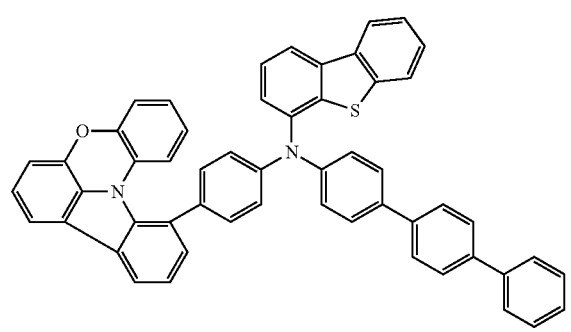
A25
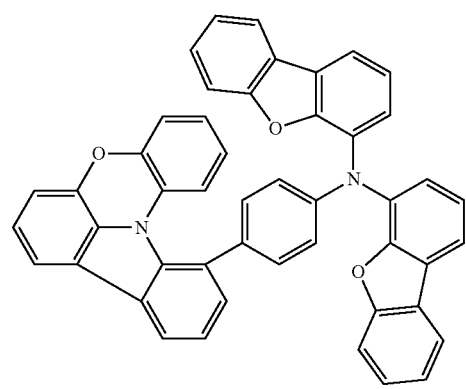
A26
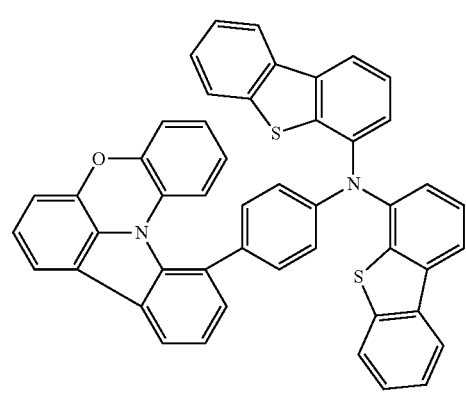
A27
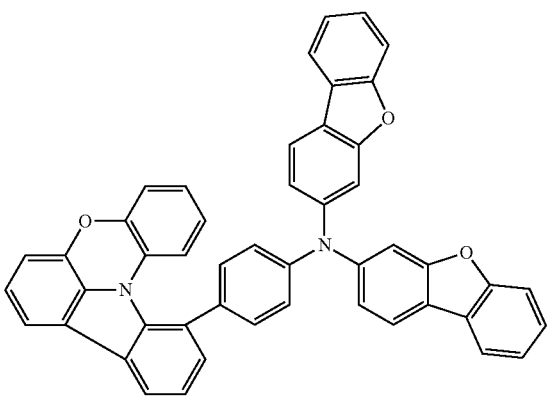
A28
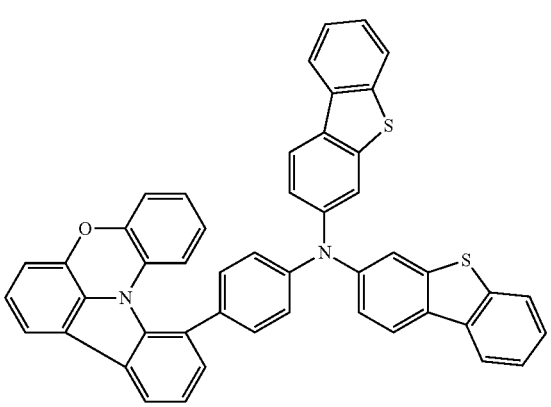
A29
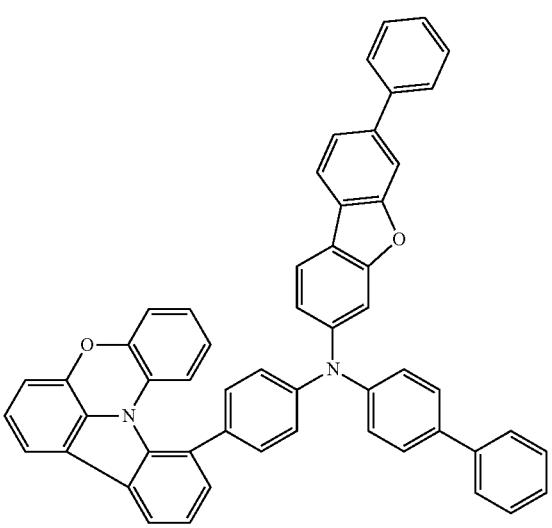

-continued
A30
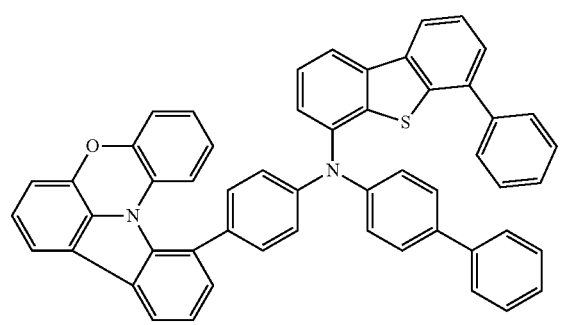
A31
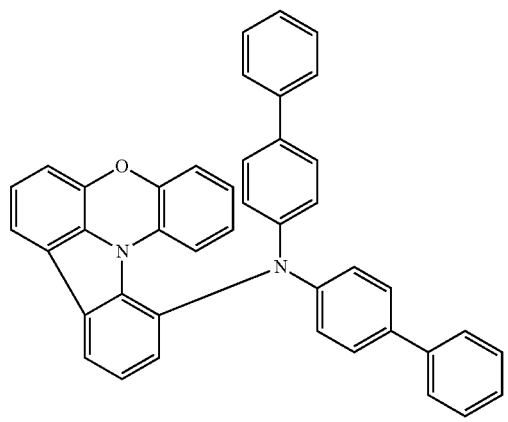
A32
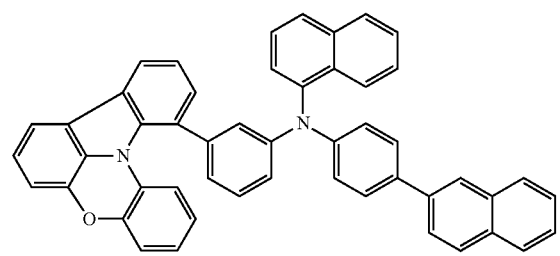
A33
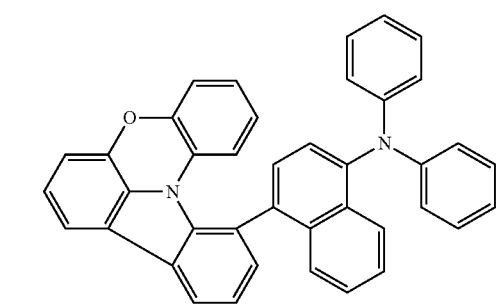
A34
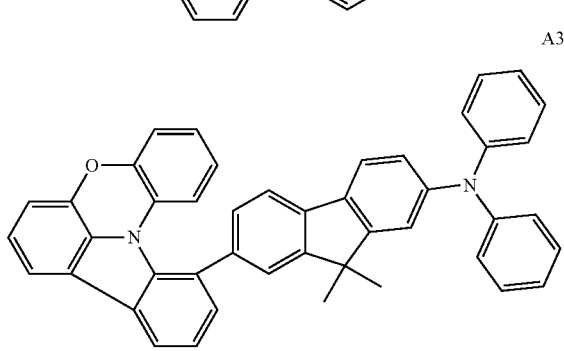
-continued
A35
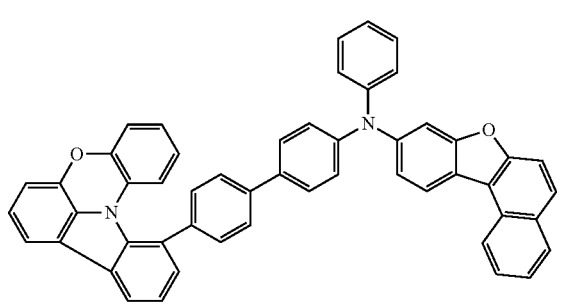
A36
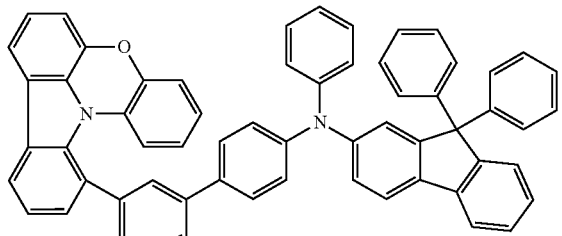
A37
A38
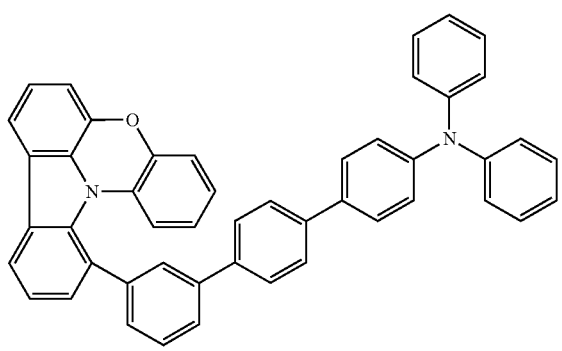

A39
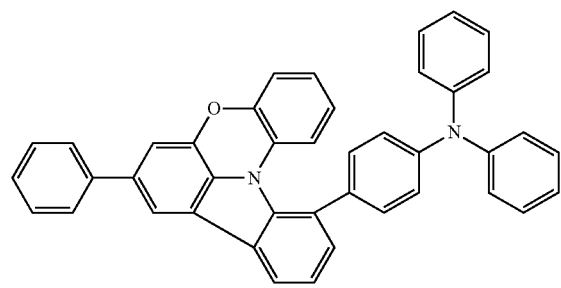
A40
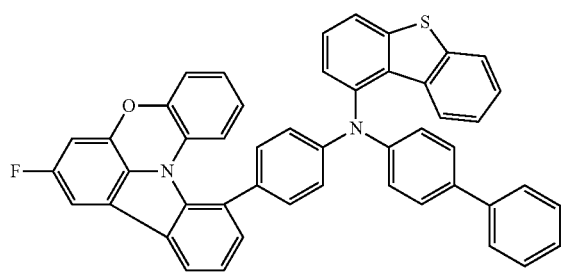
A41
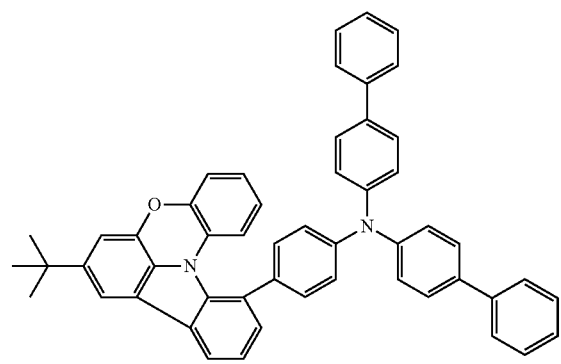
A42
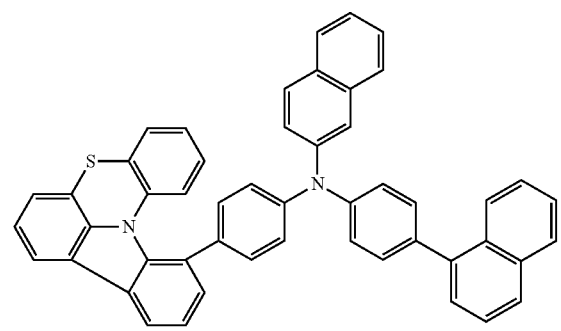
A43
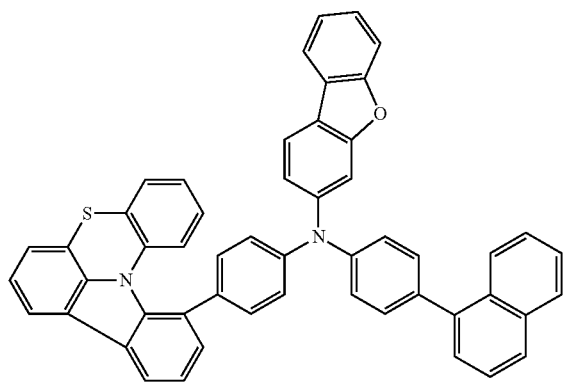
A44
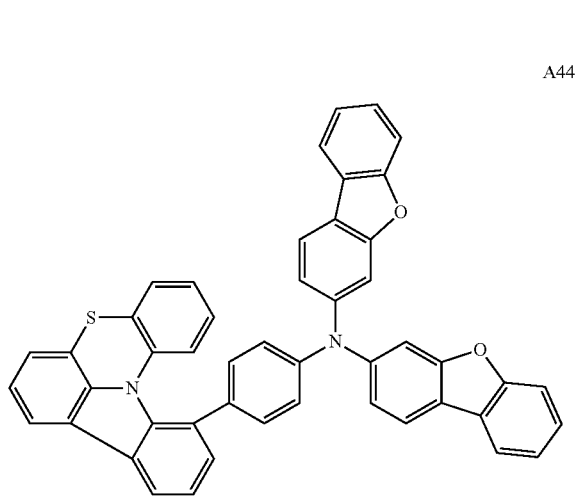
A45
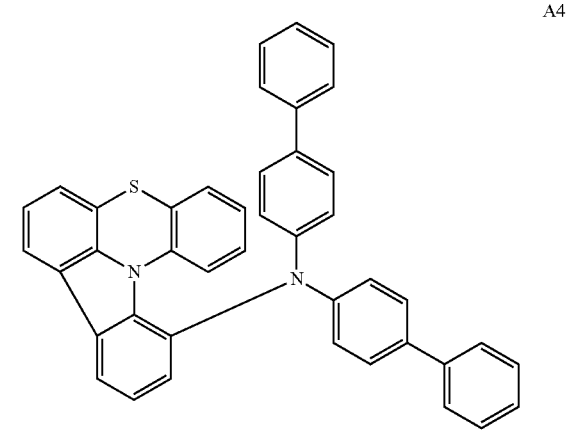
A46
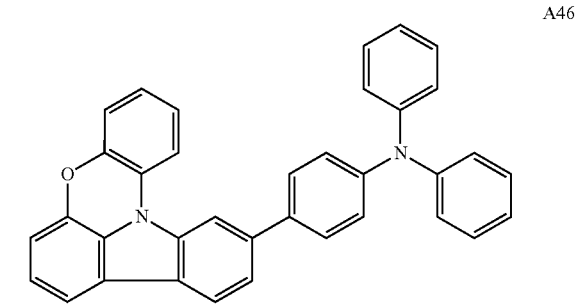

A47
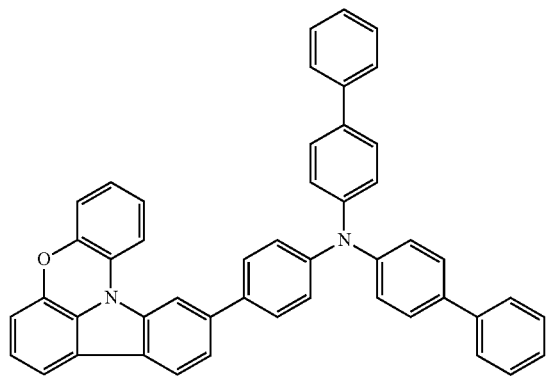
A48
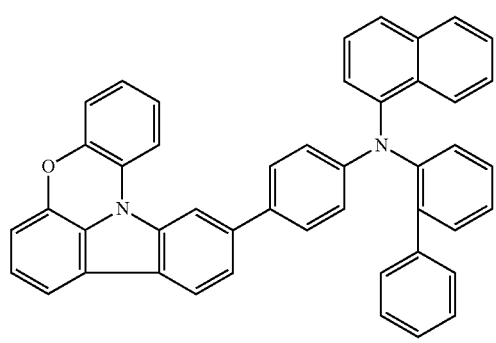
A49
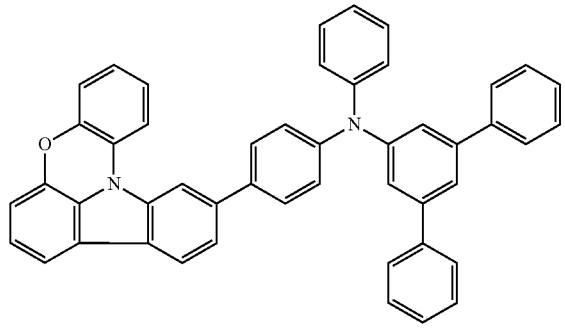
A50
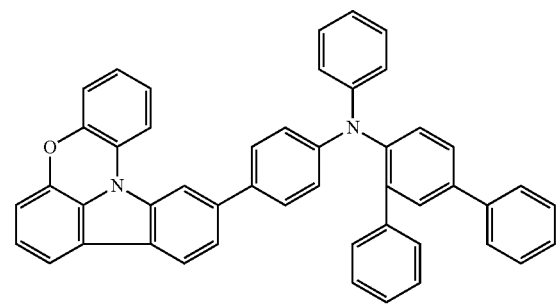
A51
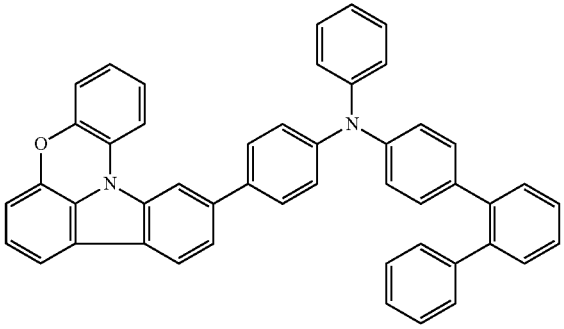
A52
A53
A54
A55
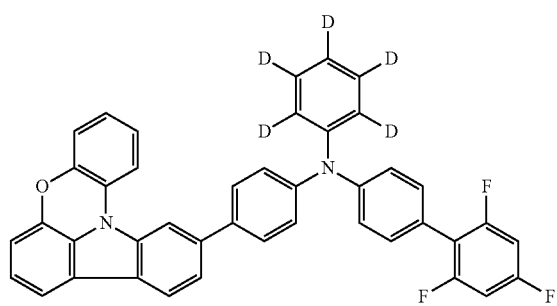

A56
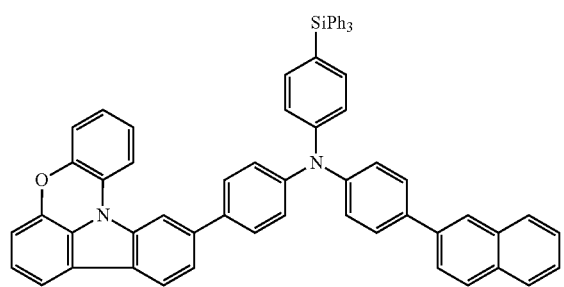
A57
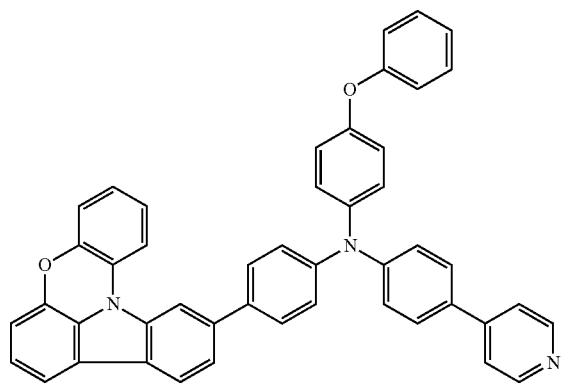
A58
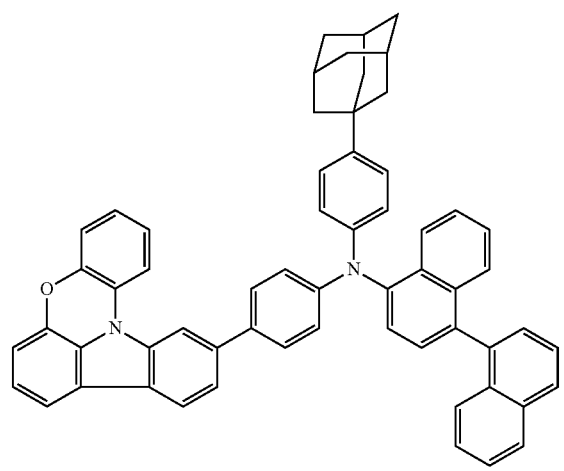
A59
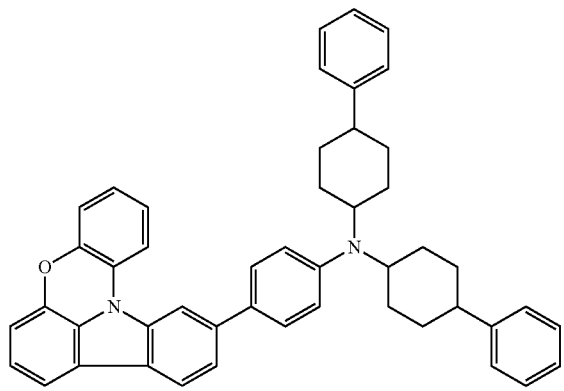
A60
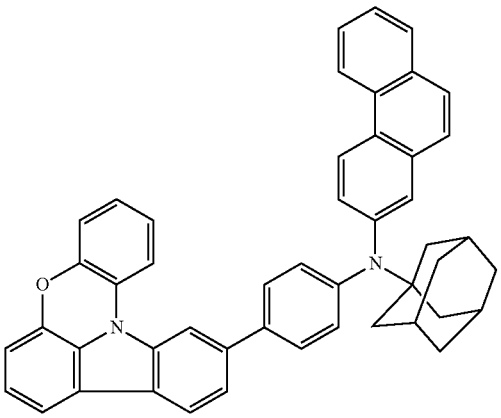
A61
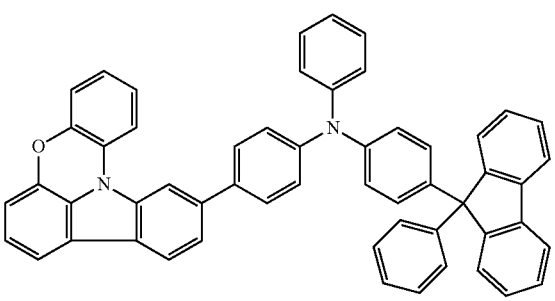
A62
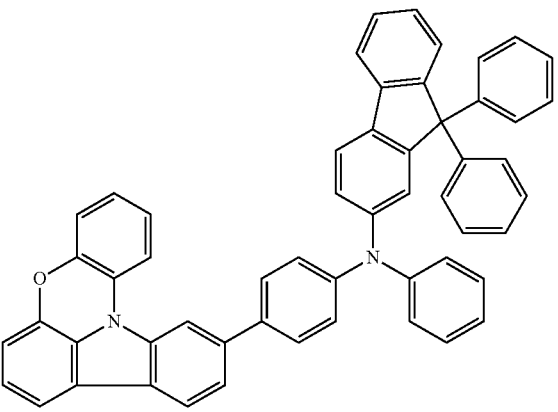
A63
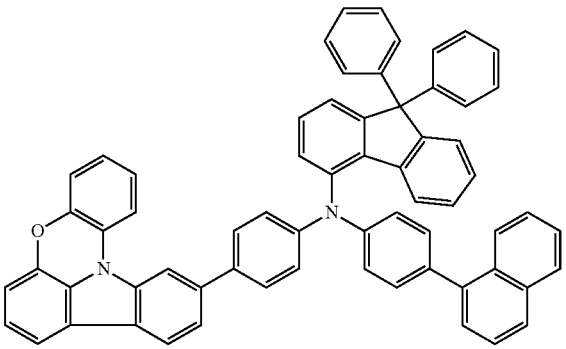

A64
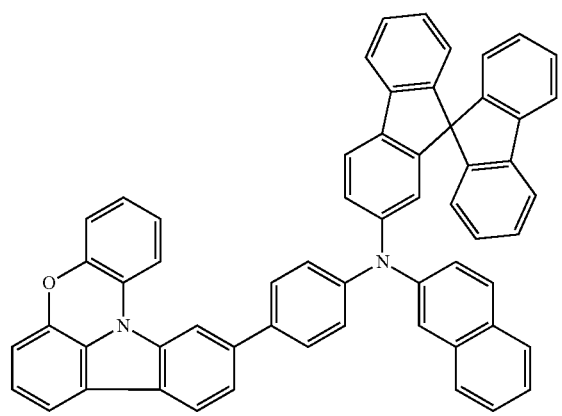
A65
A66
A67
A68
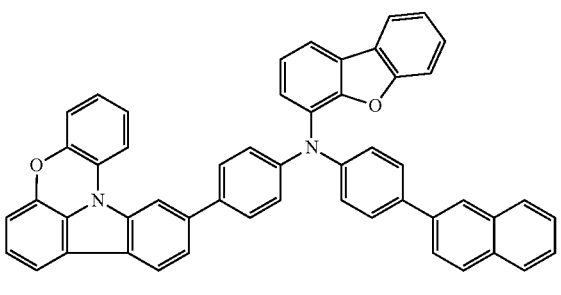
A69
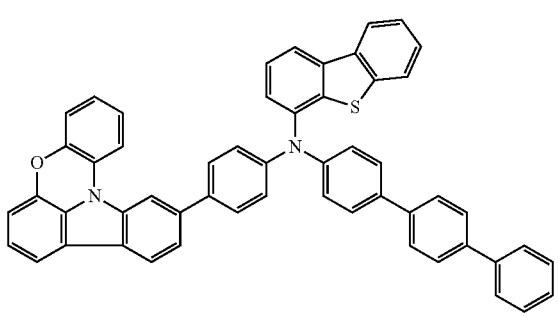
A70
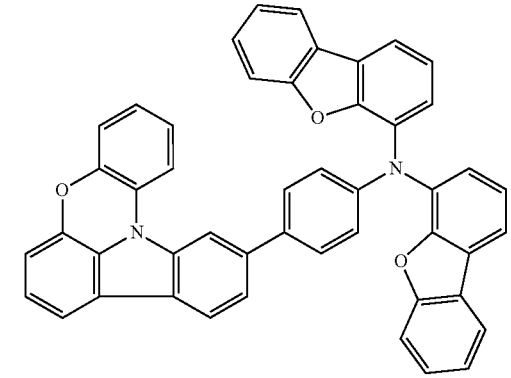
A71
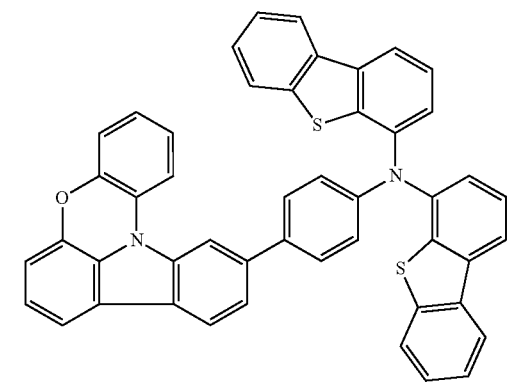

-continued
A72
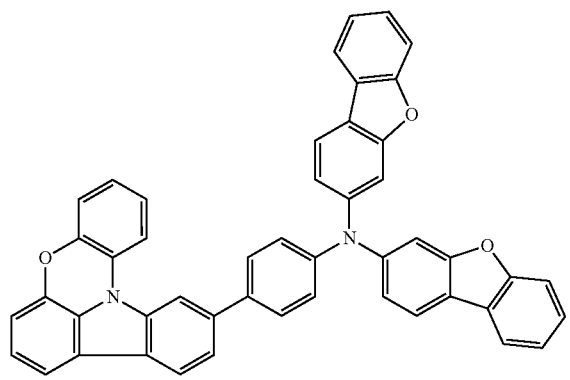
A73
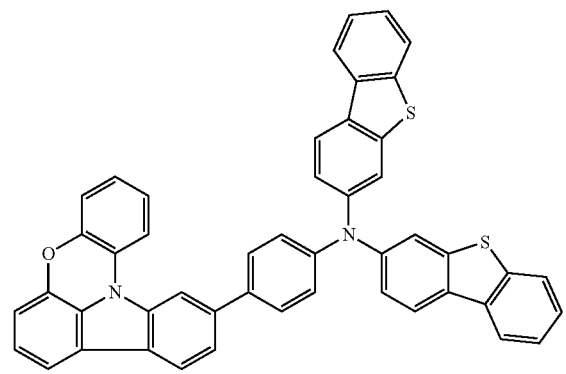
A74
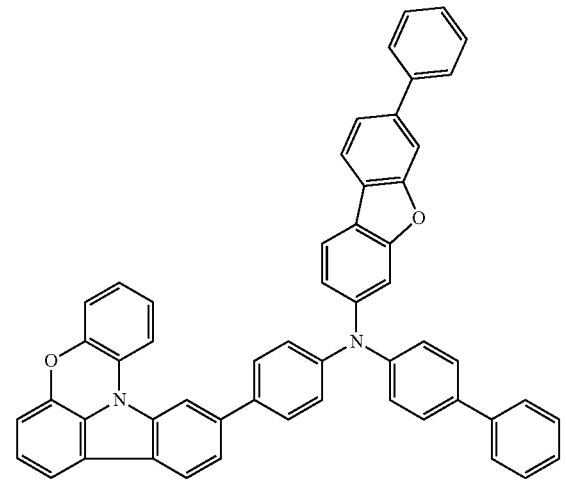
A75
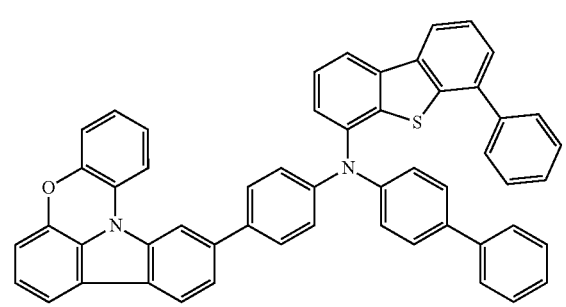
A76
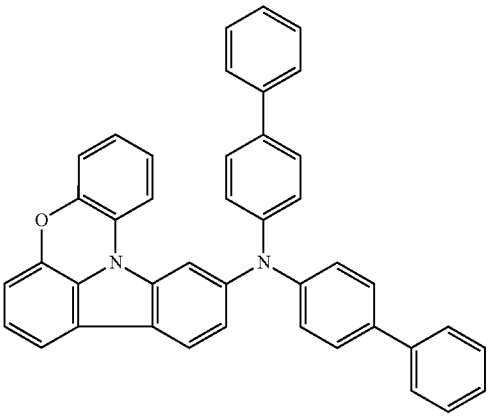
A77
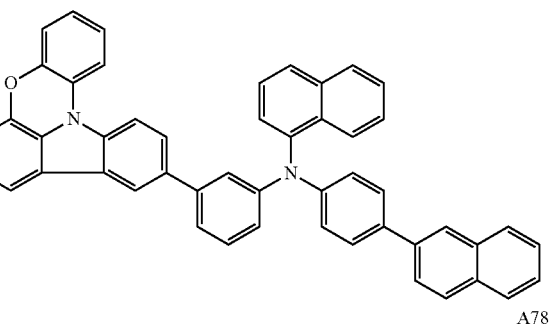
A78
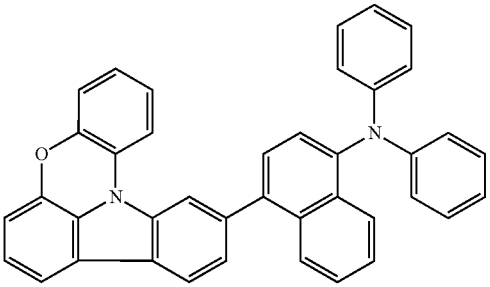
A79
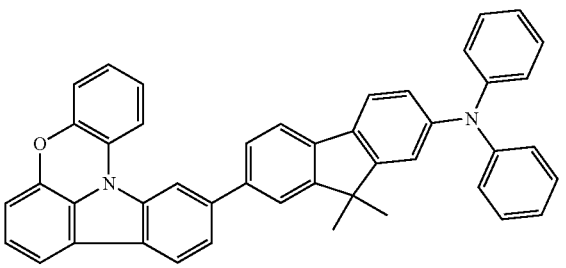
A80
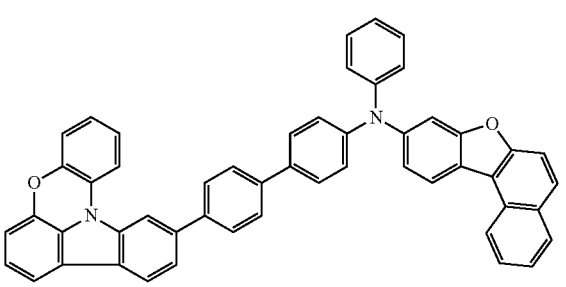

A81
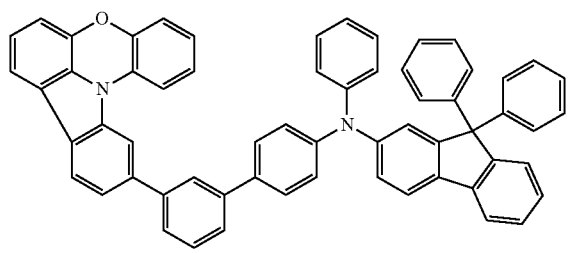
A82
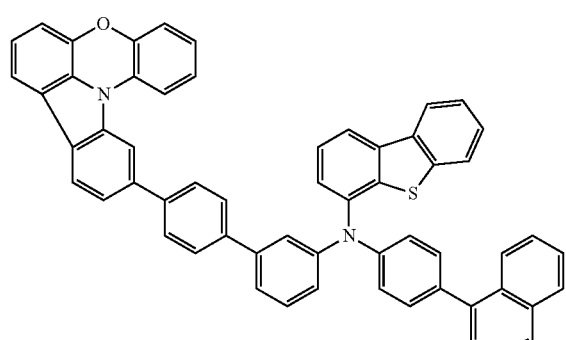
A83
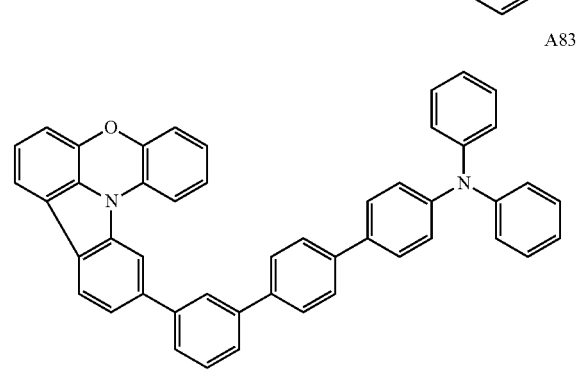
A84
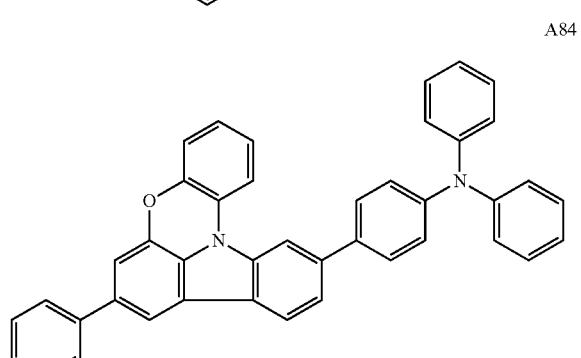
A85
A86
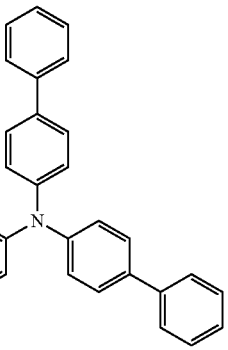
A87
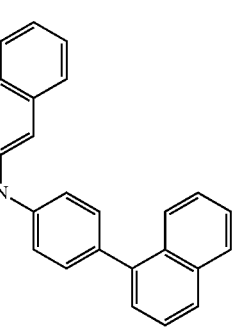
A88
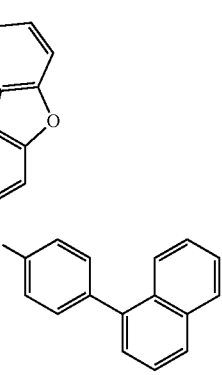
A89
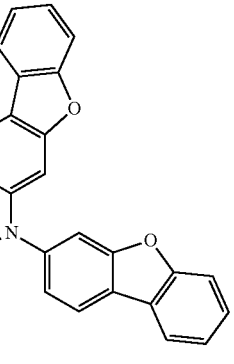

-continued
A90
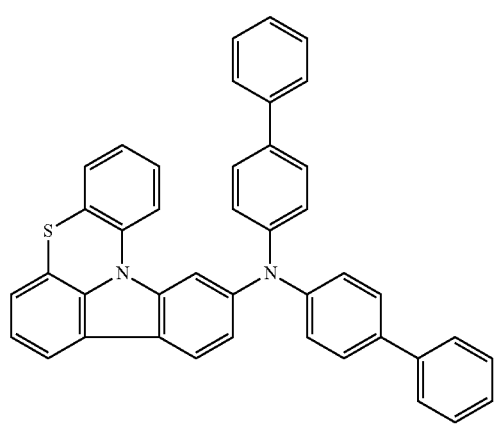
A136
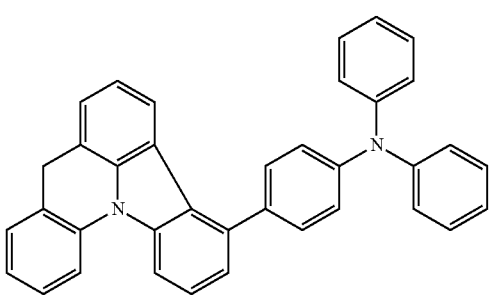
A137
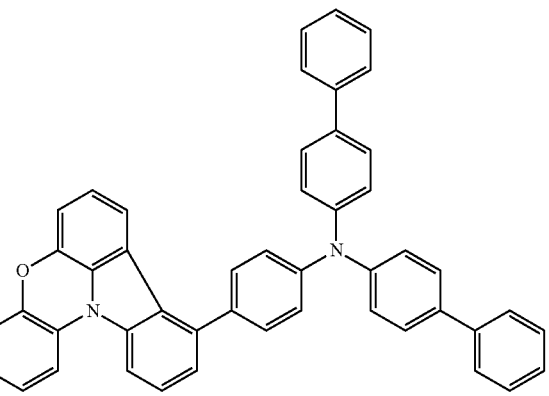
A138
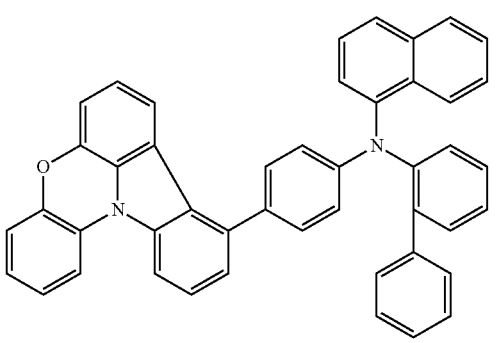
-continued
A139
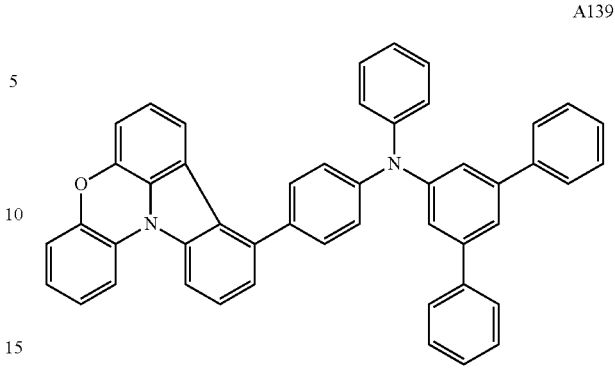
A140
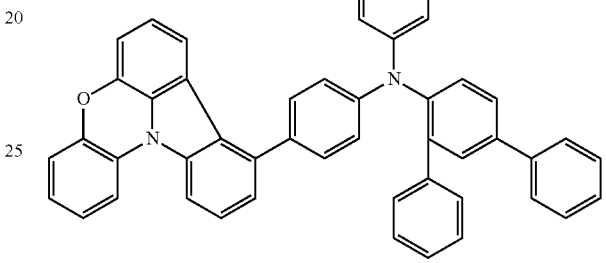
A141
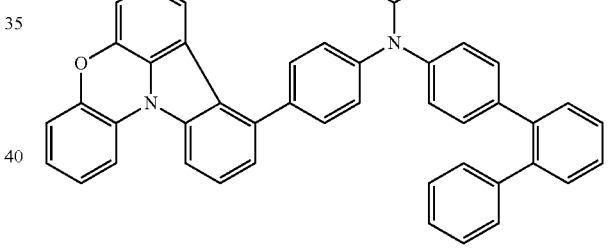
A142
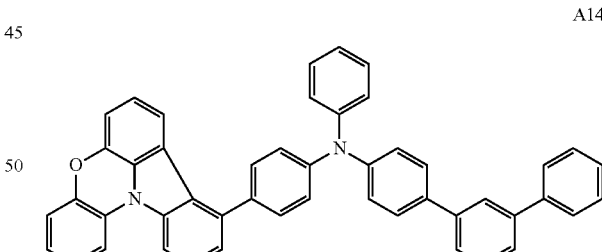
A143
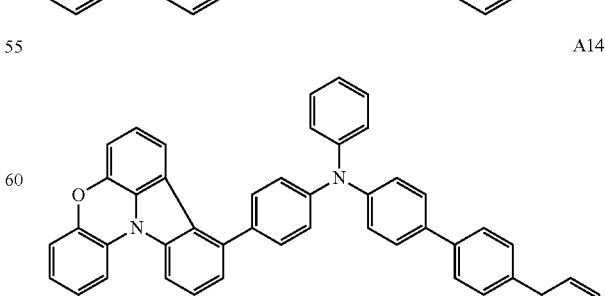

A144
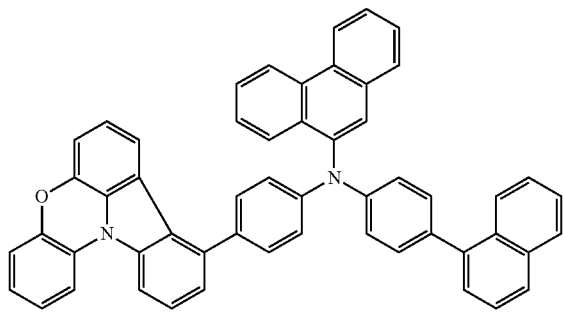
A145
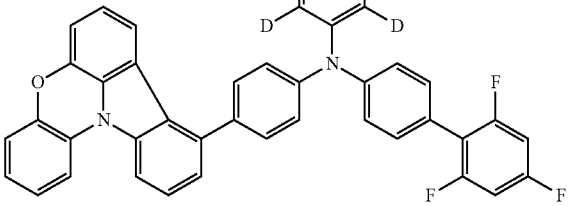
A146
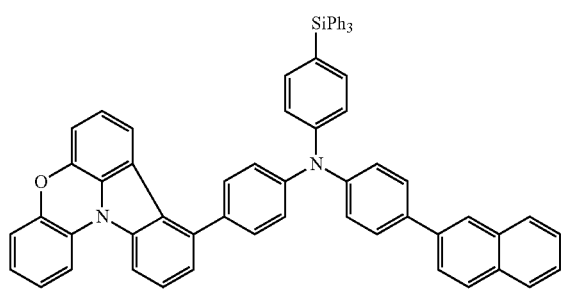
A147
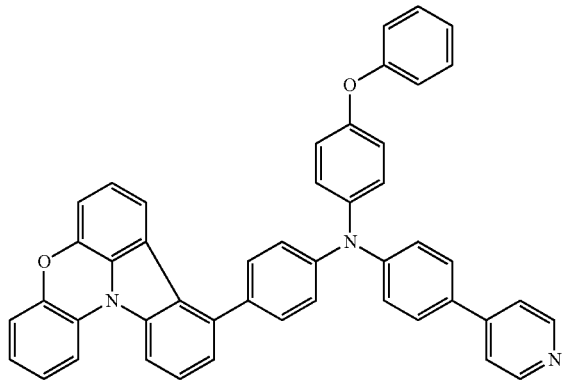
A148
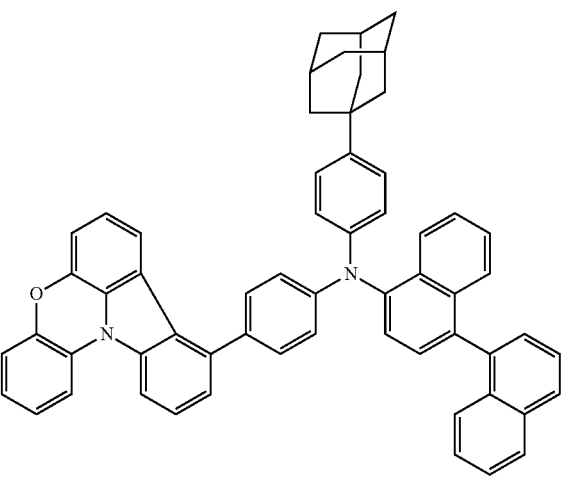
A149
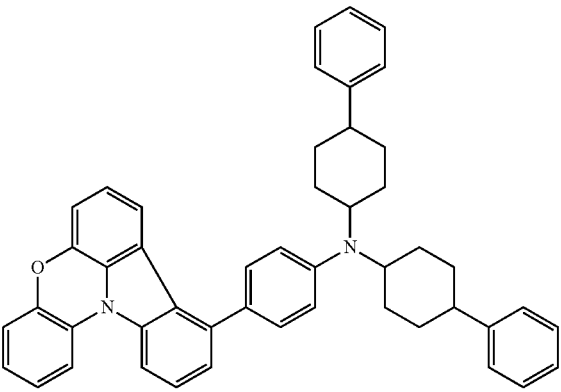
A150
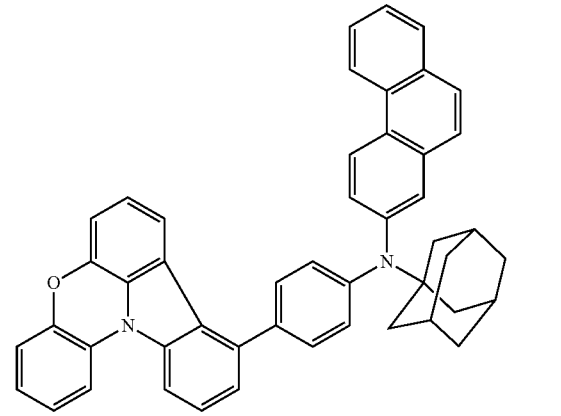
A151
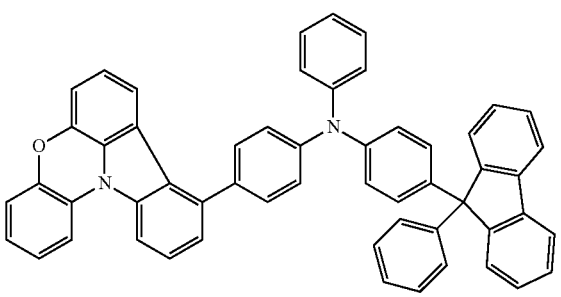

A152
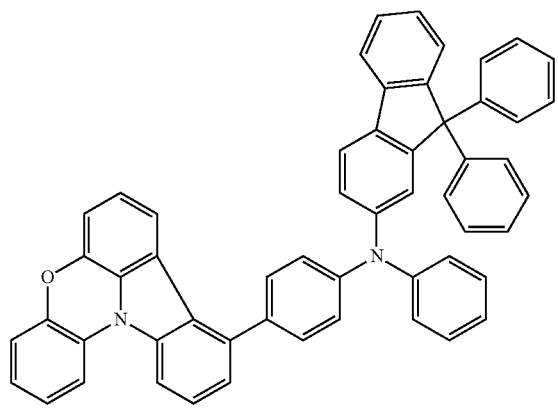
A153
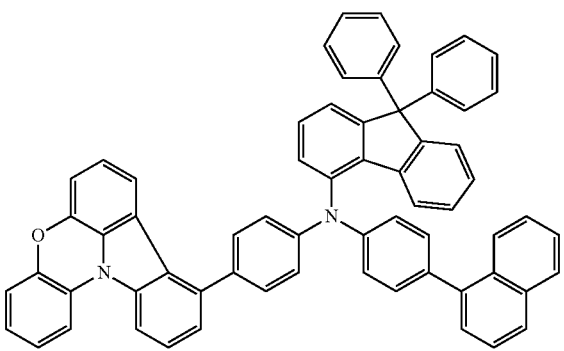
A154
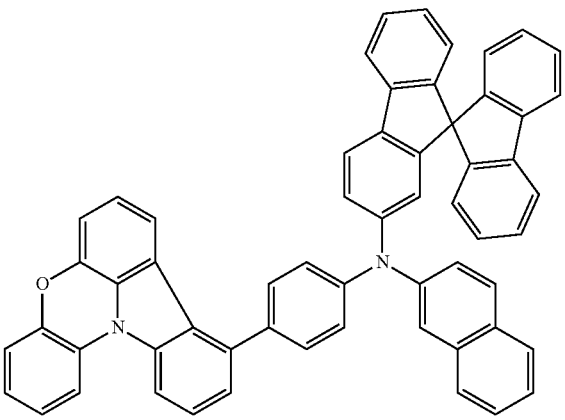
A155
A156
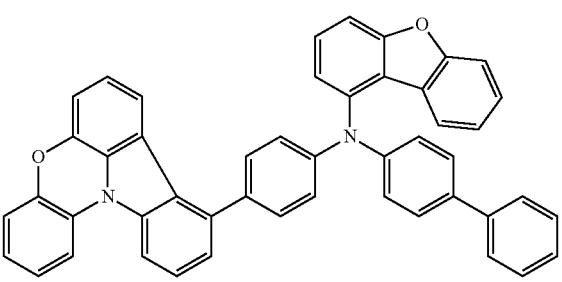
A157
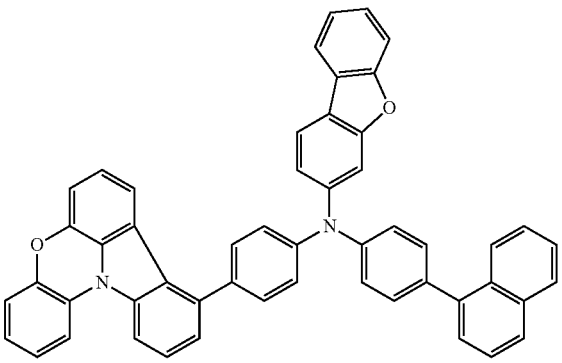
A158
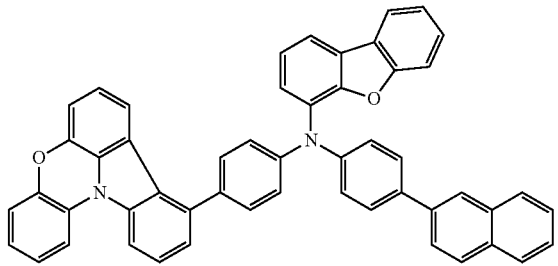
A159
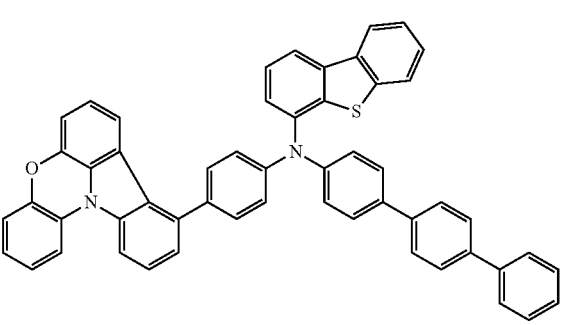

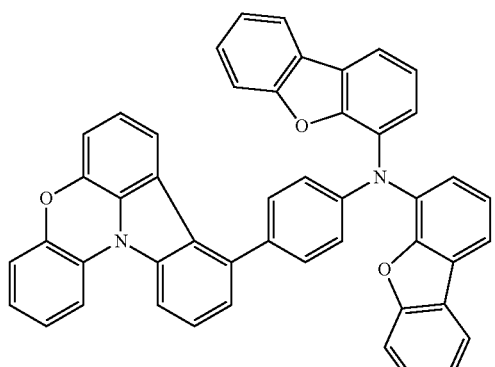 A160
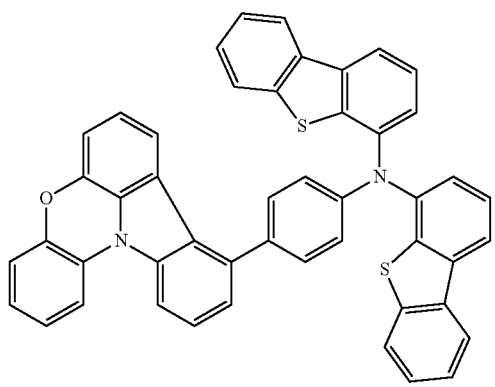 A161
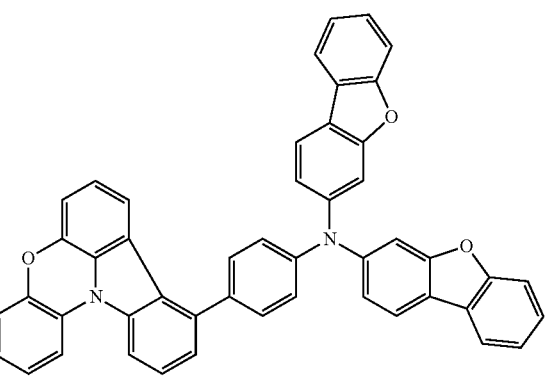 A162
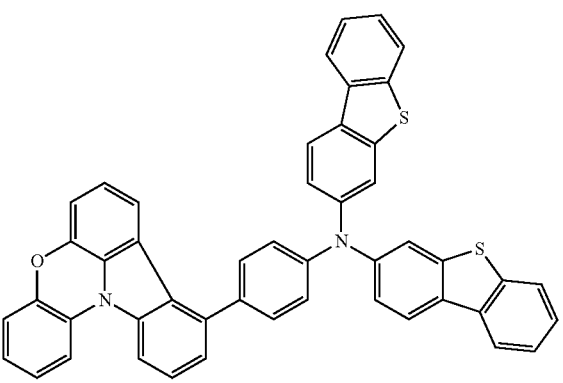 A163
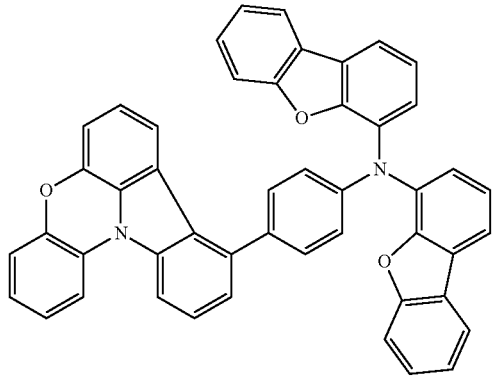 A164
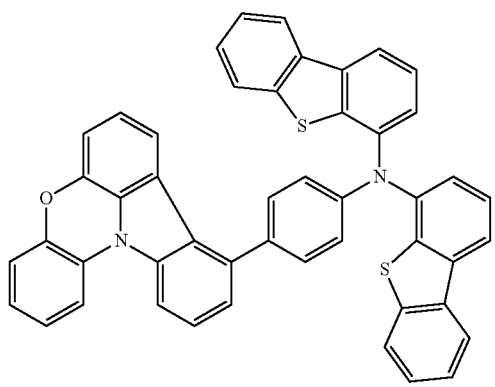 A165
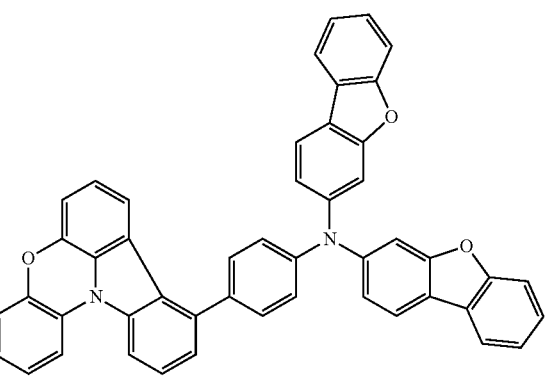 A166
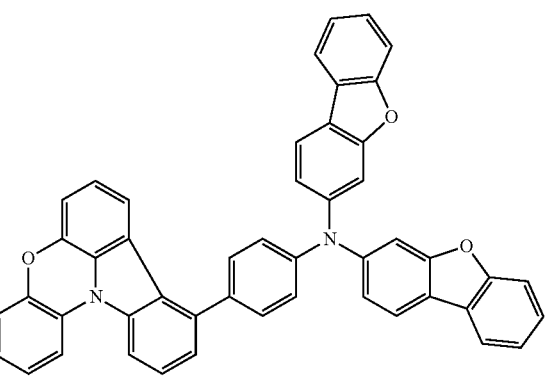 A167

A168
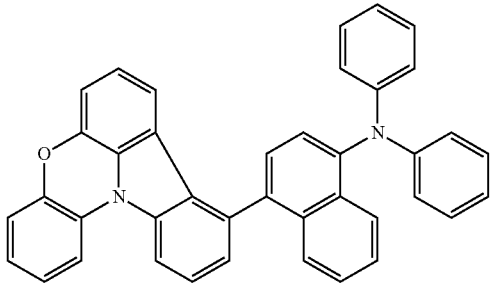
A169
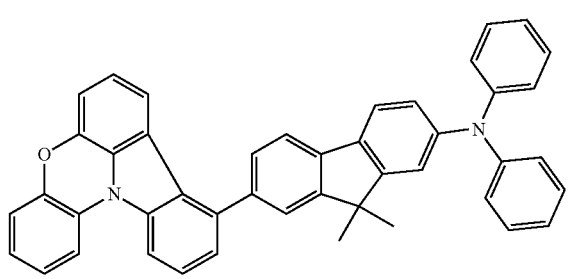
A170
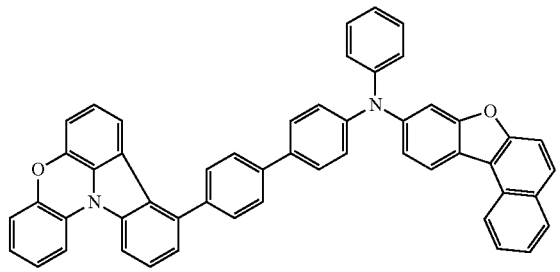
A171
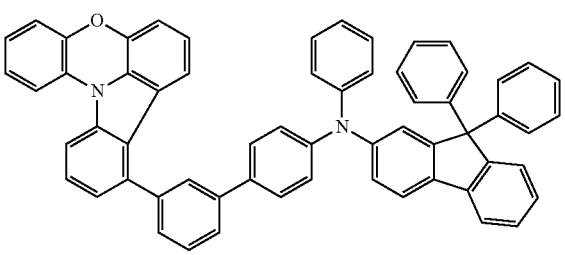
A172
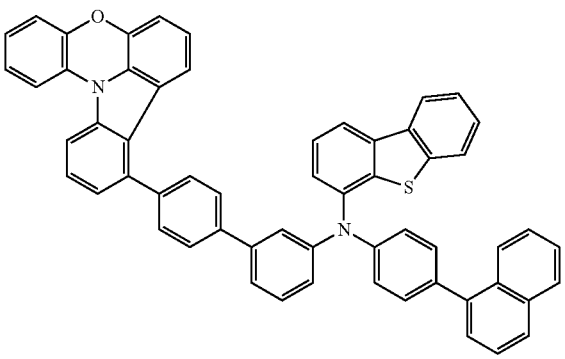
A173
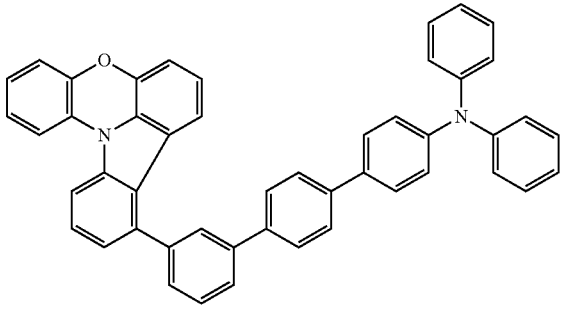
A174
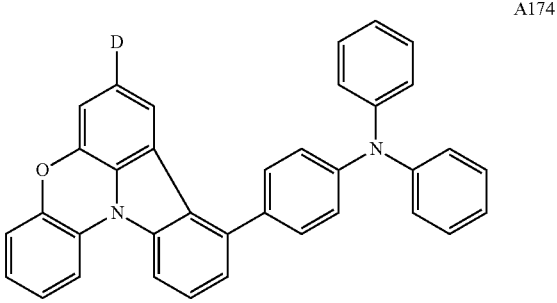
A175
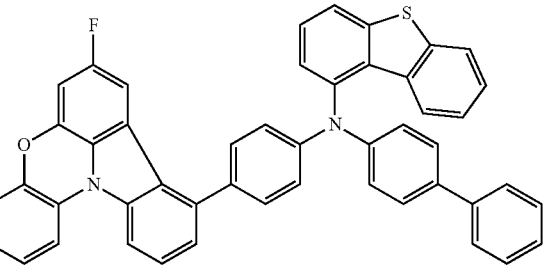
A176
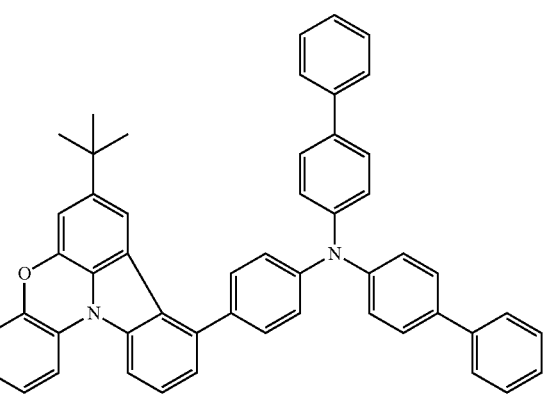

-continued
A177
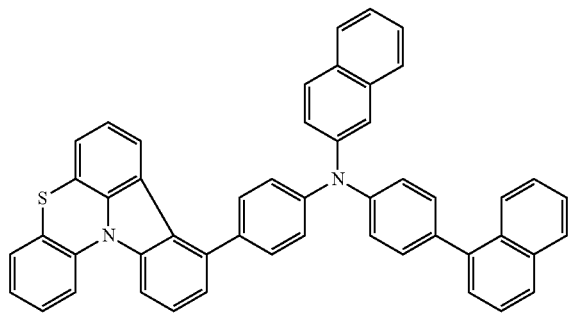
A178
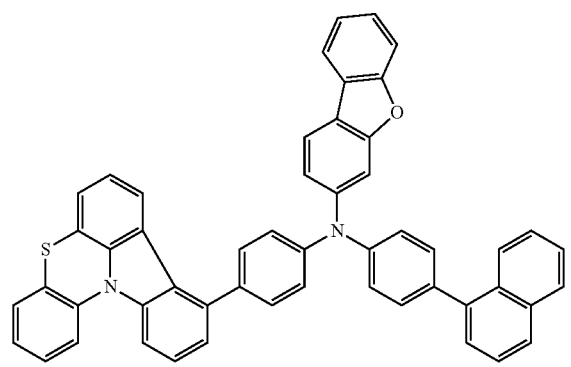
A179
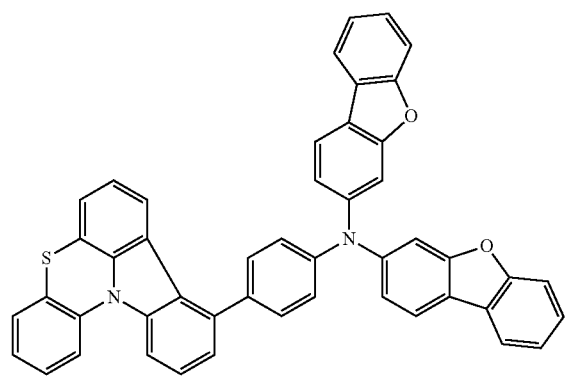
A180
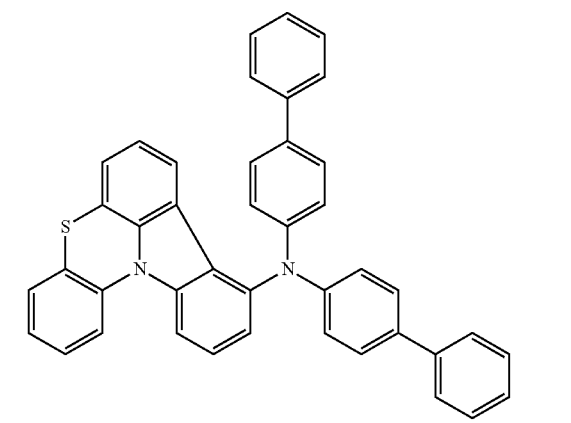
Compound Group 2
B1
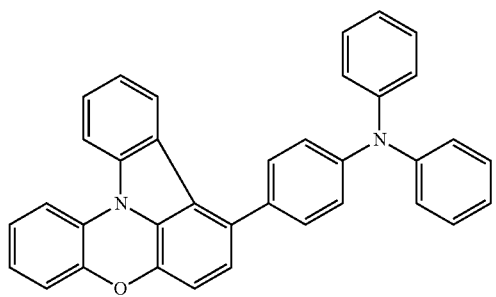
B2
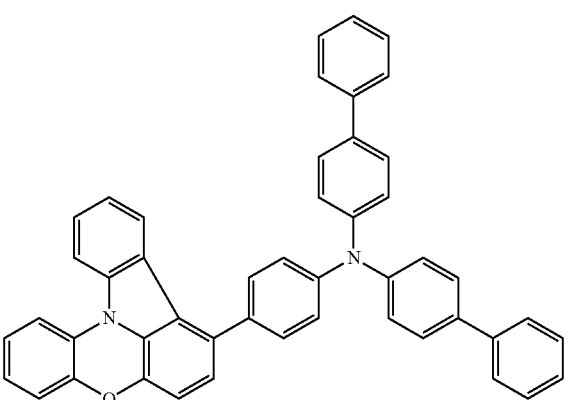
B3
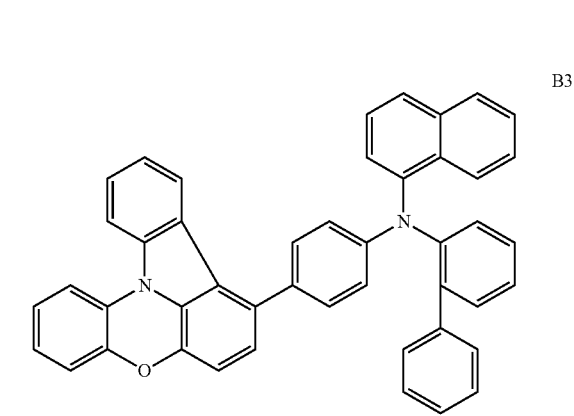
B4
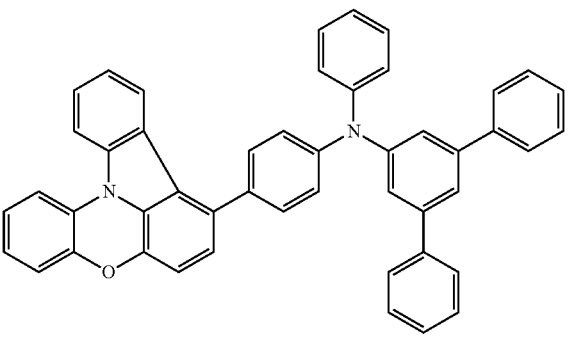

B5
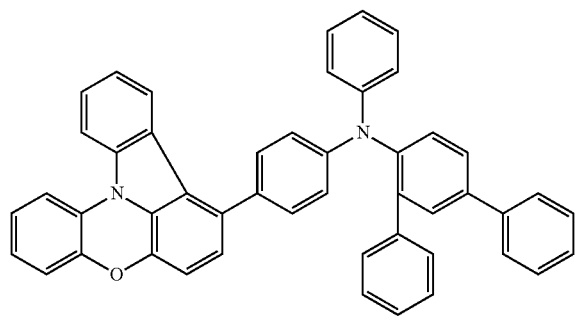
B6
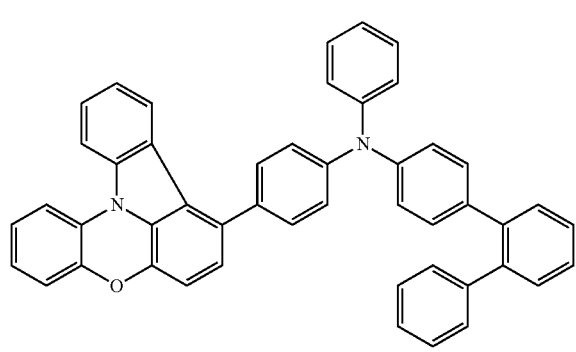
B7
B8
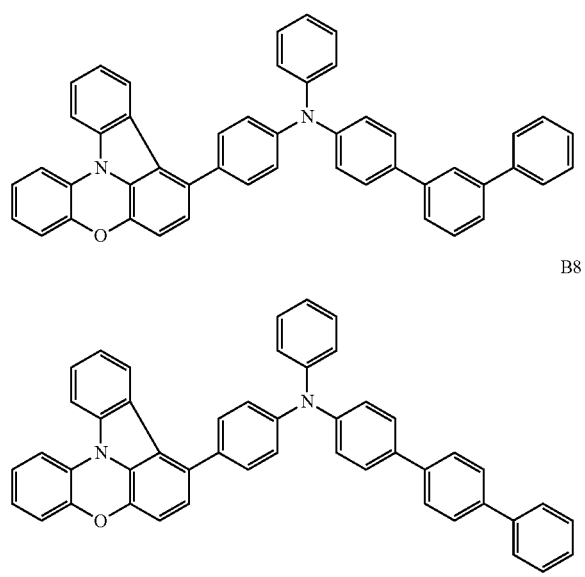
B9
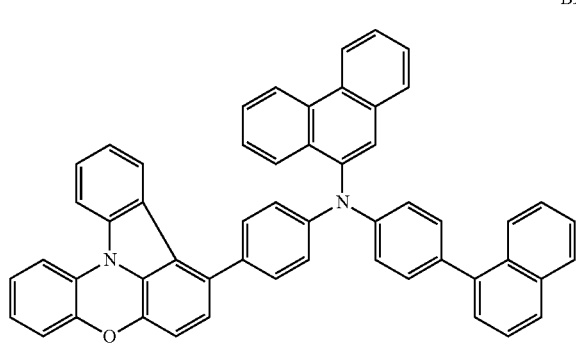
B10
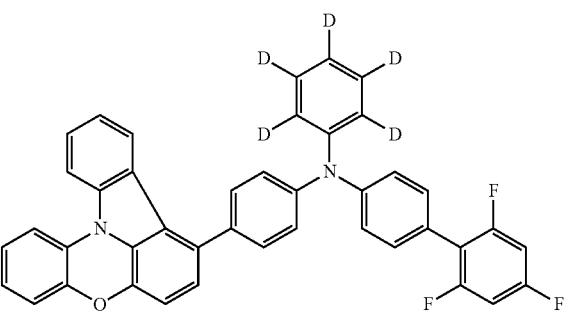
B11
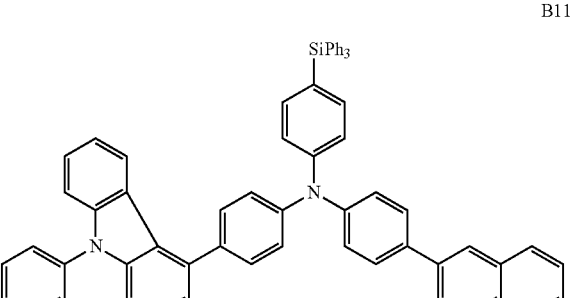
B12
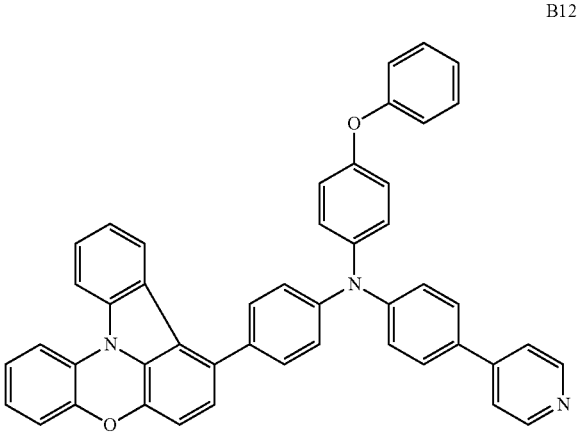
B13
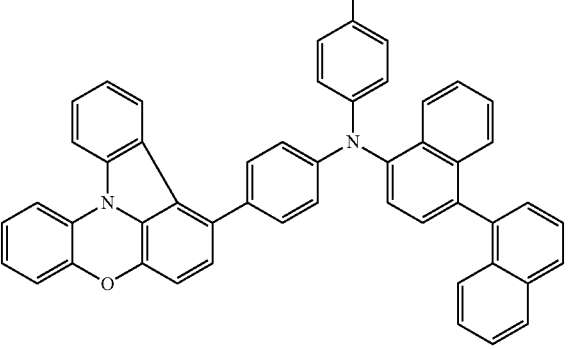

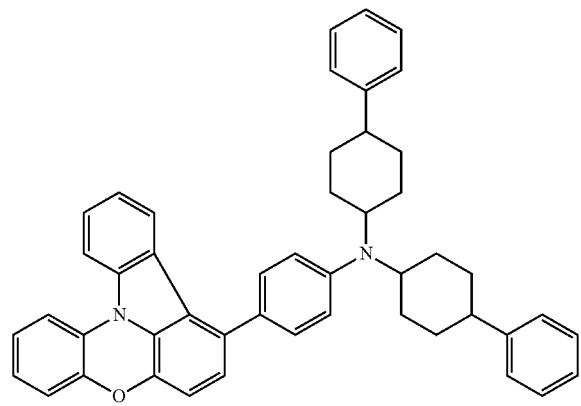
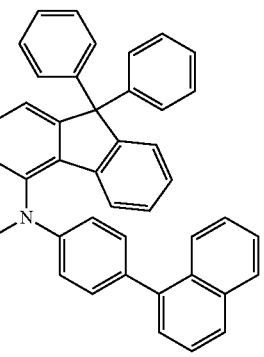
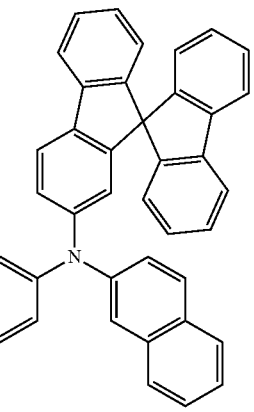
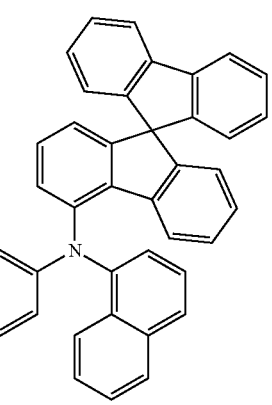
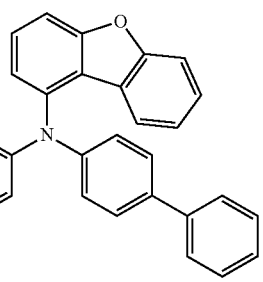

B22
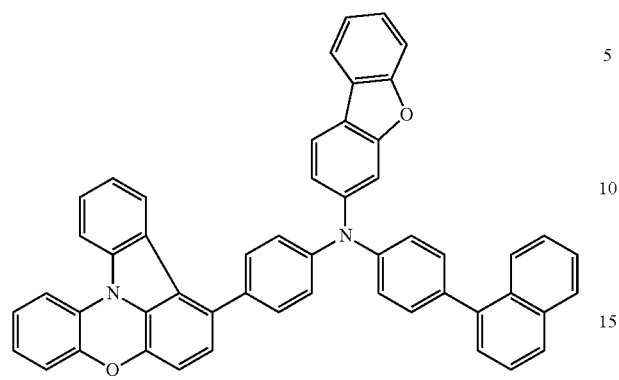
B23
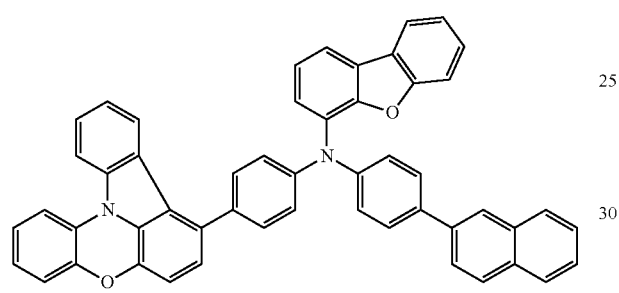
B24
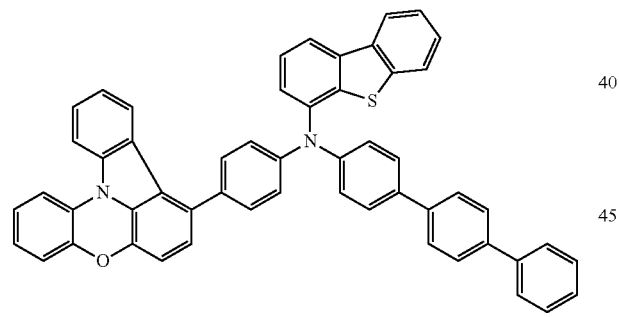
B25
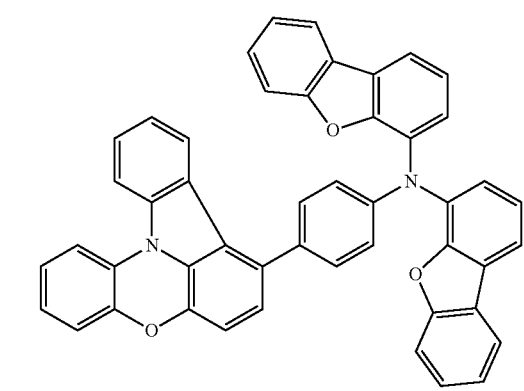
B26
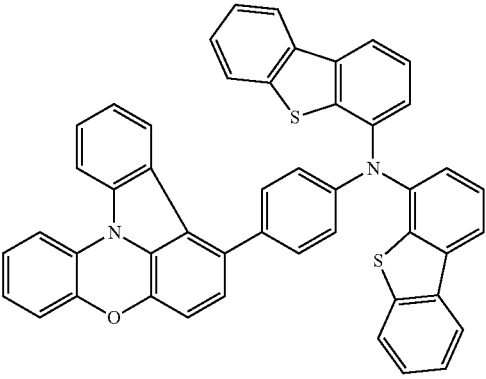
B27
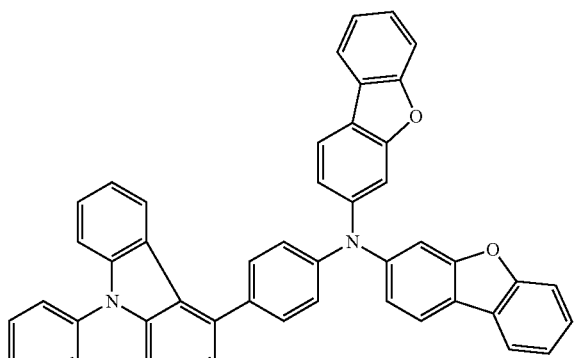
B28
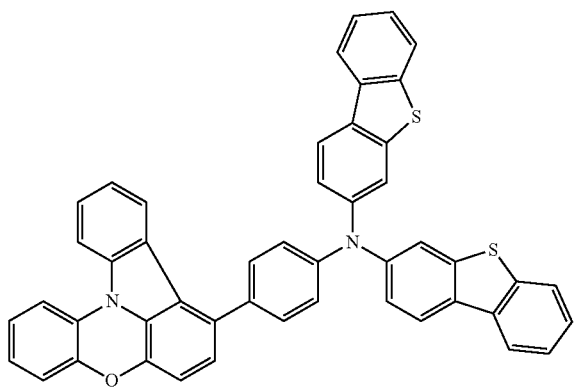

B29
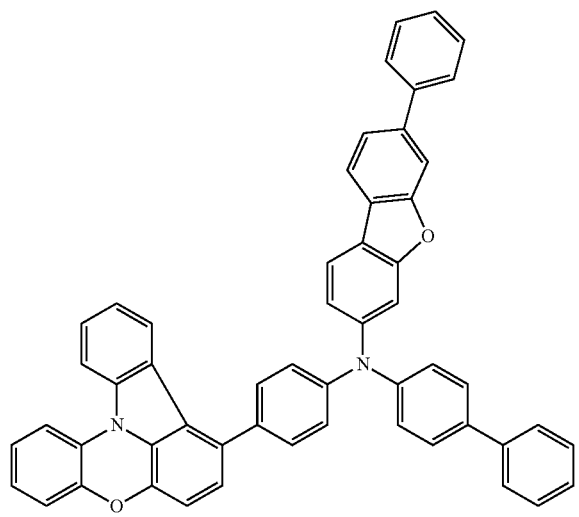
B30
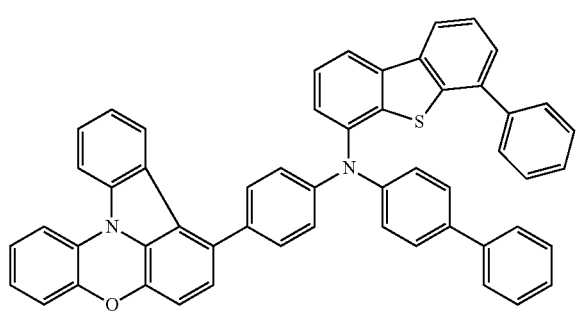
B31
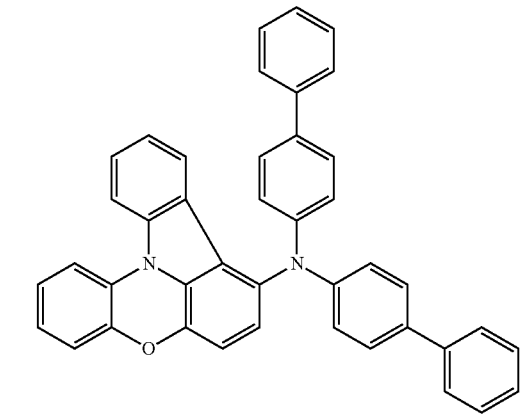
B32
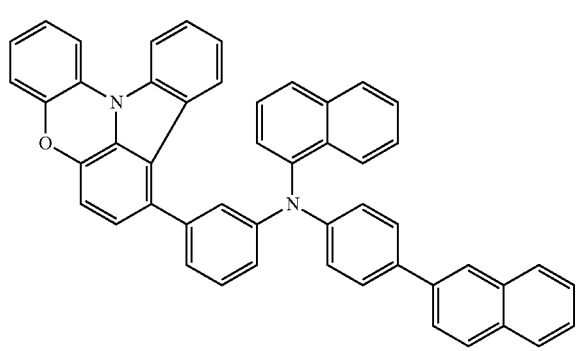
B33
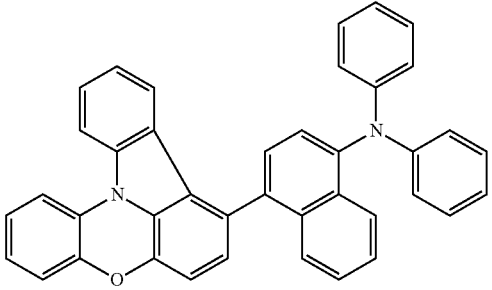
B34
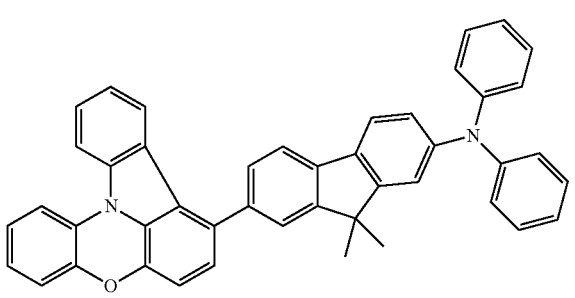
B35
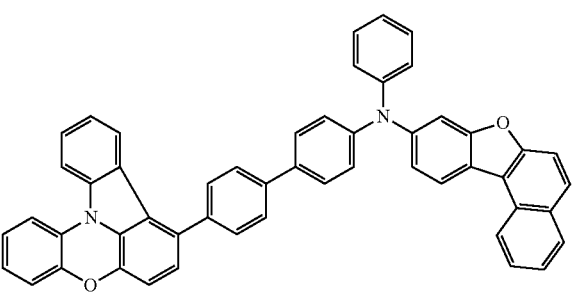
B36
B37
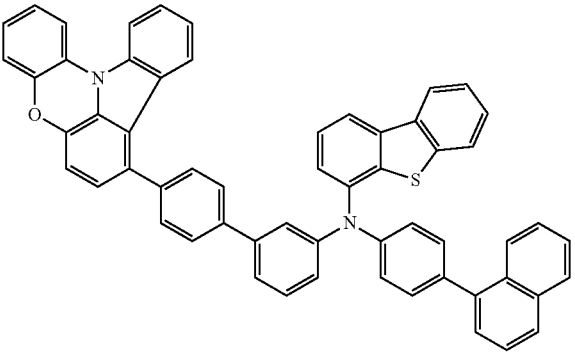

B38
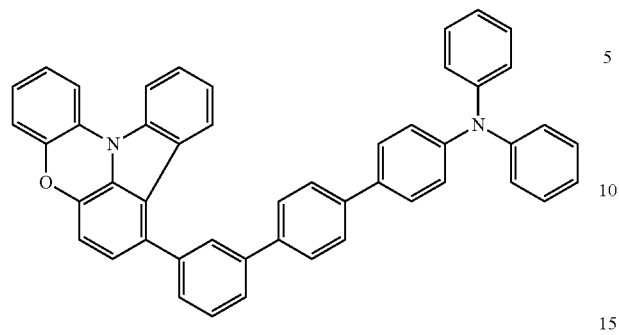
B42
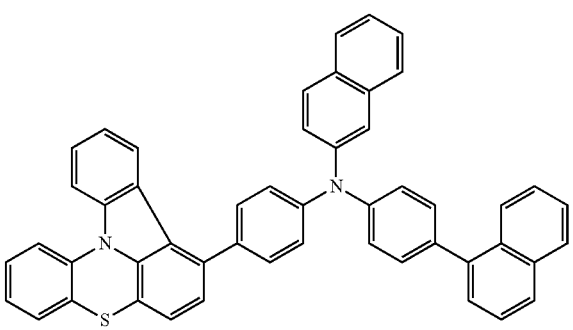
B39
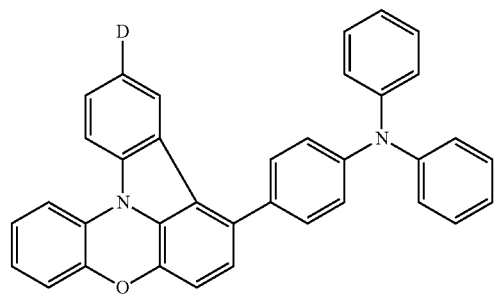
B43
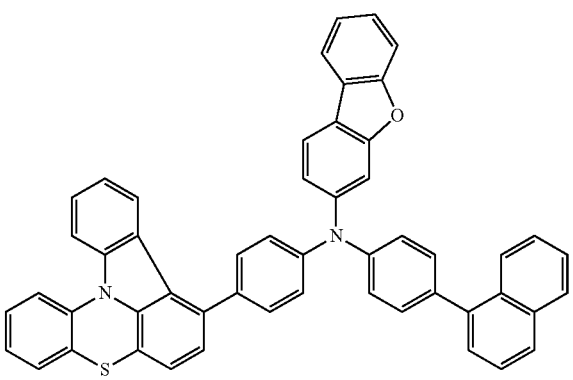
B40
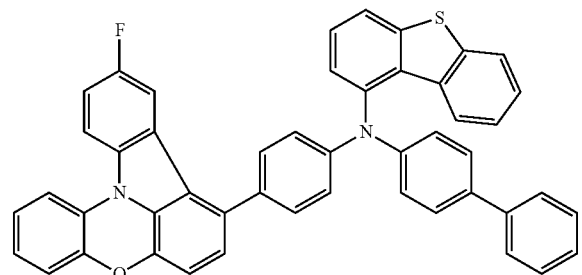
B44
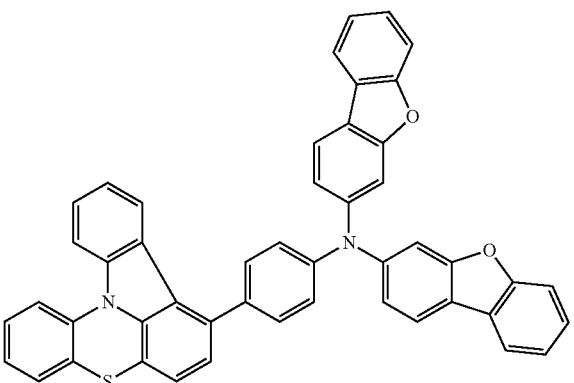
B41
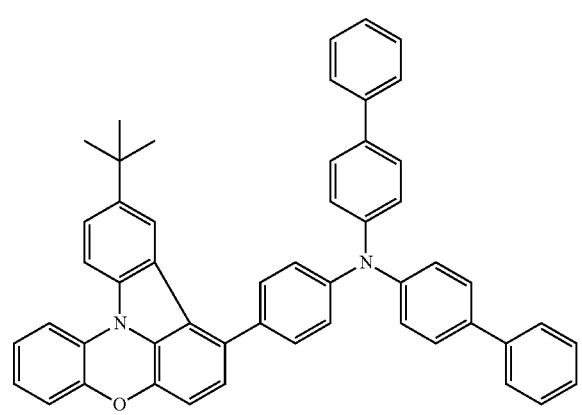
B45
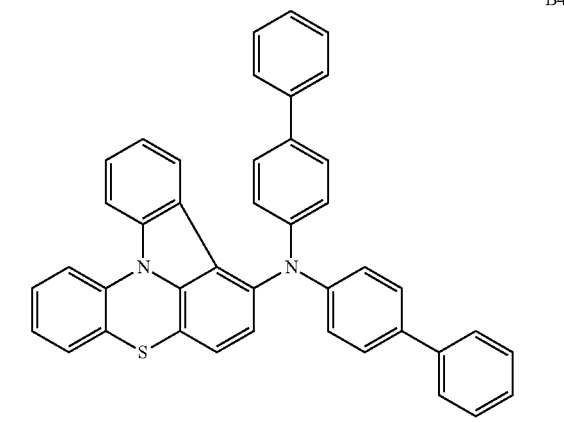

B91
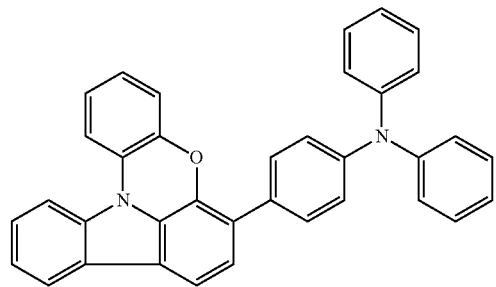
B92
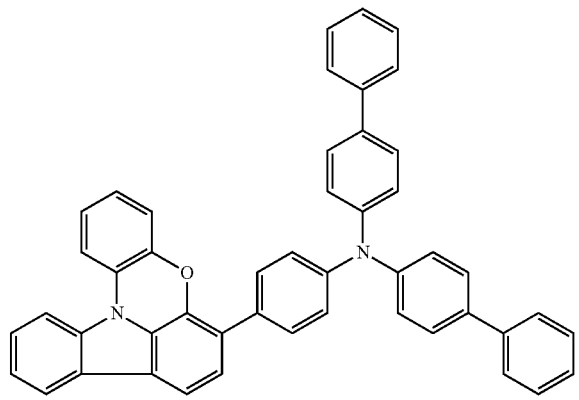
B93
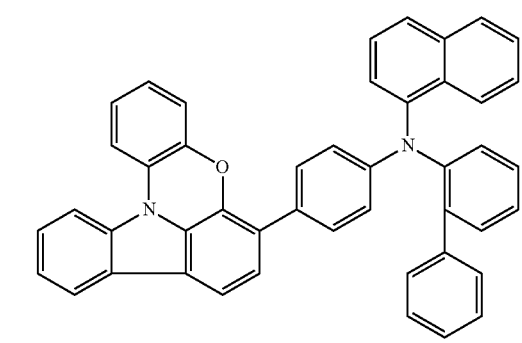
B94
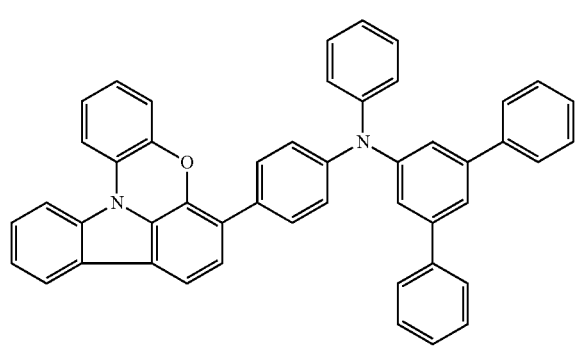
B95
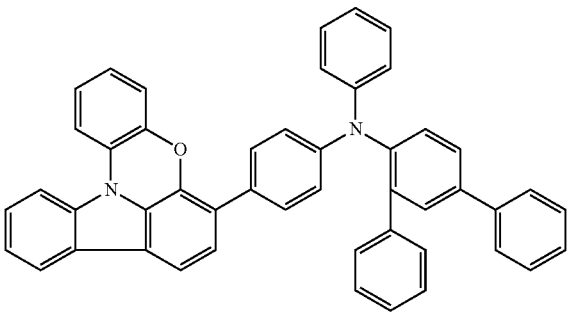
B96
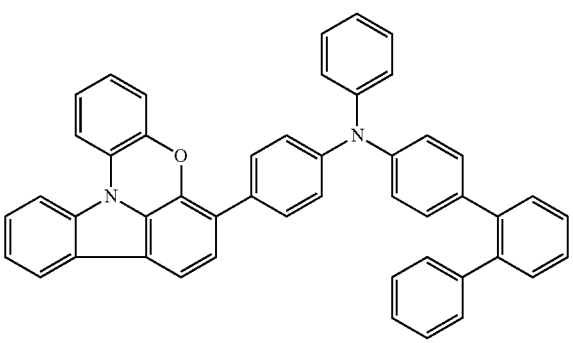
B97
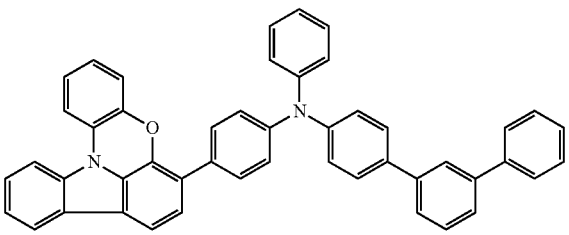
B98
B99
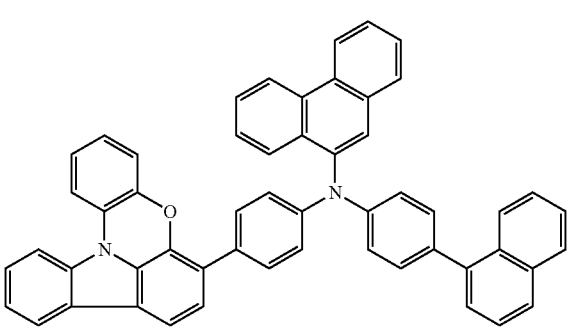

B100
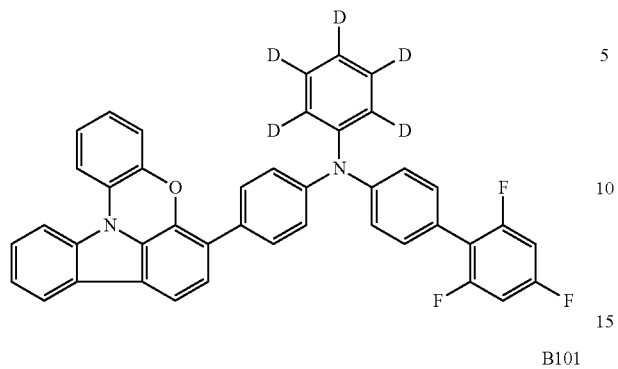
B101
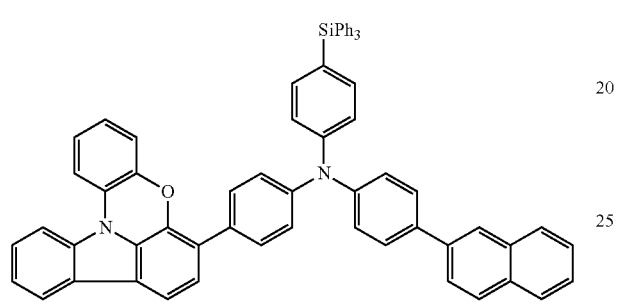
B102
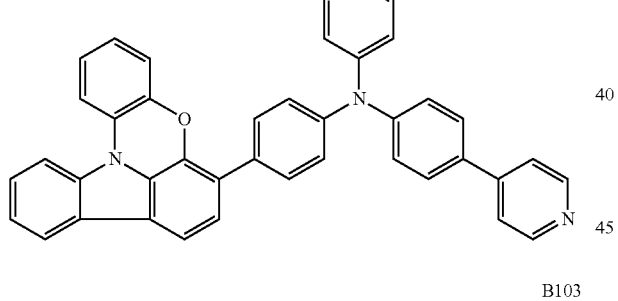
B103
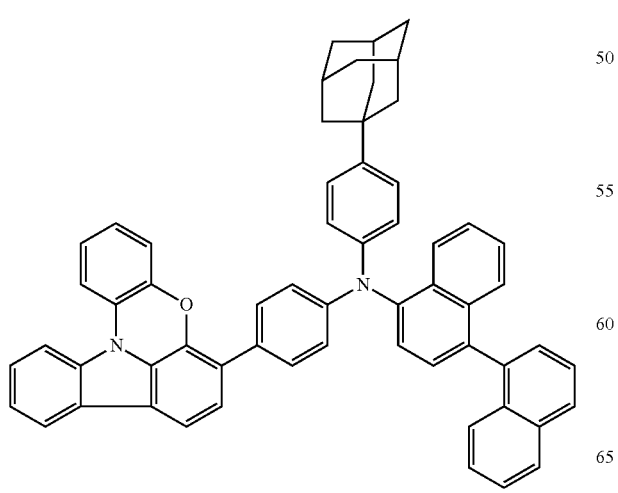
B104
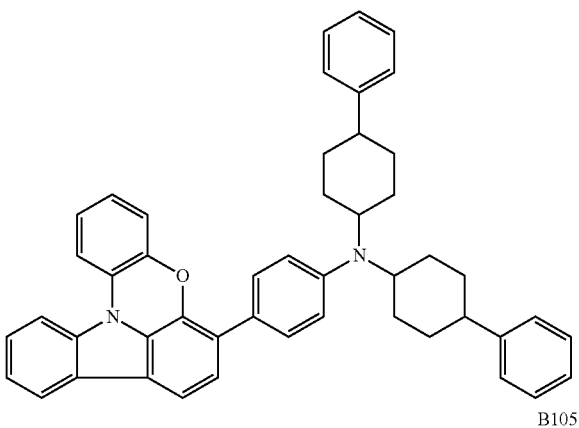
B105
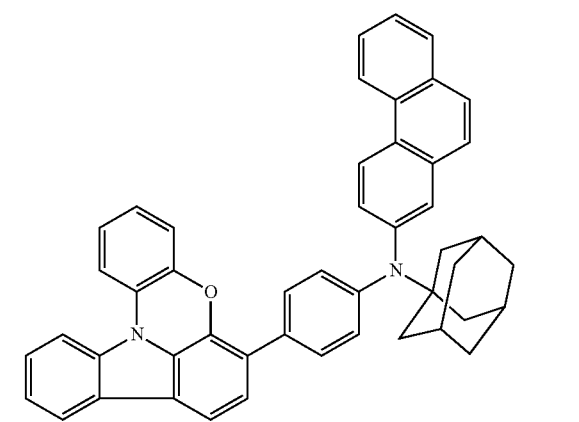
B106
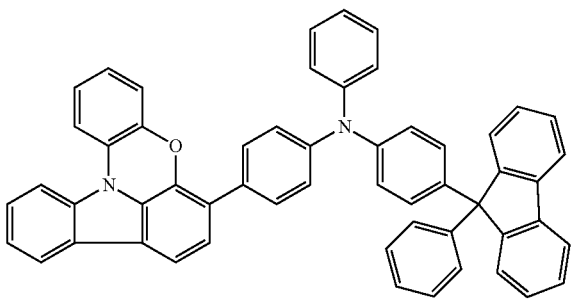
B107
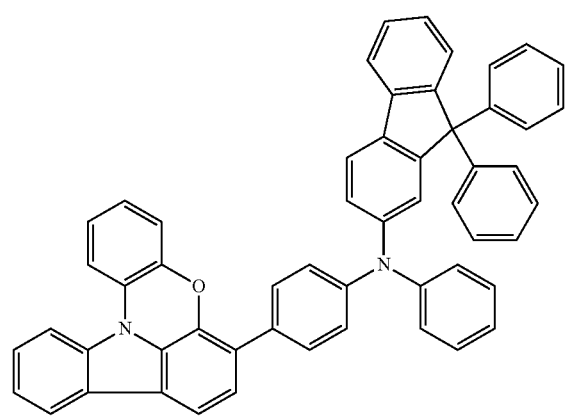

-continued
B108
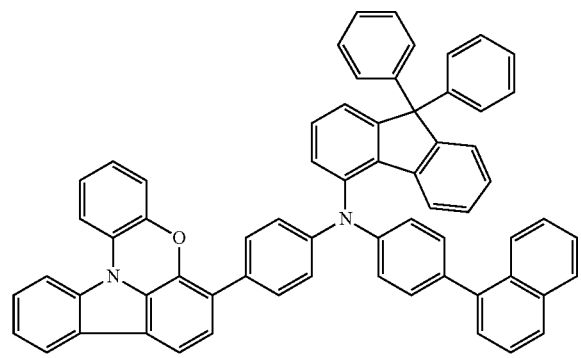
B109
B110
B111
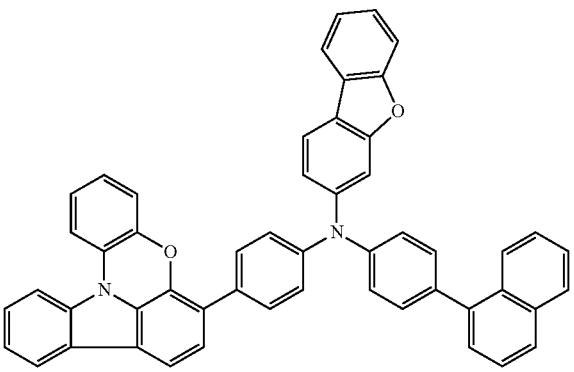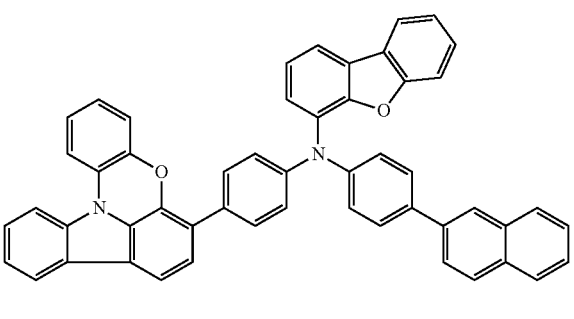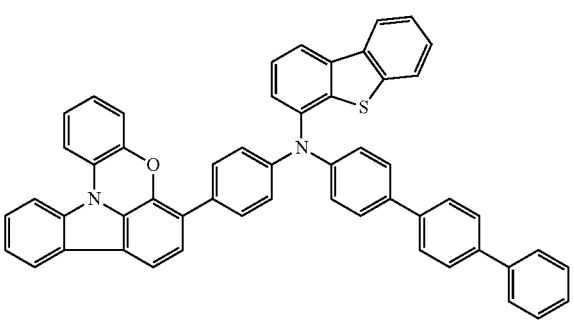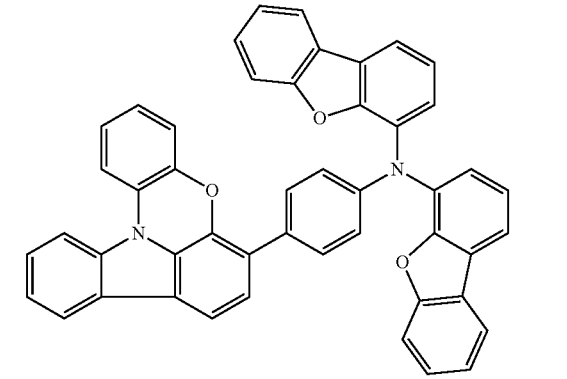
B112
B113
B114
B115

B116
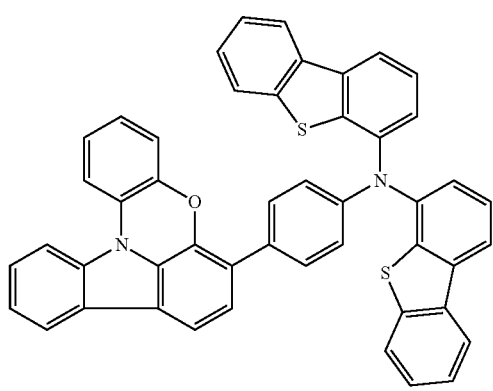
B117
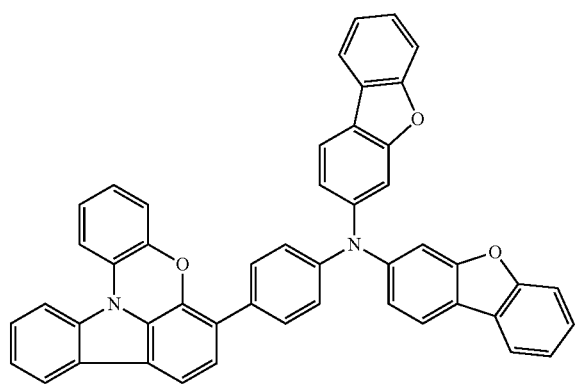
B118
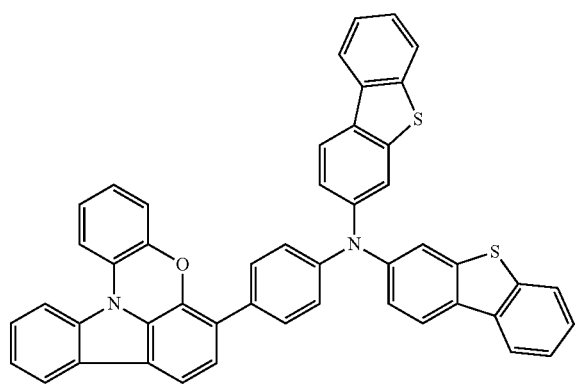
B119
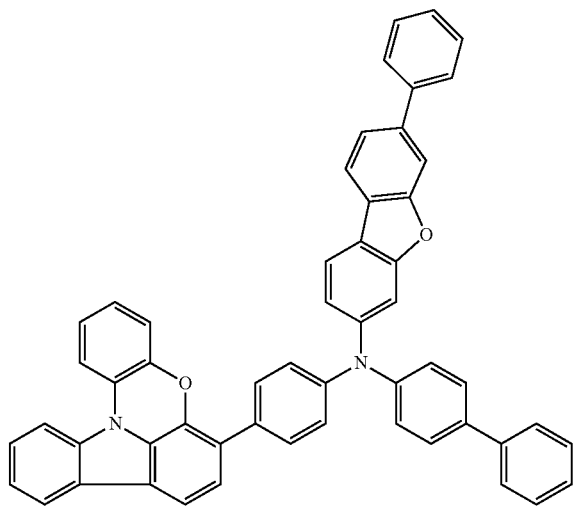
B120
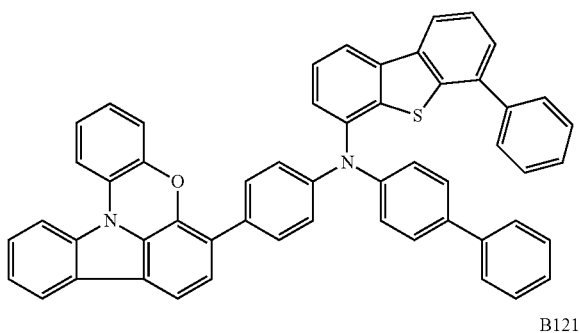
B121
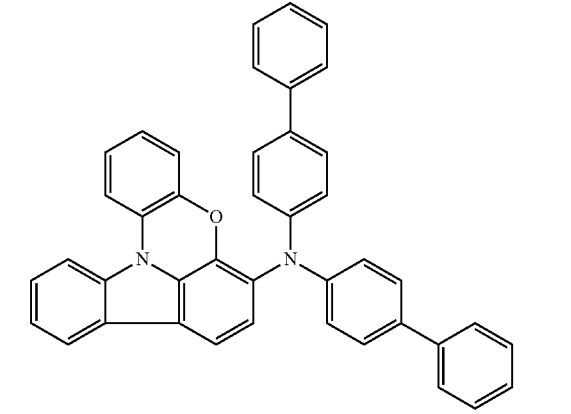
B122
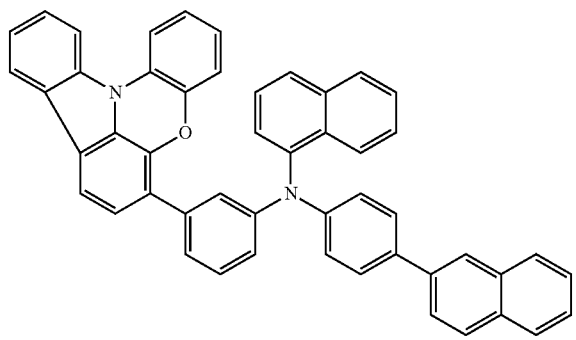

71
-continued
B123
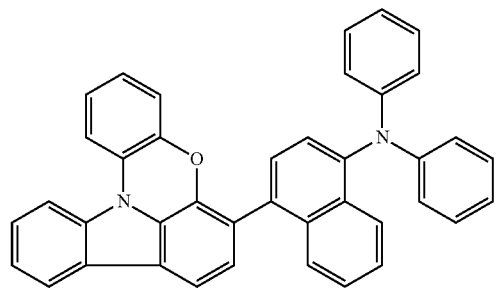
B124
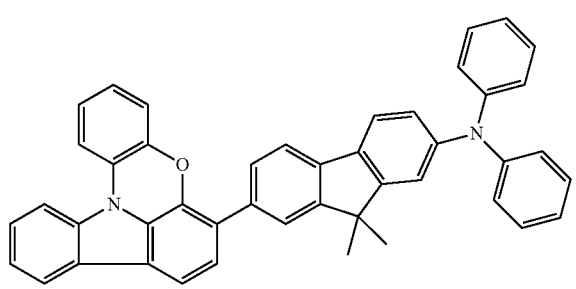
B125
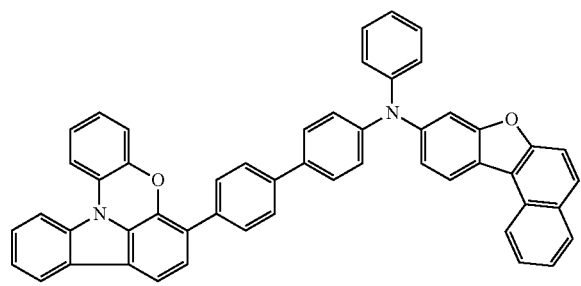
B126
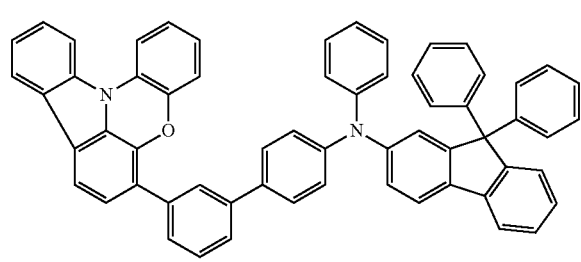
B127
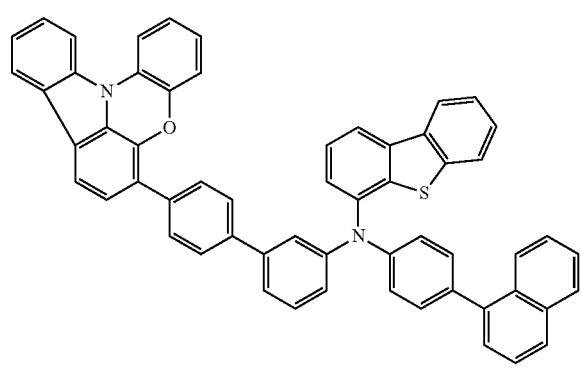
72
-continued
B128
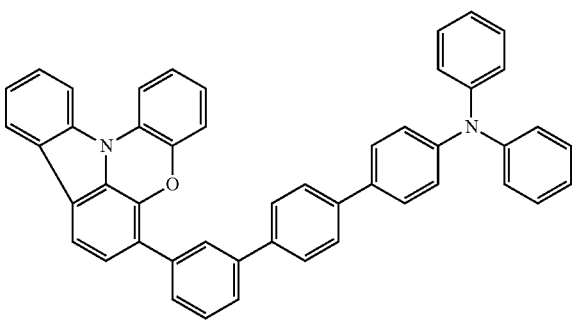
B129
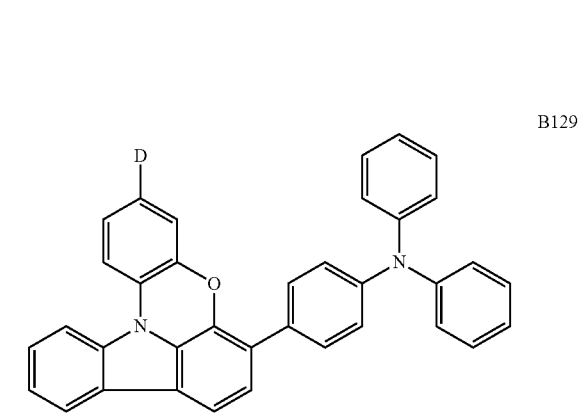
B130
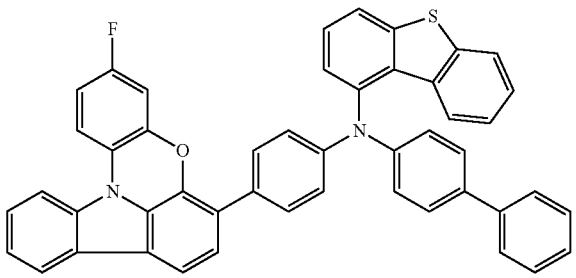
B131
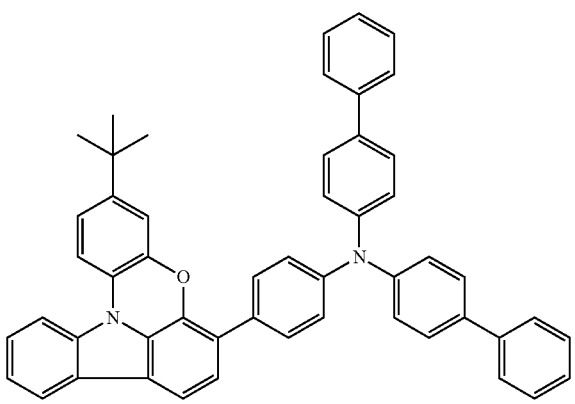

B132
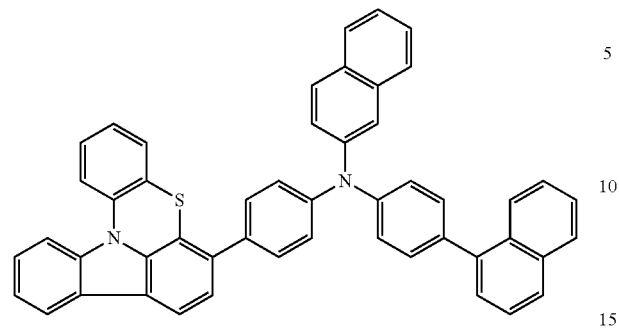
Compound Group 3
C1
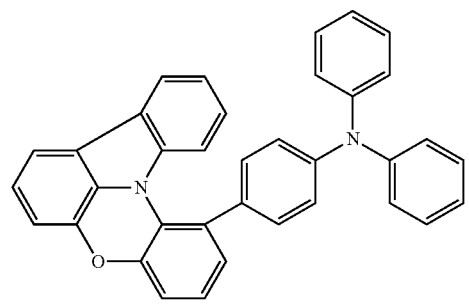
B133
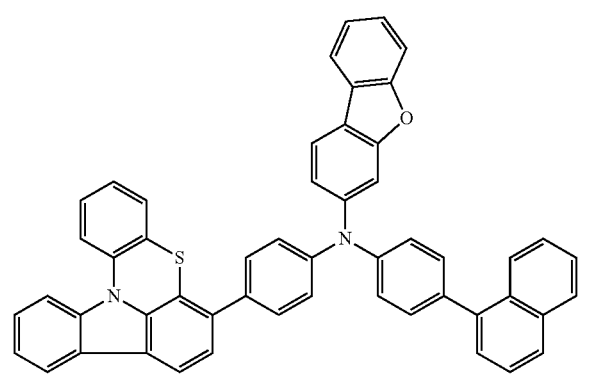
C2
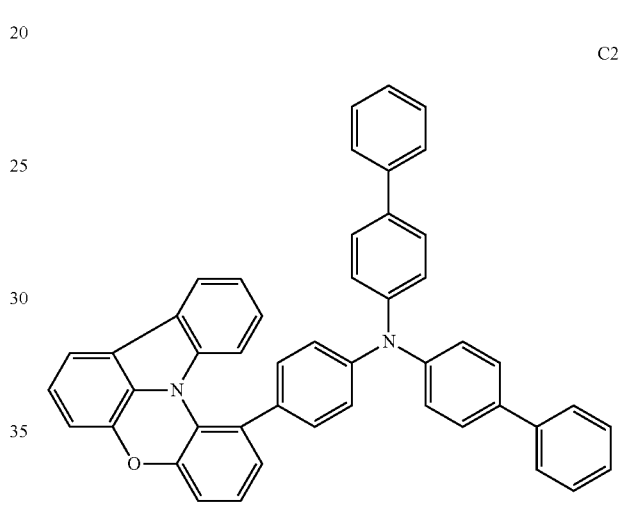
B134
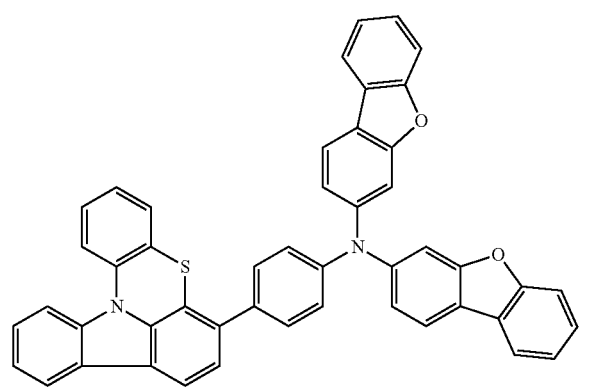
C3
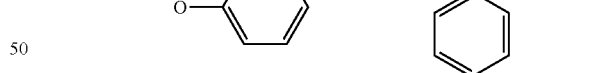
B135
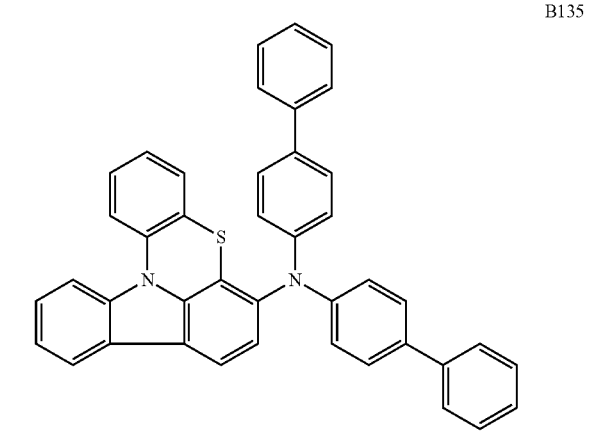
C4
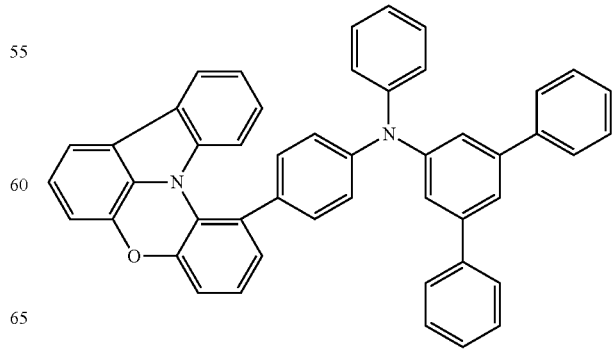

C5
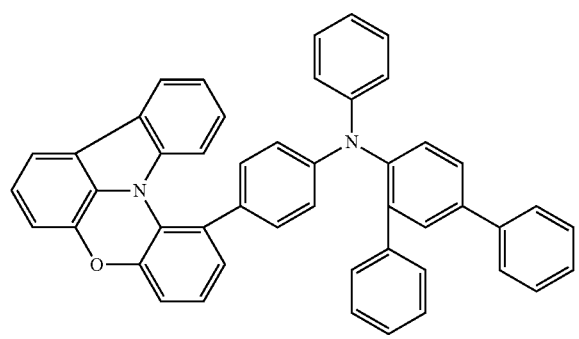
C9
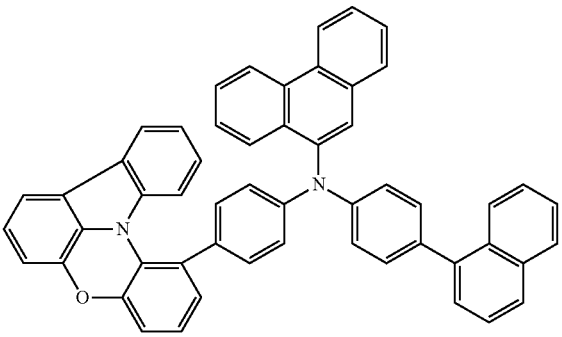
C6
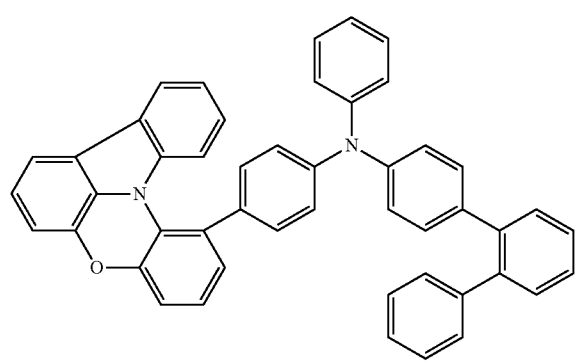
C10
C7
C11
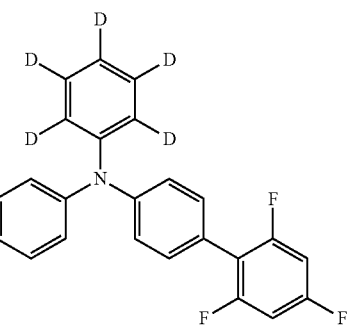
C8
C12
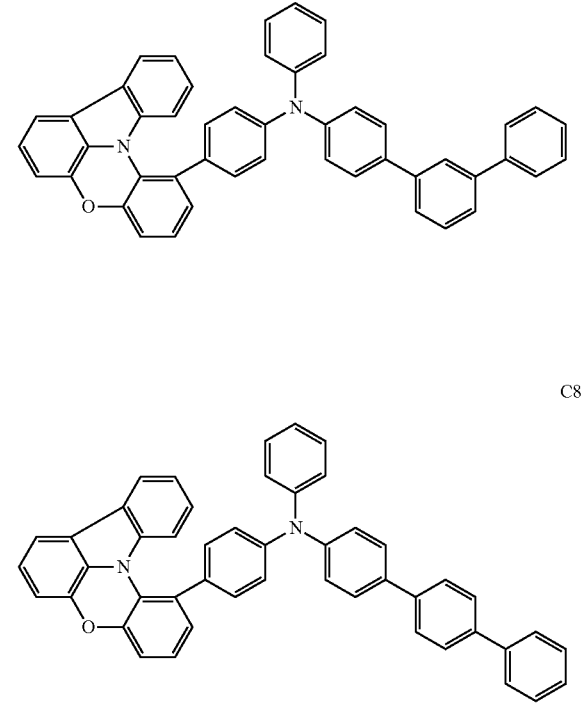
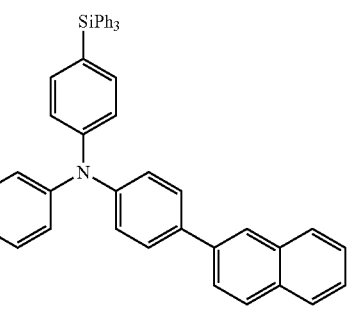
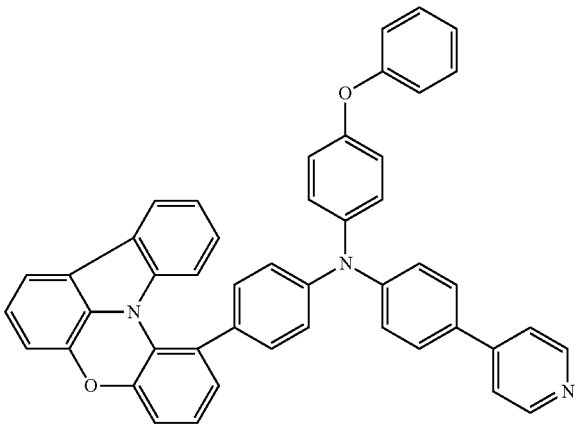

C13
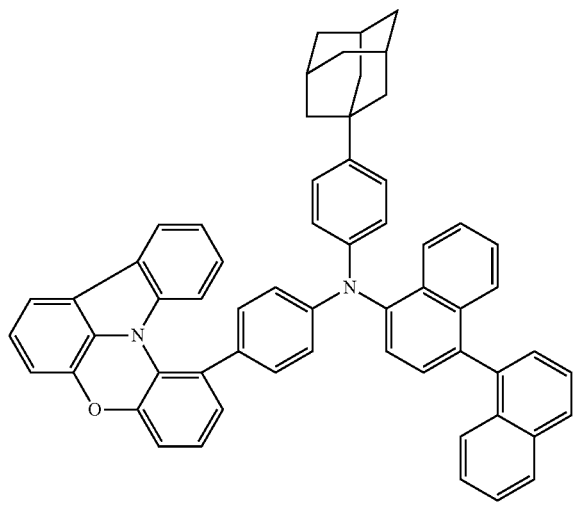
C14
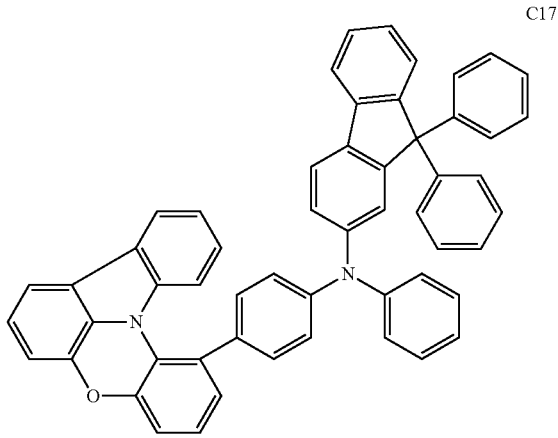
C15
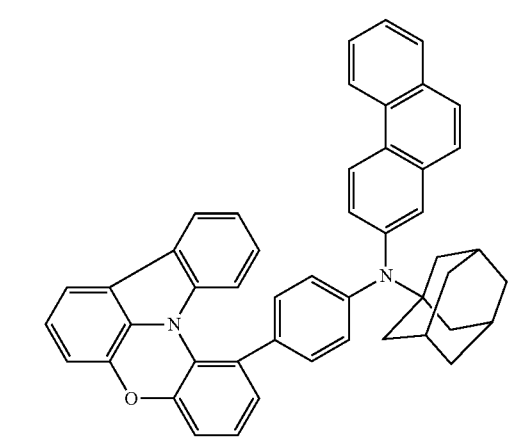
C16
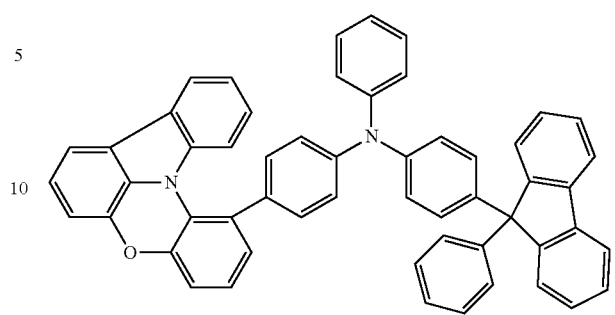
C17
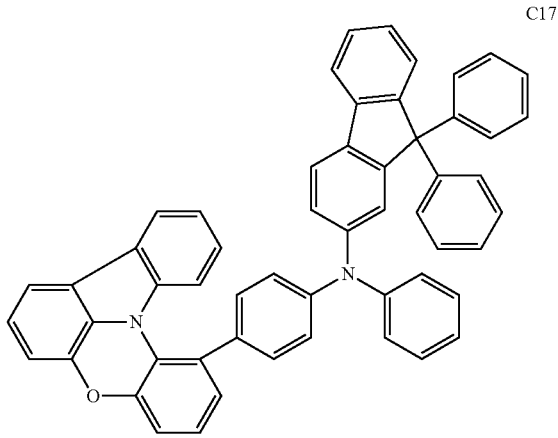
C18
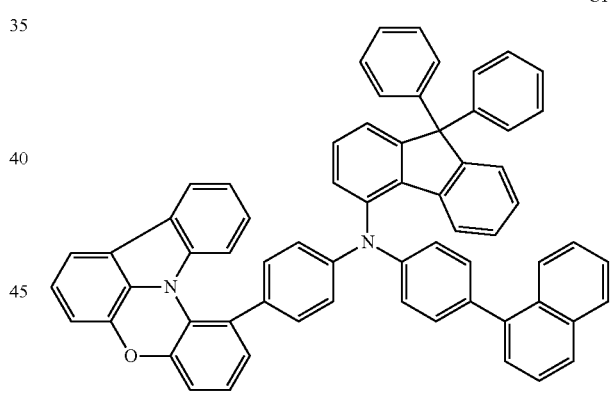
C19
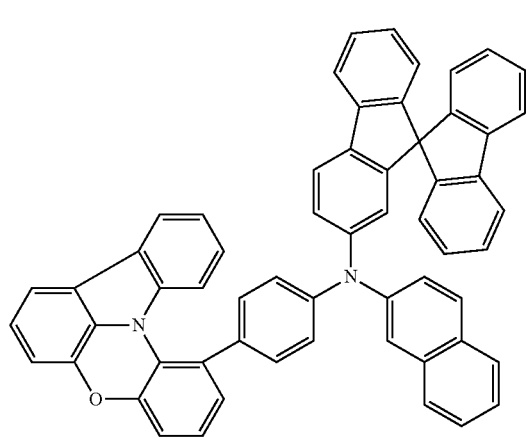

C20
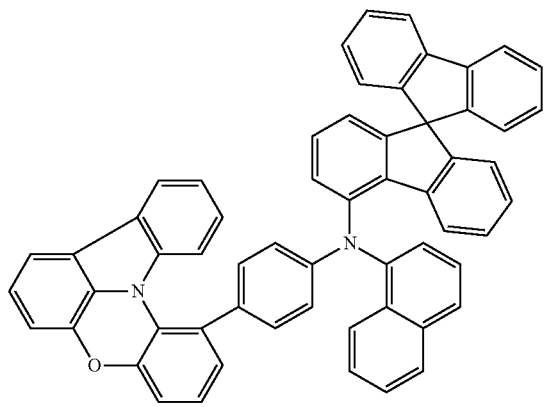
C21
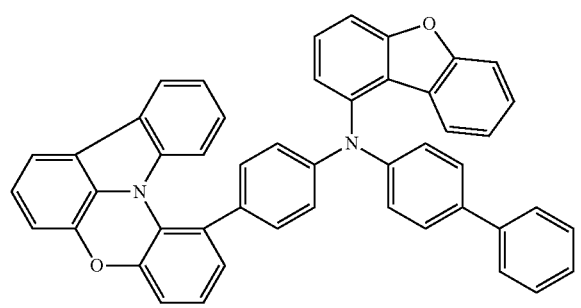
C22
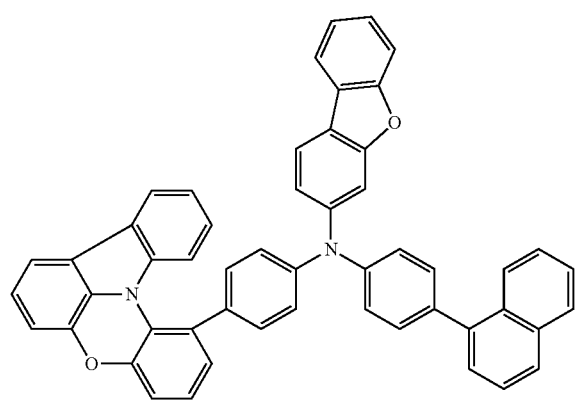
C23
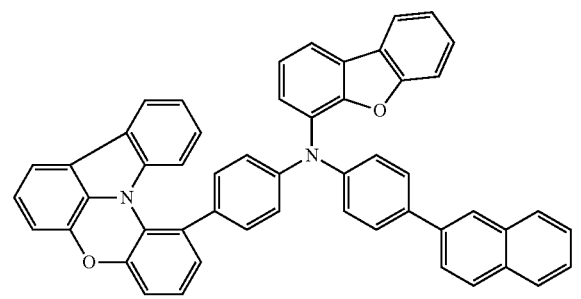
C24
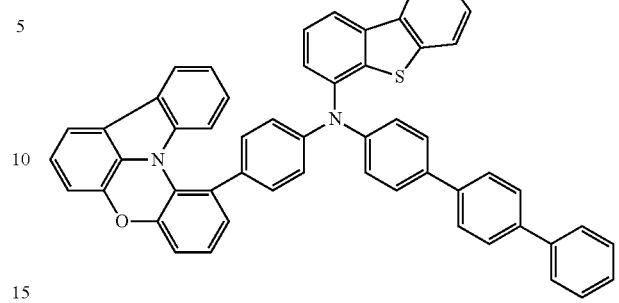
C25
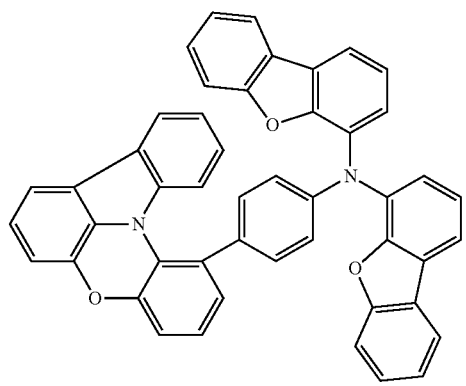
C26
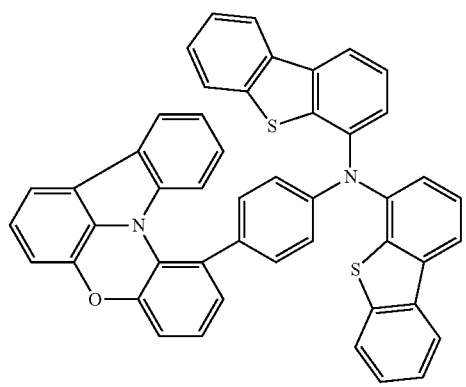
C27
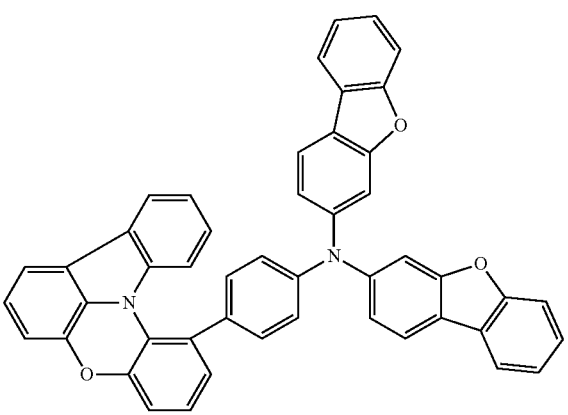

-continued
C28
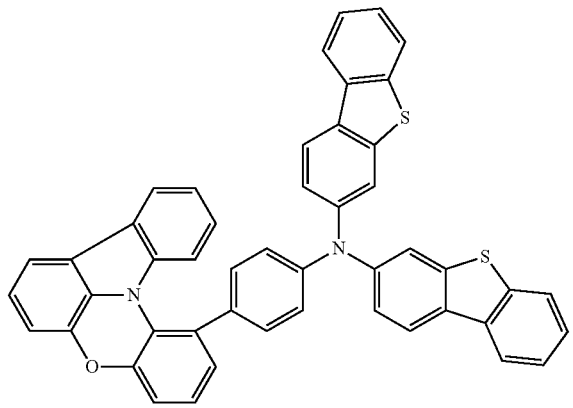
C29
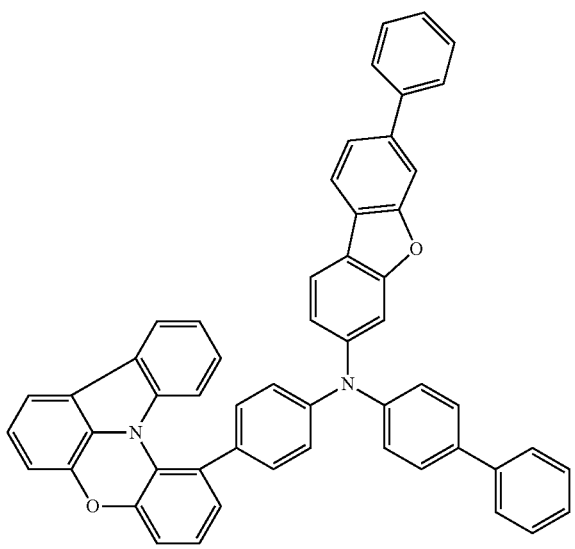
C30
C31
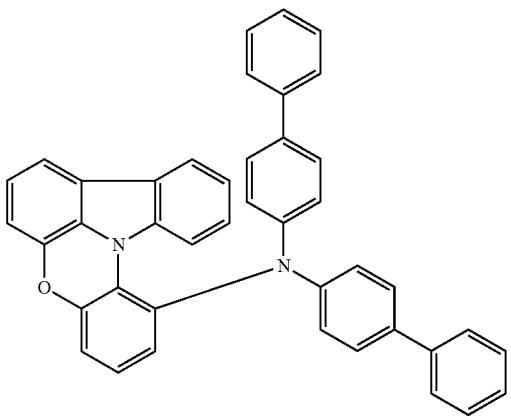
C32
C33
C34
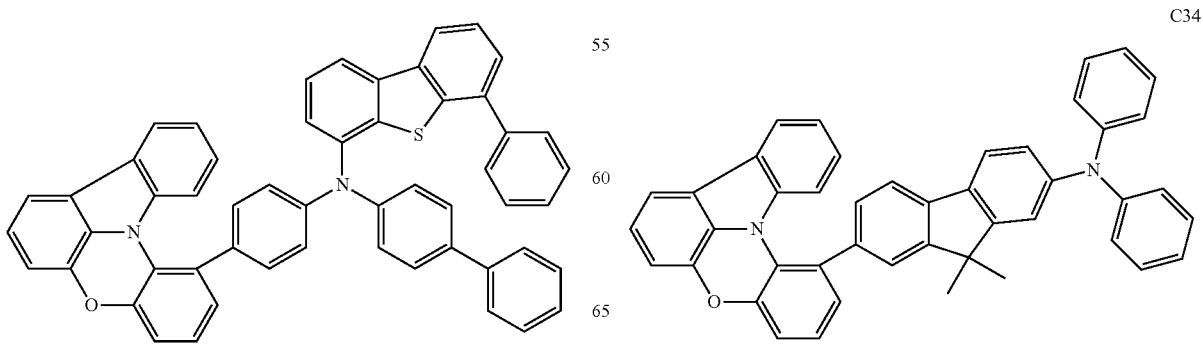

C35
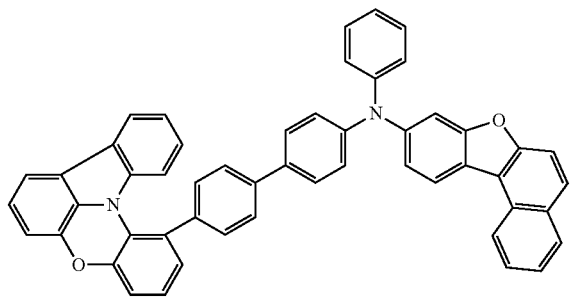
C39
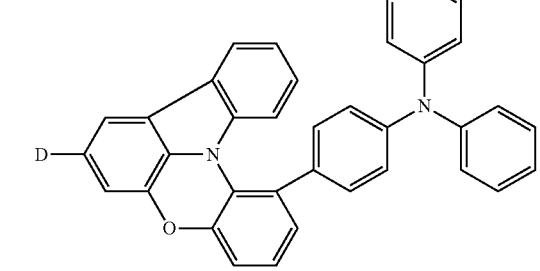
C36
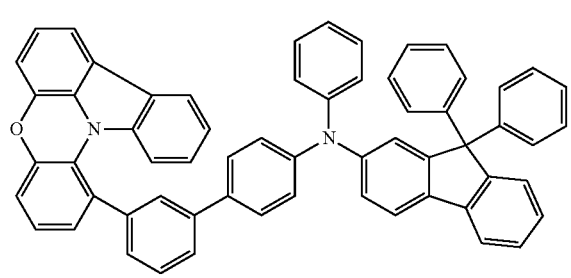
C40
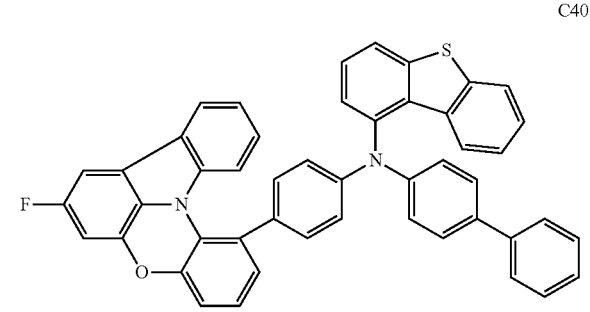
C37
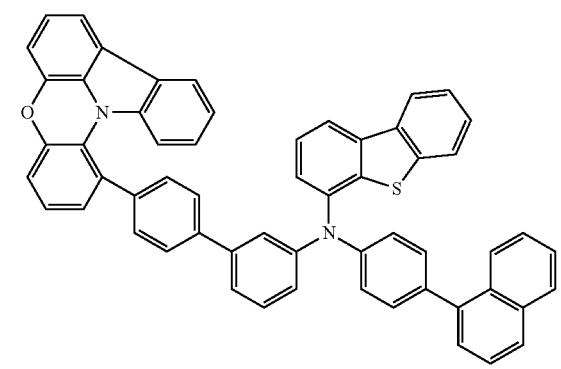
C41
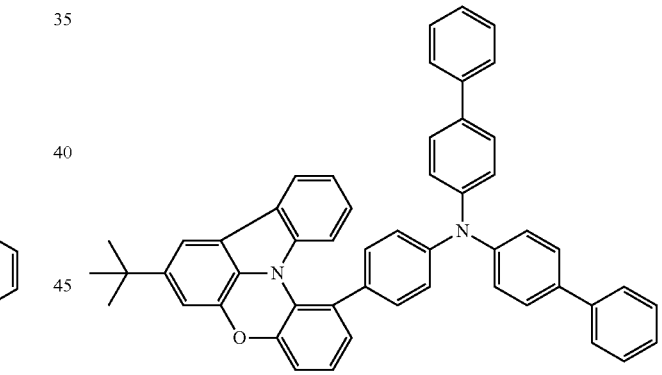
C38
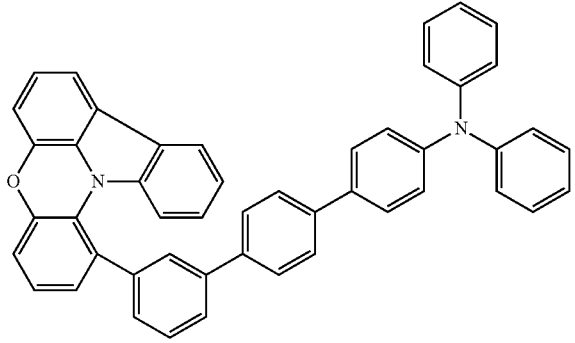
C42
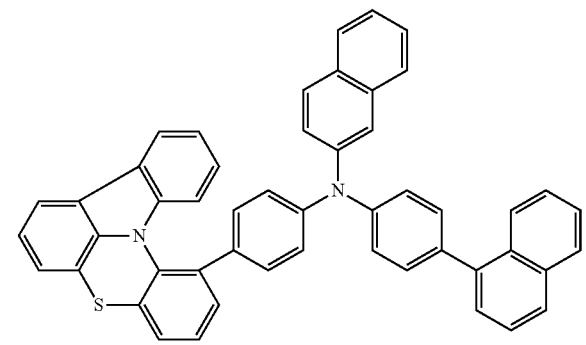

C43
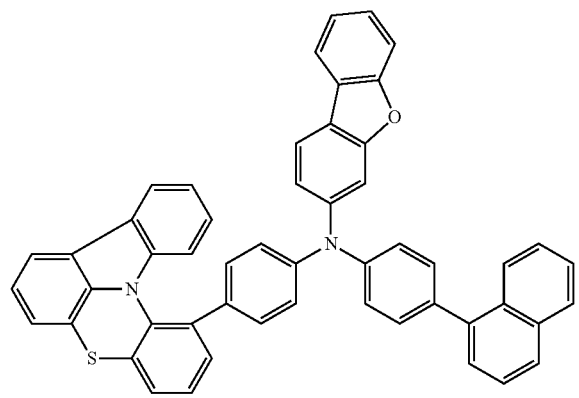
C44
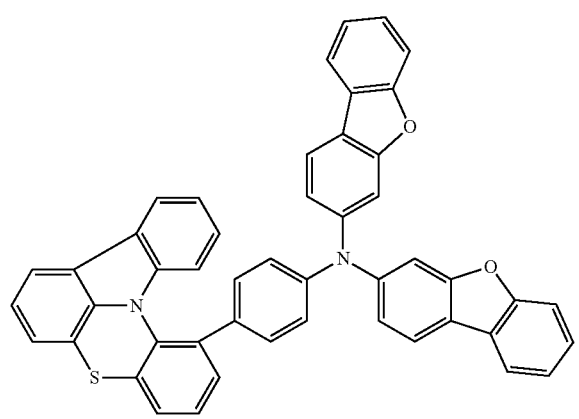
C45
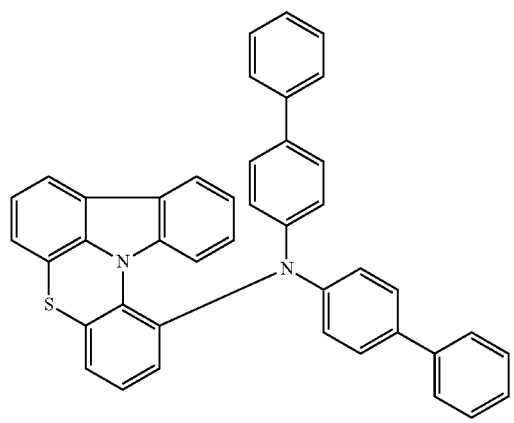
C46
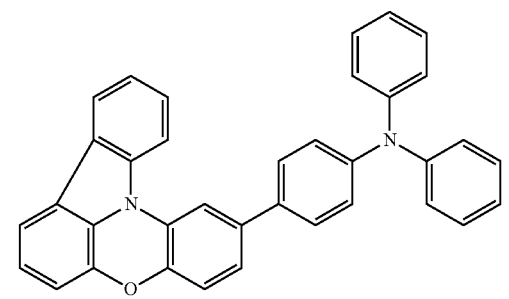
C47
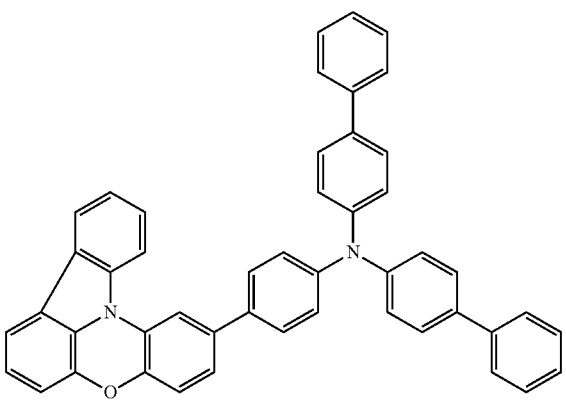
C48
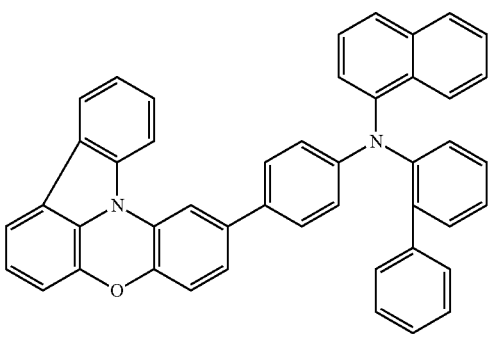
C49
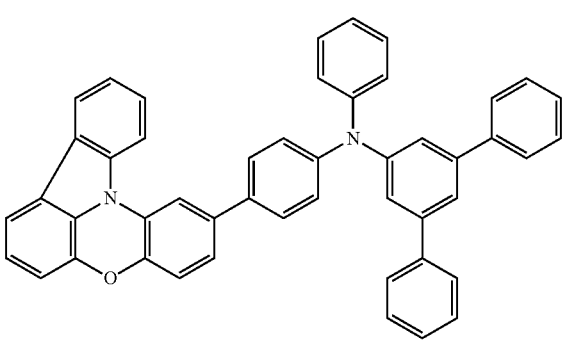
C50
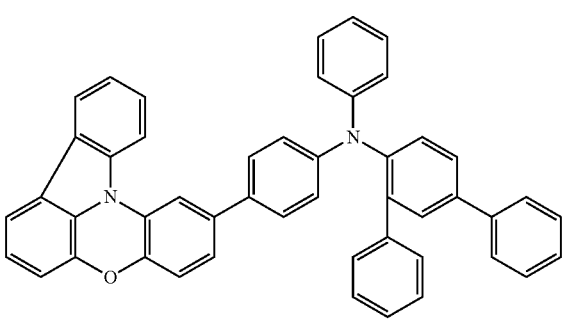

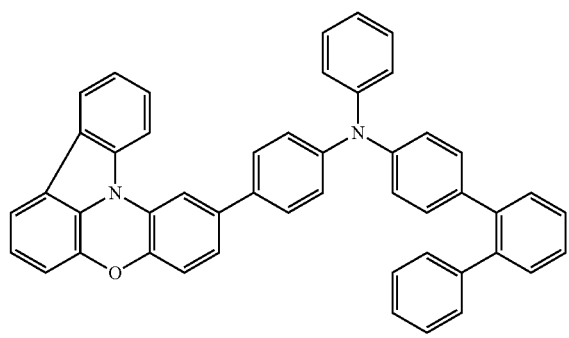
C51
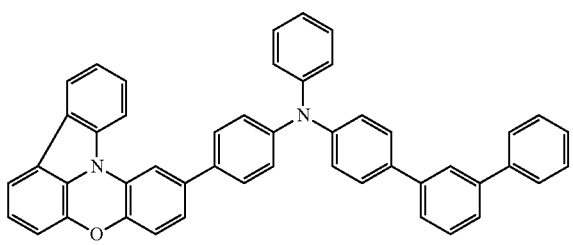
C52
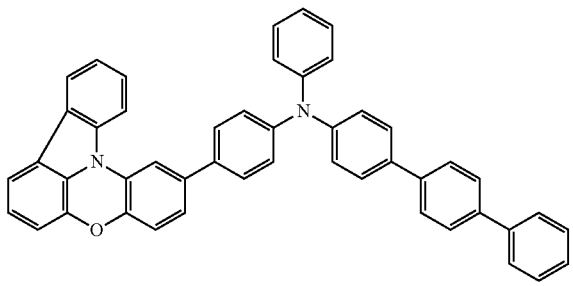
C53
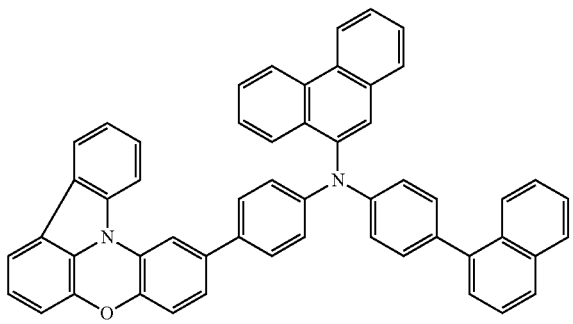
C54
C55
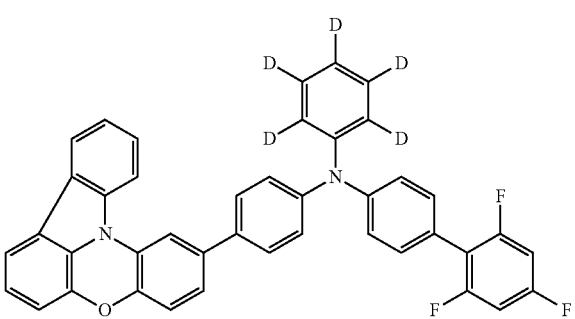
C56
C57
C58
C59

C60
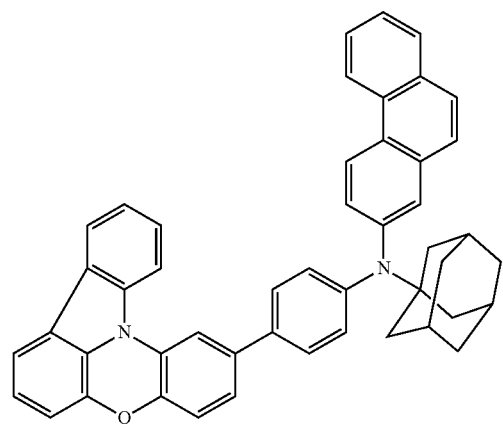
C61
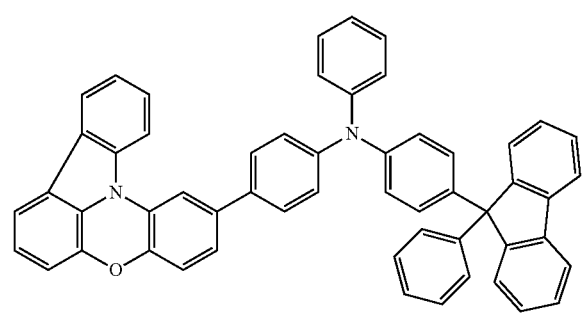
C62
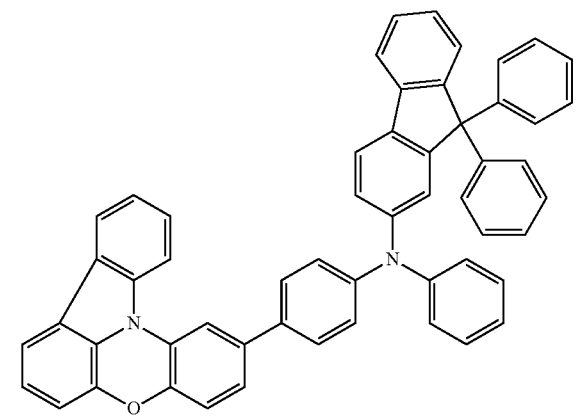
C63
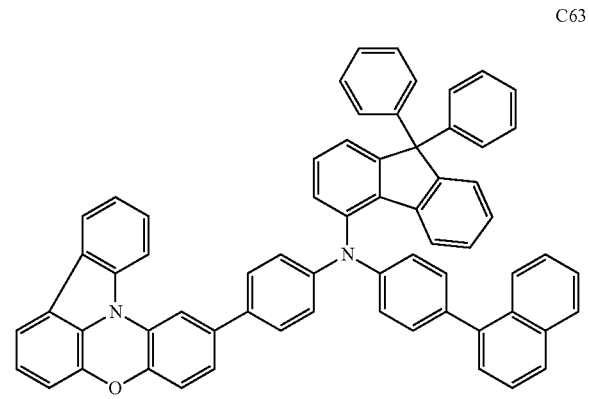
C64
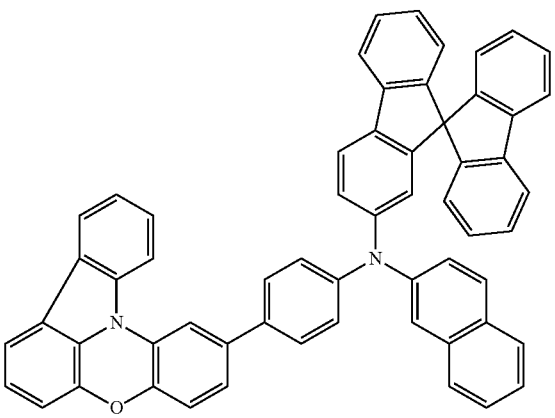
C65
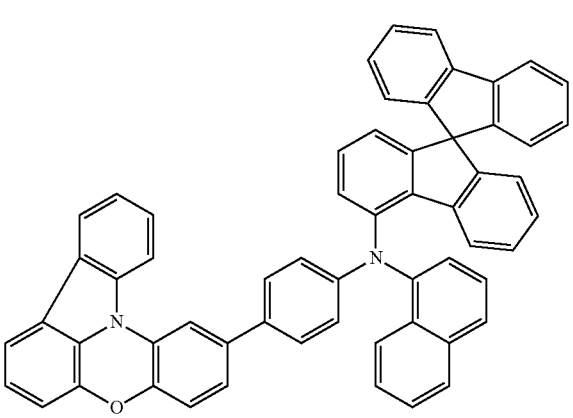
C66
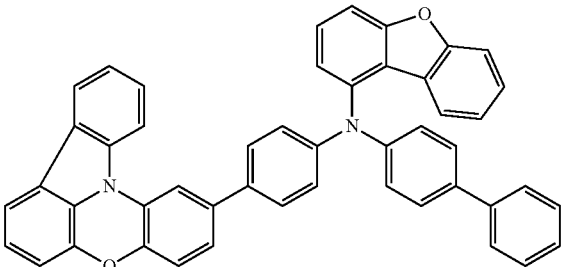
C67
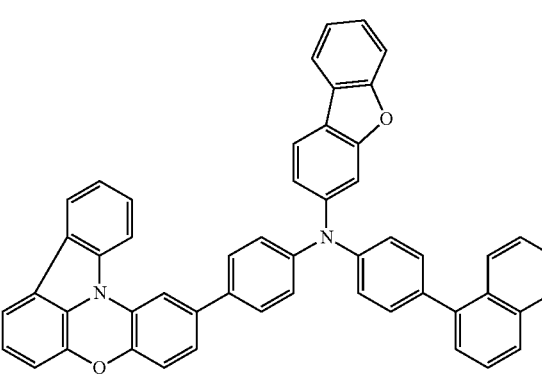

C68
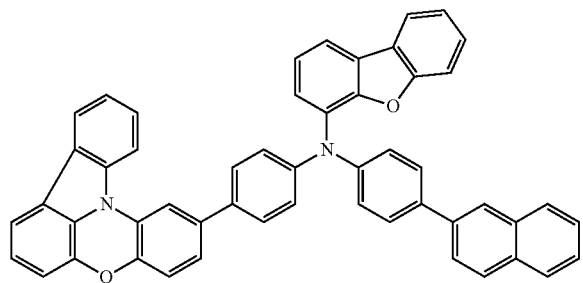
C69
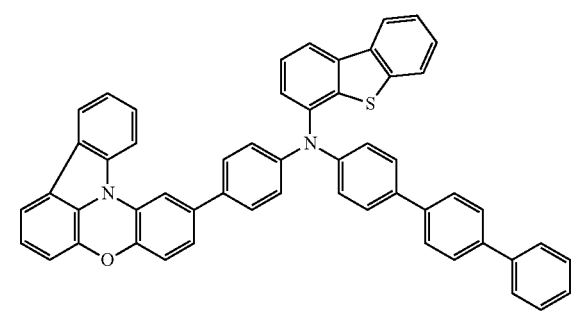
C70
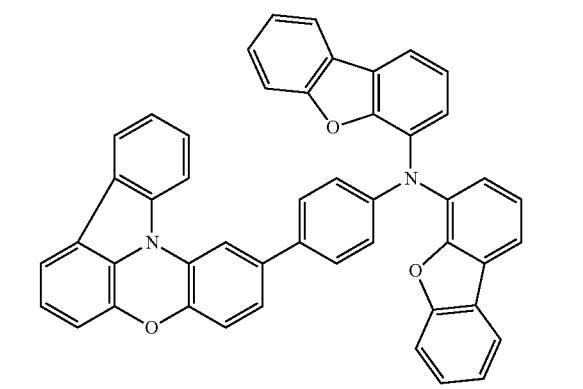
C71
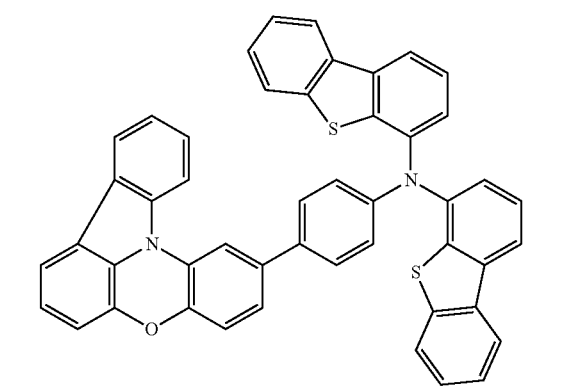
C72
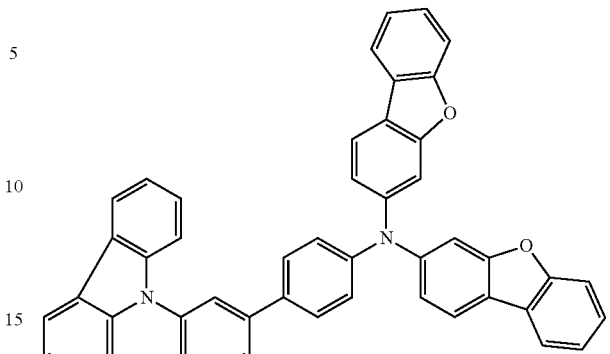
C73
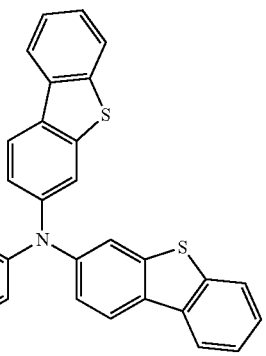
C74
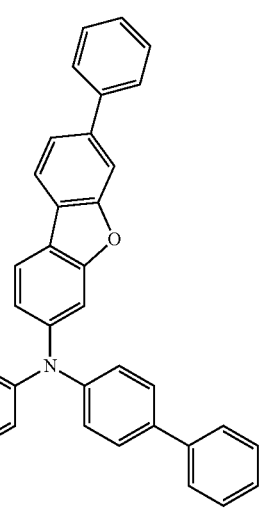

C75
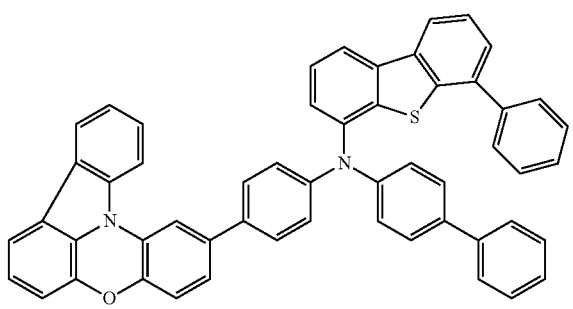
C76
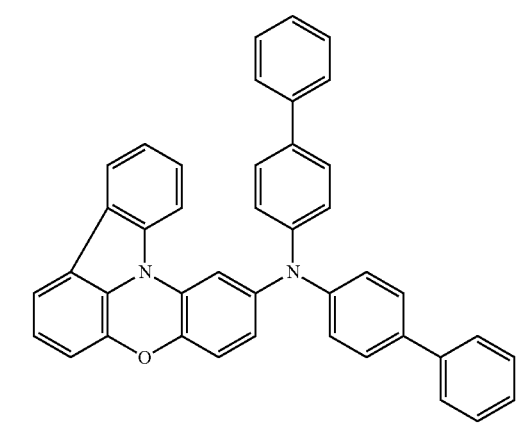
C77
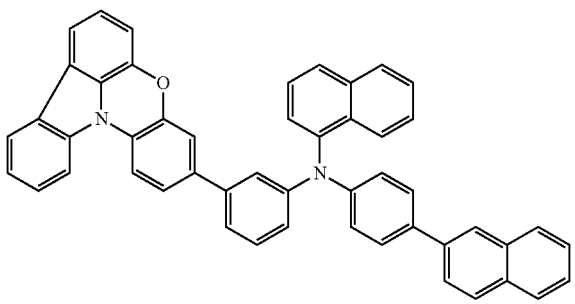
C78
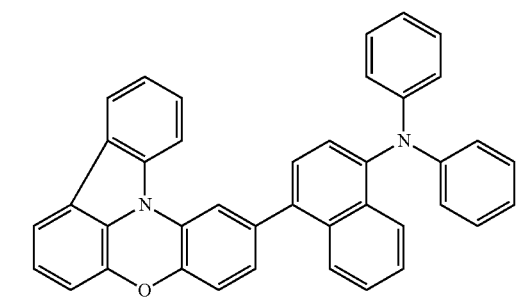
C79
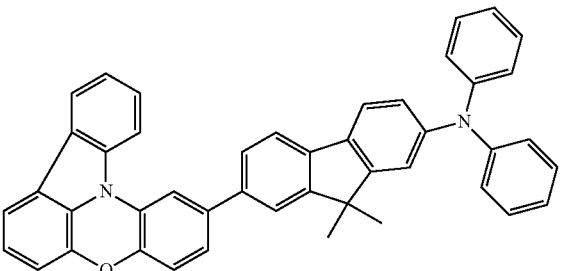
C80
C81
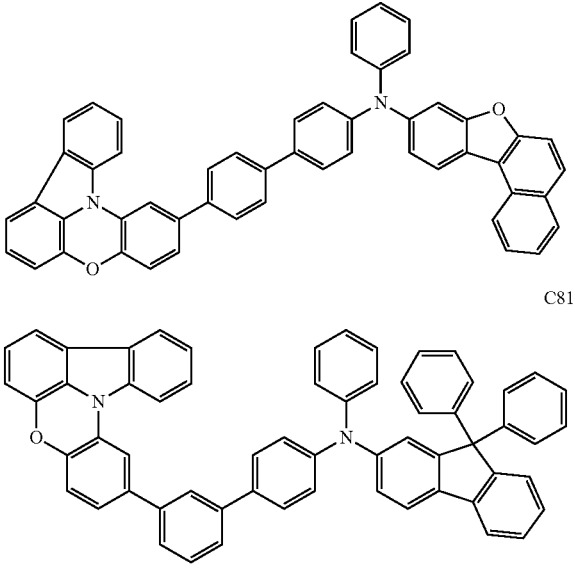
C82
C83
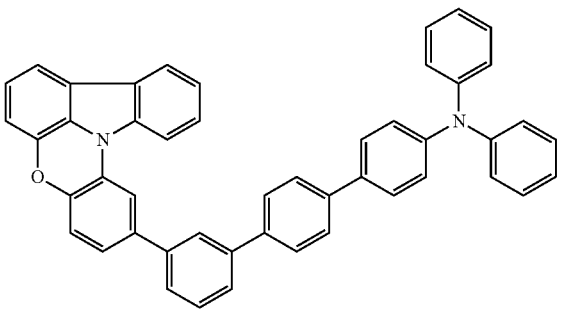

C84
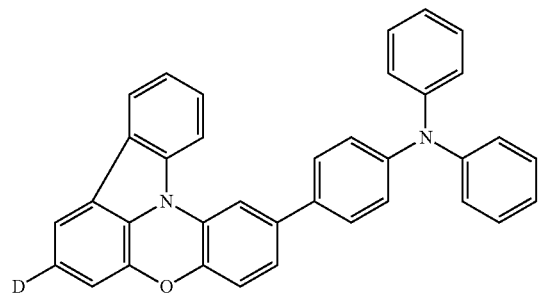
C85
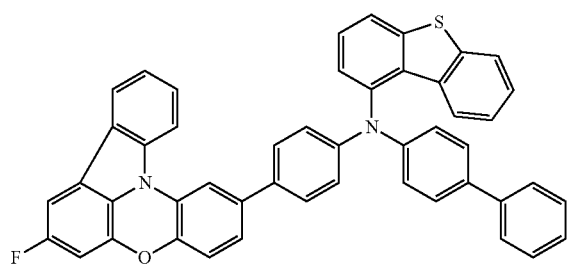
C86
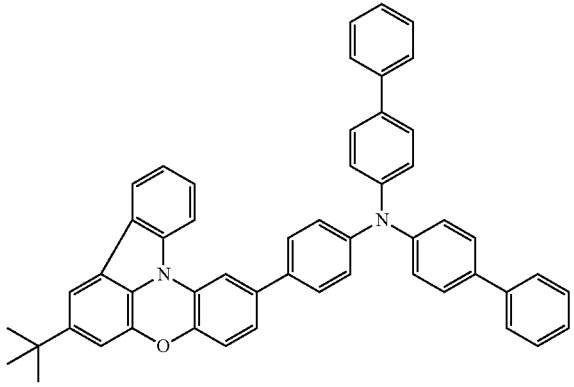
C87
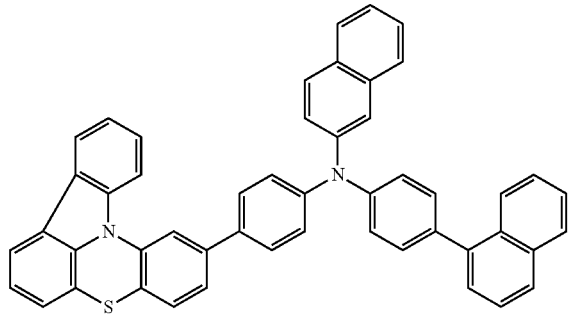
C88
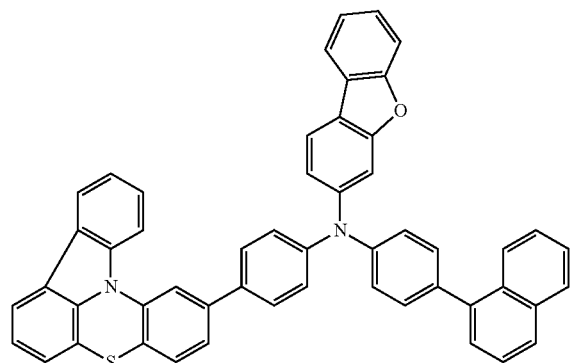
C89
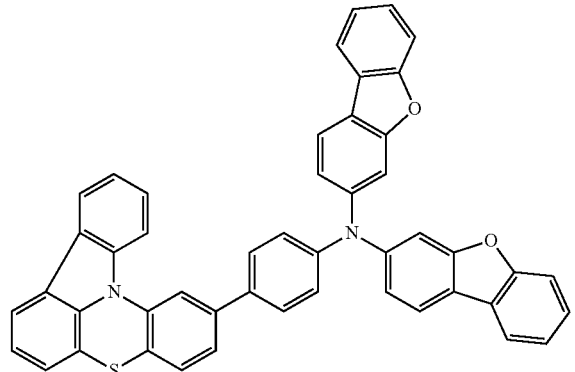
C90
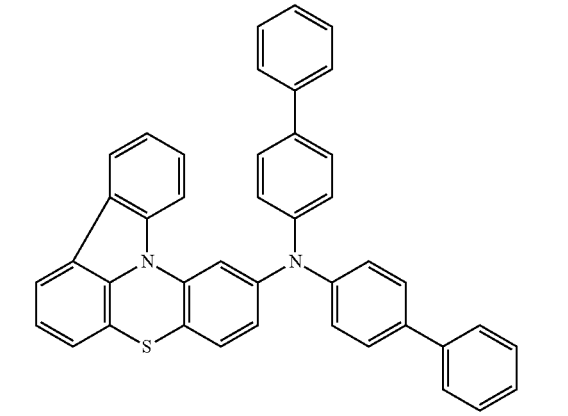
C91
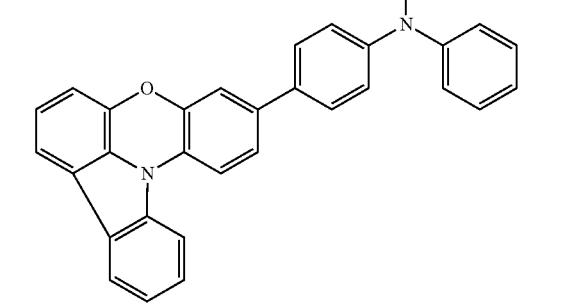

C92
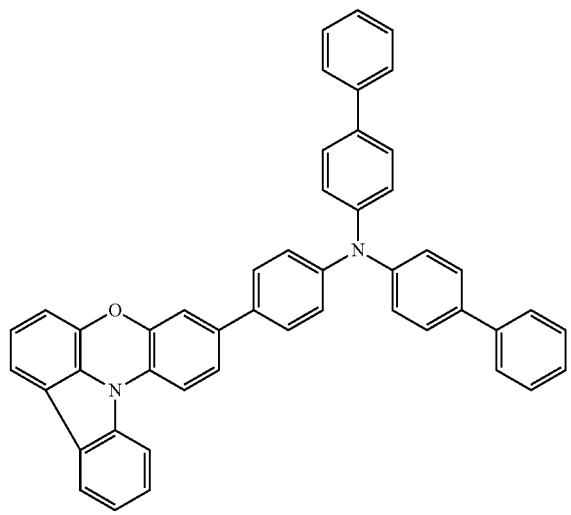
C93
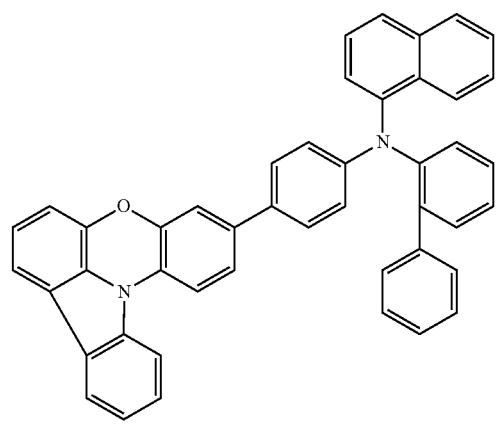
C94
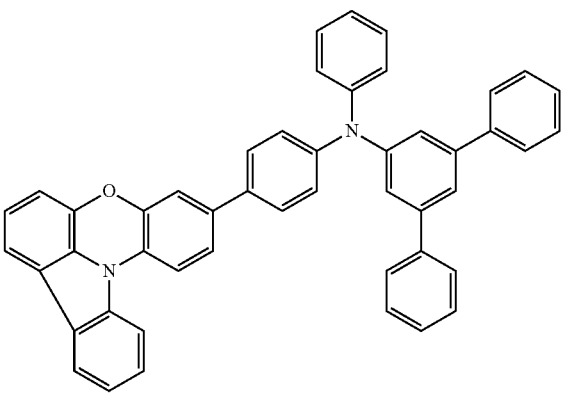
C95
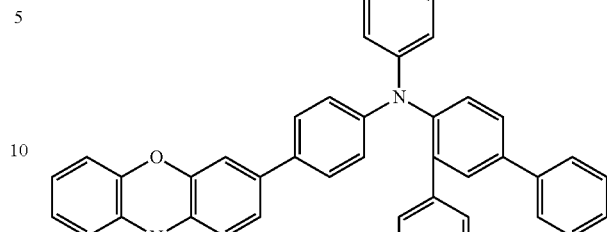
C96
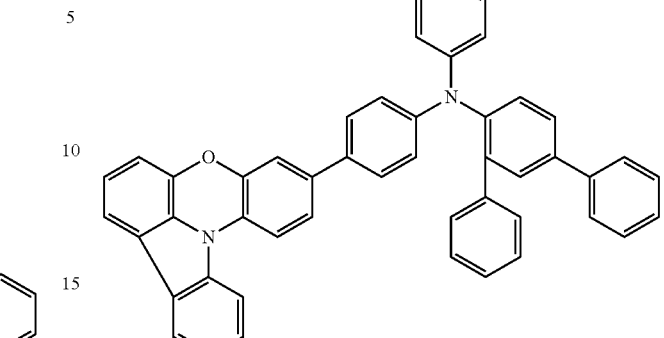
C97
C98
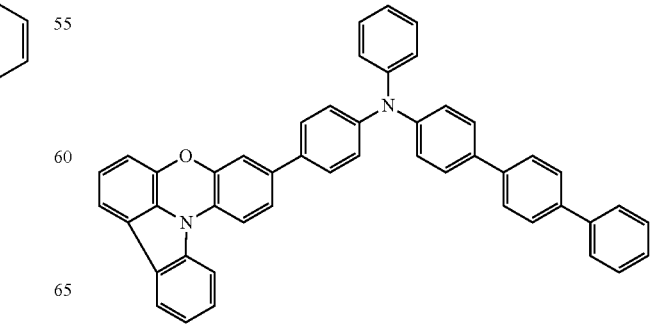

C99
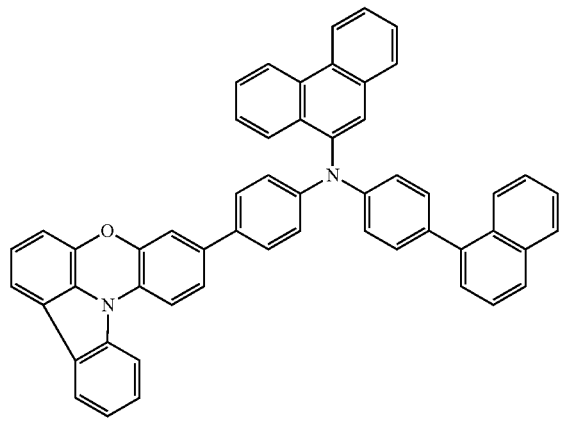
C100
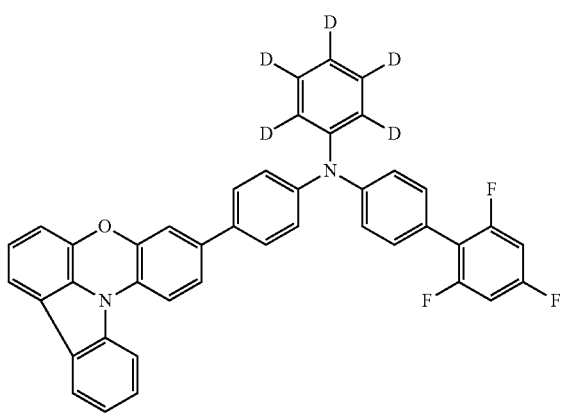
C101
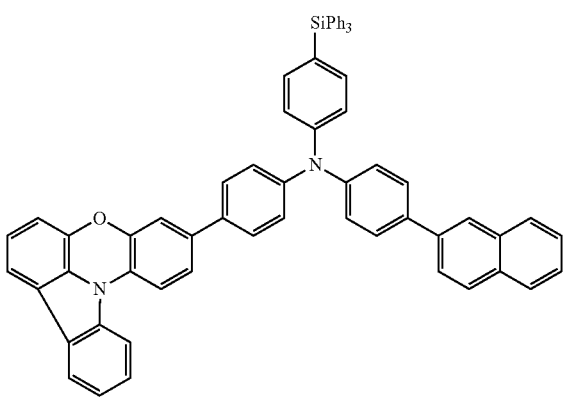
C102
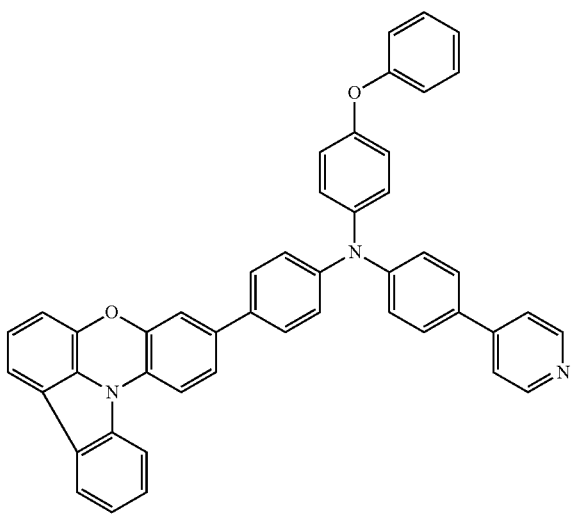
C103
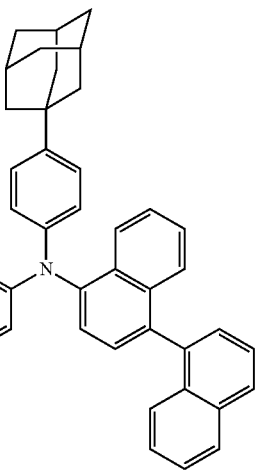
C104
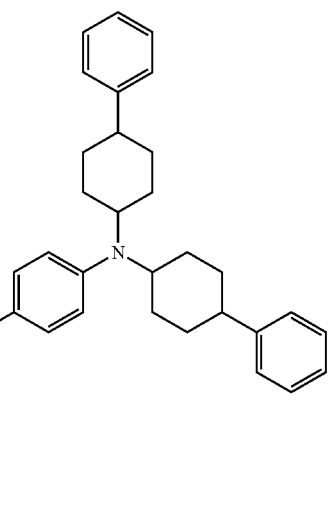

C105
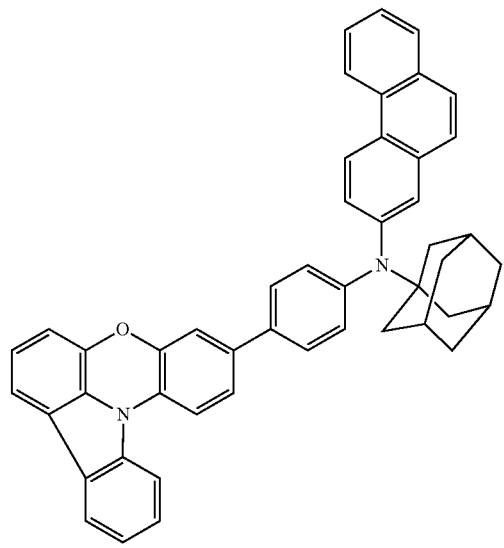
C106
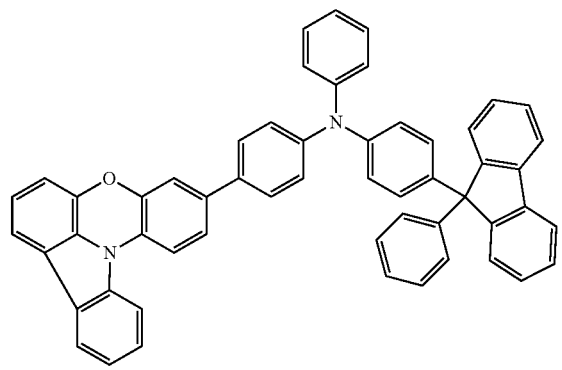
C107
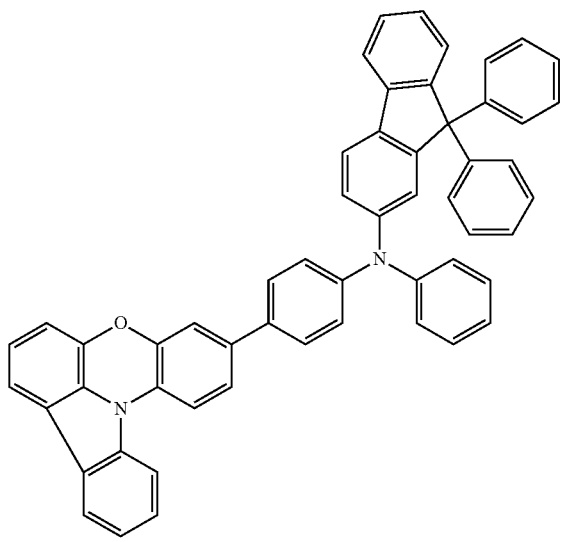
C108
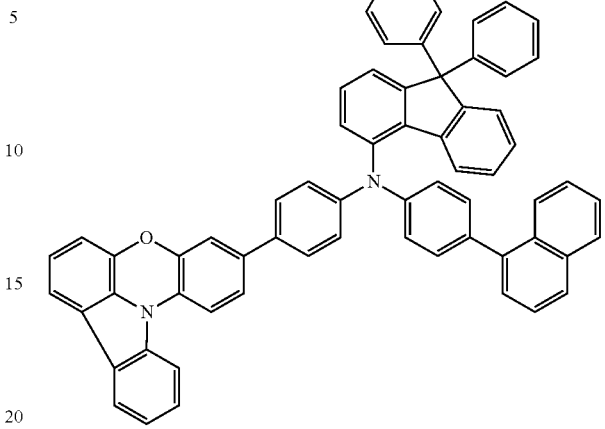
C109
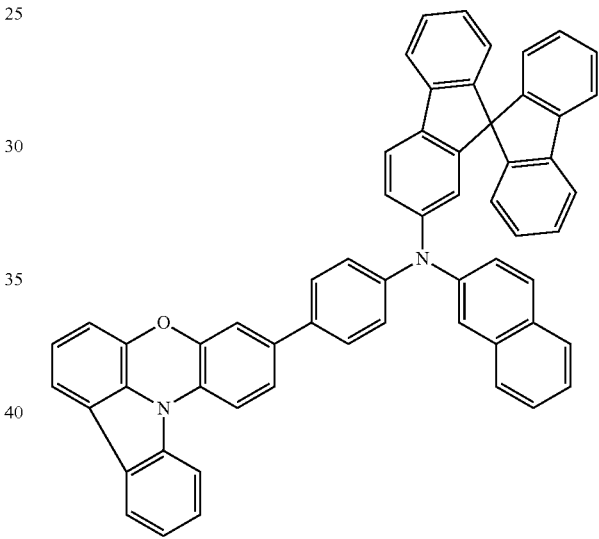
C110
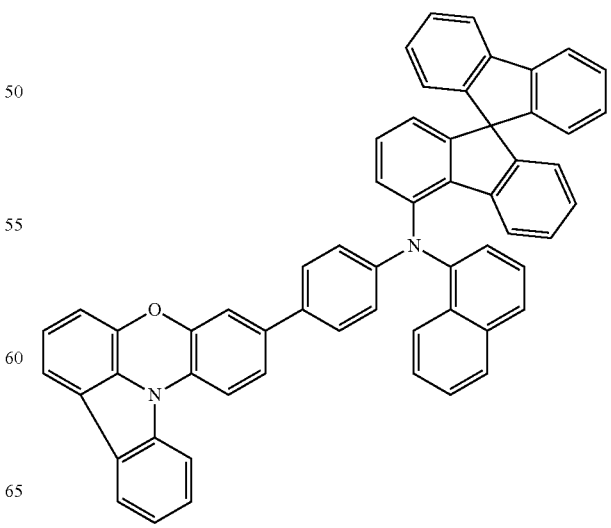

-continued
C111
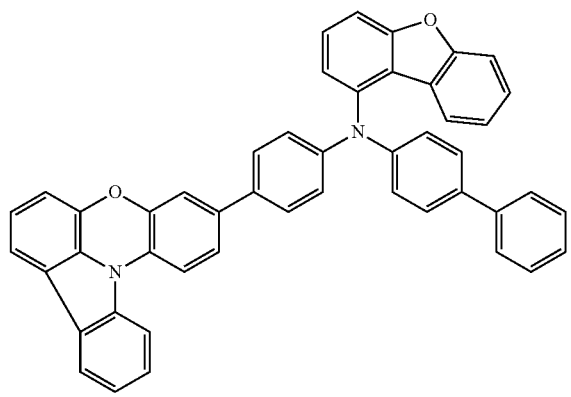
C112
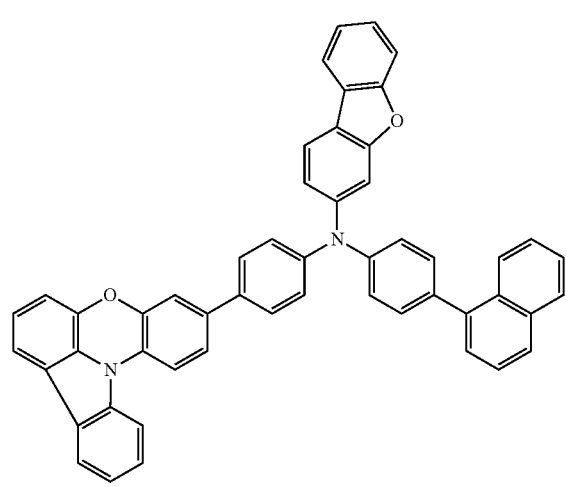
C113
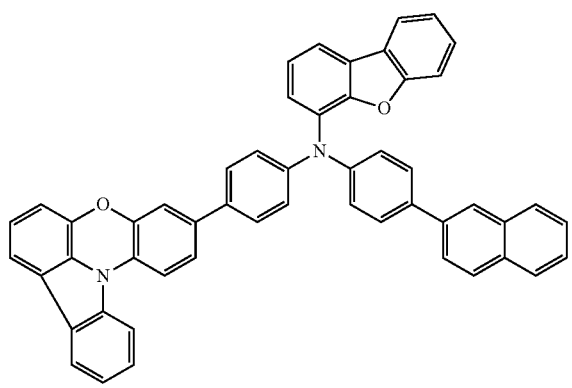
-continued
C114
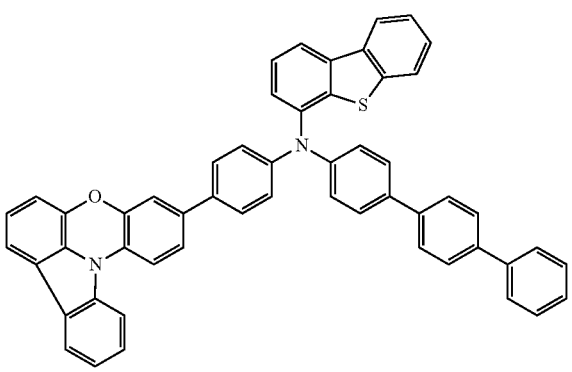
C115
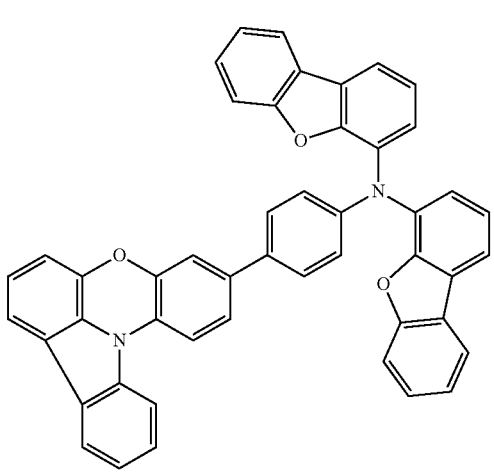
C116
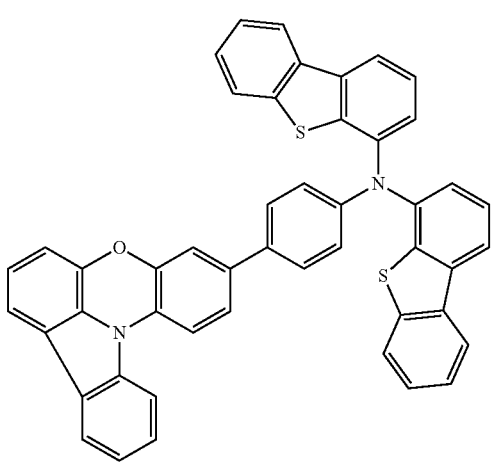

-continued
C117
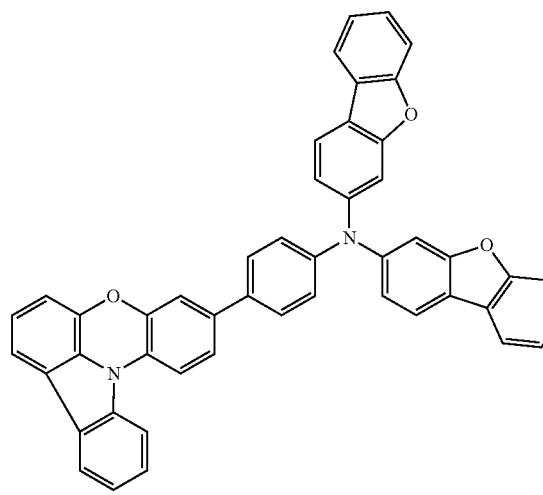
C118
C120
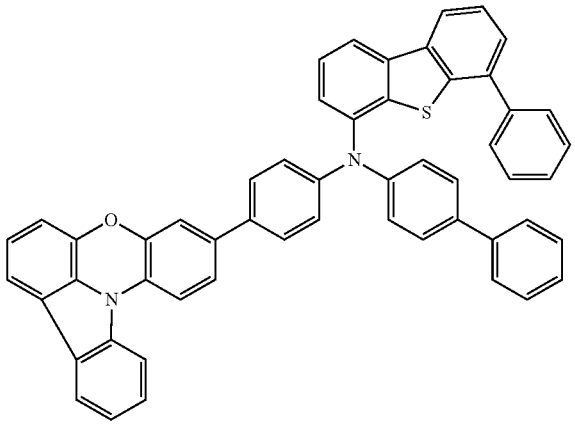
C121
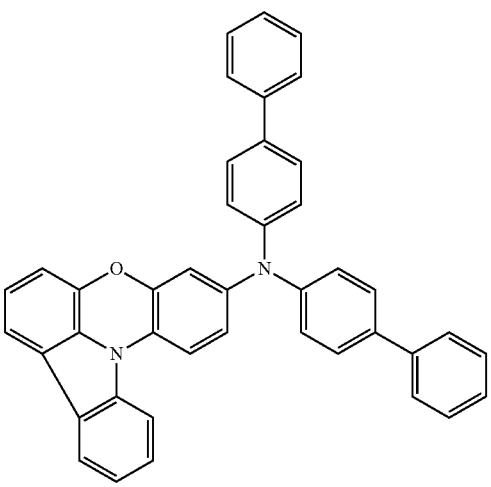
C119
C122
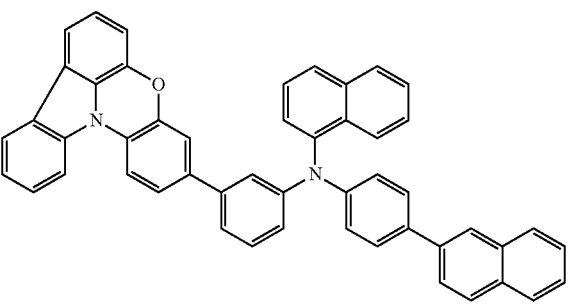

C123
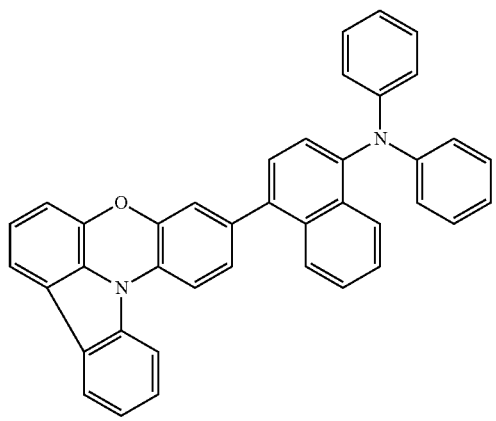
C127
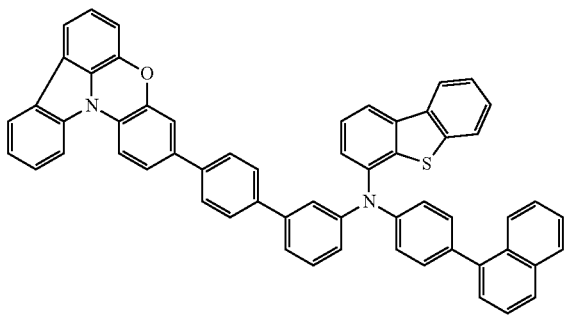
C124
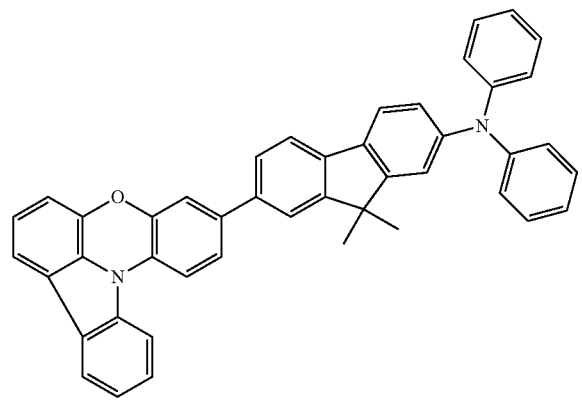
C128
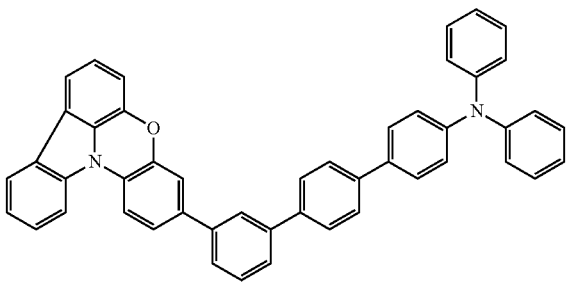
C129
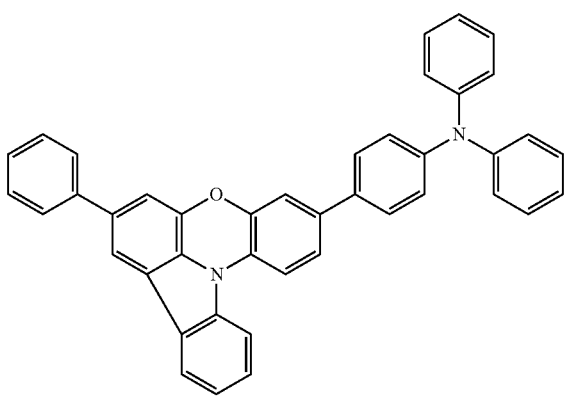
C125
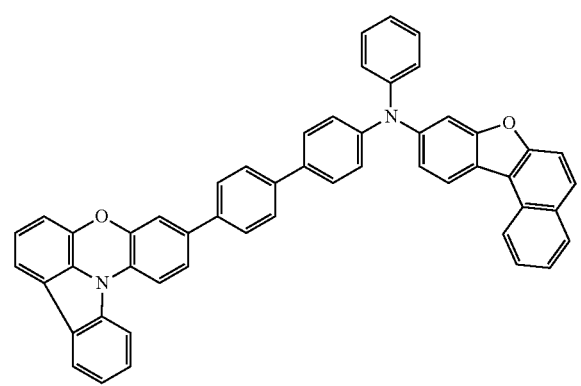
C130
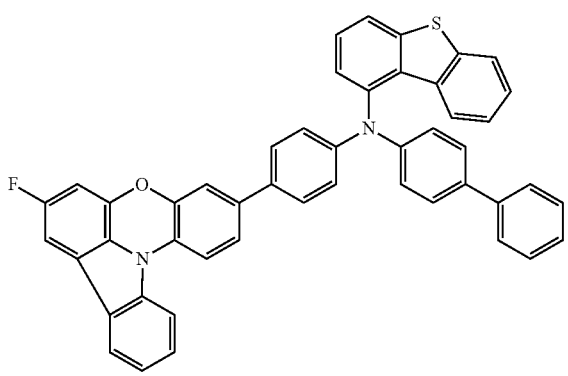
C126

C131
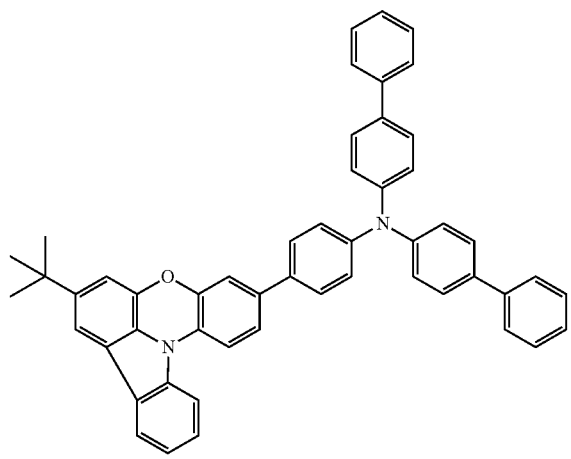
C132
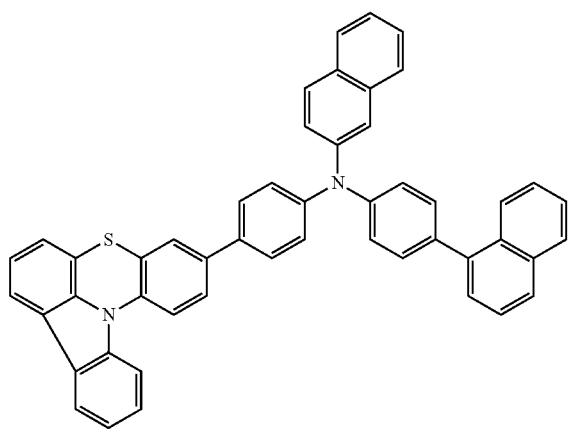
C133
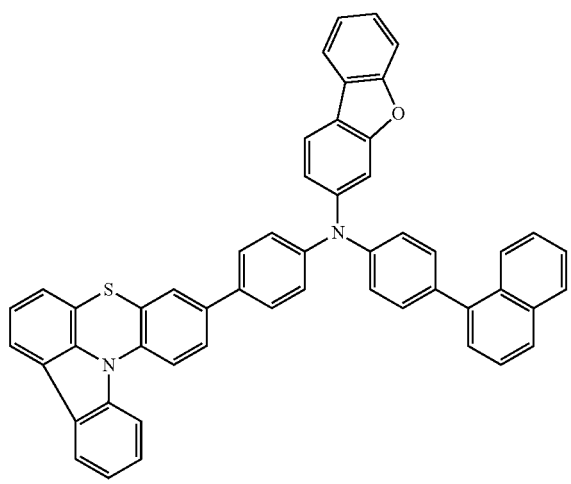
C134
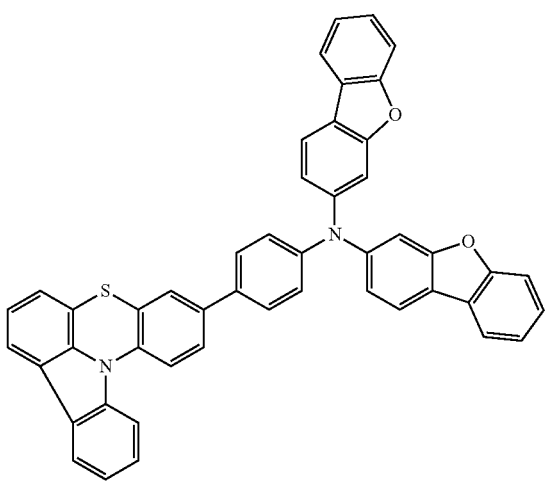
C135
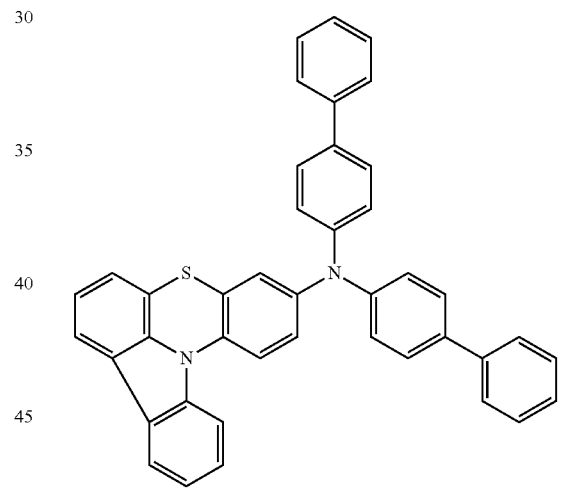
C136
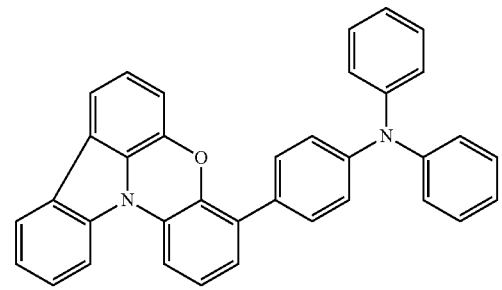

C137
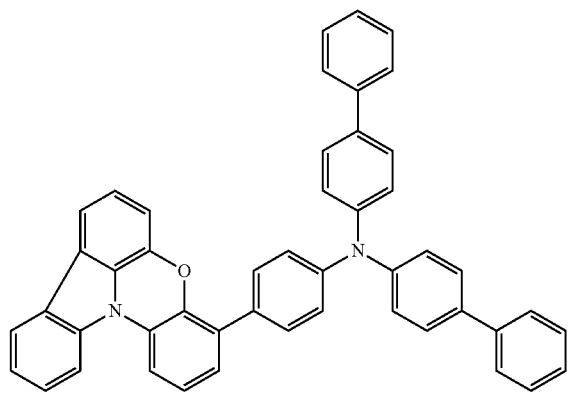
C138
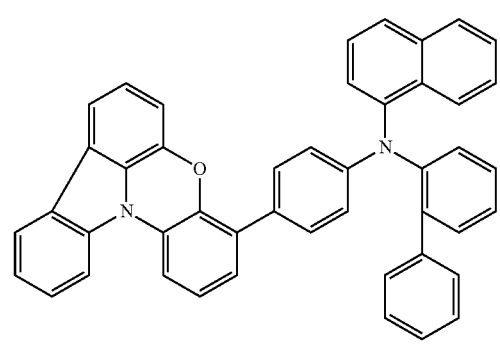
C139
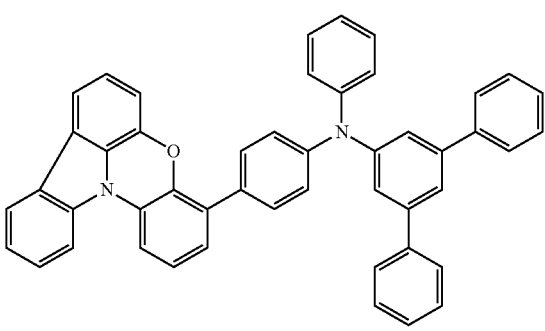
C140
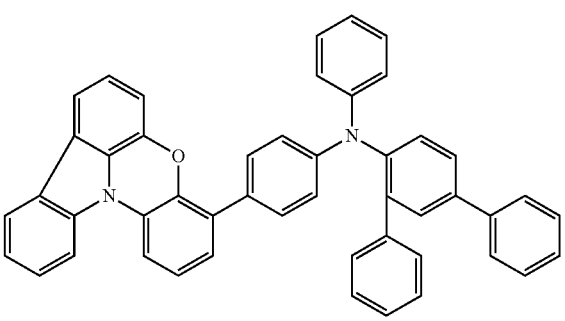
C141
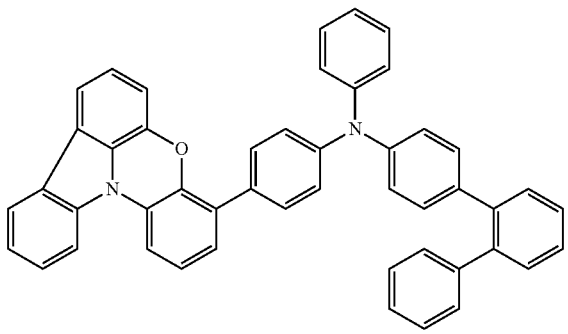
C142
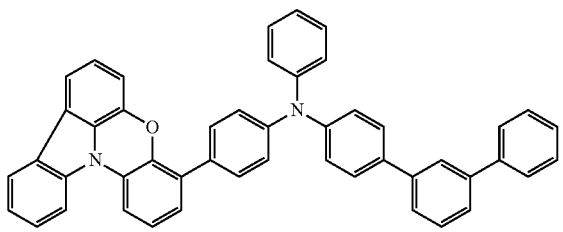
C143
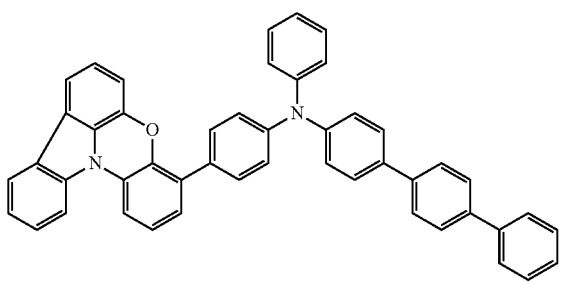
C144
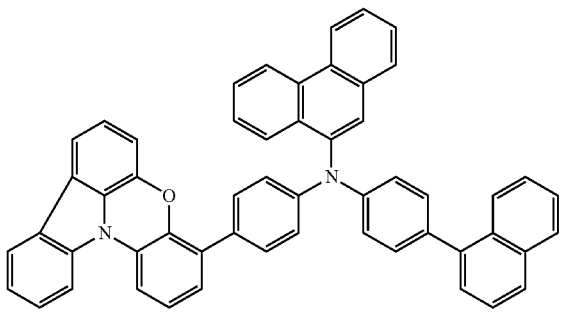
C145
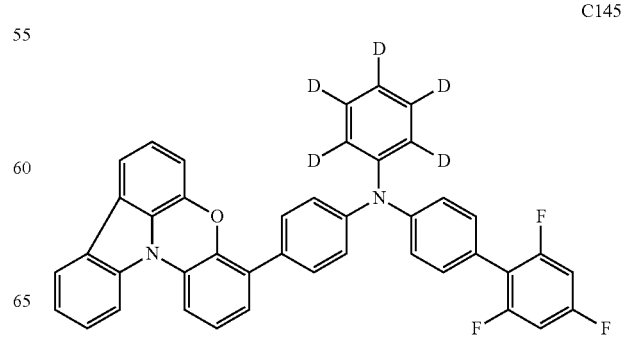

C146
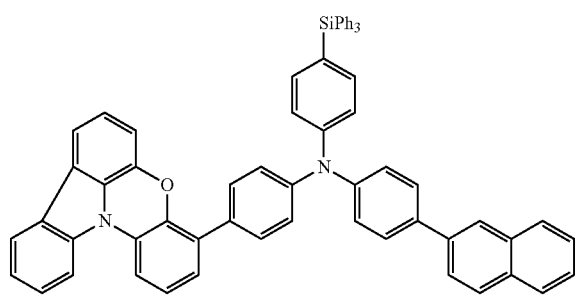
C147
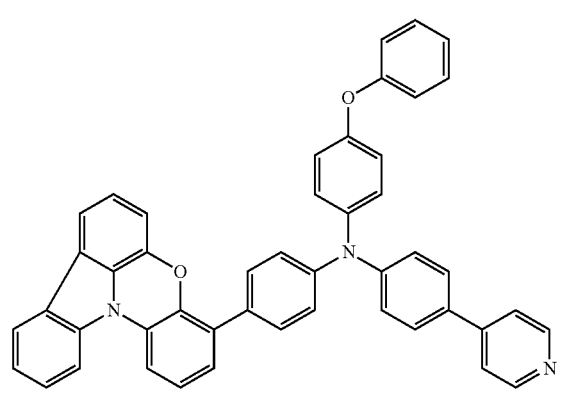
C148
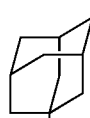
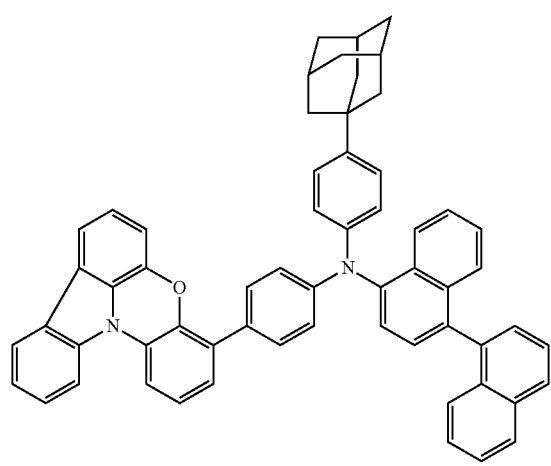
C149
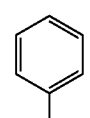
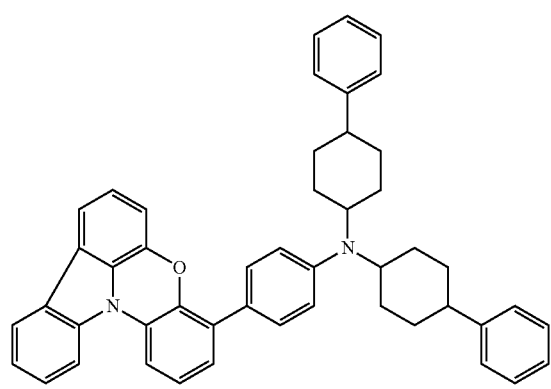
C150
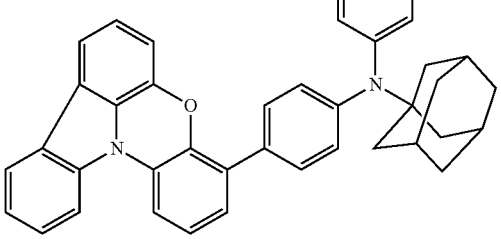
C151
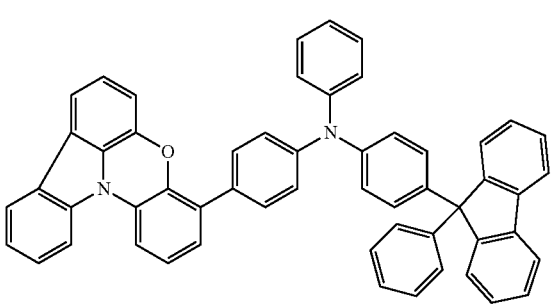
C152
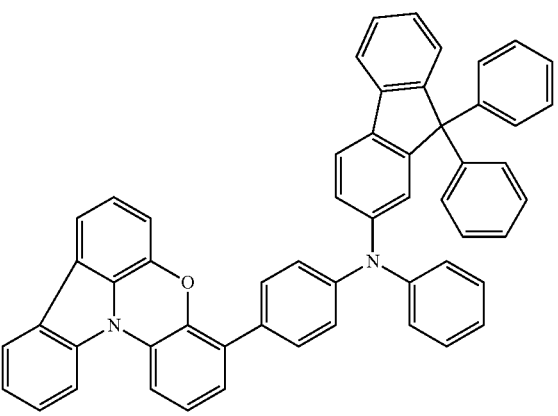
C153
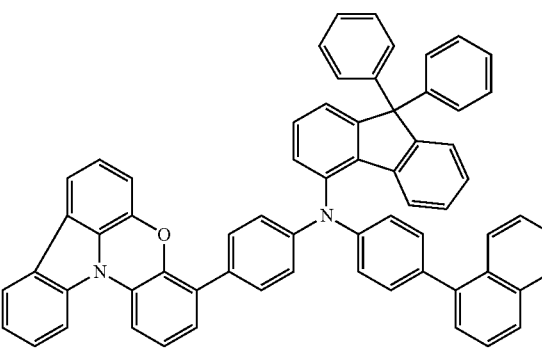

C154
C155
C156
C157
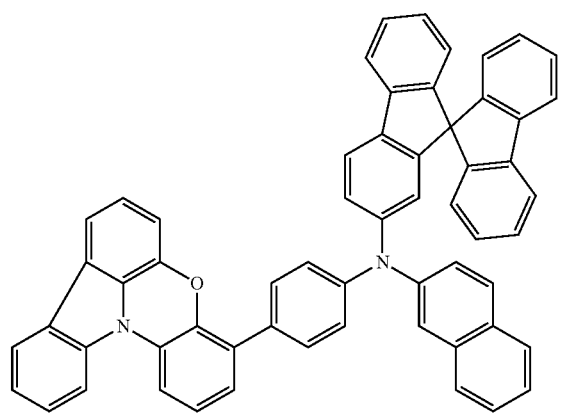
C158
C159
C160
C161
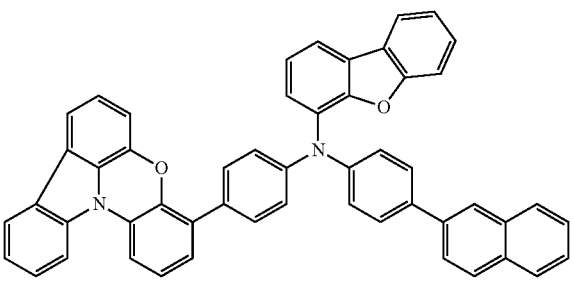
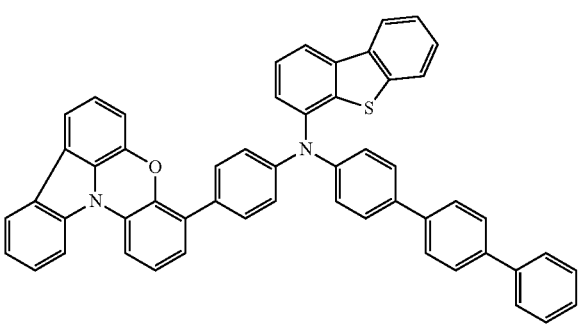
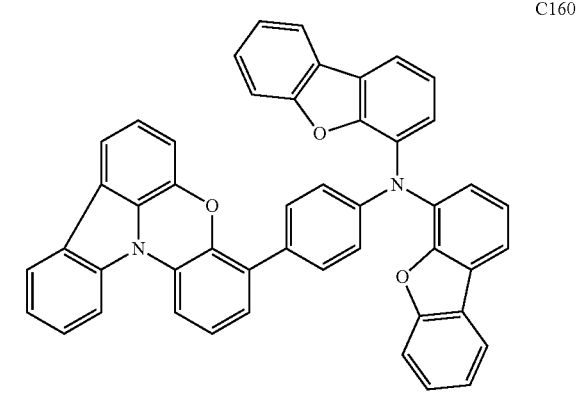
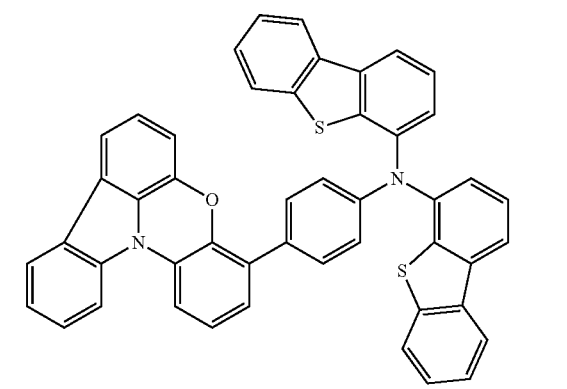

-continued
C162
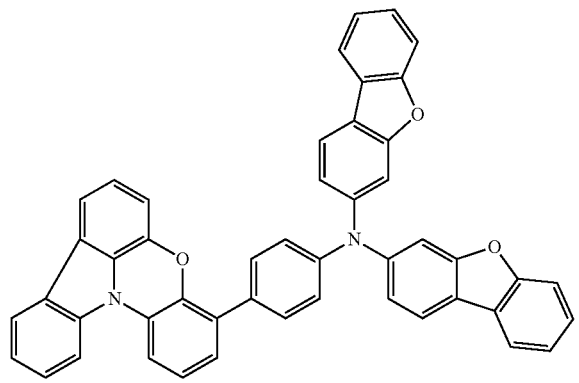
C163
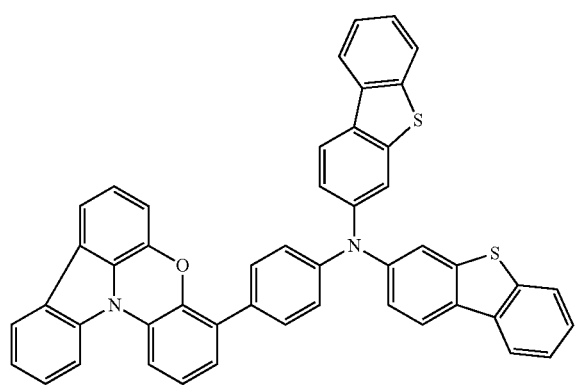
C164
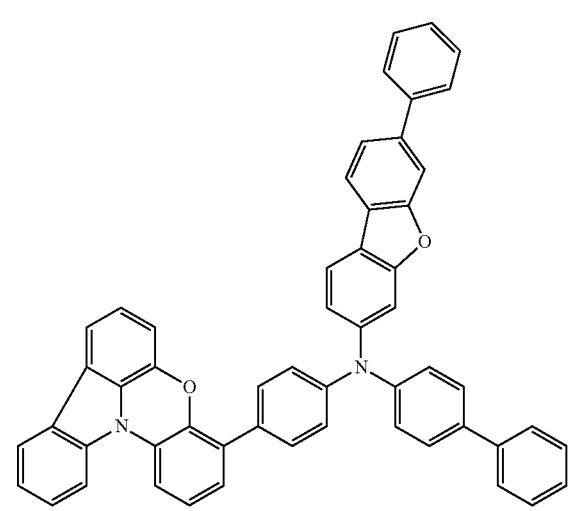
C165
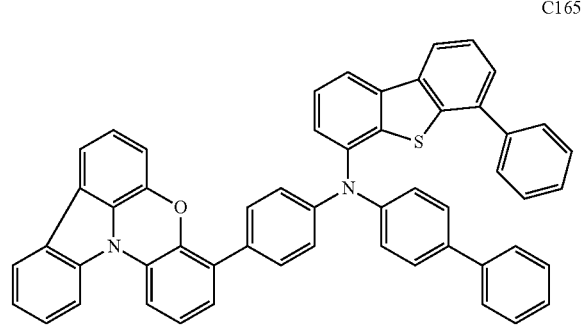
-continued
C166
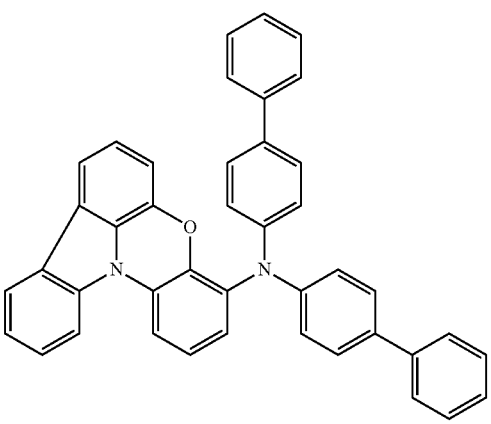
C167
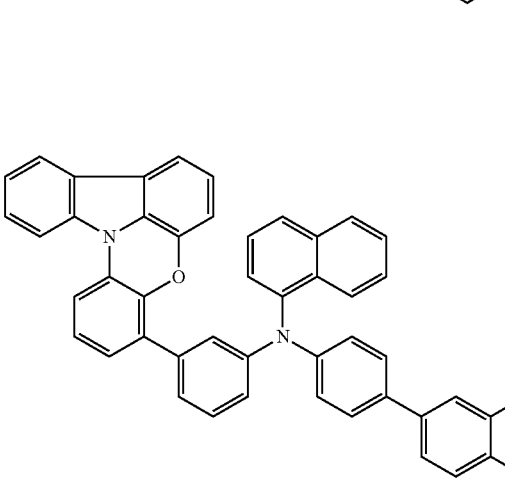
C168
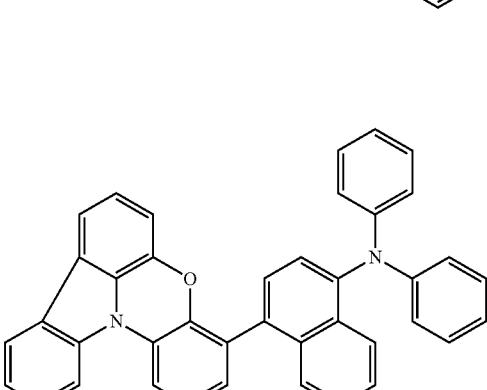
C169
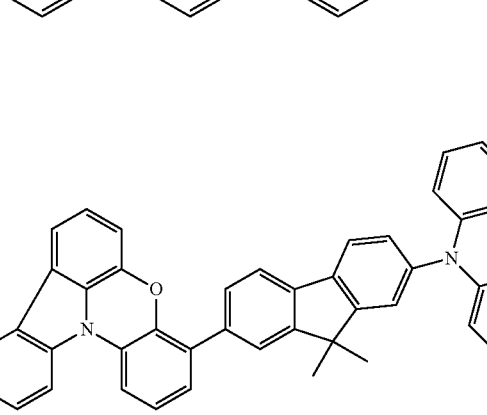

-continued
C170
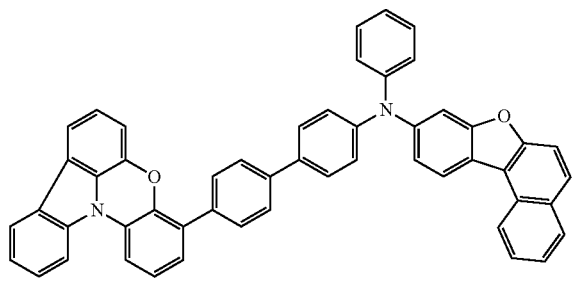
C171
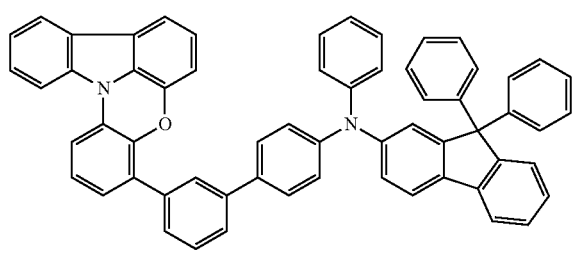
C172
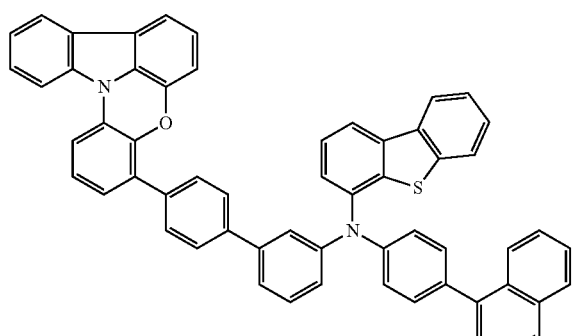
C173
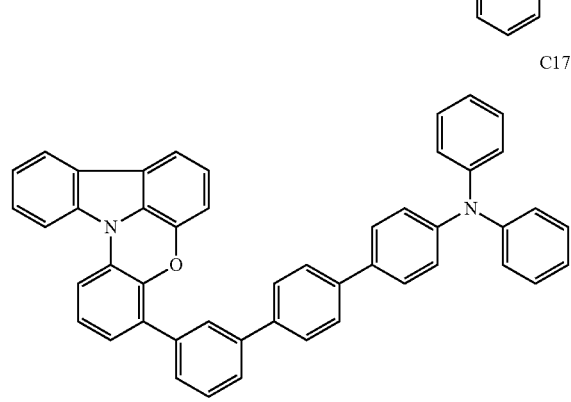
C174
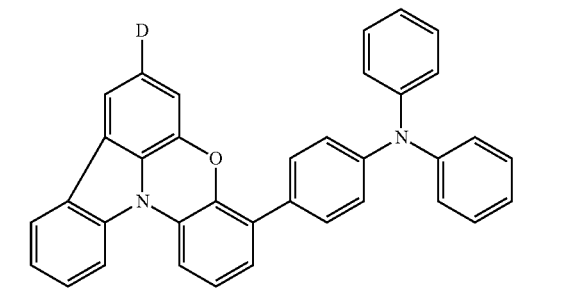
-continued
C175
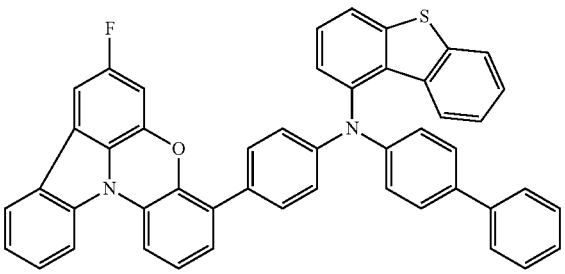
C176
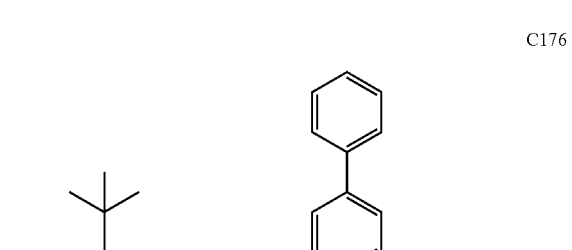
C177
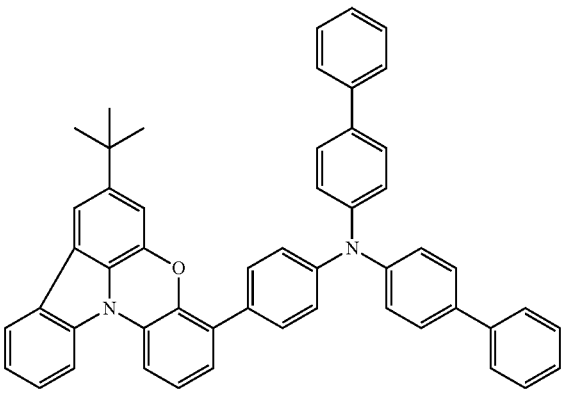
C178
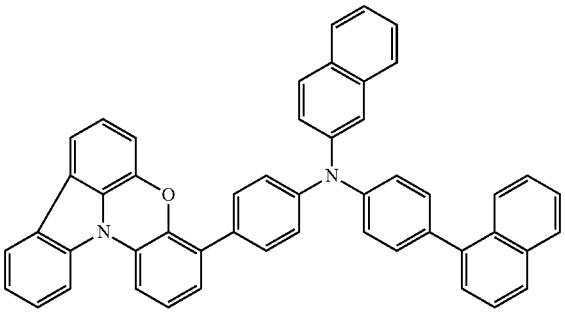
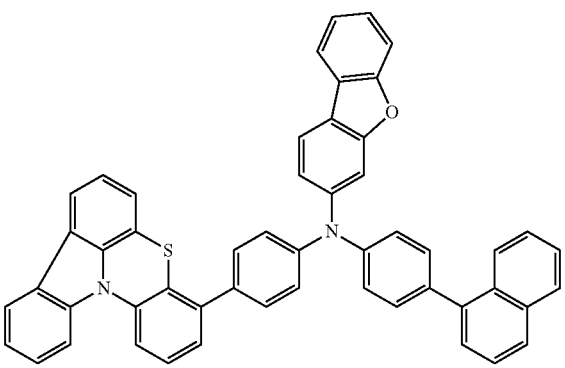

-continued

C179

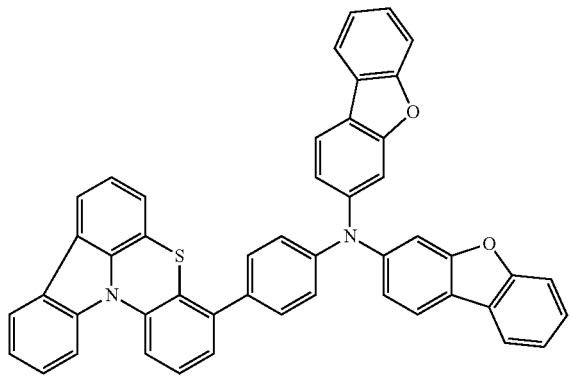

C180

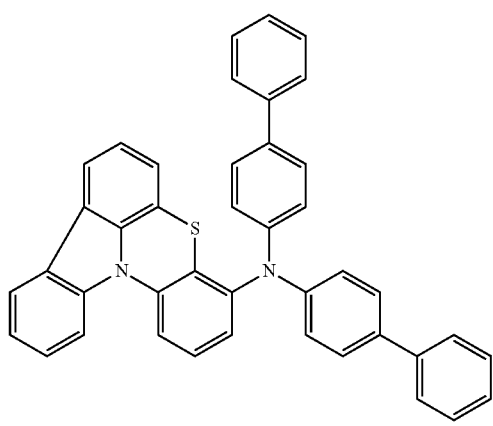

However, any hydrogen atom in a molecule in the polycyclic compound according to some exemplary embodiments may be substituted with a deuterium atom.

Referring to FIGS. 1 to 3, the organic electroluminescence devices 10 according to some exemplary embodiments has the hole transport region HTR including the polycyclic compound. For example, the hole transport region HTR includes the polycyclic compound represented by Formula 1.

When the hole transport region HTR is a multilayer structure having a plurality of layers, any one layer of the plurality of layers may include a polycyclic compound represented by Formula 1. For example, the hole transport region HTR may include the hole injection layer HIL disposed on the first electrode EL1 and the hole transport layer HTL disposed on the hole injection layer HIL, wherein the hole transport layer HTL may include a polycyclic compound represented by Formula 1. However, the exemplary embodiments are not limited thereto, for example, the hole injection layer HIL may include a polycyclic compound represented by Formula 1.

The hole transport region HTR may include one or two or more of polycyclic compounds represented by Formula 1. For example, the hole transport region HTR may include at least one selected from among compounds represented by Compound Groups 1 to 3 as described above.

The hole transport region HTR may be formed by using various methods such as a vacuum deposition method, a spin coating method, a casting method, a Langmuir-Blodgett (LB) method, an inject printing method, a laser printing method, and a laser induced thermal imaging (LITI) method.

The hole transport region HTR may further include materials below in each layer.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-[tris(3-methylphenyl)phenylamino]triphenylamine] (m-MTDATA), 4,4',4"-tris(N,N-diphenylamino)triphenylamine (TDATA), 4,4',4"-tris{N,-(2-naphthyl-N-(phenyl)amino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPD), triphenylamine-containing polyetherketone (TPAPEK), 4-isopropyl-4'-methyldiphenyliodonium tetrakis(pentafluorophenyl)borate, dipyrazino[2,3-f 2',3'-h]quinoxaline-2,3,6,7,10,11-hexacarbonitrile (HAT-CN), etc.

The hole transport layer HTL may include a material that is well known to the art. The hole transport layer HTL may further include, for example, one or more carbazole derivatives such as N-phenyl carbazole and polyvinyl carbazole, one or more fluorene derivatives, N,N'-bis(3-methylphenyl)-N,N'-diphenyl-[1,1-biphenyl]-4,4'-diamine (TPD), triphenylamine derivatives such as 4,4',4"-tris(N-carbazolyl)triphenylamine (TCTA), N,N'-di(naphthalene-1-yl)-N,N'-diphenyl-benzidine (NPD), 4,4'-cyclohexylidene bis[N,N-bis(4-methylphenyl]benzenamine] (TAPC), 3,3'-Dimethyl-N4,N4,N4',N4'-tetra-m-tolyl-[1,1'-biphenyl]-4,4'-diamine (HMTPD), 1,3-Bis(N-carbazolyl)benzene (mCP), etc.

The hole transport region HTR may have a thickness from about 50 Å to about 15,000 Å, for example, from about 100 Å to about 5,000 Å. The hole injection region HIL may have a thickness, for example, from about 30 Å to about 1,000 Å, the hole transport layer HTL may have a thickness from about 30 Å to about 1,000 Å. For example, the electron blocking layer EBL may have a thickness from about 10 Å to about 1,000 Å. If the thickness of each of the hole transport region HTR, the hole injection layer HIL, the hole transport layer HTL, and the electron blocking layer EBL satisfies the above-described range, satisfactory hole transport characteristics may be achieved without a substantial increase in driving voltage.

The hole transport region HTR may further include a charge generating material in addition to the above-described materials to improve conductivity. The charge generating material may be uniformly or non-uniformly dispersed into the hole transport region HTR. The charge generating material may be, for example, a p-dopant. The p-dopant may be one of quinone derivatives, metal oxides, and cyano group-containing compounds, but is not limited thereto. For example, non-limiting examples of the p-dopant may include, but are not limited to, quinone derivatives such as tetracyanoquinodimethane (TCNQ) and 2,3,5,6-tetrafluoro-7,7,8,8-tetracyanoquinodimethane (F4-TCNQ), one or more metal halides such as $MgF_2$, CuI, and RbI, and one or more metal oxides such as at least one of tungsten and/or molybdenum oxides.

As described above, the hole transport region HTR may further include at least one of the hole buffer layer or the electron blocking layer EBL. The hole buffer layer may compensate the resonance distance according to the wavelength of light emitted from the emission layer EML to increase light emission efficiency. A material that may be contained in the hole transport region HTR may be used as a material to be contained in the hole buffer layer. The electron blocking layer EBL is a layer playing the role of blocking the electron injection from the electron transport region ETR to the hole transport region HTR.

The emission layer EML is disposed on the hole transport region HTR. The emission layer EML may have a thickness, for example, from about 100 Å to about 1,000 Å, or from about 100 Å to about 600 Å. The emission layer EML may have a multilayer structure having a single layer formed of a single material, a single layer formed of materials different from each other, or a plurality of layers formed of materials different from each other.

As materials of the emission layer EML, known materials may be used, and one selected among one or more of fluoranthene derivatives, pyrene derivatives, arylacetylene derivatives, anthracene derivatives, fluorene derivatives, perylene derivatives, chrysene derivatives, etc. may be used, without specific limitation. Preferably, the host materials may include one or more of pyrene derivatives, perylene derivatives, and anthracene derivatives. For example, as the host materials of the emission layer EML, one or more anthracene derivatives represented by the following Formula 10 may be used.

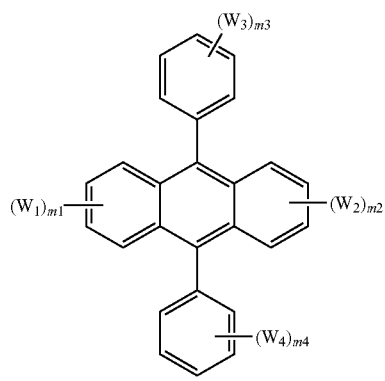

Formula 10

In Formula 10, W1 to W4 may be each independently a hydrogen atom, a deuterium atom, a halogen atom, a substituted or unsubstituted silyl group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be combined with an adjacent group to form a ring, where m1 and m2 are each independently an integer of 0 to 4, and m3 and m4 are each independently an integer of 0 to 5.

If the variable m1 is 1, W1 may not be a hydrogen atom; if the variable m2 is 1, W2 may not be a hydrogen atom; if the variable m3 is 1, W3 may not be a hydrogen atom; and if the variable m4 is 1, W4 may not be a hydrogen atom.

If the variable m1 is 2 or more, a plurality of W1 groups are the same or different. If the variable m2 is 2 or more, a plurality of W2 groups are the same or different. If the variable m3 is 2 or more, a plurality of W3 groups are the same or different. If the variable m4 is 2 or more, a plurality of W4 groups are the same or different.

The compound represented by Formula 10 may include, for example, a compound represented by the following structures. However, the compound represented by Formula 10 is not limited thereto.

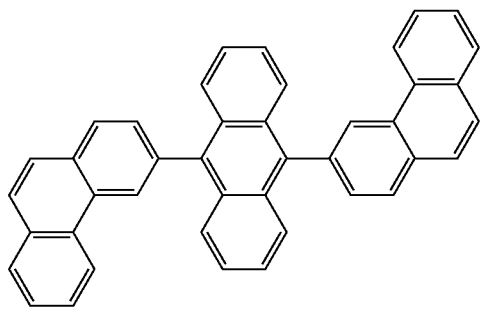

a-1

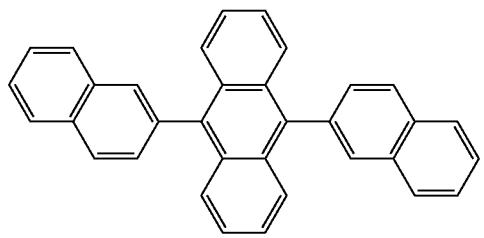

a-2

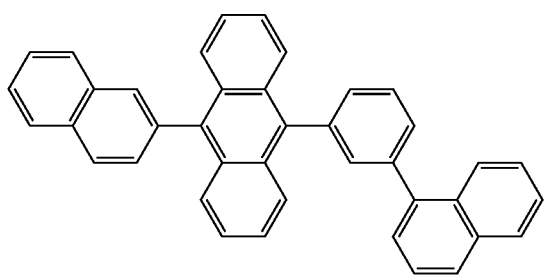

a-3

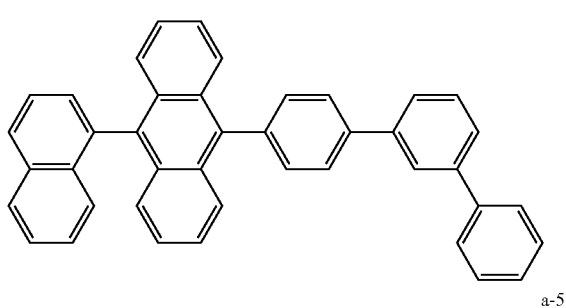

a-4

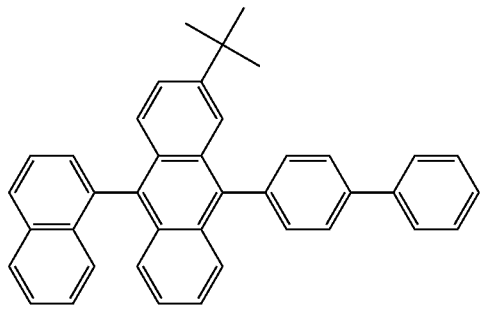

a-5

-continued
a-6
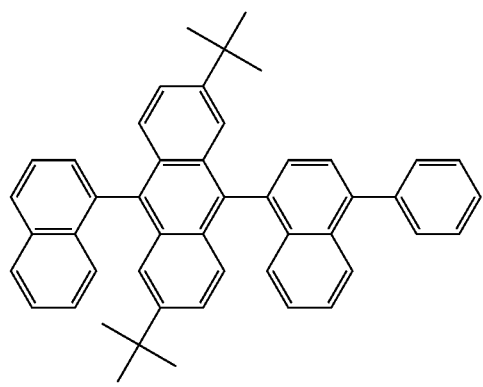
a-7
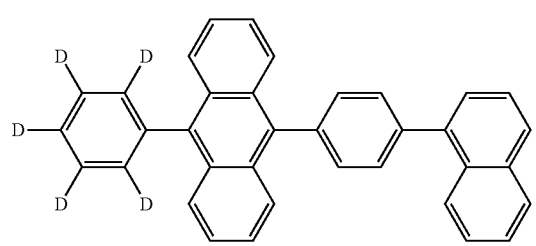
a-8
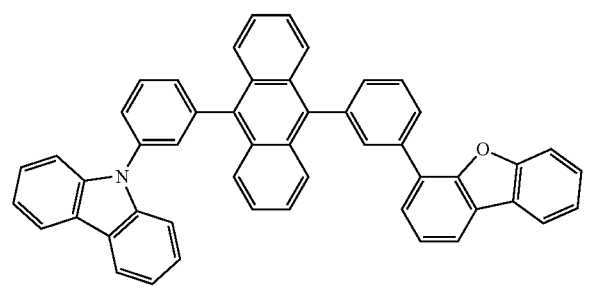
a-9
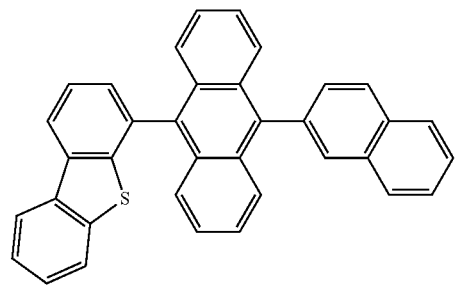
a-10
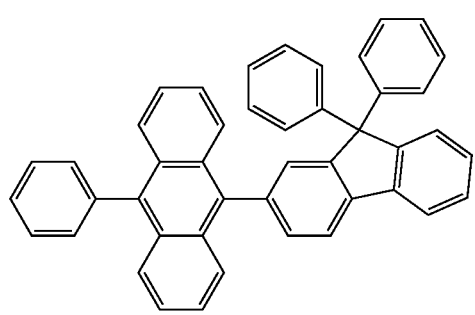
-continued
a-11
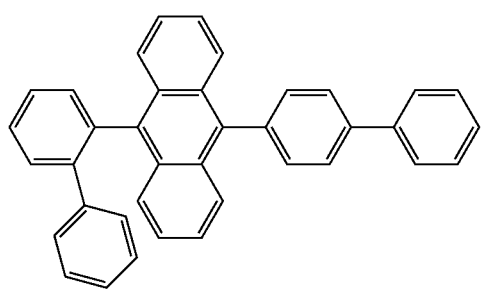
a-12
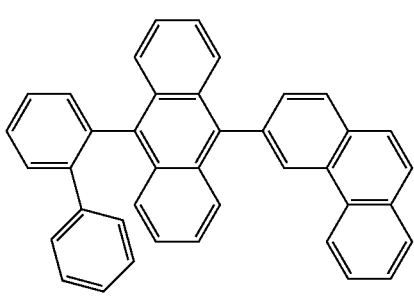
a-13
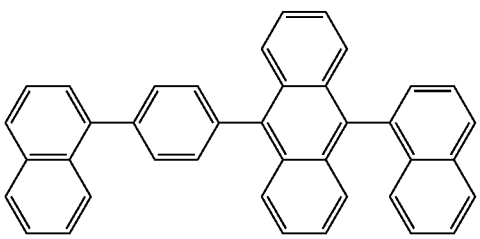
a-14
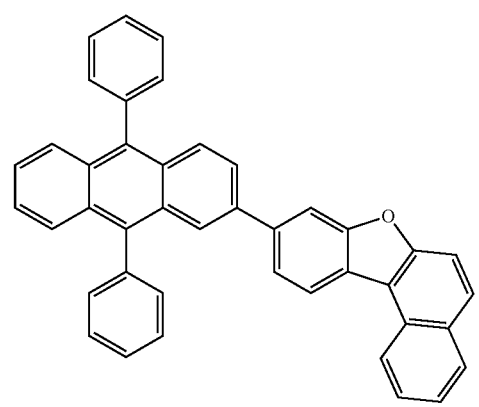

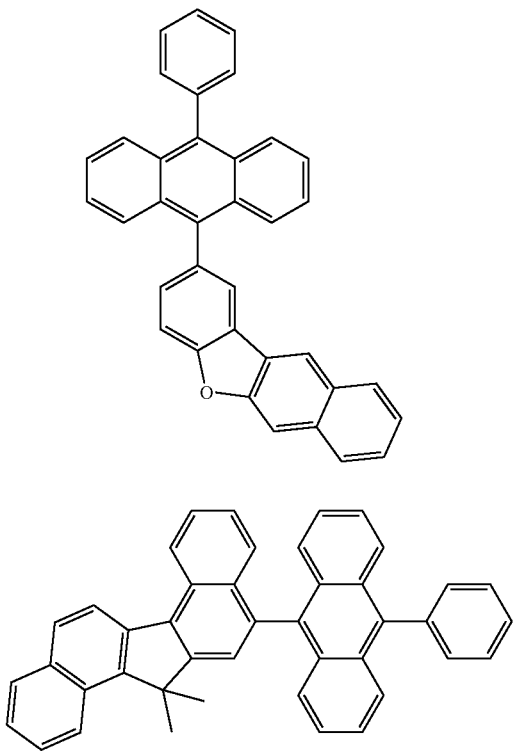

a-15 a-16

The emission layer EML may include a dopant, know materials may be used as the dopant. For example, at least one among styryl derivatives (e.g., 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and one or more derivatives thereof (e.g., 2,5,8,11-tetra-t-butylperylene (TBPe)), pyrene and one or more derivatives thereof (e.g., 1,1-dipyrene, 1,4-dipyrenylbenzene, 1,4-bis(N,N-diphenylamino)pyrene, 1,6-bis(N,N-diphenylamino)pyrene), 2,5,8,11-tetra-t-butylperylene (TBP), and 1,3,5-tris(1-phenyl-1H-benzo[d]imidazole-2-yl)benzene (TPBi) may be used as a dopant, but the exemplary embodiments are not limited thereto.

The emission layer EML may include a host material. For example, the emission layer EML may include, but is not limited to, as a host material, at least one of tris(8-hydroxyquinolino)aluminum (Alq3), bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4''-tris(carbazol-9-yl)-triphenylamine (TCTA), poly(n-vinylcabazole (PVK), 9,10-di(naphthalene-2-yl)anthracene (ADN), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH-2), hexaphenylcyclotrisiloxane (DPSiO3), octaphenylcyclotetra siloxane (DPSiO4), 2,8-bis(diphenylphosphoryl)dibenzofuran (PPF), or 1,3,5-tris(1-phenyl-1H-benzo[d]imidazole-2-yl)benzene (TPBi).

In some exemplary embodiments, the emission layer EML emits red light and may include, for example, a fluorescent material including tris(dibenzoylmethanato) phenanthoroline europium (PBD:Eu(DBM)3(Phen)) and perylene. When the emission layer EML emits red light, the dopant contained in the emission layer EML may be, for example, selected from among a metal complex or organometallic complex such as bis(1-phenylisoquinoline)acetylacetonate iridium (PIQIr(acac)), bis(1-phenylquinoline) acetylacetonate iridium (PQIr(acac)), tris(1-phenylquinoline)iridium (PQIr), and octaethylporphyrin platinum (PtOEP), rubrene and one or more derivatives thereof, and 4-dicyanomethylene-2-(p-dimethylaminostyryl)-6-methyl-4H-pyran (DCM) and one or more derivatives thereof.

In some exemplary embodiments, the emission layer EML emits green light and may further include, for example, a fluorescent material including tris(8-hydroxyquinolino) aluminum (Alq3). When the emission layer EML emits green light, the dopant contained in the emission layer EML may be, for example, selected from among a metal complex or organometallic complex such as fac-tris(2-phenylpyridine)iridium (Ir(ppy)3), and coumarin and one or more derivatives thereof.

In some exemplary embodiments, the emission layer EML emits blue light and may further include a fluorescence material including any one selected from the group consisting of spiro-DPVBi, spiro-6P, distyryl-benzene (DSB), distyryl-arylene (DSA), polyfluorene (PFO)-based polymer and poly(p-phenylene vinylene (PPV)-based polymer. When the light emitting layer EML emits the blue light, the dopant contained in the light emitting layer EML may be selected derivatives thereof, for example, a metal complex or organometallic complex such as (4,6-F2ppy)2Irpic, perylene and one or more derivatives thereof.

The electron transport region ETR is disposed on the emission layer EML. Referring to FIG. 3, the electron transport region ETR may include, but is not limited to, at least one of the hole blocking layer HBL, the electron transport layer ETL, or the electron injection layer EIL.

The electron transport region ETR may have a multilayer structure having a single layer formed of a single material, a single layer formed of materials different from each other, or a plurality of layers formed of materials different from each other.

For example, the electron transport region HTR may have a single layer structure of an electron injection layer EIL or an electron transport layer ETL, or a single layer structure formed of electron injection materials or electron transport materials. In addition, the electron transport region ETR may have a single layer structure formed of materials different from each other, or a structure of electron transport layer ETL/electron injection layer EIL, hole blocking layer HBL/electron transport layer ETL/electron injection layer (EIL) which are sequentially laminated from the emission layer EML, but the exemplary embodiments are not limited thereto. The electron transport region ETR may have a thickness, for example, from about 100 Å to about 1,500 Å.

The electron transport region ETR may be formed by using various methods such as a vacuum deposition method, a spin coating method, a casting method, a Langmuir-Blodgett (LB) method, an inkject printing method, a laser printing method, and a laser induced thermal imaging (LITI) method.

If the electron transport region ETR includes the electron transport layer ETL, the electron transport region ETR may include an anthracene-based compound. However, the exemplary embodiments are not limited thereto, and the electron transport region ETR may include, for example, tris(8-hydroxyquinolinato)aluminum (Alq3), 1,3,5-tri[(3- pyridyl)-phen-3-yl]benzene, 2,4,6-tris(3'-(pyridin-3-yl)biphenyl-3-yl)-1,3,5-triazine, bis[2-(diphenylphosphino)phenyl]ether oxide (DPEPO), 2-(4-(N-phenylbenzoimidazolyl-1-yl phenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebg2), 9,10-di(naphthalene-2-yl)anthracene (ADN), or a mixture thereof. The thickness of the electron transport layers ETL may be from about 100 Å to about 1,000 Å, for example, from about 150 Å to about 500 Å. If the thickness of the electron transport layer ETL satisfies the above-described range, satisfactory electron transport characteristics may be achieved without a substantial increase in driving voltage.

If the electron transport region ETR includes the electron injection layer EIL, the electron transport region ETR may be formed using metal halides such as LiF, NaCl, CsF, RbCl, and RbI, lanthanum metals such as Yb, metal oxides such as Li$_2$O and BaO, lithium quinolate (LiQ), etc., but the exemplary embodiments are not limited thereto. The electron injection layer EIL may be also formed of a mixture of an electron transport material and an organo metal salt. The organo metal salt may be a material having an energy band gap of about 4 eV or more. For example, the organo metal salt may include at least one of a metal acetate, a metal benzoate, a metal acetoacetate, a metal acetylacetonate or a metal stearate. The electron injection layers EIL may have a thickness from about 1 Å to about 100 Å, and from about 3 Å to about 90 Å. If the thickness of the electron injection layers EIL satisfies the above-described range, satisfactory electron injection characteristics may be achieved without a substantial increase in driving voltage.

As described above, the electron transport region ETR may include the hole blocking layer HBL. The hole blocking layer HBL may include, but is not limited to, for example, at least one of 2,9-dimethyl-4,7-diphenyl-1,10-phenanthroline (BCP), bis[2-(diphenylphosphino)phenyl]ether oxide (DPEPO), or 4,7-diphenyl-1,10-phenanthroline (Bphen).

The second electrode EL2 may be disposed on the electron transport region HTR. The second electrode EL2 may be a common electrode or a negative electrode. The second electrode EL2 may be a transmissive electrode, a transflective electrode, or a reflective electrode. When the second electrode EL2 is the transmissive electrode, the second electrode EL2 may be formed of transparent metal oxides, for example, at least one of an indium tin oxide (ITO), an indium zinc oxide (IZO), a zinc oxide (ZnO), an indium tin zinc oxide (ITZO), etc.

When the second electrode EL2 is the transflective electrode or the reflective electrode, the second electrode EL2 may include Ag, Mg Cu, Al, Pt, Pd, Au, Ni, Nd, Ir, Cr, Li, Ca, LiF/Ca, LiF/Al, Mo, Ti, or a compound or mixture (e.g., a mixture of Ag and Mg) including the same. Alternatively, the first electrode EL1 may have a multi-layered structure including a reflective layer or transflective layer and a transparent conductive layer formed of at least one of an indium tin oxide (ITO), an indium zinc oxide (IZO), a zinc oxide (ZnO), or an indium tin zinc oxide (ITZO).

The second electrode EL may be connected to an auxiliary electrode. When the second electrode EL2 is connected to the auxiliary electrode, resistance of the second electrode EL2 may be decreased.

Referring to FIG. 4, a capping layer CPL may be further included on the second electrode EL2 of the organic electroluminescence device 10 of some exemplary embodiments. The capping layer CPL may include, for example, 2,2'-Dimethyl-N,N'-di-[(1-naphthyl)-N,N'-diphenyl]-1,1'-biphenyl-4,4'-diamine (α-NPD), N,N'-di(1-naphthalene-1-yl)-N,N'-diphenyl-benzidine (NPB), TPD, m-MTDATA, Alq3, copper(II) phthalocyanine (CuPc), N4,N4,N4',N4'-tetra (biphenyl-4-yl) biphenyl-4,4'-diamine (TPD15), 4,4', 4"-Tris (carbazol sol-9-yl) triphenylamine (TCTA), N, N'-bis (naphthalen-1-yl), etc.

In the organic electroluminescence device 10 as a voltage is applied to the first electrode EL1 and the second electrode EL2, respectively, the holes injected from the first electrode EL1 are moved through the hole transport region HTR to the emission layer EML, and the electrons injected from the second electrode EL2 are moved through the electron transport region ETR to the emission layer EML. The electrons and holes are recombined in the emission layer EML to generate excitons and emit light when the excitons return to a ground state from an excited state.

In some exemplary embodiments, the organic electroluminescence device 10 is a front emission type, and the first electrode EL1 may be the reflective electrode, and the second electrode EL2 may be the transmissive electrode or transflective electrode. In some exemplary embodiments, the organic electroluminescence device 10 is a rear emission type and the first electrode EL1 may be the transmissive electrode or transflective electrode, and the second electrode EL2 may be the reflective electrode.

The organic electroluminescence device 10 according to some exemplary embodiments is characterized by including the polycyclic compound represented by Formula 1, and thereby achieving high efficiency and long service life. In addition, a low driving voltage may be achieved.

Examples

Although not wanting to be bound by theory, a polycyclic compound according to at least some exemplary embodiments may be synthesized as, for example, by the following. However, a synthetic method of the polycyclic compound is not limited to the exemplary embodiments.

1. Synthesis of Compound A2

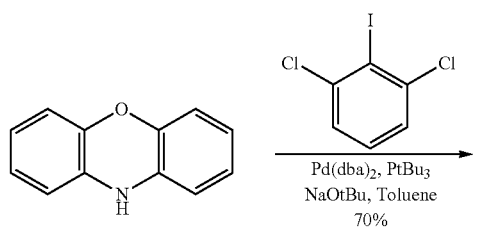

-continued

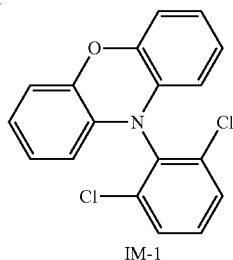
IM-1

In an argon atmosphere, in a 1000 mL three-neck flask, phenoxazine (20.00 g, 109.2 mmol), palladium(0) bis(dibenzylideneacetone) (Pd(dba)$_2$) (1.88 g, 0.03 weight equivalent, 3.3 mmol), sodium tert-butoxide (NaOtBu) (31.47 g, 3.0 weight equivalent, 327.5 mmol), toluene (545 mL), 1,3-dichloro-2-iodobenzene (32.77 g, 1.1 weight equivalent, 120.1 mmol), and tri-tert-butylphosphine (tBu$_3$P) (2.09 g, 0.1 weight equivalent, 10.9 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO$_4$. The MgSO$_4$ was filtered off and the organic layers were concentrated, and then the resulting crude product was purified by a silica gel column chromatography (using mixture solvent of hexane and toluene as an eluent) to obtain Intermediate IM-1 (25.08 g, yield 70%).

By measuring with fast atom bombardment-mass spectroscopy (FAB-MS), a mass number of m/z=328 was observed by molecular ion peak, thereby identifying Intermediate IM-1.

Synthesis of Intermediate IM-2

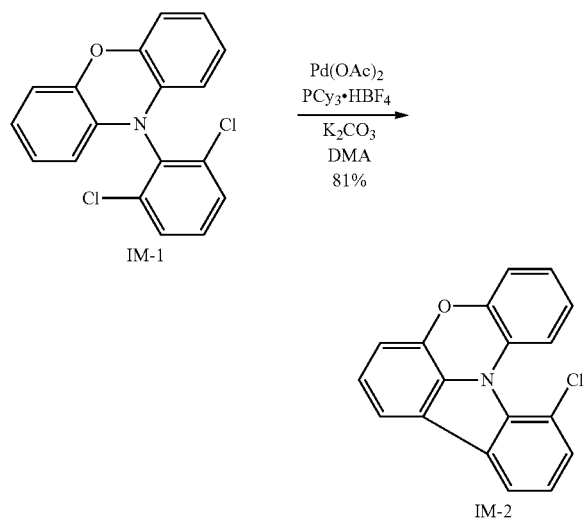

In an argon atmosphere, in a 500 mL three-neck flask, IM-1 (20.00 g, 60.9 mmol), palladium(II) acetate (Pd(OAc)$_2$) (0.82 g, 0.06 weight equivalent, 3.7 mmol), K$_2$CO$_3$ (16.85 g, 2.0 weight equivalent, 121.9 mmol), N,N-dimethylacetamide (DMA) (305 mL), and tricyclohexylphosphine (PCy$_3$)·tetrafluoroboric acid solution (HBF$_4$) solution (2.69 g, 0.12 weight equivalent, 7.3 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO$_4$. The MgSO$_4$ was filtered off and the organic layers were concentrated, and then the resulting crude product was purified by a silica gel column chromatography (using mixture solvent of hexane and toluene as an eluent) to obtain Intermediate IM-2 (14.40 g, yield 81%).

By measuring with FAB-MS, a mass number of m/z=291 was observed by molecular ion peak, thereby identifying Intermediate IM-2.

Synthesis of Compound A2

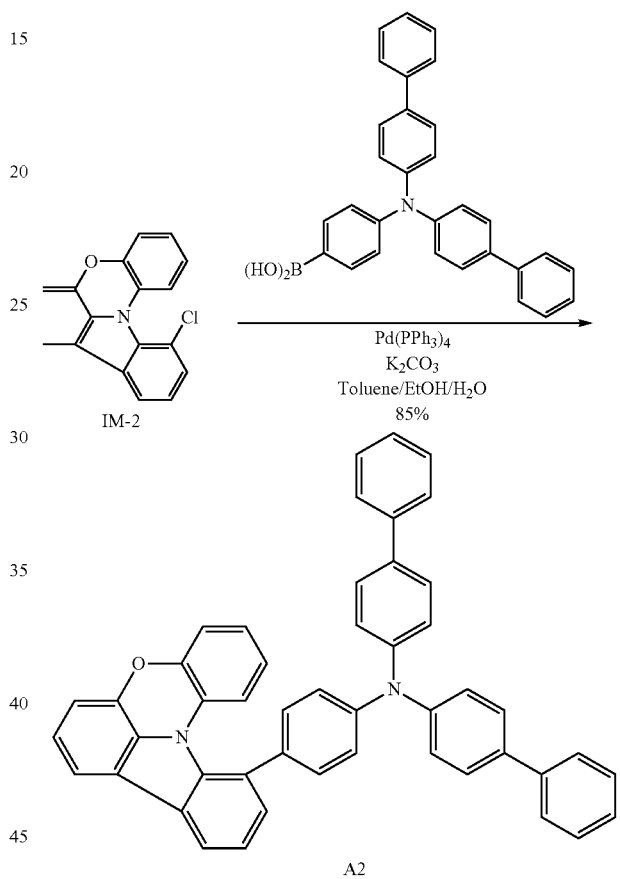

64 In an argon atmosphere, in a 300 mL three-neck flask, IM-2 (5.00 g, 17.1 mmol), {4-[di(1,1'-biphenyl)-4-yl]amino}phenylboronic acid (8.32 g, 1.1 weight equivalent, 18.9 mmol), K$_2$CO$_3$ (7.11 g, 3.0 weight equivalent, 51.4 mmol), tetrakis(triphenylphosphine)-palladium(0) (Pd(PPh$_3$)$_4$) (0.99 g, 0.05 weight equivalent, 0.9 mmol), and the mixture solution of toluene/ethanol/H$_2$O (volumetric ratio: 4/2/1) (120 mL) were sequentially added, and heated and stirred at about 80° C. After air cooling to room temperature, the reaction solution was extracted with toluene. A water layer was removed, the organic layer was washed with saturated saline, and then dried with MgSO$_4$. The MgSO$_4$ was filtered off and the organic layers were concentrated, and then the resulting crude product was purified by a silica gel column chromatography (using mixture solvent of hexane and toluene as an eluent) to obtain Compound A2 (9.51 g, yield 85%).

By measuring with FAB-MS, a mass number of m/z=652 was observed by molecular ion peak, thereby identifying Compound A2.

2. Synthesis of Compound A68
Synthesis of Intermediate IM-3

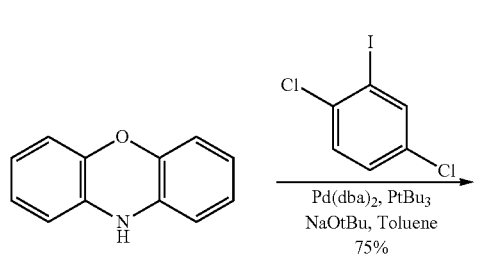

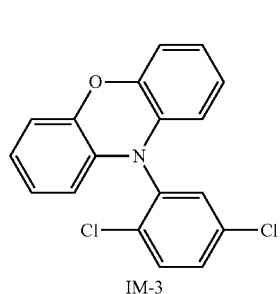

Synthesis of Intermediate IM-4

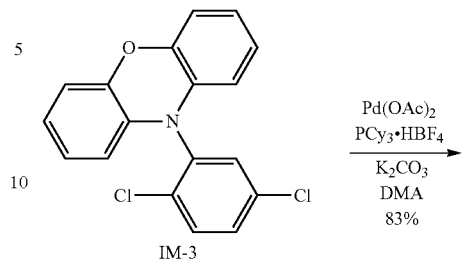

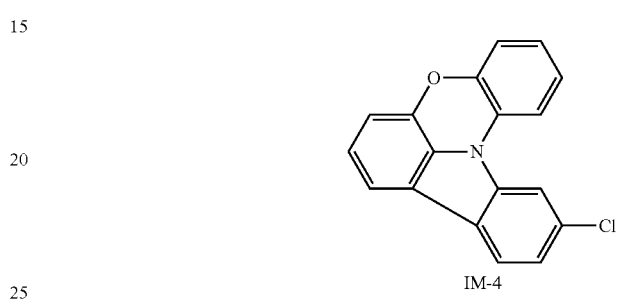

In an argon atmosphere, in a 1000 mL three-neck flask, phenoxazine (20.00 g, 109.2 mmol), Pd(dba)$_2$ (1.88 g, 0.03 weight equivalent, 3.3 mmol), sodium tert-butoxide (NaOtBu) (31.47 g, 3.0 weight equivalent, 327.5 mmol), toluene (545 mL), 1,4-dichloro-2-iodobenzene (32.77 g, 1.1 weight equivalent, 120.1 mmol), and (tBu$_3$P) (2.09 g, 0.1 weight equivalent, 10.9 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO$_4$. The MgSO$_4$ was filtered off and the organic layers were concentrated, and then the resulting crude product was purified by a silica gel column chromatography (using mixture solvent of hexane and toluene as eluent) to obtain Intermediate IM-3 (26.87 g, yield 75%).

By measuring FAB-MS, a mass number of m/z=328 was observed by molecular ion peak, thereby identifying Intermediate IM-3.

In an argon atmosphere, in a 500 mL three-neck flask, IM-3 (20.00 g, 60.9 mmol), Pd(OAc)$_2$ (0.82 g, 0.06 weight equivalent, 3.7 mmol), K$_2$CO$_3$ (16.85 g, 2.0 weight equivalent, 121.9 mmol), N,N-dimethylacetamide (DMA) (305 mL), and PCy$_3$·HBF$_4$ (2.69 g, 0.12 weight equivalent, 7.3 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO$_4$. The MgSO$_4$ was filtered off and the organic layers were concentrated, and then the resulting crude product was purified by a silica gel column chromatography (using mixture solvent of hexane and toluene as eluent) to obtain Intermediate IM-4 (14.76 g, yield 83%).

By measuring with FAB-MS, a mass number of m/z=291 was observed by molecular ion peak, thereby identifying Intermediate IM-4.

Synthesis of Compound A68

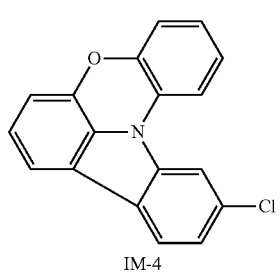

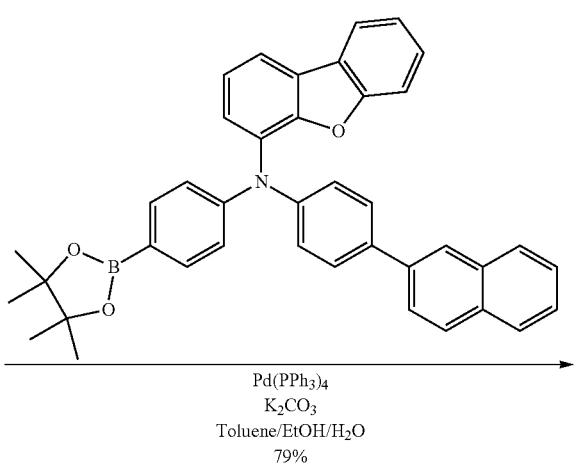

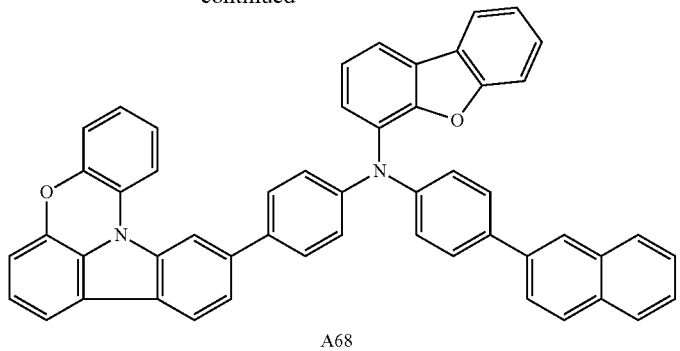

A68

In an argon atmosphere, in a 300 mL three-neck flask, IM-4 (5.00 g, 17.1 mmol), N-[4-(naphthalen-2-yl)phenyl]-N-[4-(4,4,5,5-tetramethyl-1,3,2-dioxaborolan-2-yl)phenyl]dibenzo[b,d]furan-4-amine (11.68 g, 1.1 weight equivalent, 18.9 mmol), K$_2$CO$_3$ (7.11 g, 3.0 weight equivalent, 51.4 mmol), Pd(PPh$_3$)$_4$ (0.99 g, 0.05 weight equivalent, 0.9 mmol), and the mixture solution of toluene/ethanol/H$_2$O (4/2/1) (120 mL) were sequentially added, and heated and stirred at about 80° C. After air cooling to room temperature, the reaction solution was extracted with toluene. A water layer was removed, the organic layer was washed with saturated saline, and then dried with MgSO$_4$. The MgSO$_4$ was filtered off and the organic layers were concentrated, and then the resulting crude product was purified by a silica gel column chromatography (using mixture solvent of hexane and toluene as an eluent) to obtain Compound A68 (9.71 g, yield 79%).

By measuring with FAB-MS, a mass number of m/z=716 was observed by molecular ion peak, thereby identifying Compound A68.

3. Synthesis of Compound A144
Synthesis of Intermediate IM-7

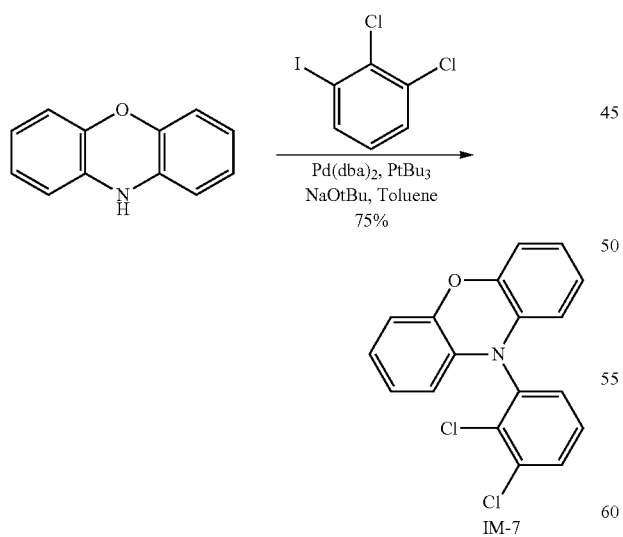

In an argon atmosphere, in a 1000 mL three-neck flask, phenoxazine (20.00 g, 109.2 mmol), Pd(dba)$_2$ (1.88 g, 0.03 weight equivalent, 3.3 mmol), NaOtBu (31.47 g, 3.0 weight equivalent, 327.5 mmol), toluene (545 mL), 1,2-dichloro-3-iodobenzene (32.77 g, 1.1 weight equivalent, 120.1 mmol), and tBu$_3$P (2.09 g, 0.1 weight equivalent, 10.9 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO$_4$. The MgSO$_4$ was filtered off and the organic layers were concentrated, and then the resulting crude product was purified by a silica gel column chromatography (using mixture solvent of hexane and toluene as an eluent) to obtain Intermediate IM-3 (26.87 g, yield 75%).

By measuring with FAB-MS, a mass number of m/z=328 was observed by molecular ion peak, thereby identifying Intermediate IM-3.

Synthesis of Intermediate IM-8

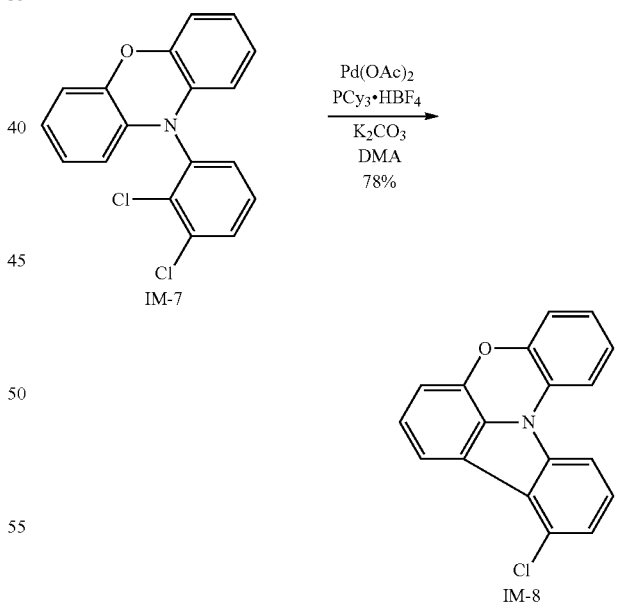

In an argon atmosphere, in a 500 mL three-neck flask, IM-7 (20.00 g, 60.9 mmol), Pd(OAc)$_2$ (0.82 g, 0.06 weight equivalent, 3.7 mmol), K$_2$CO$_3$ (16.85 g, 2.0 weight equivalent, 121.9 mmol), N,N-dimethylacetamide (DMA) (305 mL), and PCy$_3$·HBF$_4$ (2.69 g, 0.12 weight equivalent, 7.3 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO$_4$. The MgSO$_4$ was filtered off and the organic layers were concentrated, and then the resulting crude product was purified by a silica gel column chromatography (using mixture solvent of hexane and toluene as an eluent) to obtain Intermediate IM-8 (13.87 g, yield 78%).

By measuring with FAB-MS, a mass number of m/z=291 was observed by molecular ion peak, thereby identifying Intermediate IM-4.

Synthesis of Compound A144 saline, and then dried with MgSO$_4$. The MgSO$_4$ was filtered off and the organic layers were concentrated, and then the resulting crude product was purified by a silica gel column chromatography (using mixture solvent of hexane and toluene as an eluent) to obtain Compound A144 (10.09 g, yield 81%).

By measuring with FAB-MS, a mass number of m/z=726 was observed by molecular ion peak, thereby identifying Compound A144.

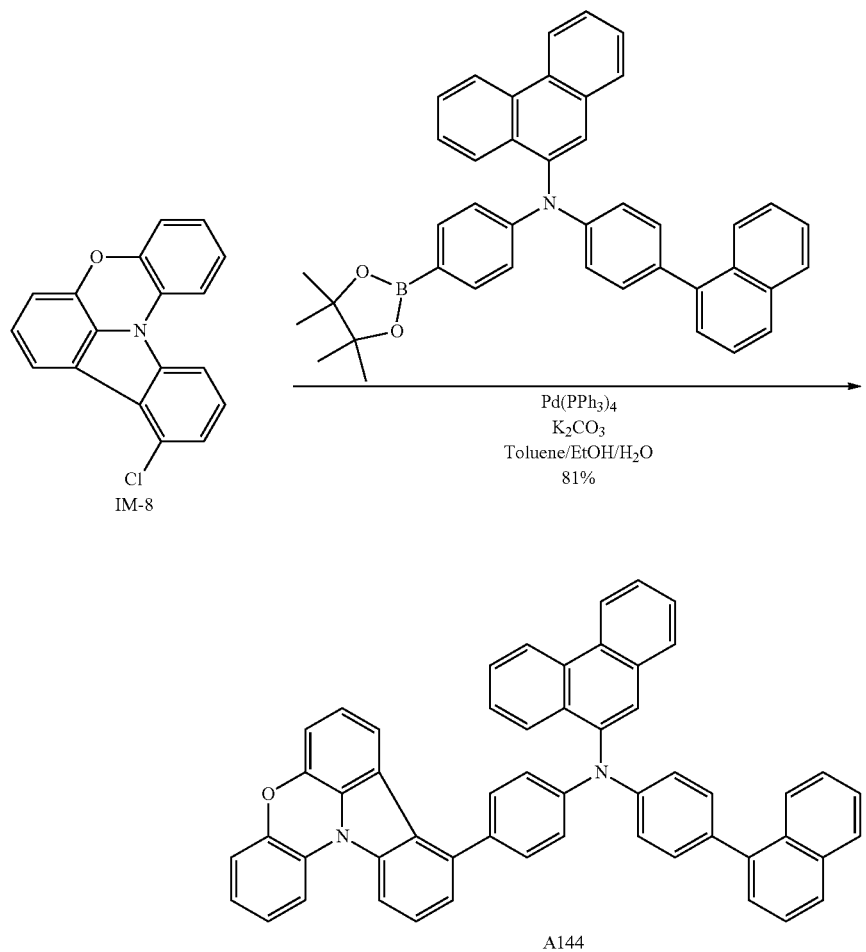

In an argon atmosphere, in a 300 mL three-neck flask, IM-8 (5.00 g, 17.1 mmol), N-[4-(naphthalen-1-yl)phenyl]-N-[4-(4,4,5,5-tetramethyl-1,3,2-dioxaborolan-2-yl)phenyl] phenanthren-9-amine (11.87 g, 1.1 weight equivalent, 18.9 mmol), K$_2$CO$_3$ (7.11 g, 3.0 weight equivalent, 51.4 mmol), Pd(PPh$_3$)$_4$ (0.99 g, 0.05 weight equivalent, 0.9 mmol), and the mixture solution of toluene/ethanol/H$_2$O (4/2/1) (120 mL) were sequentially added, and heated and stirred at about 80° C. After air cooling to room temperature, the reaction solution was extracted with toluene. A water layer was removed, the organic layer was washed with saturated 4. Synthesis of Compound B31
Synthesis of Intermediate IM-9

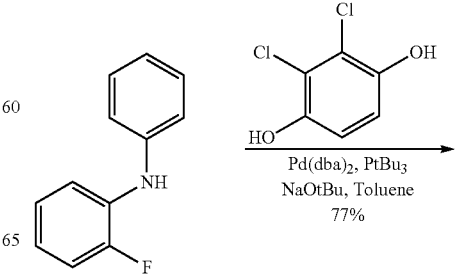

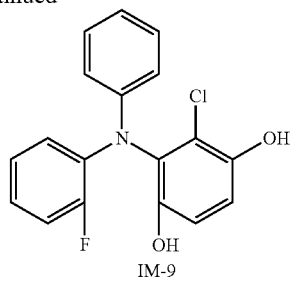

In an argon atmosphere, in a 1000 mL three-neck flask, 2-fluoro-N-phenylaniline (20.00 g, 106.8 mmol), Pd(dba)$_2$ (1.84 g, 0.03 weight equivalent, 3.9 mmol), NaOtBu (11.29 g, 1.1 weight equivalent, 117.8 mmol), toluene (534 mL), p-biphenylamine (21.03 g, 1.1 weight equivalent, 117.5 mmol), and tBu$_3$P (2.16 g, 0.1 weight equivalent, 10.7 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO$_4$. The MgSO$_4$ was filtered off and the organic layers were concentrated, and then the resulting crude product was purified by a silica gel column chromatography (using mixture solvent of hexane and toluene as an eluent) to obtain Intermediate IM-9 (27.12 g, yield 77%).

By measuring with FAB-MS, a mass number of m/z=329 was observed by molecular ion peak, thereby identifying Intermediate IM-9.

Synthesis of Intermediate IM-10

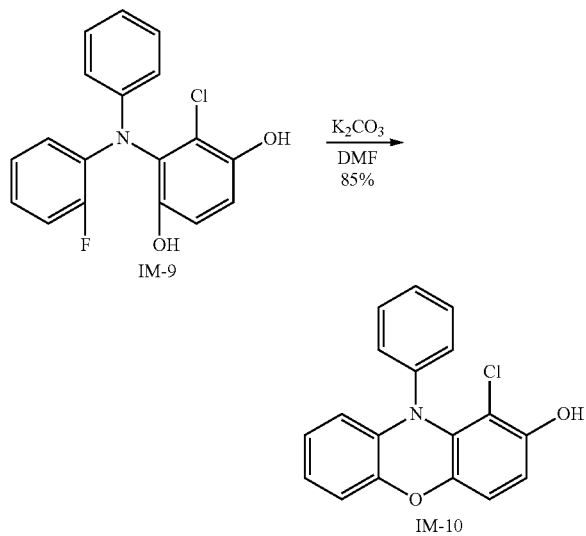

In an argon atmosphere, in a 500 mL three-neck flask, IM-9 (20.00 g, 60.7 mmol), N,N-dimethylformamide (DMF) (303 mL) and K$_2$CO$_3$ (33.53 g, 4 weight equivalent, 242.6 mmol) were sequentially added and heated and stirred at about 140° C. After air cooling to room temperature, H$_2$O was added to the reaction solution, the reaction solution was extracted with toluene, and organic layers were washed with saturated saline, and then dried with MgSO$_4$. The MgSO$_4$ was filtered off and the organic layers were concentrated, and then the resulting crude product was purified by a silica gel column chromatography (using mixture solvent of hexane and toluene as an eluent) to obtain Intermediate IM-10 (15.97 g, yield 85%).

By measuring with FAB-MS, a mass number of m/z=309 was observed by molecular ion peak, thereby identifying Intermediate IM-10.

Synthesis of Intermediate IM-11

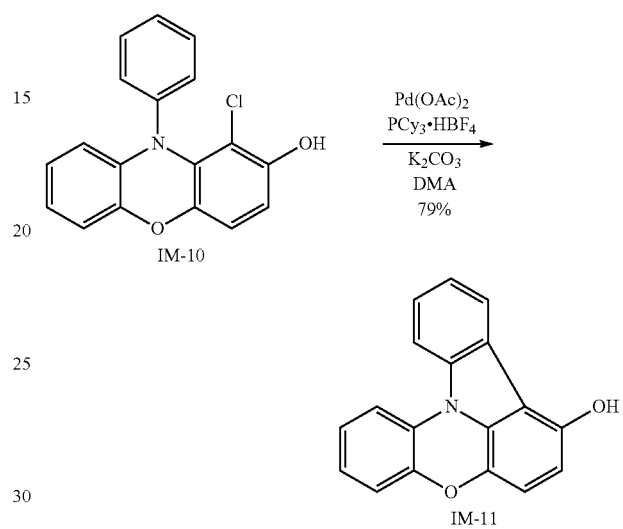

In an argon atmosphere, in a 500 mL three-neck flask, IM-10 (15.00 g, 48.4 mmol), Pd(OAc)$_2$ (0.65 g, 0.06 weight equivalent, 2.9 mmol), K$_2$CO$_3$ (13.39 g, 2.0 weight equivalent, 96.9 mmol), N,N-dimethylacetamide (DMA) (242 mL), and PCy3·HBF$_4$ (2.14 g, 0.12 weight equivalent, 5.8 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO$_4$. The MgSO$_4$ was filtered off and the organic layers were concentrated, and then the resulting crude product was purified by a silica gel column chromatography (using mixture solvent of hexane and toluene as an eluent) to obtain Intermediate IM-11 (10.46 g, yield 79%).

By measuring with FAB-MS, a mass number of m/z=273 was observed by molecular ion peak, thereby identifying Intermediate IM-11.

Synthesis of Intermediate IM-12

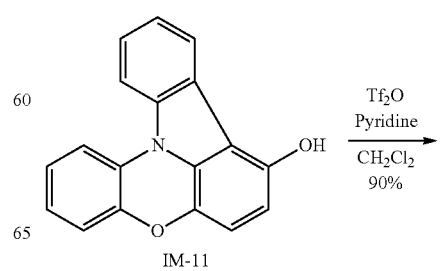

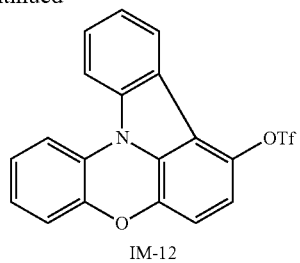

IM-12

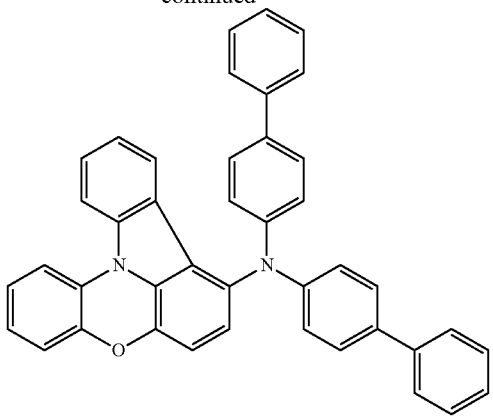

B31

In an argon atmosphere, in a 500 mL three-neck flask, IM-11 (10.00 g, 36.6 mmol), pyridine 8.68 g (3.0 weight equivalent, 109.8 mmol), CH$_2$Cl$_2$ (282 mL), and trifluoromethanesulfonic anhydride (T20) (15.49 g, 1.5 weight equivalent, 54.9 mmol) were sequentially added and stirred at room temperature. After reaction was completed, H$_2$O was added to the reaction solution, the reaction solution was extracted with CH$_2$Cl$_2$, and organic layers were washed with saturated saline, and then dried with MgSO$_4$. The MgSO$_4$ was filtered off and the organic layers were concentrated, and then the resulting crude product was purified by a silica gel column chromatography (using mixture solvent of hexane and toluene as an eluent) to obtain Intermediate IM-12 (13.35 g, yield 90%).

By measuring with FAB-MS, a mass number of m/z=405 was observed by molecular ion peak, thereby identifying Intermediate IM-12.

Synthesis of Compound B31

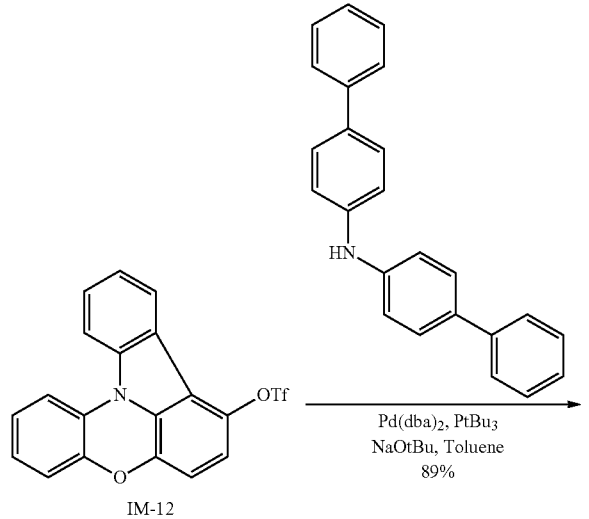

In an argon atmosphere, in a 300 mL three-neck flask, IM-12 (5.00 g, 12.3 mmol), Pd(dba)$_2$ (0.21 g, 0.03 weight equivalent, 0.4 mmol), NaOtBu (3.56 g, 3.0 weight equivalent, 37.0 mmol), toluene (62 mL), di[(1,1'-biphenyl)-4-yl] amine (4.36 g, 1.1 weight equivalent, 13.6 mmol), and tBu$_3$P (0.25 g, 0.1 weight equivalent, 1.2 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO$_4$. The MgSO$_4$ was filtered off and the organic layers were concentrated, and then the resulting crude product was purified by a silica gel column chromatography (using mixture solvent of hexane and toluene as an eluent) to obtain Compound B31 (6.62 g, yield 89%).

By measuring with FAB-MS, a mass number of m/z=602 was observed by molecular ion peak, thereby identifying Compound B31.

5. Synthesis of Compound B101

Synthesis of Intermediate IM-16

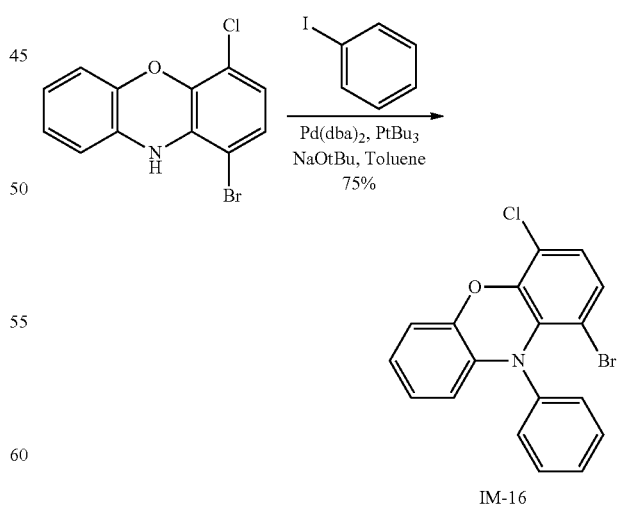

IM-16

In an argon atmosphere, in a 1000 mL three-neck flask, 1-bromo-4-chloro-10H-phenoxazine (20.00 g, 67.4 mmol), Pd(dba)$_2$ (1.16 g, 0.03 weight equivalent, 2.0 mmol), NaOtBu (7.13 g, 3.0 weight equivalent, 74.2 mmol), toluene (337 mL), iodobenzene (15.13 g, 1.1 weight equivalent, 74.2 mmol), and tBu₃P (1.36 g, 0.1 weight equivalent, 6.7 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO₄. The MgSO₄ was filtered off and the organic layers were concentrated, and then the resulting crude product was purified by a silica gel column chromatography (using mixture solvent of hexane and toluene as an eluent) to obtain Intermediate IM-16 (18.85 g, yield 75%).

By measuring with FAB-MS, a mass number of m/z=372 was observed by molecular ion peak, thereby identifying Intermediate IM-16.

Synthesis of Intermediate IM-17

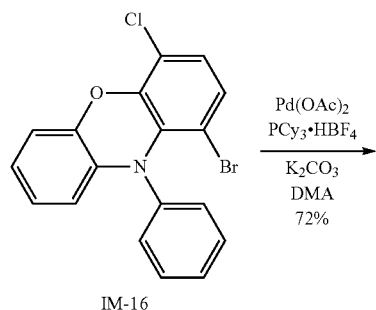

IM-16

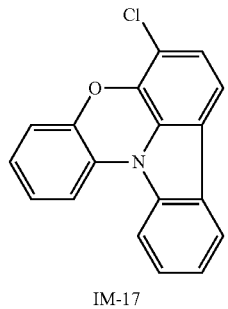

IM-17

In an argon atmosphere, in a 500 mL three-neck flask, IM-16 (15.00 g, 40.3 mmol), Pd(OAc)₂ (0.54 g, 0.06 weight equivalent, 2.4 mmol), K₂CO₃ (11.13 g, 2.0 weight equivalent, 80.5 mmol), N,N-dimethylacetamide (DMA) (201 mL), and PCy₃·HBF₄ (1.78 g, 0.12 weight equivalent, 4.8 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO₄. The MgSO₄ was filtered off and the organic layers were concentrated, and then the resulting crude product was purified by a silica gel column chromatography (using mixture solvent of hexane and toluene as an eluent) to obtain Intermediate IM-17 (8.45 g, yield 72%).

By measuring with FAB-MS, a mass number of m/z=291 was observed by molecular ion peak, thereby identifying Intermediate IM-17.

Synthesis of Compound B101

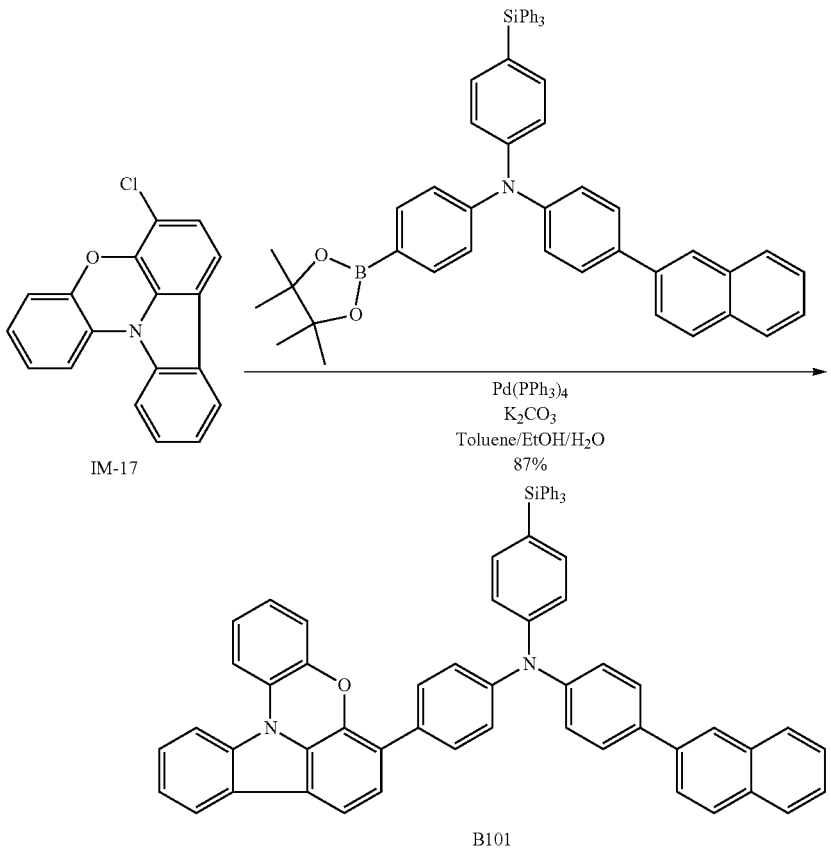

In an argon atmosphere, in a 300 mL three-neck flask, IM-17 (5.00 g, 17.1 mmol), 4-(naphthalen-2-yl)-N-[4-(4,4,5,5-tetramethyl-1,3,2-dioxaborolan-2-yl)phenyl]-N-[4-(triphenylsilyl)phen yl]aniline (14.25 g, 1.1 weight equivalent, 18.9 mmol), K₂CO₃ (7.11 g, 3.0 weight equivalent, 51.4 mmol), Pd(PPh₃)₄ (0.99 g, 0.05 weight equivalent, 0.9 mmol), and the mixture solution of toluene/ethanol/H₂O (4/2/1) (120 mL) were sequentially added, and heated and stirred at 80° C. After air cooling to room temperature, the reaction solution was extracted with toluene. A water layer was removed, the organic layer was washed with saturated saline, and then dried with MgSO₄. The MgSO₄ was filtered off and the organic layers were concentrated, and then the resulting crude product was purified by a silica gel column chromatography (using mixture solvent of hexane and toluene as an eluent) to obtain Compound B101 (13.20 g, yield 87%).

By measuring with FAB-MS, a mass number of m/z=885 was observed by molecular ion peak, thereby identifying Compound B101.

6. Synthesis of Compound C26
Synthesis of Intermediate IM-18

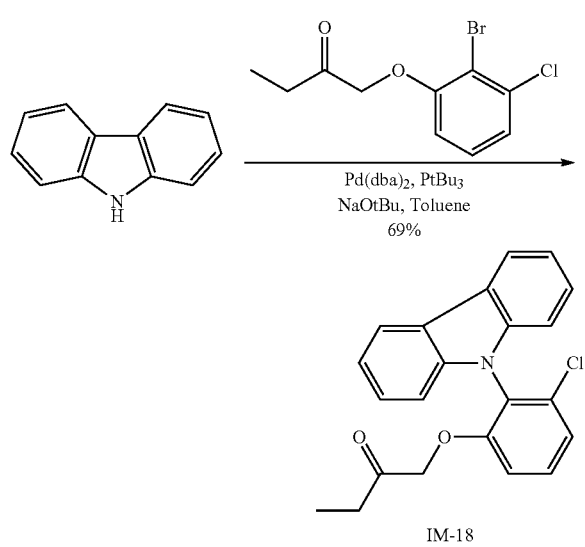

In an argon atmosphere, in a 1000 mL three-neck flask, carbazole (20.00 g, 119.6 mmol), Pd(dba)₂ (2.06 g, 0.03 weight equivalent, 3.6 mmol), NaOtBu (12.6 g, 1.1 weight equivalent, 131.6 mmol), toluene (590 mL), 1-(2-bromo-3-chlorophenoxy)butan-2-one (36.52 g, 1.1 weight equivalent, 131.6 mmol), and tBu₃P (2.42 g, 0.1 weight equivalent, 12.0 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO₄. The MgSO₄ was filtered off and the organic layers were concentrated, and then the resulting crude product was purified by a silica gel column chromatography (using mixture solvent of hexane and toluene as an eluent) to obtain Intermediate IM-18 (30.03 g, yield 69%).

By measuring with FAB-MS, a mass number of m/z=363 was observed by molecular ion peak, thereby identifying Intermediate IM-18.

Synthesis of Intermediate IM-19

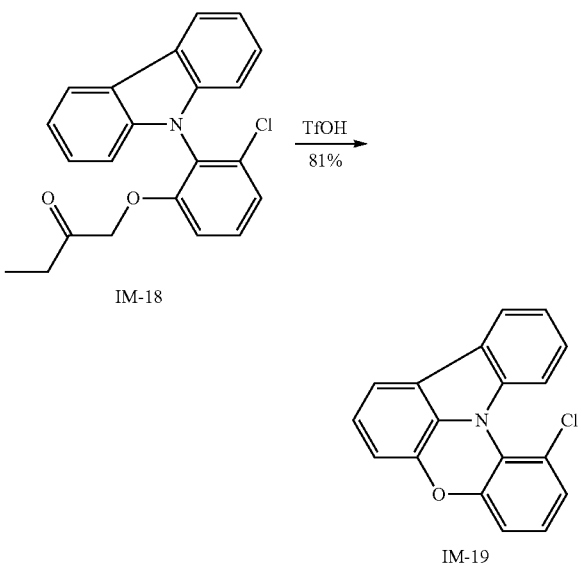

In an argon atmosphere, in a 500 mL three-neck flask, IM-16 (15.00 g, 41.2 mmol), and trifluoromethanesulfonic acid (TfOH) 61.87 g (10.0 weight equivalent, 412.3 mmol) were sequentially added and stirred at room temperature. After the reaction was completed, the mixture solvent of pyridine (106 mL, 0.2 M) and H₂O (41 mL, 1 M) was slowly added to the reaction solution and stirred for 1 hour, and then CH₂Cl₂ was added to the reaction solution to fractionate an organic layer. The organic layer was further extracted by adding CH₂Cl₂ to a water layer, and then the combined organic layers were washed with saline and dried with MgSO₄. The MgSO₄ was filtered off and the organic layers were concentrated, and then the resulting crude product was purified by a silica gel column chromatography (using mixture solvent of hexane and toluene as an eluent) to obtain Intermediate IM-19 (9.74 g, yield 81%).

By measuring with FAB-MS, a mass number of m/z=291 was observed by molecular ion peak, thereby identifying Intermediate IM-19.

Synthesis of Compound C26

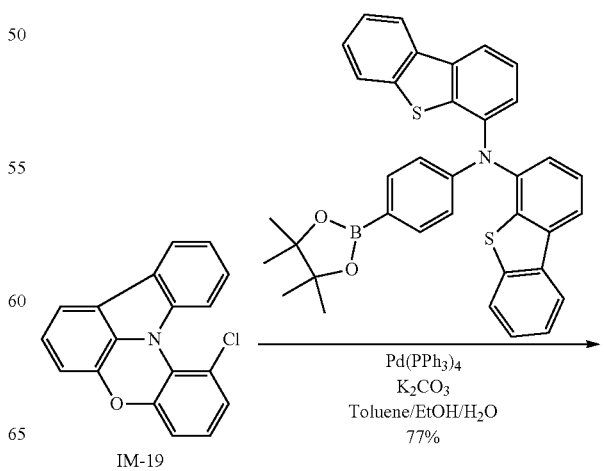

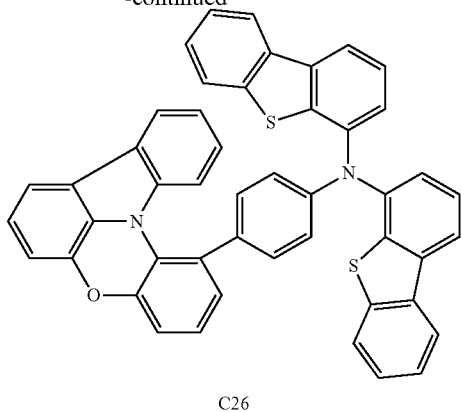

C26

In an argon atmosphere, in a 300 mL three-neck flask, IM-19 (5.00 g, 17.1 mmol), N-(dibenzo[b,d]thiophen-4-yl)-N-[4-(4,4,5,5-tetramethyl-1,3,2-dioxaborolan-2-yl)phenyl] dibenzo[b,d]thiophen-4-amine (11.01 g, 1.1 weight equivalent, 18.9 mmol), $K_2CO_3$ (7.11 g, 3.0 weight equivalent, 51.4 mmol), $Pd(PPh_3)_4$ (0.99 g, 0.05 weight equivalent, 0.9 mmol), and the mixture solution of toluene/ethanol/H2O (4/2/1) (120 mL) were sequentially added, and heated and stirred at about 80° C. After air cooling to room temperature, the reaction solution was extracted with toluene. A water layer was removed, the organic layer was washed with saturated saline, and then dried with $MgSO_4$. The $MgSO_4$ was filtered off and the organic layers were concentrated, and then the resulting crude product was purified by a silica gel column chromatography (using mixture solvent of hexane and toluene as an eluent) to obtain Compound C26 (9.41 g, yield 77%).

By measuring with FAB-MS, a mass number of m/z=712 was observed by molecular ion peak, thereby identifying Compound C26.

7. Synthesis of Compound C61
Synthesis of Intermediate IM-20

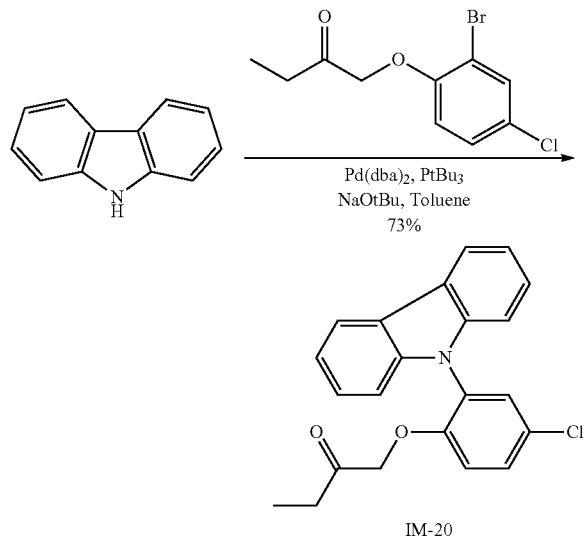

IM-20

In an argon atmosphere, in a 1000 mL three-neck flask, carbazole (20.00 g, 119.6 mmol), $Pd(dba)_2$ (2.06 g, 0.03 weight equivalent, 3.6 mmol), NaOtBu (12.6 g, 1.1 weight equivalent, 131.6 mmol), toluene (590 mL), 1-(2-bromo-4-chlorophenoxy)butan-2-one (36.52 g, 1.1 weight equivalent, 131.6 mmol), and $tBu_3P$ (2.42 g, 0.1 weight equivalent, 12.0 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with $MgSO_4$. The $MgSO_4$ was filtered off and the organic layers were concentrated, and then the resulting crude product was purified by a silica gel column chromatography (using mixture solvent of hexane and toluene as an eluent) to obtain Intermediate IM-20 (31.77 g, yield 73%).

By measuring with FAB-MS, a mass number of m/z=363 was observed by molecular ion peak, thereby identifying Intermediate IM-20.

Synthesis of Intermediate IM-21

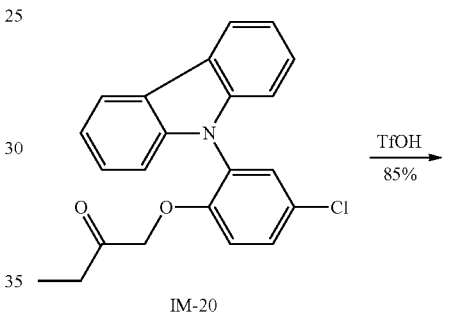

IM-20

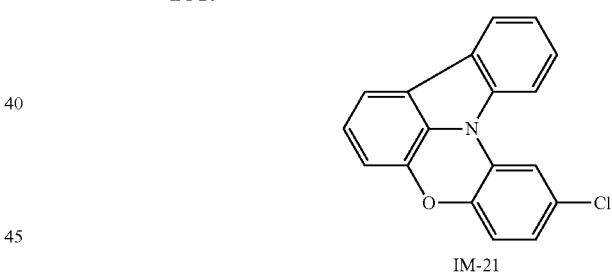

IM-21

In an argon atmosphere, in a 500 mL three-neck flask, IM-20 (15.00 g, 41.2 mmol), and TfOH 61.87 g (10.0 weight equivalent, 412.3 mmol) were sequentially added and stirred at room temperature. After the reaction was completed, the mixture solvent of pyridine (106 mL, 0.2 M) and $H_2O$ (41 mL, 1 M) was slowly added to the reaction solution and stirred for 1 hour, and then $CH_2Cl_2$ was added to the reaction solution to fractionate an organic layer. The organic layer was further extracted by adding $CH_2Cl_2$ to a water layer, and then the combined organic layers were washed with saline and dried with $MgSO_4$. The $MgSO_4$ was filtered off and the organic layers were concentrated, and then the resulting crude product was purified by a silica gel column chromatography (using mixture solvent of hexane and toluene as an eluent) to obtain Intermediate IM-21 (10.22 g, yield 85%).

By measuring with FAB-MS, a mass number of m/z=291 was observed by molecular ion peak, thereby identifying Intermediate IM-21.

Synthesis of Compound C61

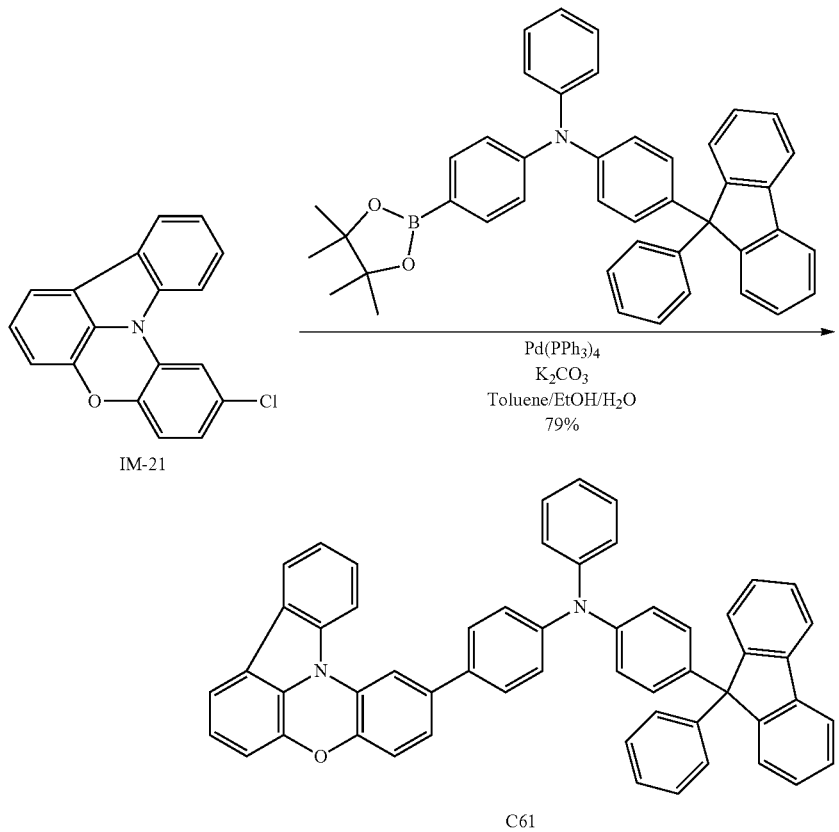

N-phenyl-4-(9-phenyl-9H-fluoren-9-yl)-N-[4-(4,4,5,5-tetramethyl-1,3,2-dioxaborolan-2-yl)phenyl]aniline (11.53 g, 1.1 weight equivalent, 18.9 mmol), K₂CO₃ (7.11 g, 3.0 weight equivalent, 51.4 mmol), Pd(PPh₃)₄ (0.99 g, 0.05 weight equivalent, 0.9 mmol), and the mixture solution of toluene/ethanol/H₂O (4/2/1) (120 mL) were sequentially added, and heated and stirred at 80° C. After air cooling to room temperature, the reaction solution was extracted with toluene. A water layer was removed, the organic layer was washed with saturated saline, and then dried with MgSO₄. The MgSO₄ was filtered off and the organic layers were concentrated, and then the resulting crude product was purified by a silica gel column chromatography (using mixture solvent of hexane and toluene as an eluent) to obtain Compound C61 (10.03 g, yield 79%).

By measuring with FAB-MS, a mass number of m/z=740 was observed by molecular ion peak, thereby identifying Compound C61.

8. Synthesis of Compound C154
Synthesis of Intermediate IM-25

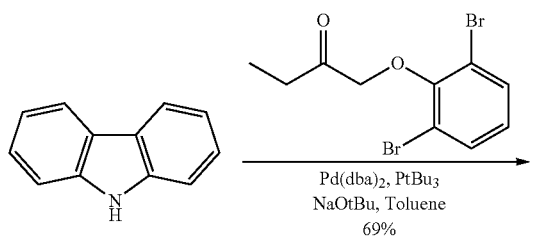

-continued

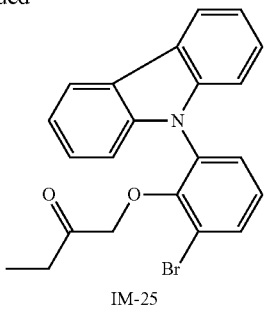

IM-25

In an argon atmosphere, in a 1000 mL three-neck flask, carbazole (20.00 g, 119.6 mmol), Pd(dba)₂ (2.06 g, 0.03 weight equivalent, 3.6 mmol), NaOtBu (12.6 g, 1.1 weight equivalent, 131.6 mmol), toluene (590 mL), 1-(2,6-dibromophenoxy)butan-2-one (42.37 g, 1.1 weight equivalent, 131.6 mmol), and tBu₃P (2.42 g, 0.1 weight equivalent, 12.0 mmol) were sequentially added and heated and stirred under reflux. After air cooling to room temperature, the organic layer was fractionated by adding water to the reaction solvent. The organic layer was further extracted by adding toluene to a water layer, and then the combined organic layers were washed with saline and dried with MgSO₄. The MgSO₄ was filtered off and the organic layers were concentrated, and then the resulting crude product was purified by a silica gel column chromatography (using mixture solvent of hexane and toluene as an eluent) to obtain Intermediate IM-25 (33.70 g, yield 69%).

By measuring with FAB-MS, a mass number of m/z=408 was observed by molecular ion peak, thereby identifying Intermediate IM-25.

Synthesis of Intermediate IM-26

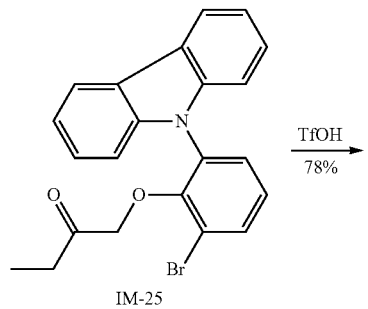

In an argon atmosphere, in a 500 mL three-neck flask, IM-20 (15.00 g, 36.7 mmol), and TfOH 55.13 g (10.0 weight equivalent, 367.4 mmol) were sequentially added and stirred at room temperature. After the reaction was completed, the mixture solvent of pyridine (184 mL, 0.2 M) and H₂O (36 mL, 1 M) was slowly added to the reaction solution and stirred for 1 hour, and then CH₂Cl₂ was added to the reaction solution to fractionate an organic layer. The organic layer was further extracted by adding CH₂Cl₂ to a water layer, and then the combined organic layers were washed with saline and dried with MgSO₄. The MgSO₄ was filtered off and the organic layers were concentrated, and then the resulting crude product was purified by a silica gel column chromatography (using mixture solvent of hexane and toluene as an eluent) to obtain Intermediate IM-26 (9.64 g, yield 78%).

By measuring with FAB-MS, a mass number of m/z=336 was observed by molecular ion peak, thereby identifying Intermediate IM-26.

Synthesis of Compound C154

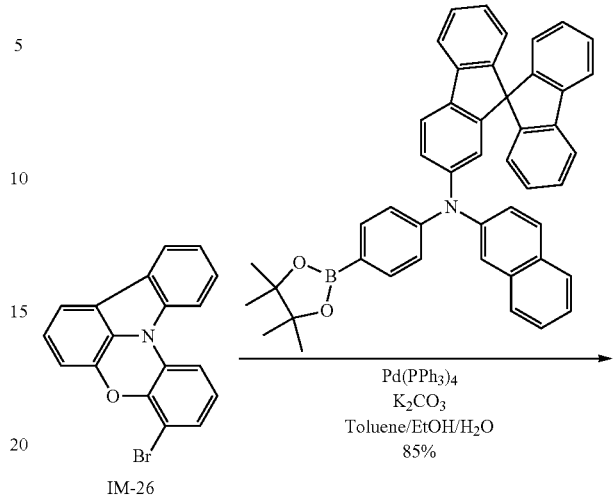

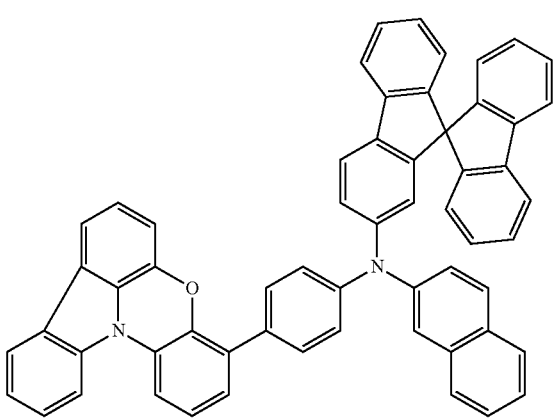

In an argon atmosphere in a 300 mL three-neck flask, IM-26 (5.00 g, 14.9 mmol), N-phenyl-4-(9-phenyl-9H-fluoren-9-yl)-N-[4-(4,4,5,5-tetramethyl-1,3,2-dioxaborolan-2-yl)phenyl]aniline (10.79 g, 1.1 weight equivalent, 16.4 mmol), K₂CO₃ (6.17 g, 3.0 weight equivalent, 44.6 mmol), Pd(PPh₃)₄ (0.86 g, 0.05 weight equivalent, 0.7 mmol), and the mixture solution of toluene/ethanol/H₂O (4/2/1) (104 mL) were sequentially added, and heated and stirred at about 80° C. After air cooling to room temperature, the reaction solution was extracted with toluene. A water layer was removed, the organic layer was washed with saturated saline, and then dried with MgSO₄. The MgSO₄ was filtered off and the organic layers were concentrated, and then the resulting crude product was purified by a silica gel column chromatography (using mixture solvent of hexane and toluene as an eluent) to obtain Compound C154 (9.97 g, yield 85%).

By measuring with FAB-MS, a mass number of m/z=788 was observed by molecular ion peak, thereby identifying Compound C154.

Device Manufactured Examples
Organic electroluminescence devices were manufactured using Example Compounds and Comparative Example Compounds below as a hole transport region material:
Example Compounds
A2
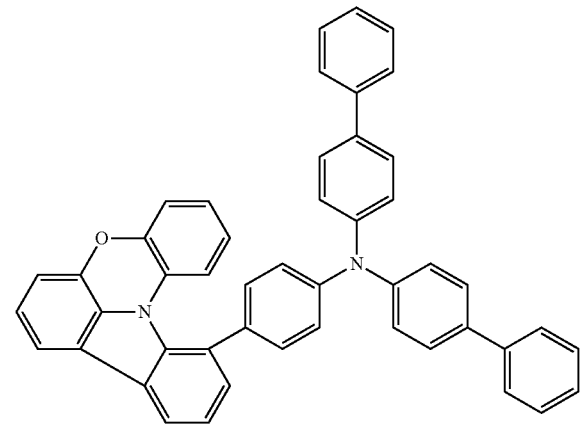
A68
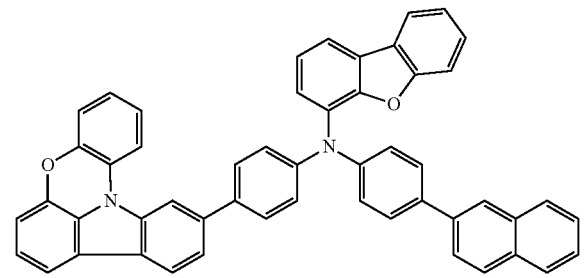
A144
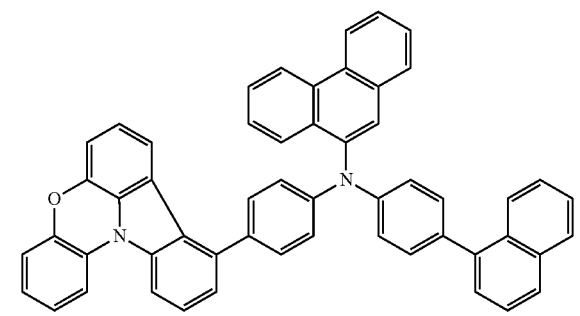
B31
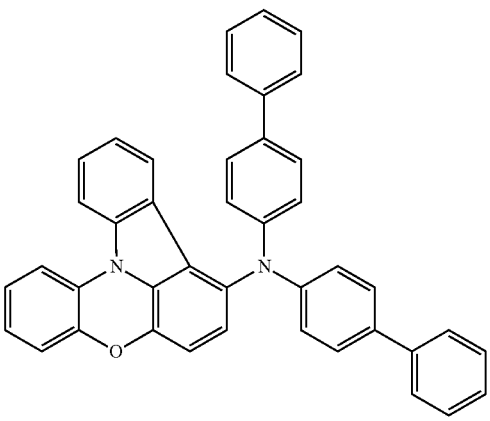
B101
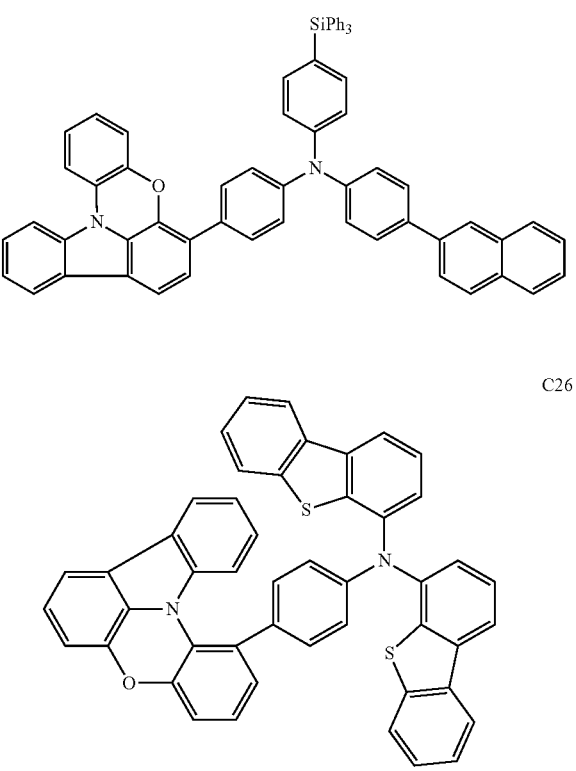
C26
C61
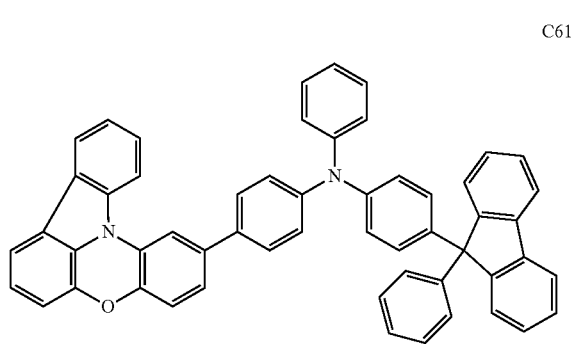

C154
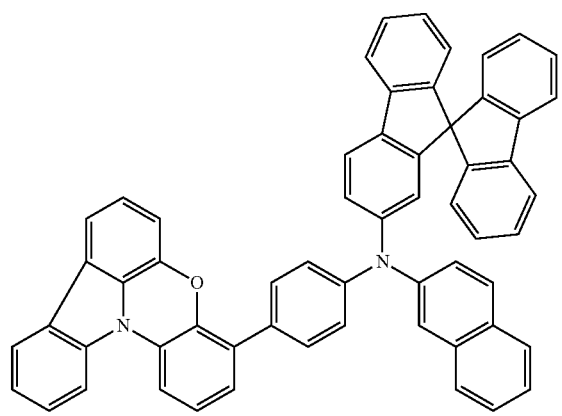
Comparative Example Compounds
R1
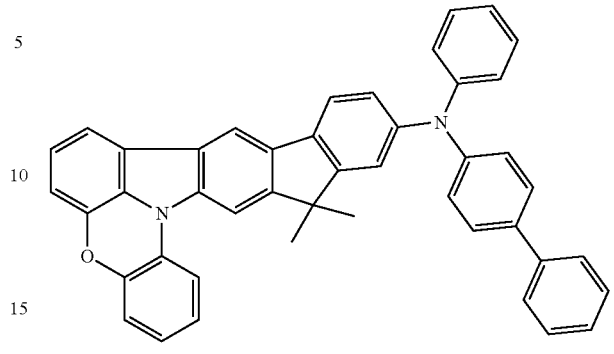
R2
R3
R4
R5
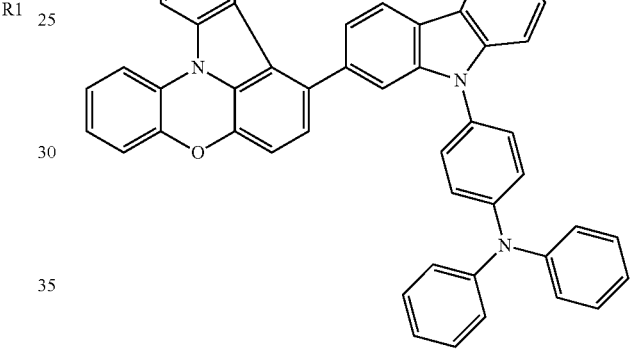
R6
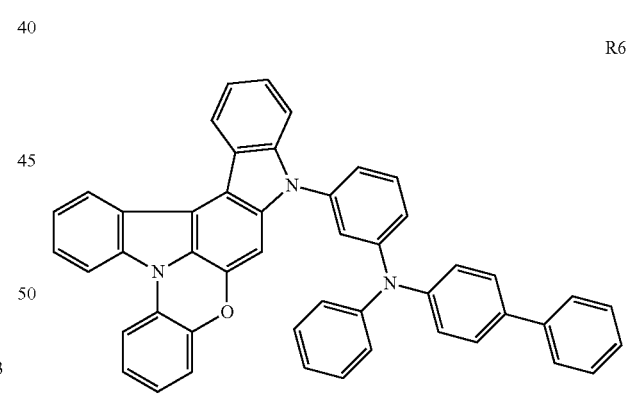
R7
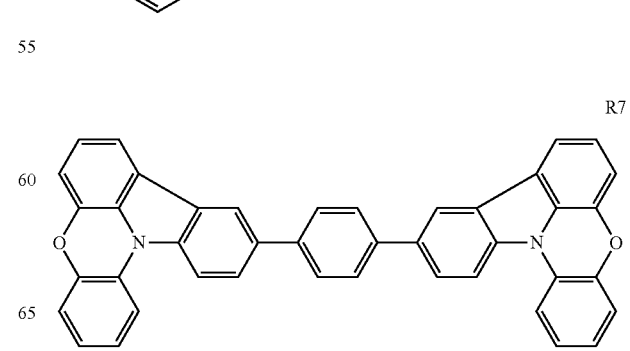

-continued

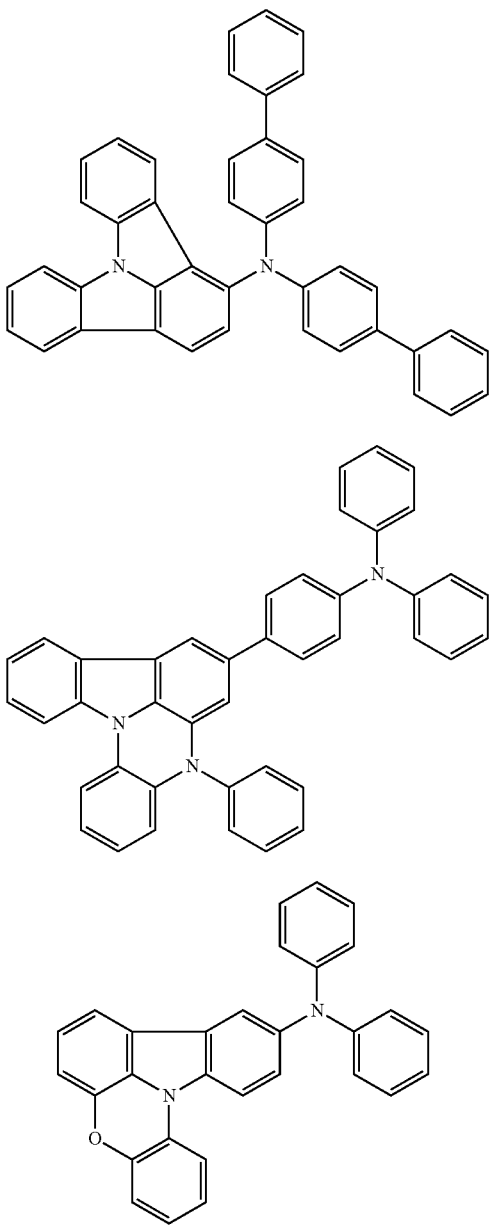

R8

R9

R10

The organic electroluminescence devices of Examples and Comparative Examples were manufactured as follows. After ITO having a thickness of about 150 nm was patterned on a glass substrate, the glass substrate was washed with pure water and treated with ultraviolet (UV) and ozone for about 10 minutes to form a first electrode. Then, 2-TNATA was deposited thereon to a thickness of about 60 nm, and Example Compounds or Comparative Example Compounds were used to form a hole transport layer having a thickness of about 30 nm. Then, 9,10-bis(2-naphthyl)anthrace (ADN) doped by 3% (mole percent) TBP is used to form an emission layer having a thickness of about 25 nm, a layer having a thickness of about 25 nm was formed with Alq3 on the emission layer, and a layer having a thickness of about 1 nm was formed with LiF to form an electron transport region. Then, a second electrode having a thickness of about 100 nm was formed with Al. Each layer was formed by a vacuum deposition method.

The luminous efficiencies of the organic electroluminescence devices according to Examples 1 to 8 and Comparative Examples 1 to 10 are shown in Table 1 below. The luminous efficiencies were measured at 10 mA/cm$^2$. Voltages and luminous efficiencies of the devices were measured in a dark room using 2400 Series source meter from Keithley Instruments, Inc., a company affiliated with Tektronix of Beaverton, Oregon, CS-200, Color and luminance meter from Konica Minolta, Inc. of Tokyo, Japan, and a software program sold under the trade designation LaVIEW 8.2 for the measurement from Japan National Instruments Co, of Minato-ku, Japan.

TABLE 1

| | Hole transport layer | Voltage (V) | Luminous efficiency (%) | Service life $LT_{50}(h)$ |
|---|---|---|---|---|
| Example 1 | Example Compound A2 | 5.7 | 7.7 | 1950 |
| Example 2 | Example Compound A68 | 5.6 | 7.6 | 2050 |
| Example 3 | Example Compound A144 | 5.7 | 7.6 | 1950 |
| Example 4 | Example Compound B31 | 5.7 | 7.5 | 2150 |
| Example 5 | Example Compound B101 | 5.7 | 7.6 | 2150 |
| Example 6 | Example Compound C26 | 5.6 | 7.8 | 1900 |
| Example 7 | Example Compound C61 | 5.6 | 7.6 | 2050 |
| Example 8 | Example Compound C154 | 5.6 | 7.7 | 2000 |
| Comparative Example 1 | Comparative Example Compound R1 | 6.4 | 5.9 | 1700 |
| Comparative Example 2 | Comparative Example Compound R2 | 6.5 | 6.0 | 1650 |
| Comparative Example 3 | Comparative Example Compound R3 | 6.6 | 5.9 | 1500 |
| Comparative Example 4 | Comparative Example Compound R4 | 6.5 | 6.1 | 1550 |
| Comparative Example 5 | Comparative Example Compound R5 | 6.1 | 6.4 | 1500 |
| Comparative Example 6 | Comparative Example Compound R6 | 6.1 | 6.5 | 1550 |
| Comparative Example 7 | Comparative Example Compound R7 | 6.8 | 5.8 | 1600 |
| Comparative Example 8 | Comparative Example Compound R8 | 6.3 | 6.6 | 1650 |
| Comparative Example 9 | Comparative Example Compound R9 | 6.2 | 6.5 | 1550 |
| Comparative Example 10 | Comparative Example Compound R10 | 6.0 | 5.9 | 1700 |

Referring to Table 1 above, Examples 1 to 8 have significantly and unexpectedly achieved low voltage, long service life, and high efficiency compared to Comparative Examples 1 to 10.

A polycyclic compound according to exemplary embodiments is used in the hole transport region to facilitate a low driving voltage, high efficiency, and long service life of organic electroluminescence devices. Specifically, an amine group is included in an indolo phenoxazine or indolophenothiazine skeleton, and thus the organic electroluminescence devices may achieve longer service life while having resistance for high temperature and charge. In addition, two hetero atoms included in the indolo phenoxazine or indolophenothiazine skeleton may improve the hole transporting ability of the entire molecule, and thus a reunion probability of holes and electrons in the emission layer may be improved to better luminous efficiency.

In Examples 1, 2, 3, 6, 7, and 8, although not wanting to be bound by theory, an amine group is substituted to a side chain of the benzene rings (A ring, C ring of Formula 11 below) present at the both ends in aromatic rings included in the indolo phenoxazine skeleton, and thus, particularly, luminous efficiencies of the devices were improved. The indolo phenoxazine has a structure which is slightly twisted in a complete plane because hydrogen atoms substituted to the benzene rings at the both ends repel stereoelectrically from each other. When the amine group is substituted to the benzene rings at the both ends of the indolo phenoxazine, the planarity of the entire molecule is reduced by the effect of a twist of the skeleton. As a result, it is found that a hole-transport property is improved by reducing crystallinity and improving film quality, and thus the reunion probability of holes and electrons in the emission layer is improved, thereby improving luminous efficiency.

In Examples 4 and 5, an amine group is substituted to the side chain of the aromatic ring (B ring of Formula 11 below) present at the center in aromatic rings included in the indolo phenoxazine skeleton, and thus, particularly, service lives of the devices were improved. The aromatic ring at the center in aromatic rings included in the indolo phenoxazine skeleton has the most electrons, HOMO orbitals are widely spread all over the molecule, and thus stability in a radical state is improved to achieve long service life.

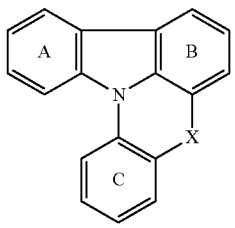

Formula 11

Comparative Examples 1 and 2 are materials having the indolo phenoxazine skeleton, but show results of reducing both efficiency and service life of the devices compared to Examples. Although not wanting to be bound by theory, it is believed that a carbazole group and an acridine group have insufficient hole transport properties compared to an amine group which is present in at least some exemplary embodiments, thereby losing a carrier balance.

Although not wanting to be bound by theory, comparative Examples 3 and 4 are materials having a fused heterocyclic ring, but show a result of reducing, in particular, service life of the devices due to thermal instability since Comparative Examples 3 and 4 have a sp3 hybridization carbon atom site in a fused structure.

Comparative Examples 5 and 6 are materials including an amine group and an indolo phenoxazine skeleton, but have a carbazole site together, thereby losing a carrier balance, and thus, in particular, service lives of the devices were reduced.

Comparative Example 7 is a material having two indolo phenoxazine skeletons, and shows a result of reducing both of efficiency and service life of the device because a hole transport property is reduced compared to Examples.

Comparative Example 8 is a material having an indolo-carbazole skeleton, Comparative Example 9 is a material having an indolophenazine skeleton, and both of Comparative Example 8 and Comparative Example 9 show a result of reducing efficiency and service life of the devices compared to Examples. Although not wanting to be bound by theory, it is reasoned that a hole transport property is lost compared to a polycyclic compound of some exemplary embodiments because materials having an indolocarbazole skeleton and an indolophenazine skeleton do not give a suitable HOMO level.

Comparative Example 10 is a material having an indolo phenoxazine skeleton and an amine group in the para-position of a nitrogen atom at the center of the indolo phenoxazine skeleton, and reduces both luminous efficiency and service life compared to Examples. Although not wanting to be bound by theory, introducing an amine group to the para-position of a nitrogen atom at the center of the indolo phenoxazine skeleton results in 6 electrons leaked out of the amine group to the indolo phenoxazine skeleton. As such, the electron density in rings of the indolo phenoxazine is relatively increased, and thereby a HOMO energy level becomes shallow to delay influx of holes into the emission layer and the electron density in the amine group is relatively decreased, and thus the effect of the amine group resulting in long service life is reduced.

Some of the advantages that may be achieved by exemplary implementations of the invention and/or exemplary methods of the invention include providing a polycyclic compound used in the hole transport region to facilitate a low driving voltage, high efficiency, and long service life of organic electroluminescence devices. Moreover, the organic electroluminescence devices according to some exemplary embodiments may have excellent efficiency. The polycyclic compound according to some exemplary embodiments may be used as a material of the hole transport region of the organic electroluminescence device, and thereby the organic electroluminescence device may have improved efficiency.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:
1. An organic electroluminescence device comprising:
a first electrode;
a hole transport region disposed on the first electrode;
an emission layer disposed on the hole transport region;
an electron transport region disposed on the emission layer; and
a second electrode disposed on the electron transport region,
wherein the hole transport region comprises a polycyclic compound of Formula 1:

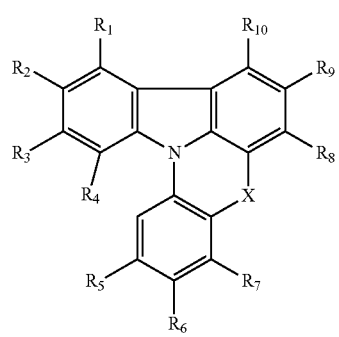

Formula 1 wherein, in Formula 1,
X is O or S;
at least one of $R_1$, $R_3$ to $R_5$, $R_7$, $R_8$, and $R_{10}$ is an amine group of Formula 2:

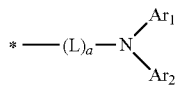

Formula 2 wherein, in Formula 2,

L is a direct linkage, a substituted or unsubstituted arylene group having 6 to 30 ring-forming carbon atoms, or a substituted or unsubstituted heteroarylene group having 2 to 30 ring-forming carbon atoms, provided that L does not include a carbazole group;

$Ar_1$ and $Ar_2$ are each, independently from one another, a substituted or unsubstituted aryl group having 6 to 30 ring-forming carbon atoms or a substituted or unsubstituted heteroaryl group having 2 to 30 ring-forming carbon atoms, where $Ar_1$ and $Ar_2$ do not bond to each other to form a ring; and a is 0, 1, 2, 3, or 4, and the remainder of $R_1$, $R_3$ to $R_5$, $R_7$, $R_8$, and $R_{10}$, which do not include an amine group of Formula 2, are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, $R_2$, $R_6$, and $R_9$ are each, independently from one another, a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and when a is 0, only one of $R_1$, $R_3$ to $R_5$, $R_7$, $R_8$, and $R_{10}$ is an amine group of Formula 2, and when a is 0, neither $Ar_1$ nor $Ar_2$ are phenyl groups having six ring-forming carbon atoms.

2. The organic electroluminescence device of claim 1, wherein only one among $R_1$, $R_3$ to $R_5$, $R_7$, $R_8$, and $R_{10}$ is an amine group of Formula 2, wherein another one among $R_1$, $R_3$ to $R_5$, $R_7$, $R_8$, and $R_{10}$ not an amine group of Formula 2 is each, independently from one another, a hydrogen atom, a deuterium atom, a halogen atom, a substituted or unsubstituted alkyl group having 1 to 20 carbon atoms, or a substituted or unsubstituted aryl group having 6 to 30 ring-forming carbon atoms.

3. The organic electroluminescence device of claim 1, wherein the compound of Formula 1 is a compound by any one among Formula 3 to Formula 5:

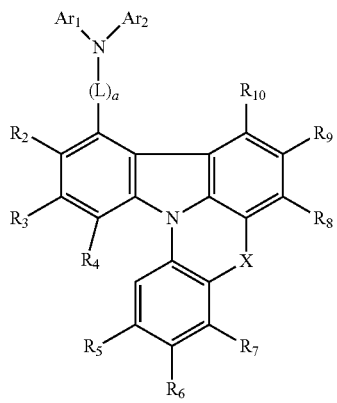

Formula 3

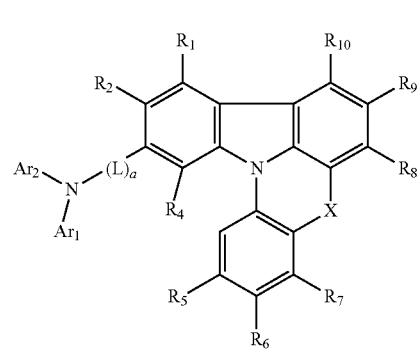

Formula 4

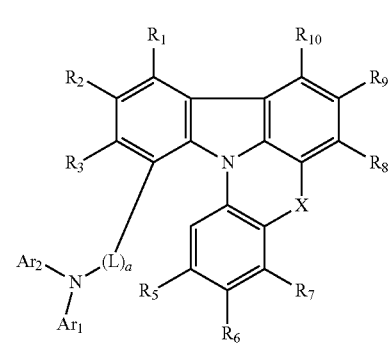

Formula 5 wherein, in Formula 3 and Formula 5 above, $R_1$ to $R_{10}$ are each, independently from one another, a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms; and X, $Ar_1$, $Ar_2$, L, and a have the same meanings as in Formula 1 and Formula 2 of claim 1.

4. The organic electroluminescence device of claim 1, wherein the compound Formula 1 is a compound of Formula 6 or Formula 7:

Formula 6

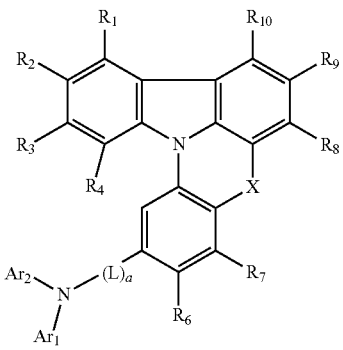

Formula 7

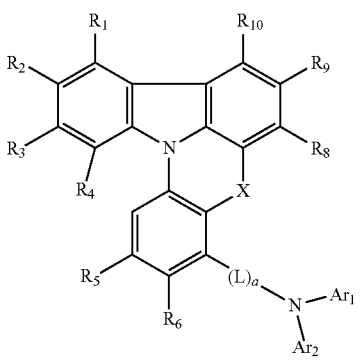

wherein, in Formula 6 and Formula 7, $R_1$ to $R_{10}$ are each, independently from one another, a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms; and X, $Ar_1$, $Ar_2$, L, and a have the same meanings as in Formula 1 and Formula 2 of claim 1.

5. The organic electroluminescence device of claim 1, wherein the compound of Formula 1 is a compound of Formula 8 or Formula 9:

Formula 8

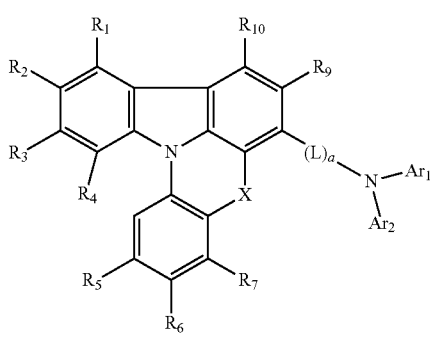

Formula 9

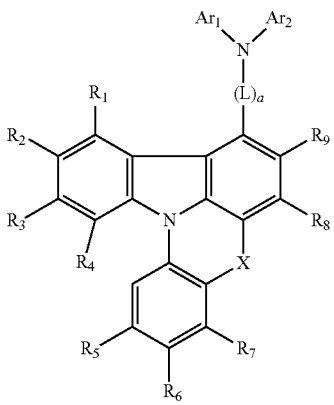

wherein, in Formula 8 and Formula 9, $R_1$ to $R_{10}$ are each, independently from one another, a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms; and X, $Ar_1$, $Ar_2$, L, and a have the same meanings as in Formula 1 and Formula 2 of claim 1.

6. The organic electroluminescence device of claim 1, wherein $R_2$, $R_6$, and Ry are each, independently from one another, a hydrogen atom, a deuterium atom, a halogen atom, or a substituted or unsubstituted alkyl group having 1 to 20 carbon atoms.

7. The organic electroluminescence device of claim 1, wherein X is O.

8. The organic electroluminescence device of claim 1, wherein L is a direct linkage, a substituted or unsubstituted phenylene group, a substituted or unsubstituted biphenylene group, a substituted or unsubstituted fluorenylene group, or a substituted or unsubstituted naphthylene group.

9. The organic electroluminescence device of claim 1, wherein $Ar_1$ and $Ar_2$ are each, independently from one another, a substituted or unsubstituted phenyl group, a substituted or unsubstituted biphenyl group, a substituted or unsubstituted triphenyl group, a substituted or unsubstituted fluorenyl group, a substituted or unsubstituted dibenzofuran group, or a substituted or unsubstituted dibenzothiophene group.

10. The organic electroluminescence device of claim 1, wherein the hole transport region comprises:

a hole injection layer disposed on the first electrode; and a hole transport layer comprising the polycyclic compound of Formula 1 disposed on the hole injection layer.

11. The organic electroluminescence device of claim 1, wherein the polycyclic compound of Formula 1 is at least one compound of Compound Group 1:

Compound Group 1
A1 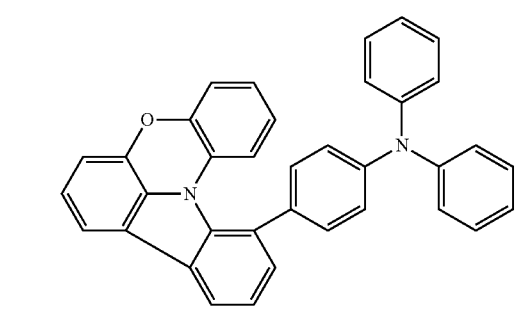
A2 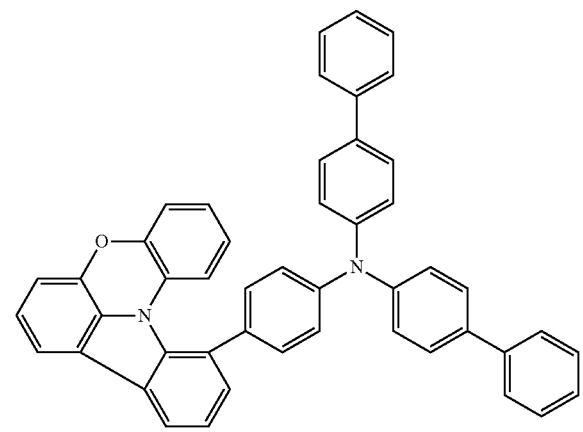
A3 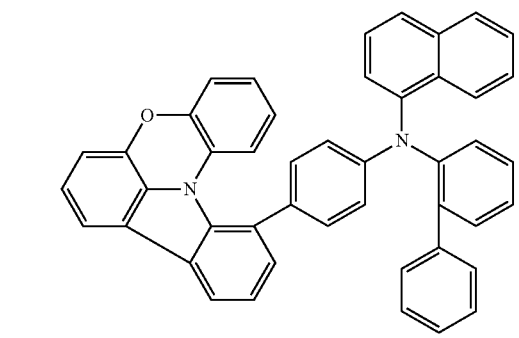
A4 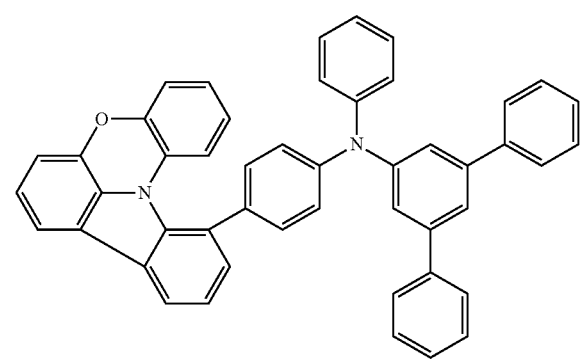
-continued
A5 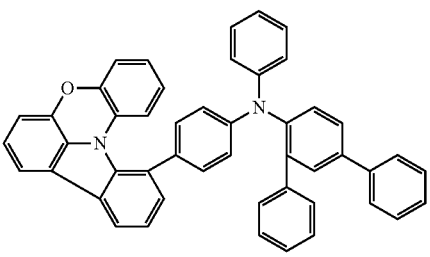
A6 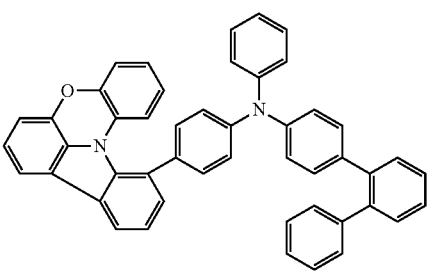
A7 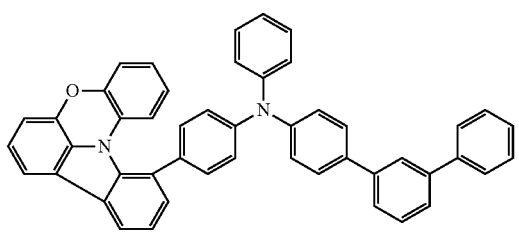
A8 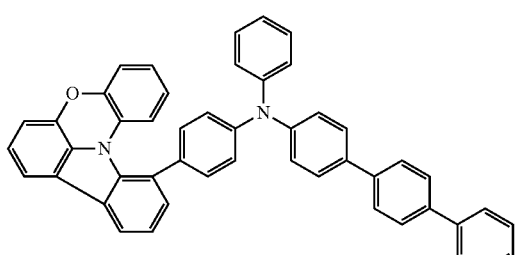
A9 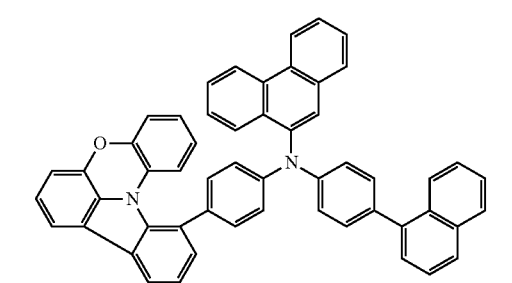
A10 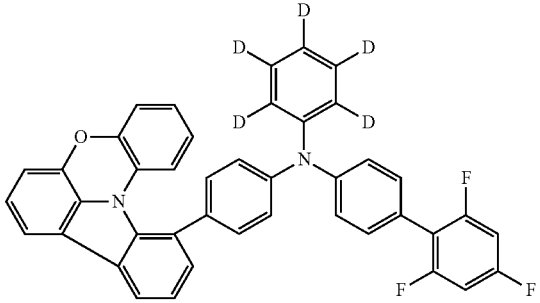

167
-continued
A11
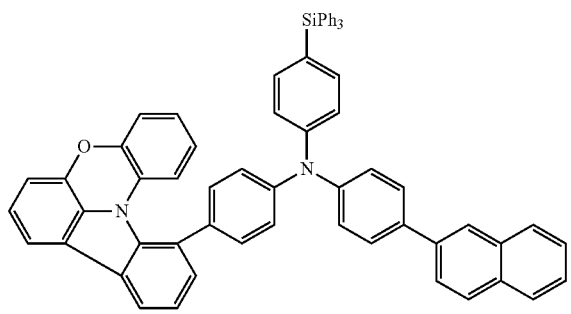
A12
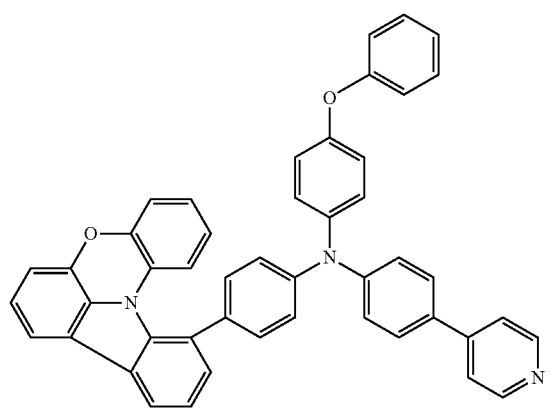
A13
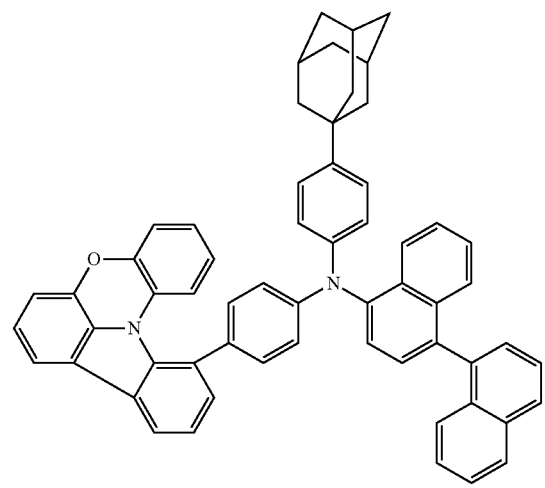
A16
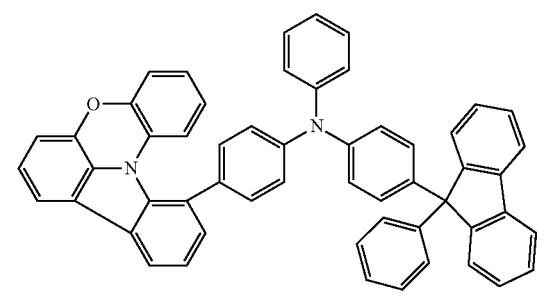
168
-continued
A17
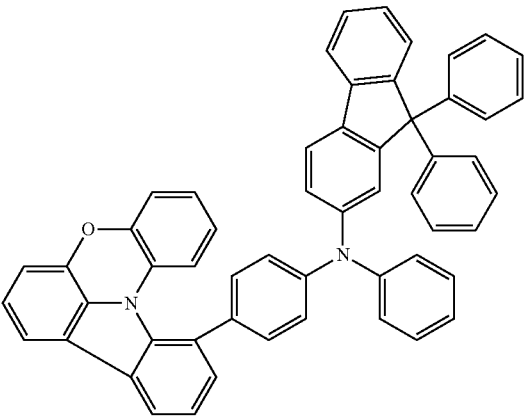
A18
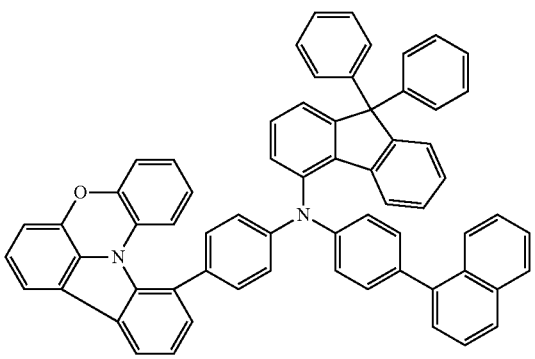
A19
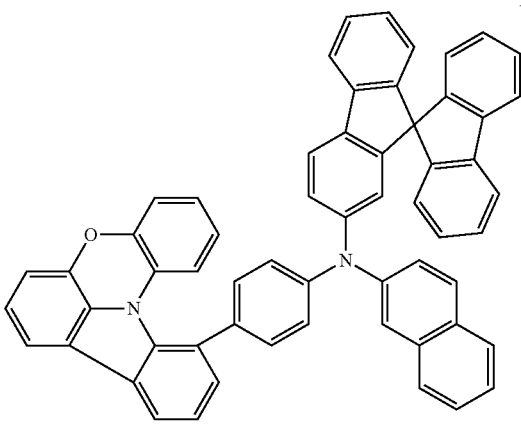
A20
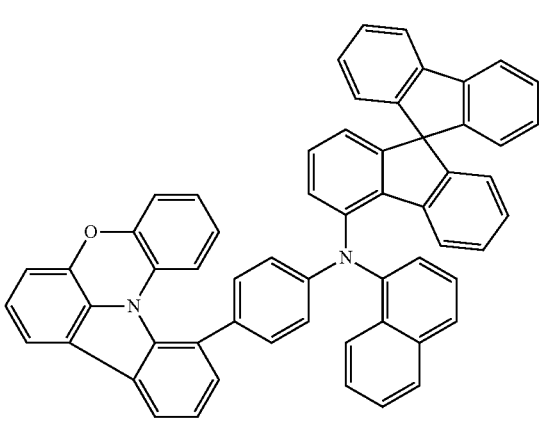

A21
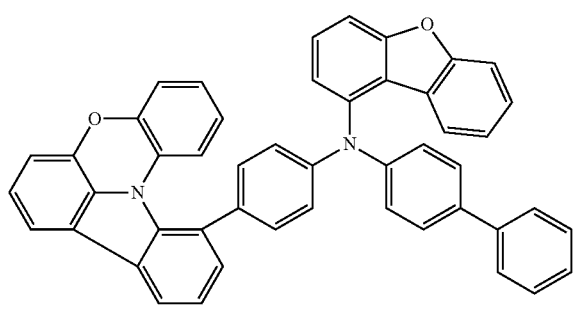
A22
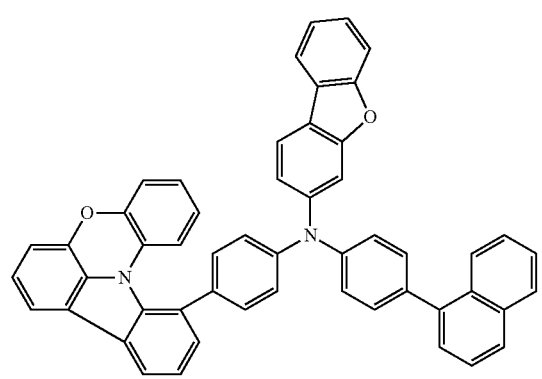
A23
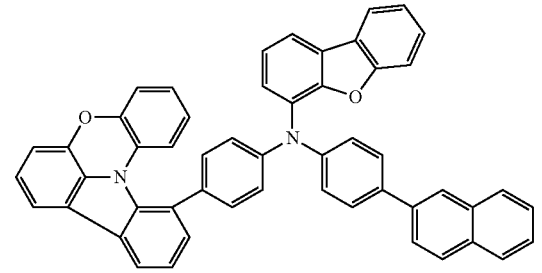
A24
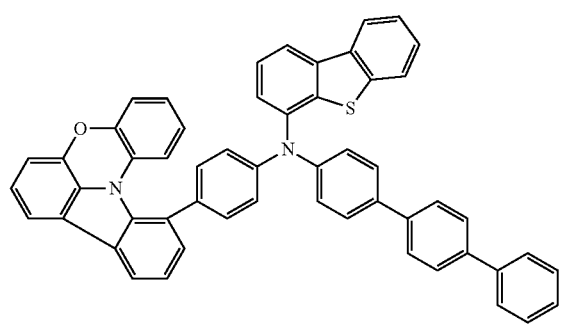
A25
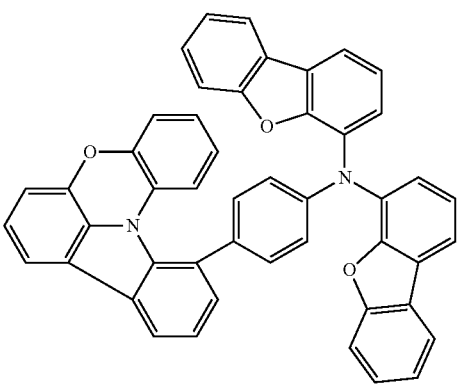
A26
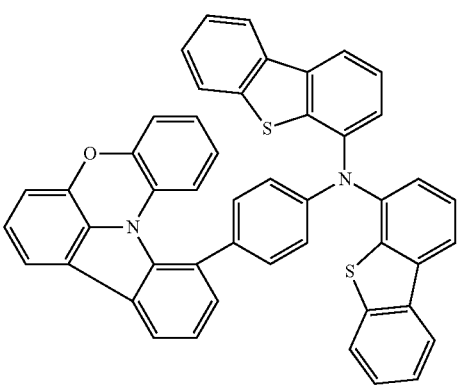
A27
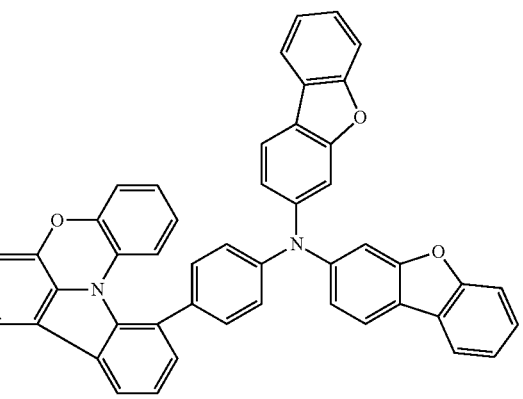
A28
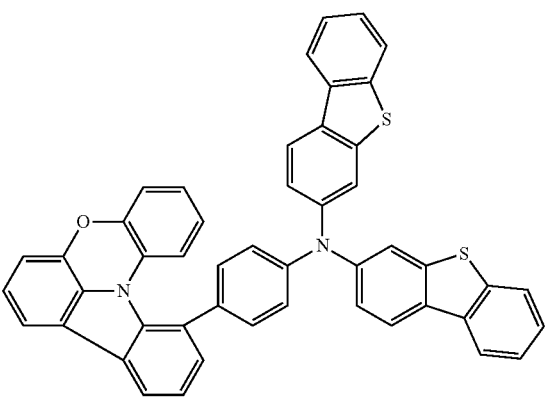

-continued
A29
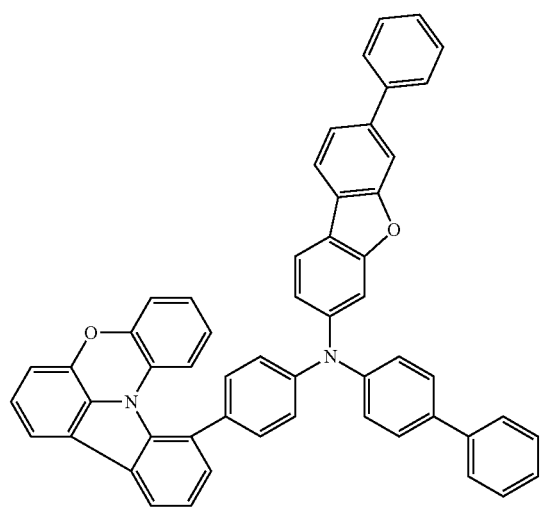
A30
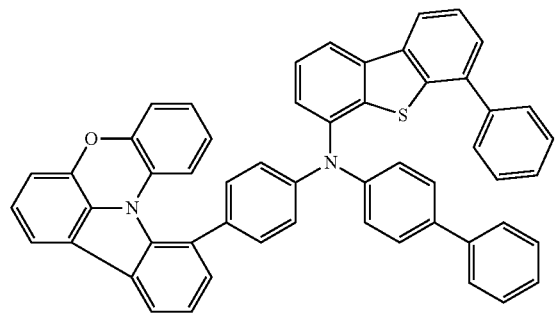
A31
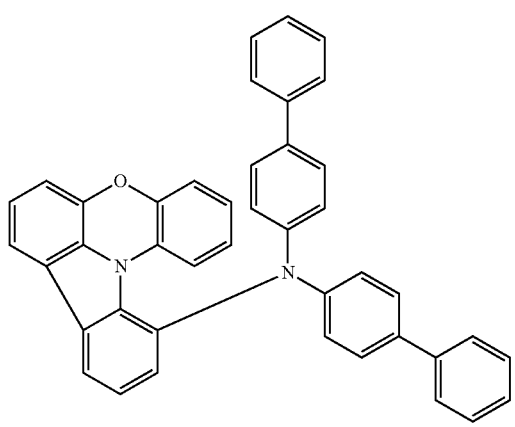
A32
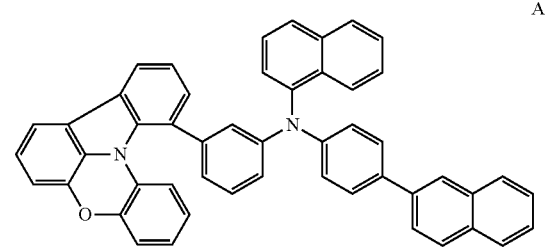
-continued
A33
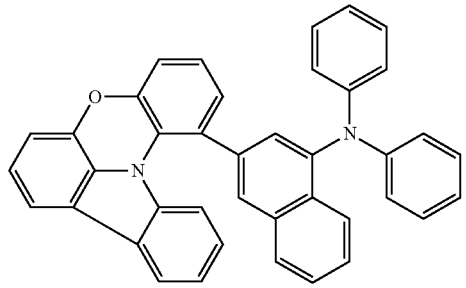
A34
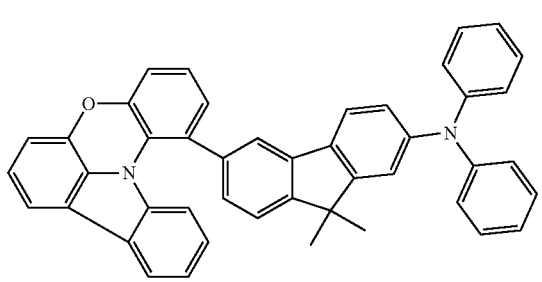
A35
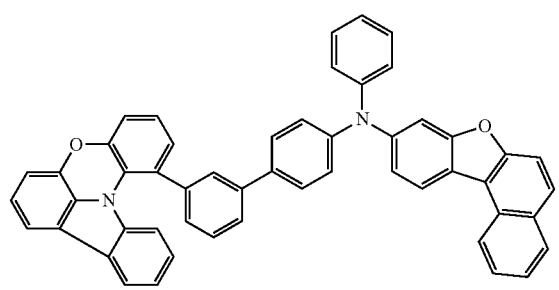
A36
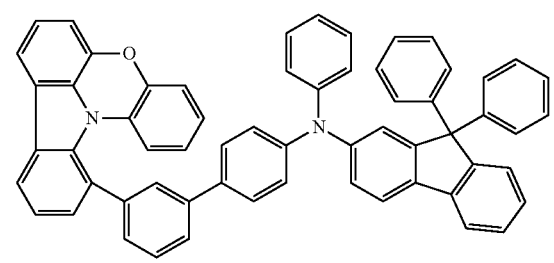
A37
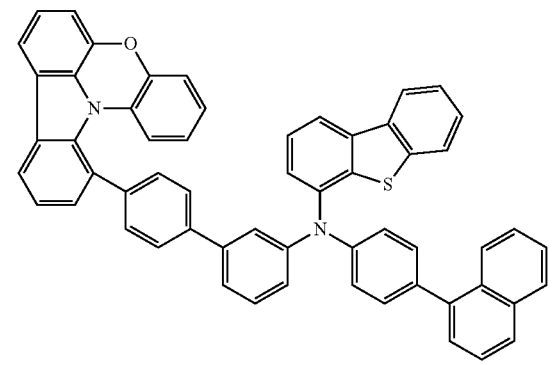

A38
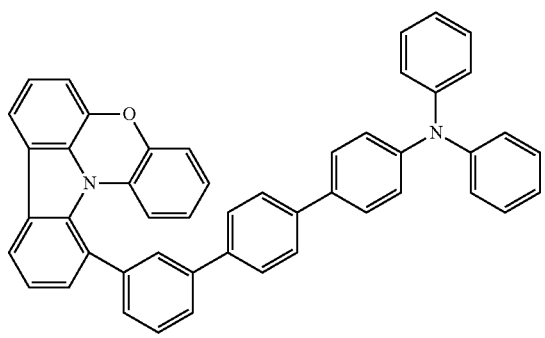
A39
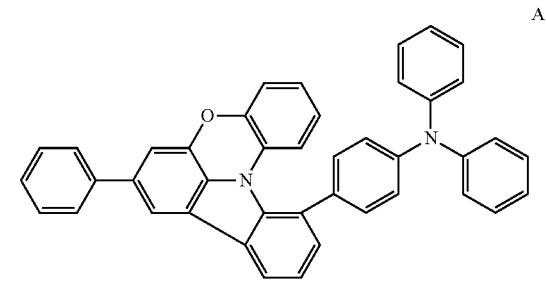
A40
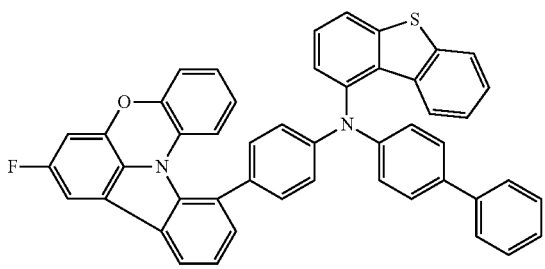
A41
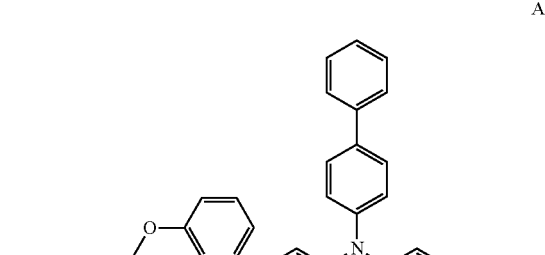
A42
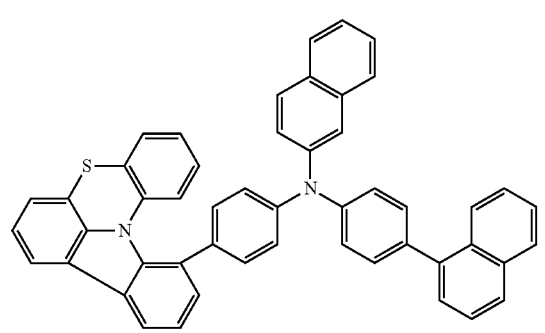
A43
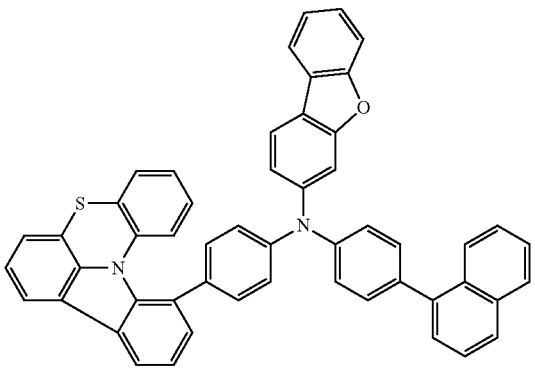
A44
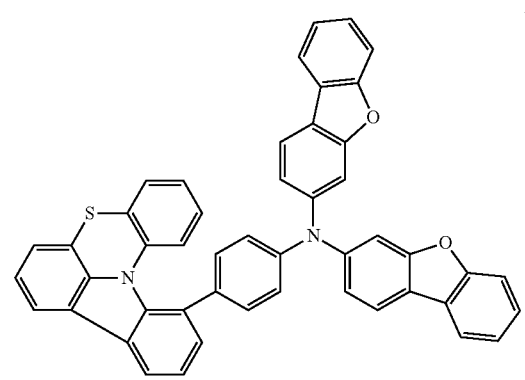
A45
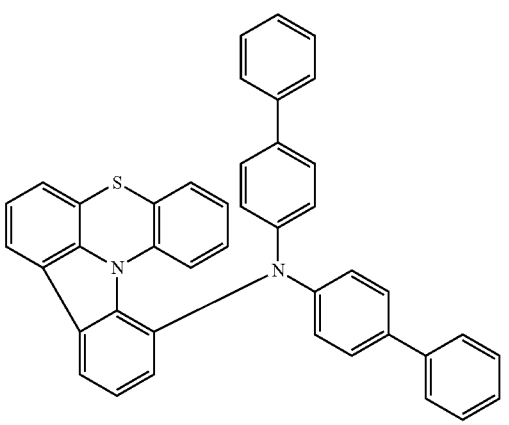
A46
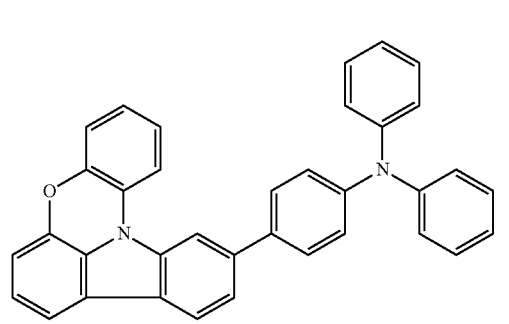

A47
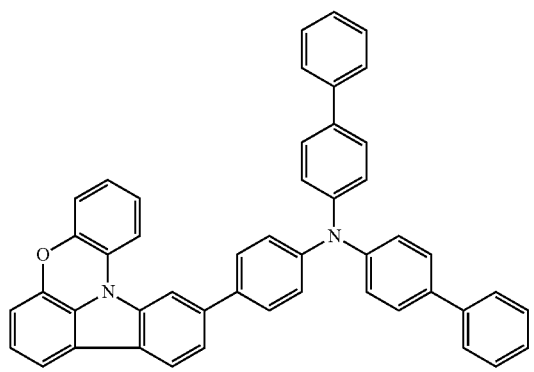
A48
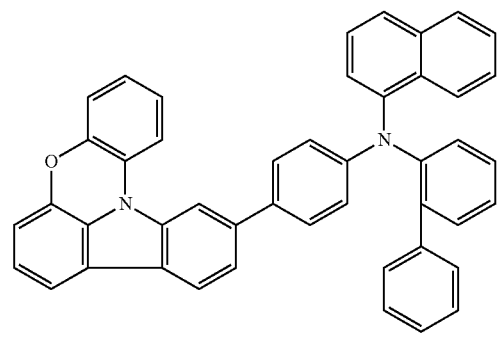
A49
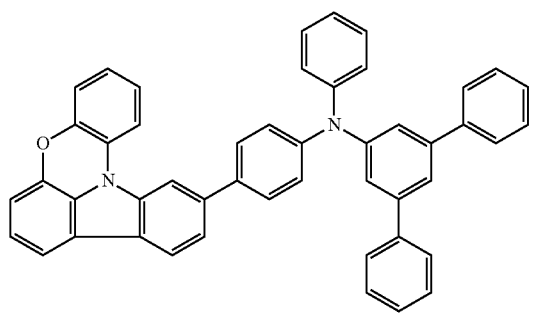
A50
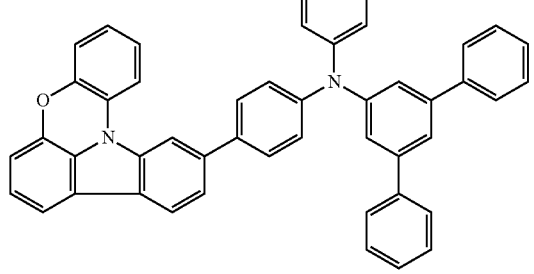
A51
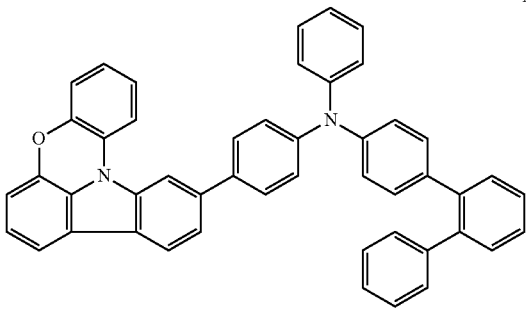
A52
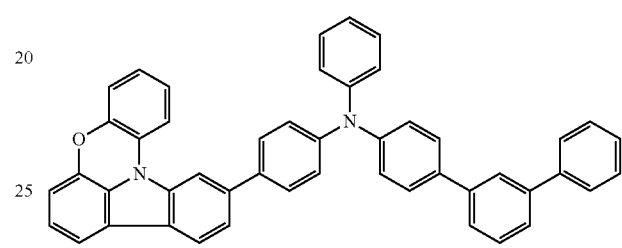
A53
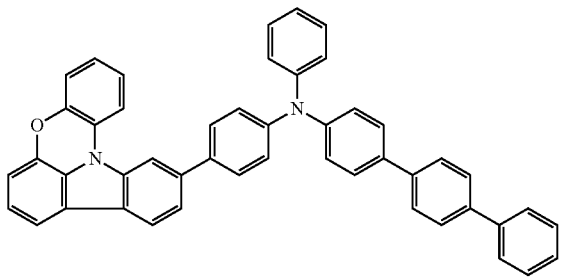
A54
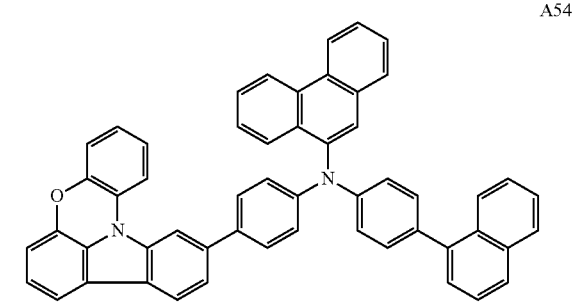
A55
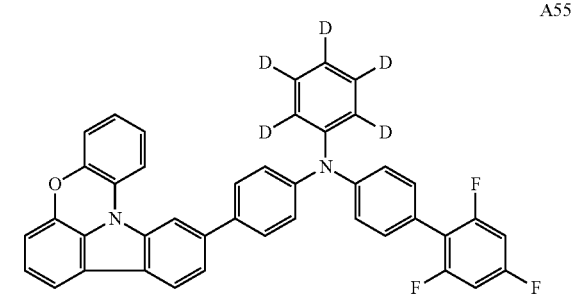

A56 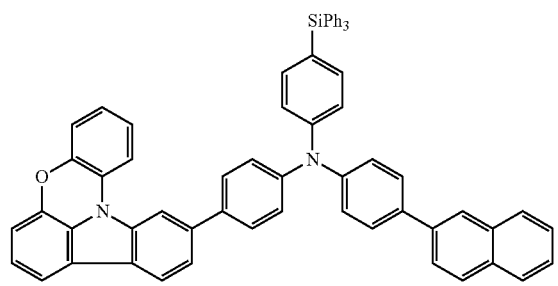
A57 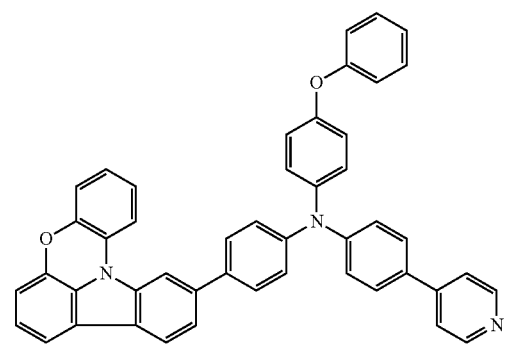
A58 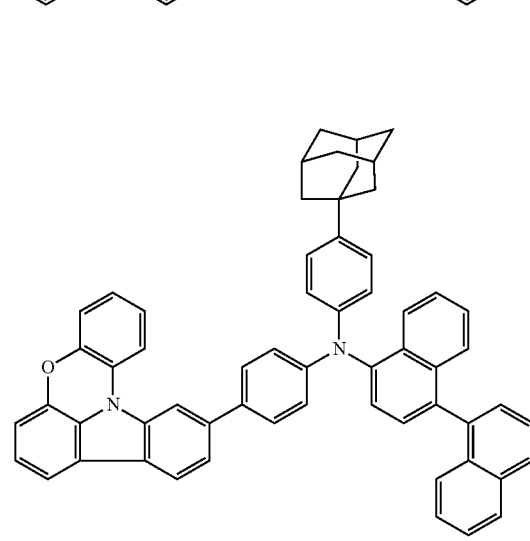
A61 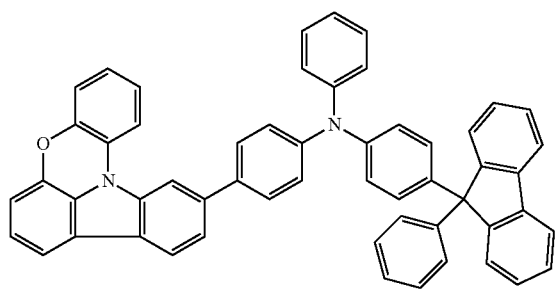
A62 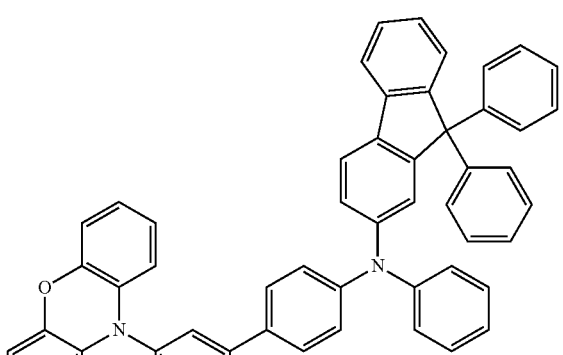
A63 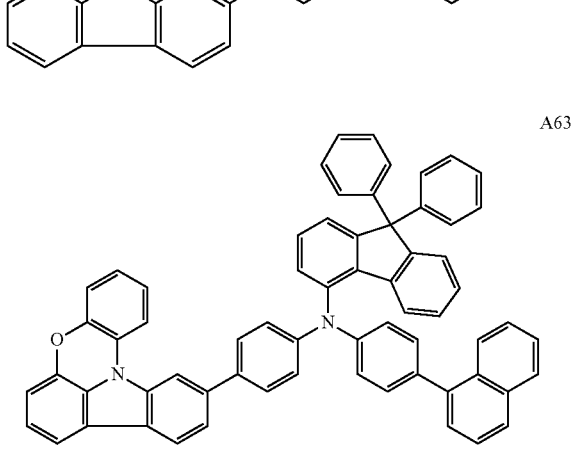
A64 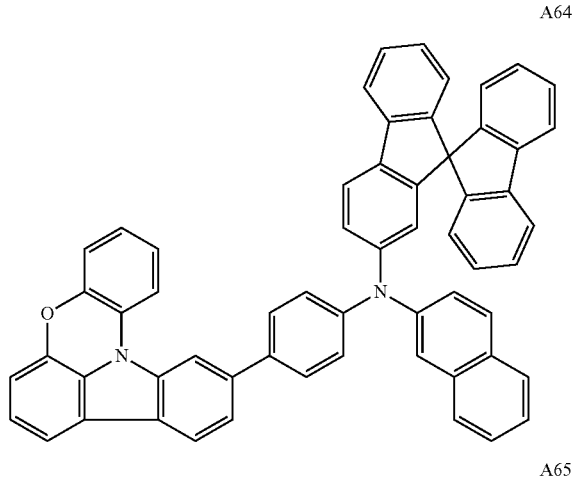
A65 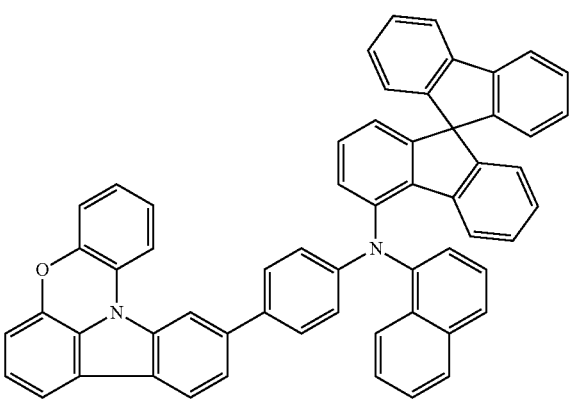

A66
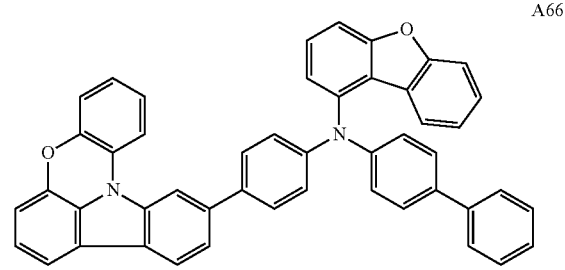
A67
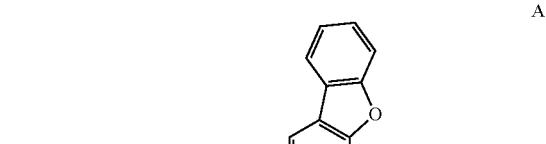
A68
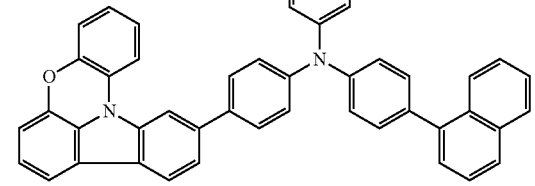
A69
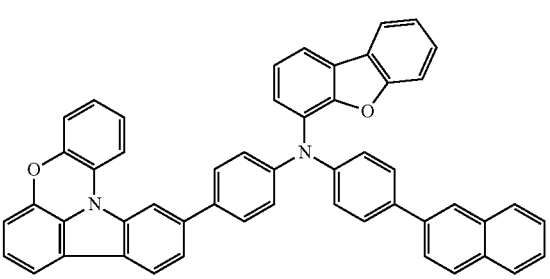
A70
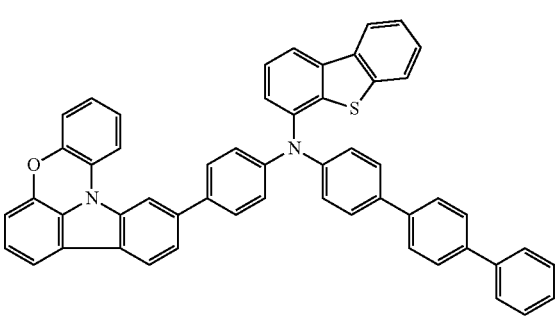
A71
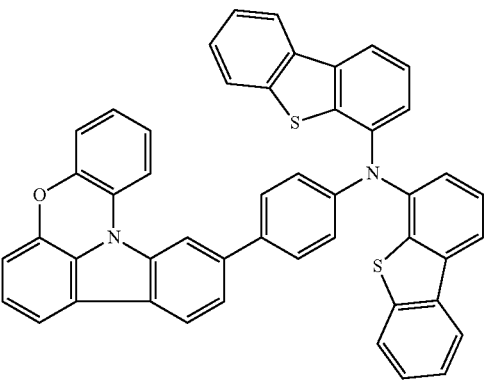
A72
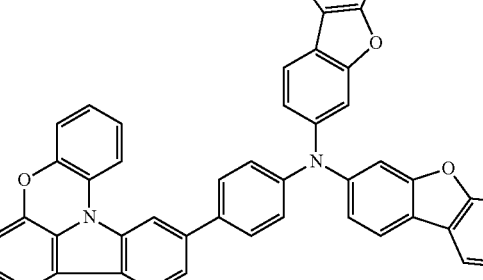
A73
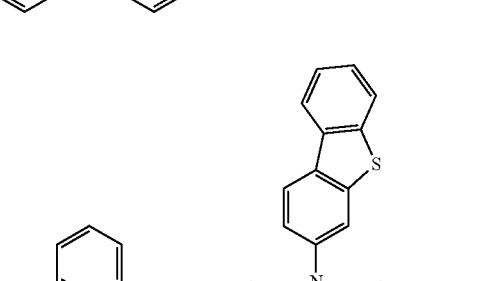
A74
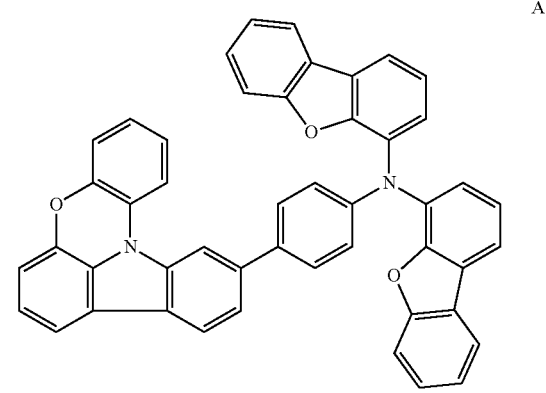

A75
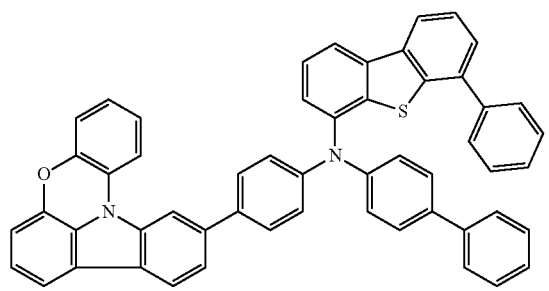
A76
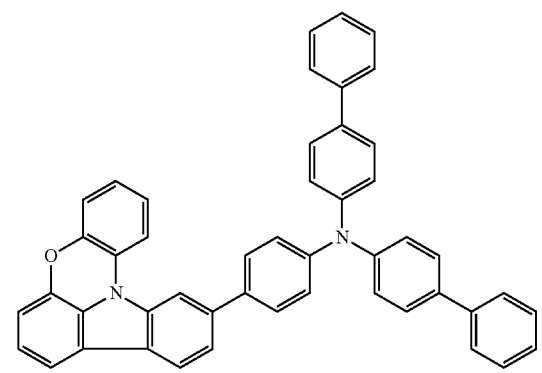
A77
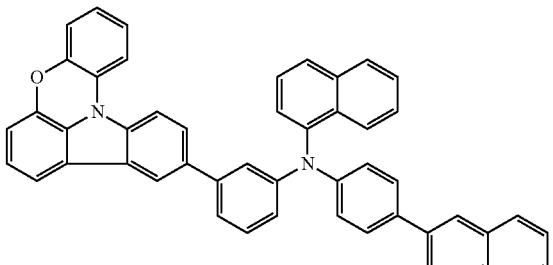
A78
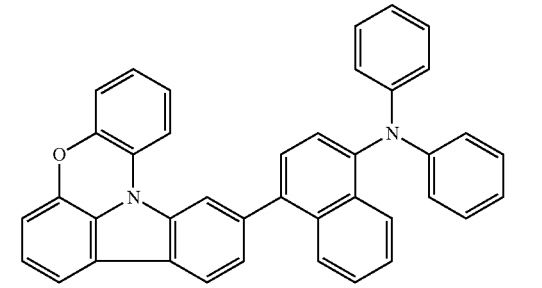
A79
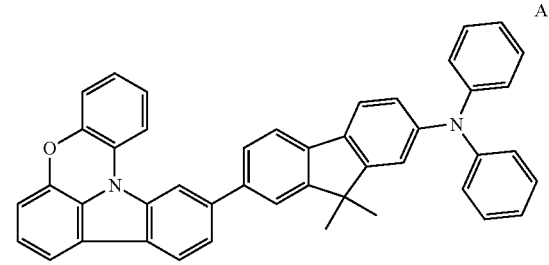
A80
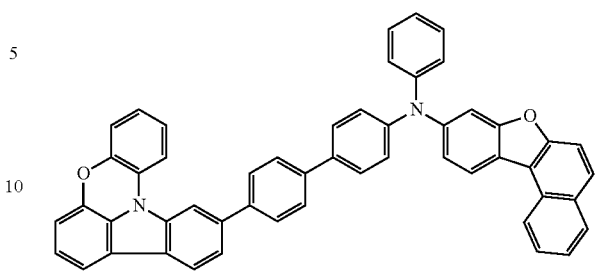
A81
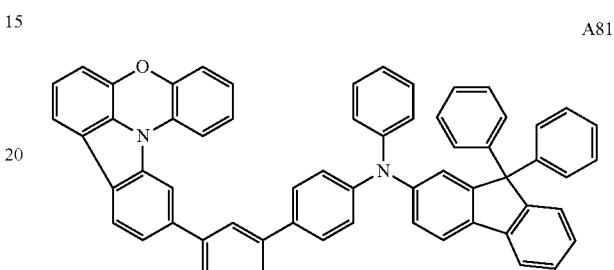
A82
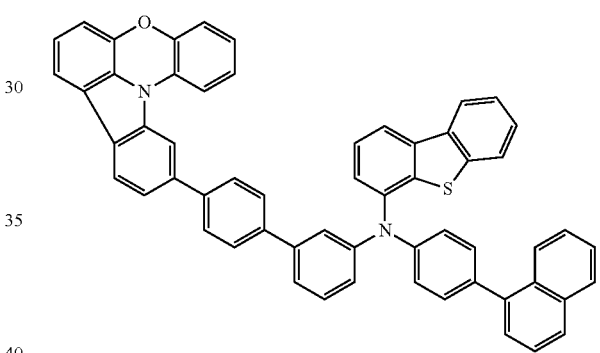
A83
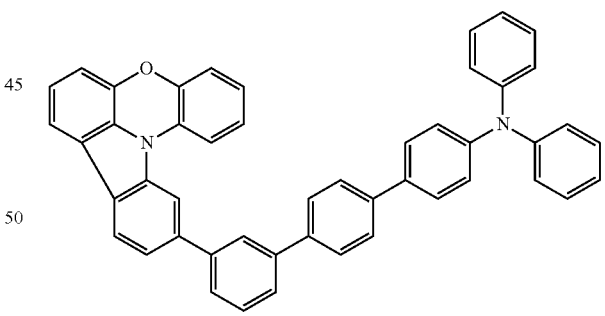
A84
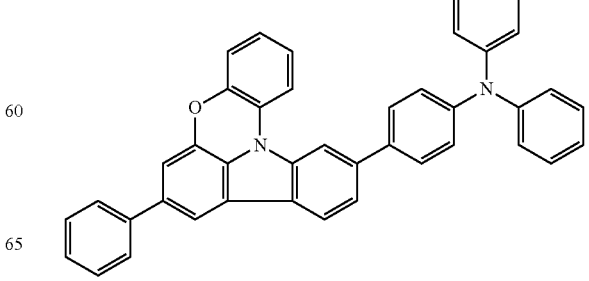

A85
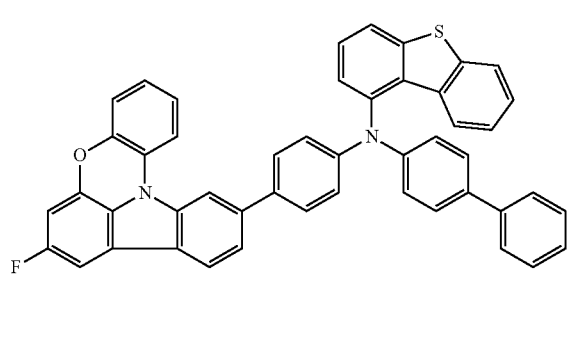
A89
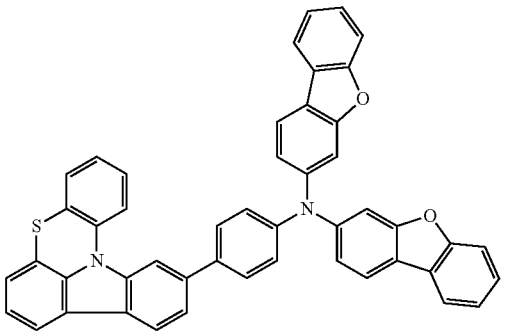
A86
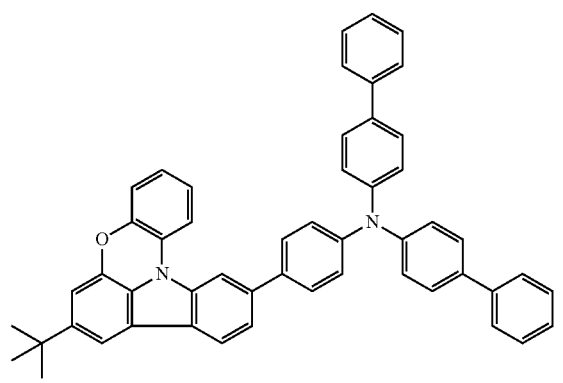
A90
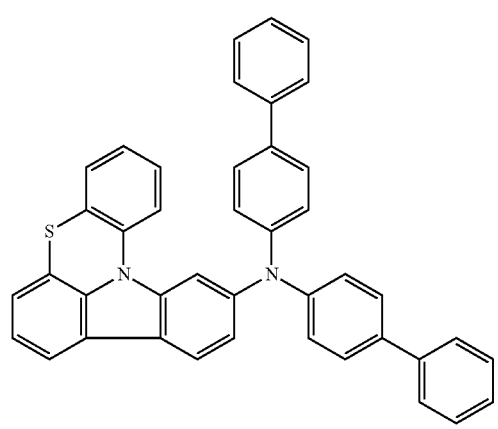
A87
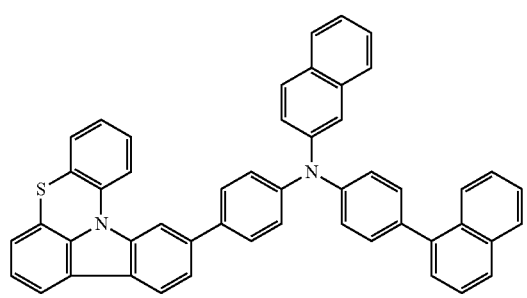
A136
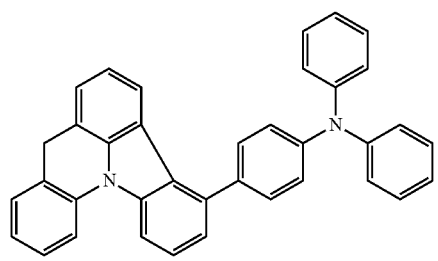
A88
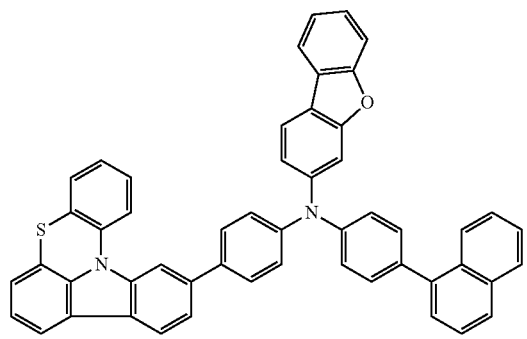
A137
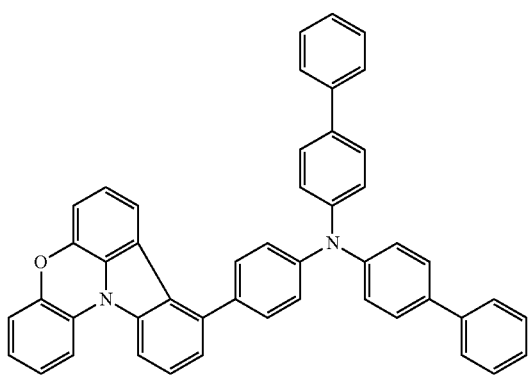

A138 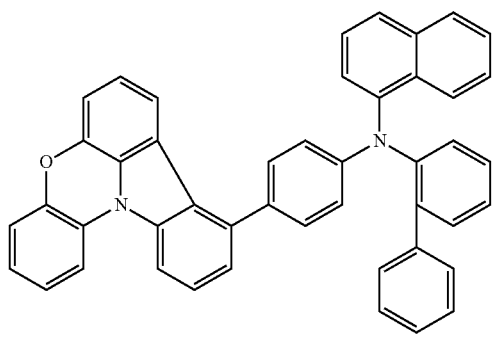
A139 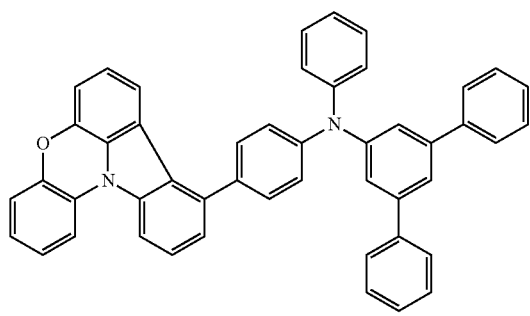
A140 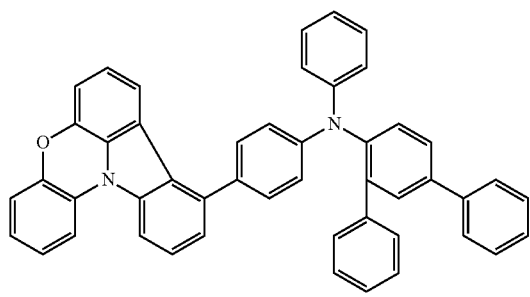
A141 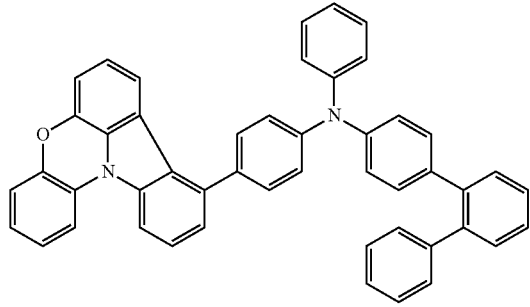
A142 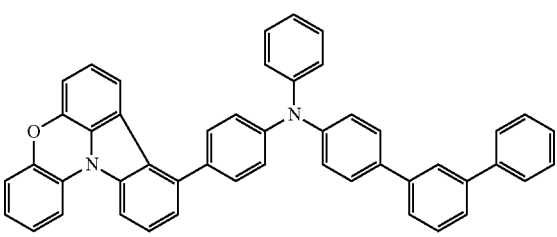
A143 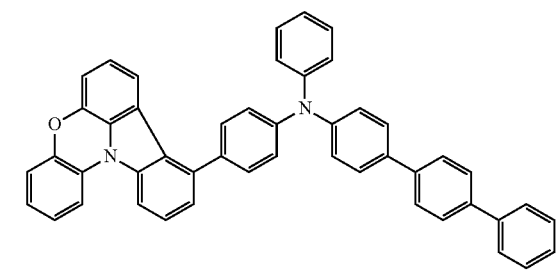
A144 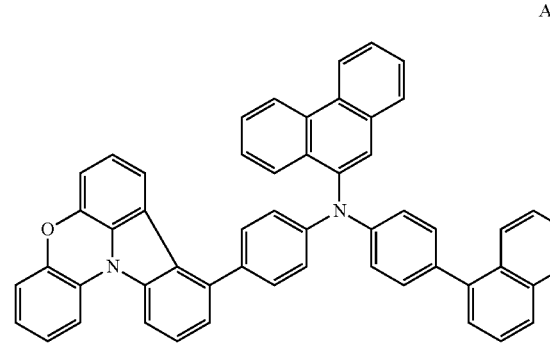
A145 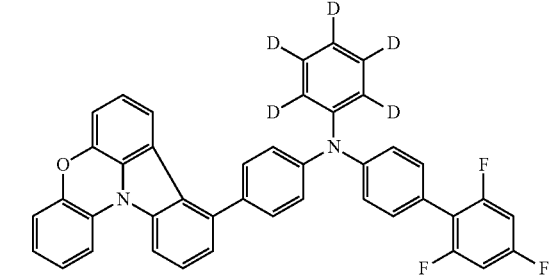
A146 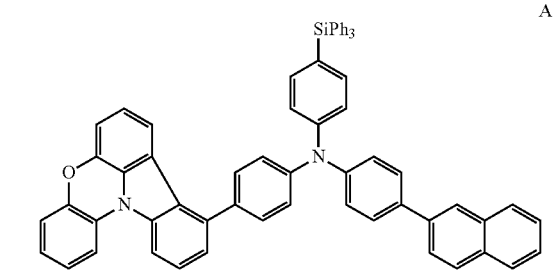
A147 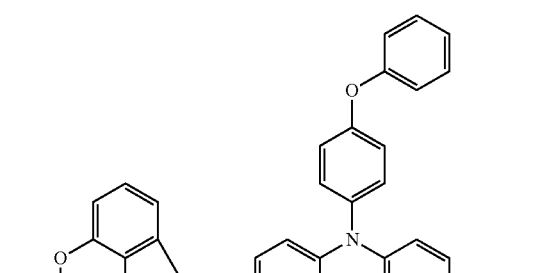

A148
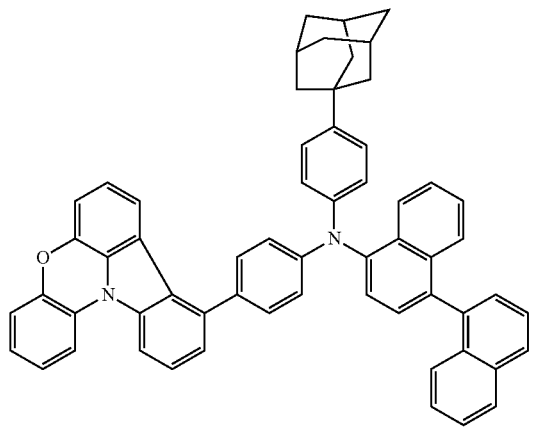
A151
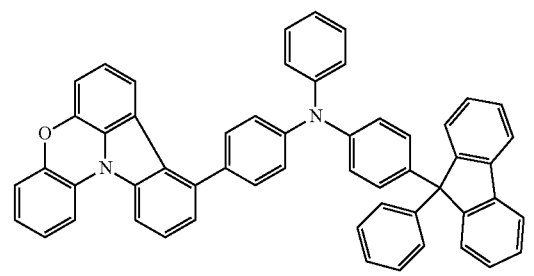
A152
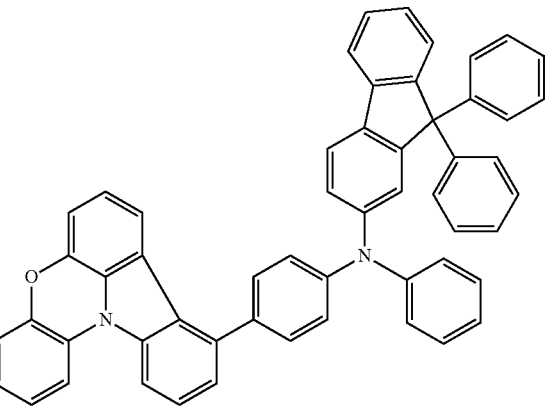
A153
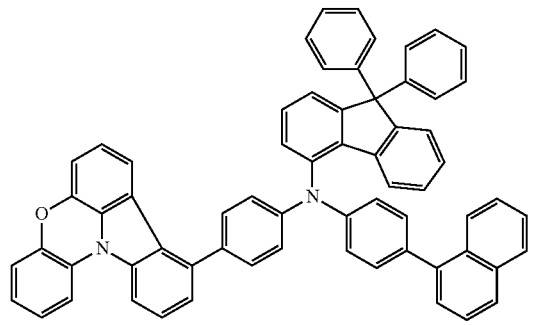
A154
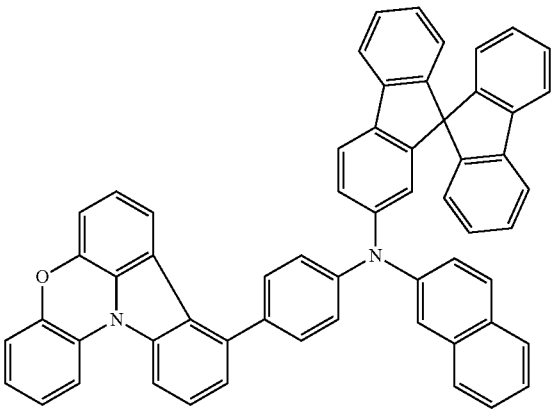
A155
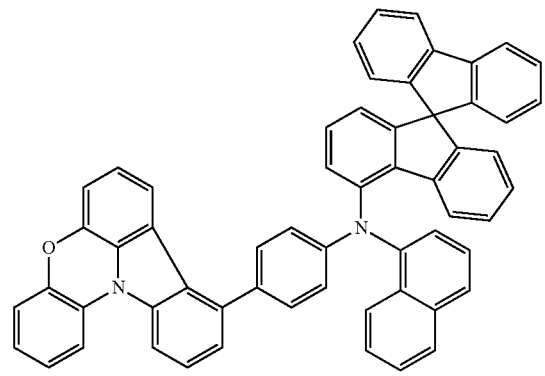
A156
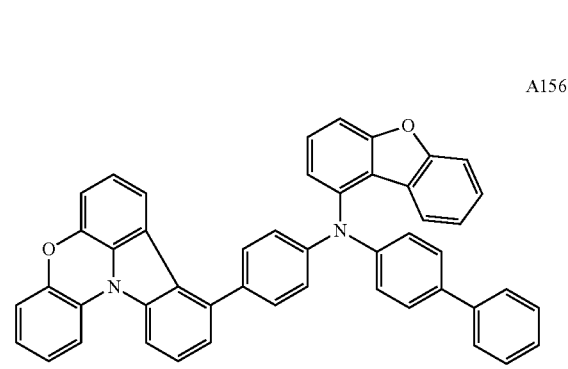
A157
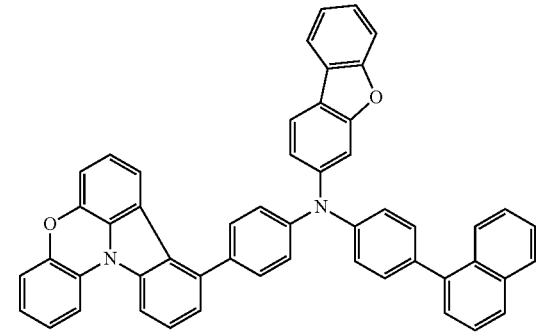

A158
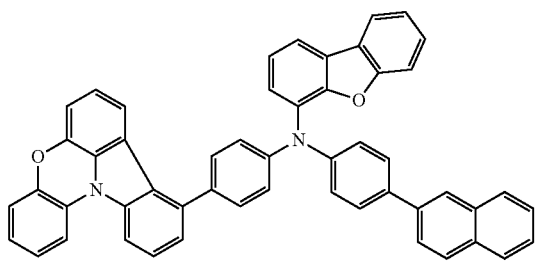
A159
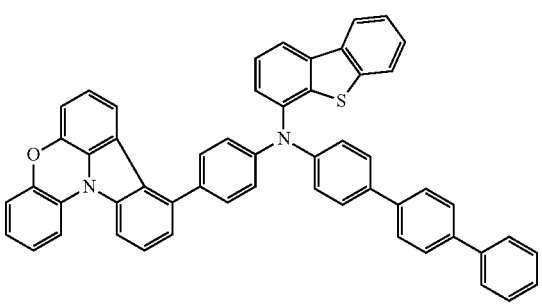
A160
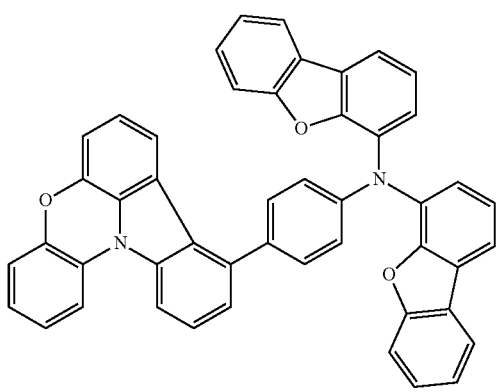
A161
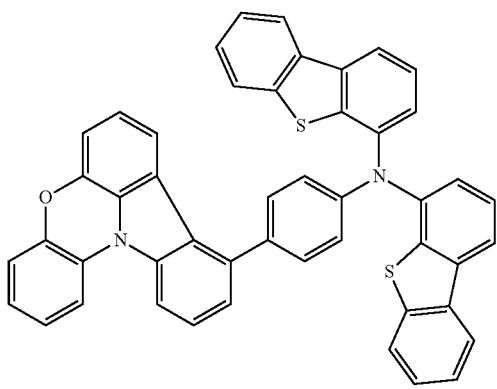
A162
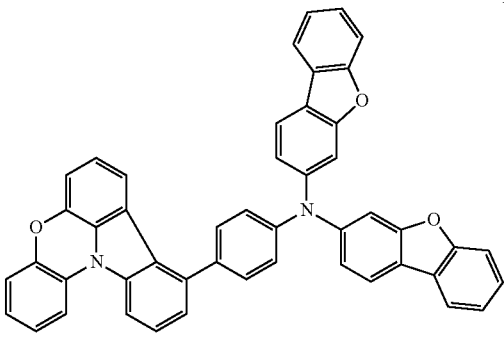
A163
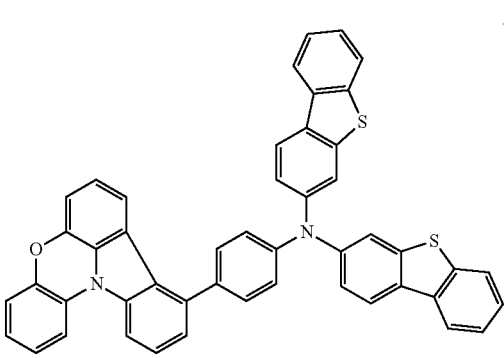
A164
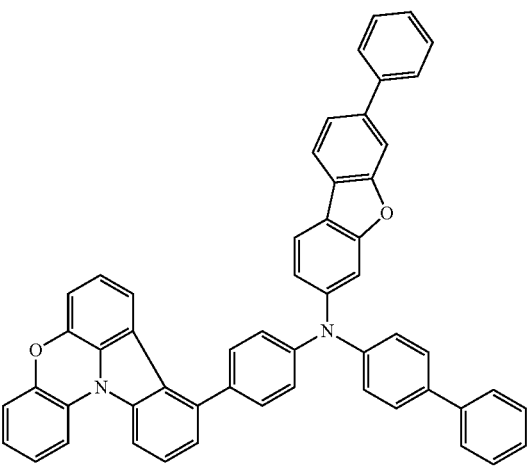
A165
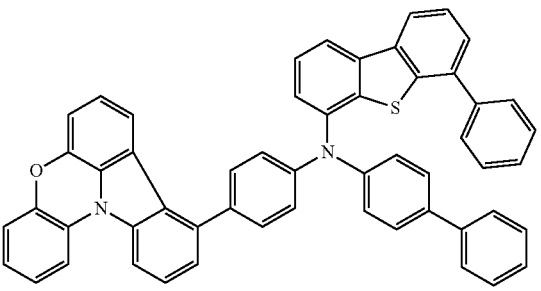

A166
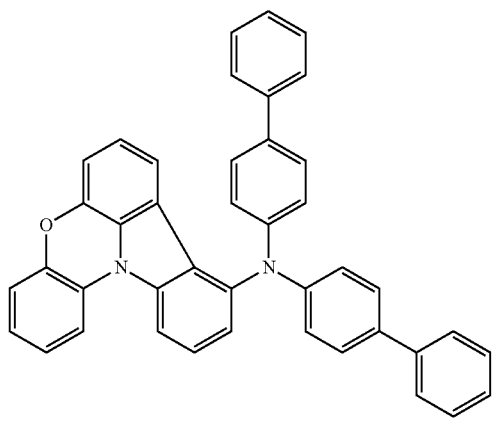
A167
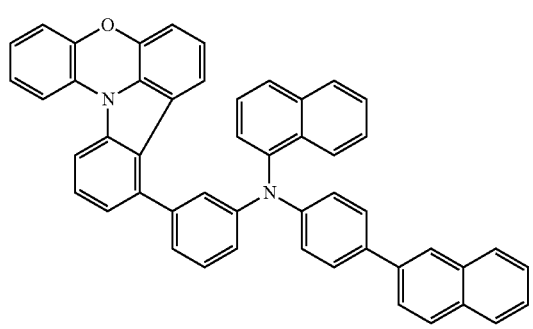
A168
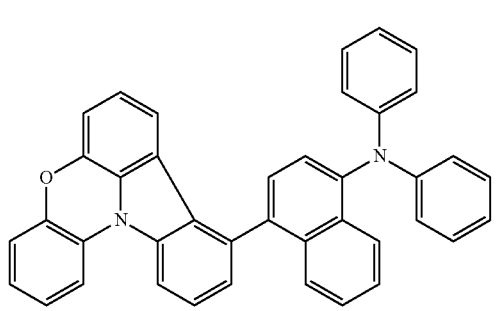
A169
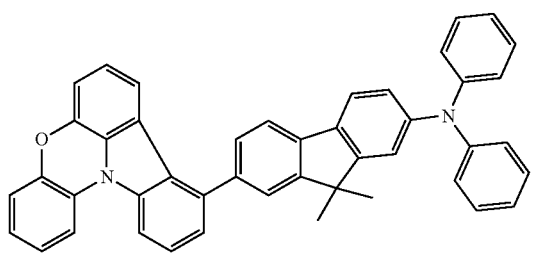
A170
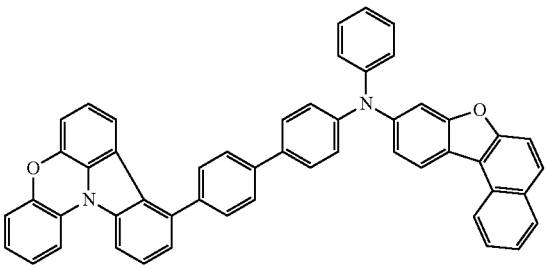
A171
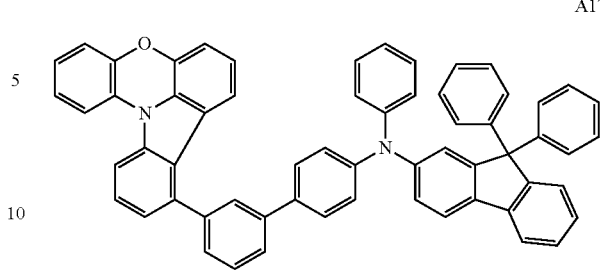
A172
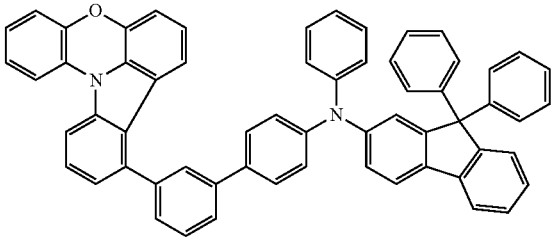
A173
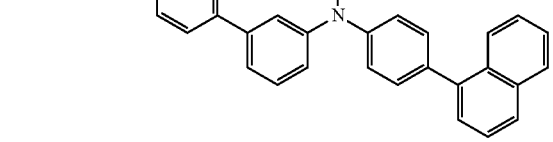
A174
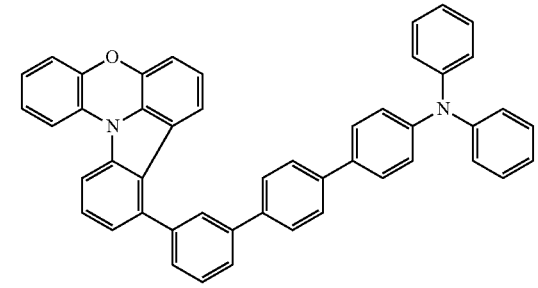
A175
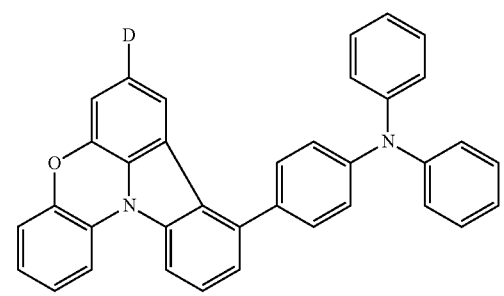

-continued
A176
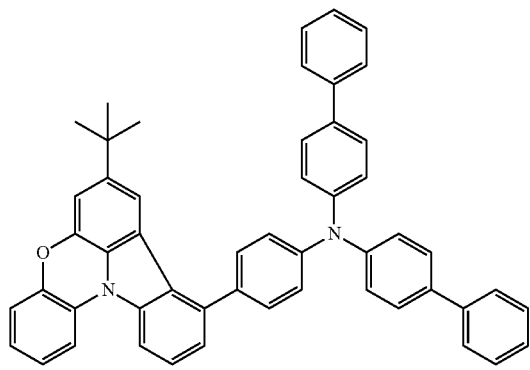
A177
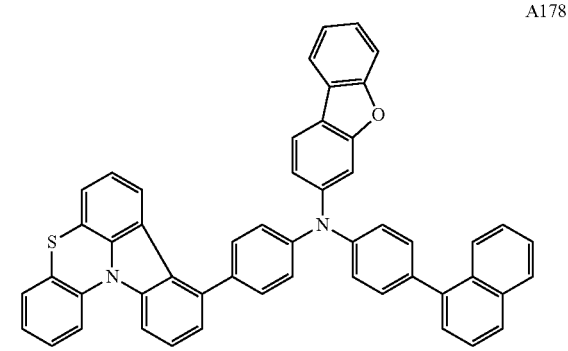
A178
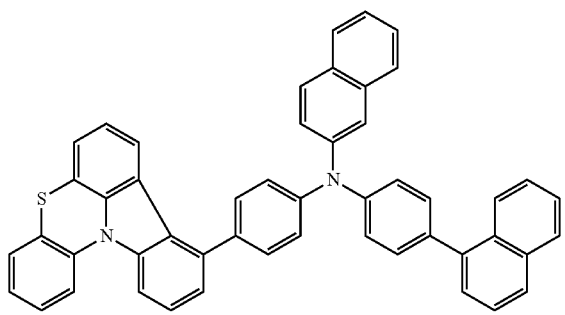
A179
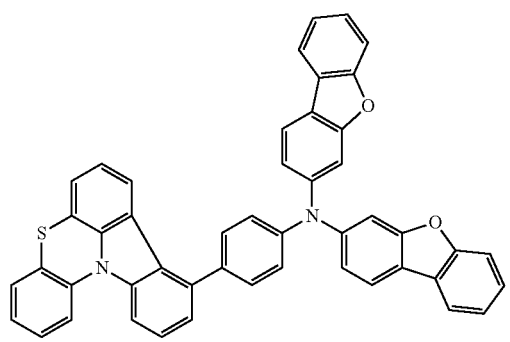
-continued
A180
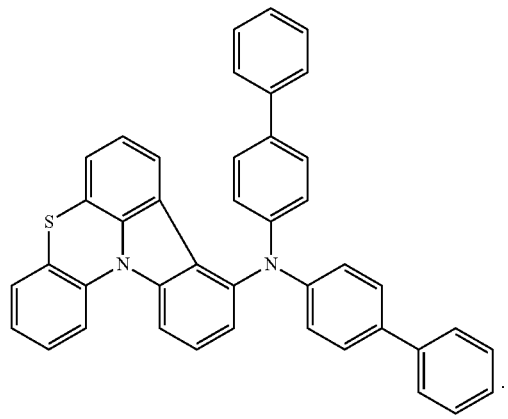
12. The organic electroluminescence device of claim 1, wherein the polycyclic compound of Formula 1 is at least one compound of Compound Group 2:
Compound Group 2
B1
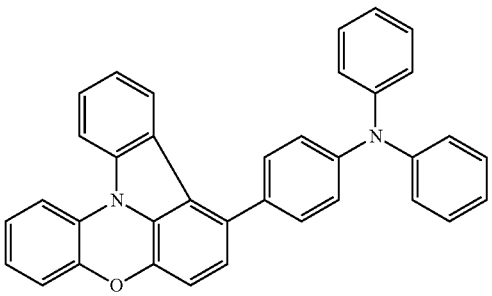
B2
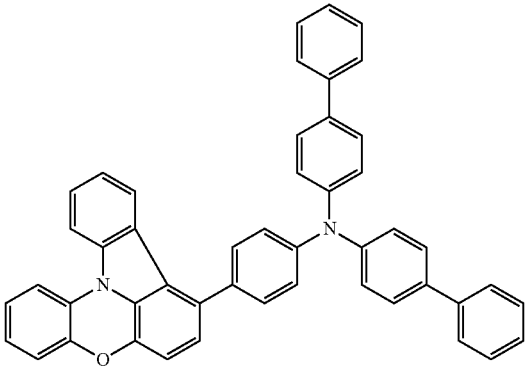
B3
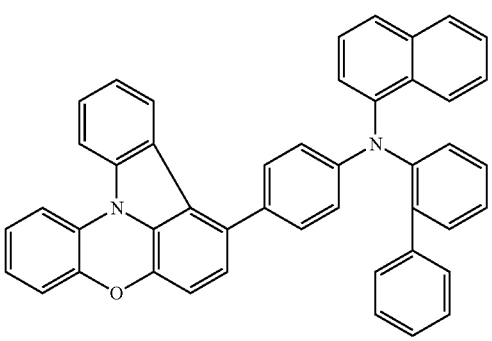

B4
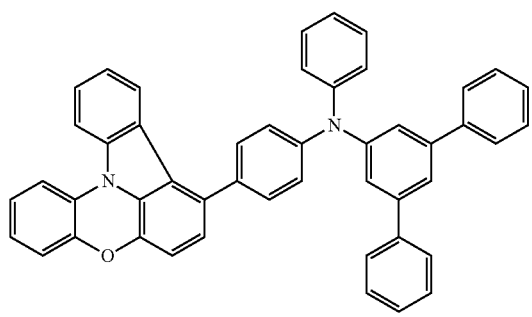
B5
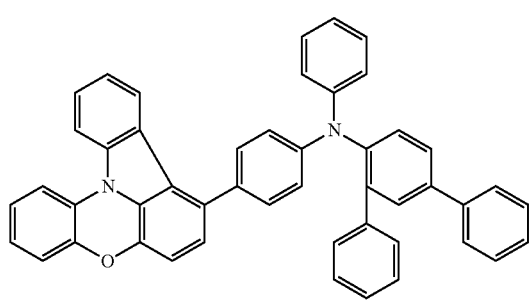
B6
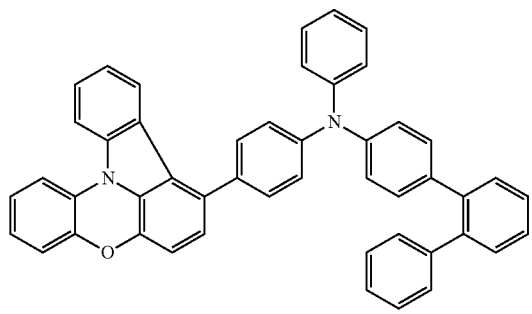
B7
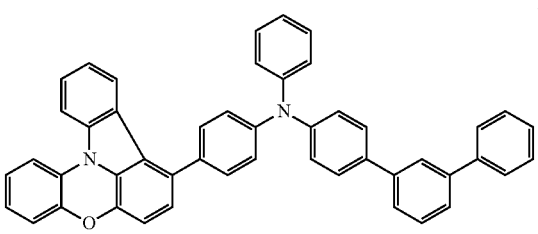
B8
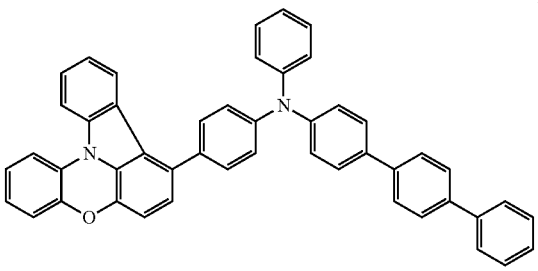
B9
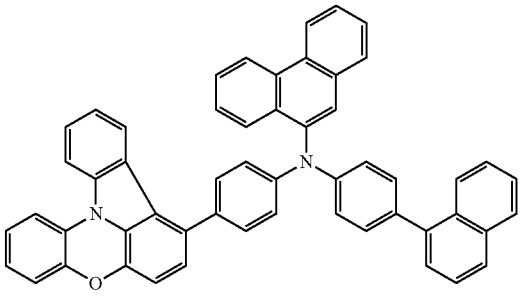
B10
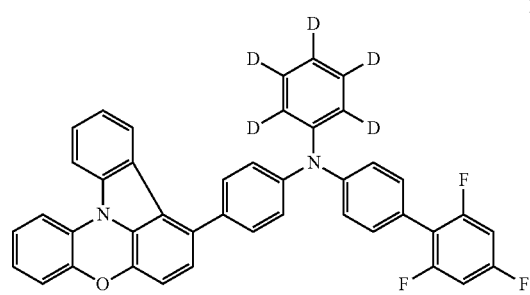
B11
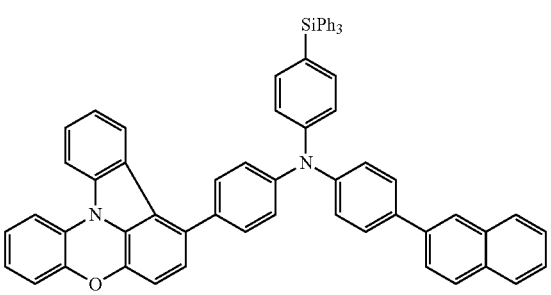
B12
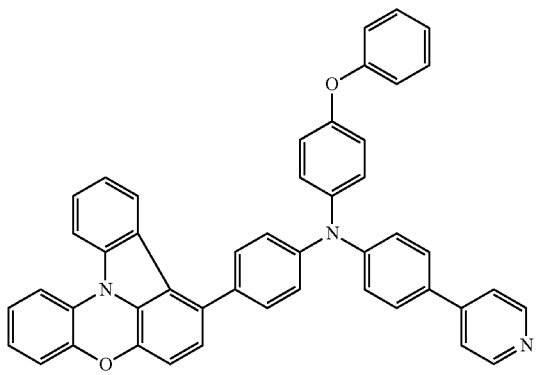

197
-continued
B13
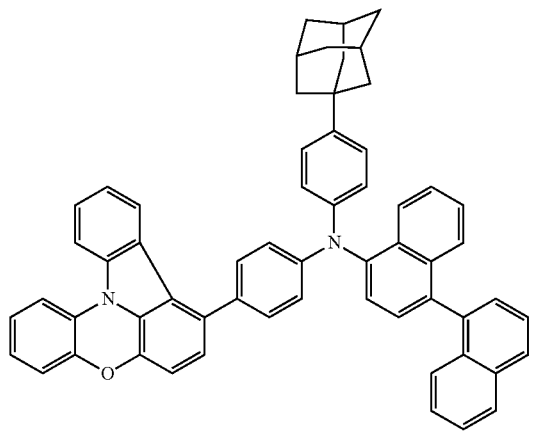
B16
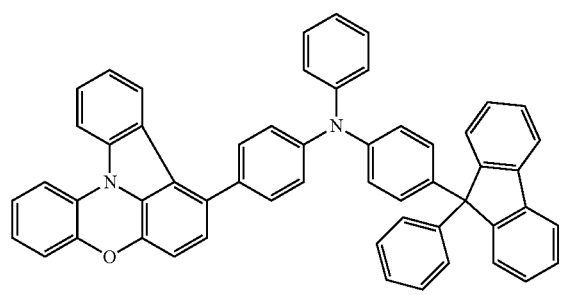
B17
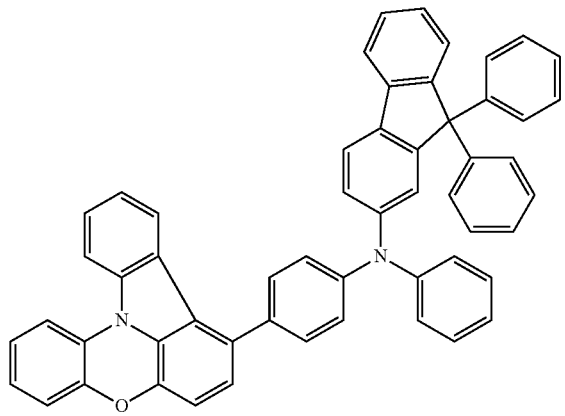
B18
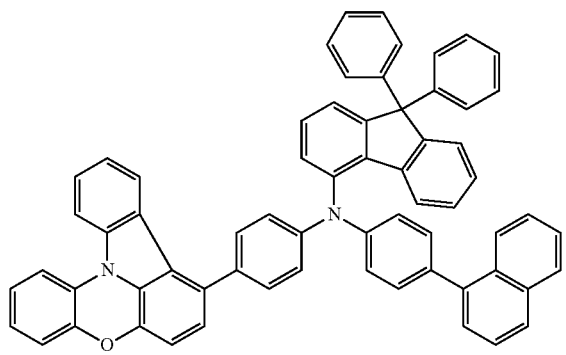
198
-continued
B19
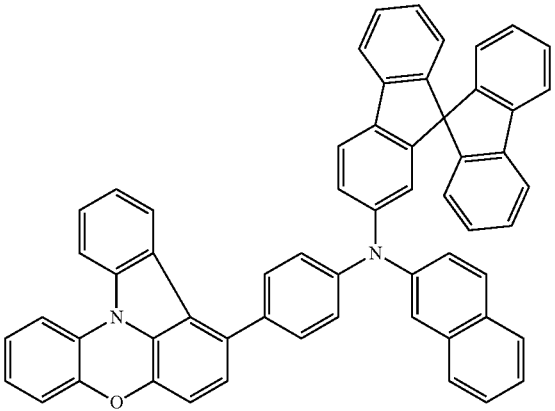
B20
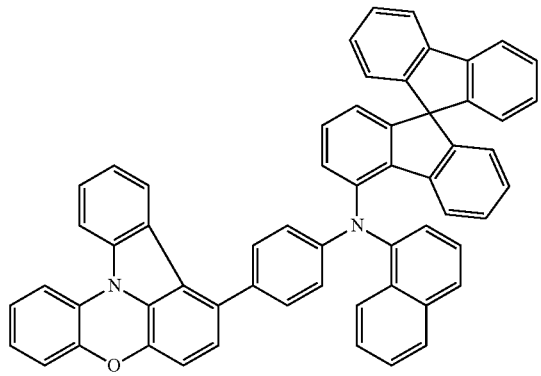
B21
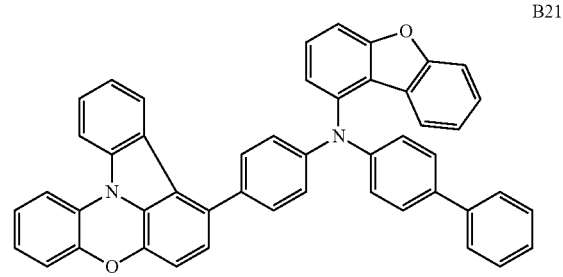
B22
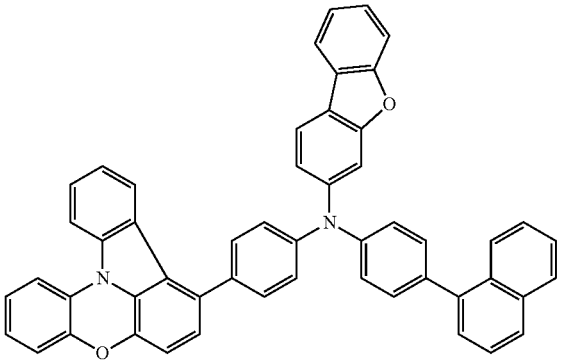

-continued
B23
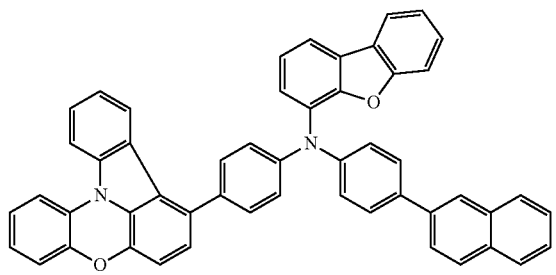
B24
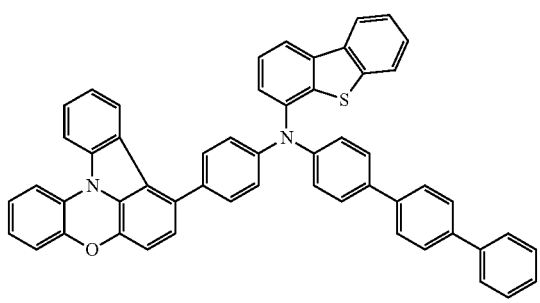
B25
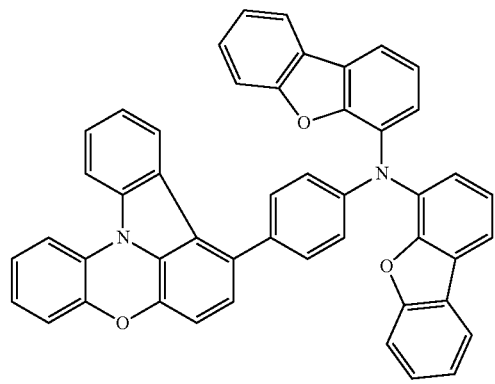
B26
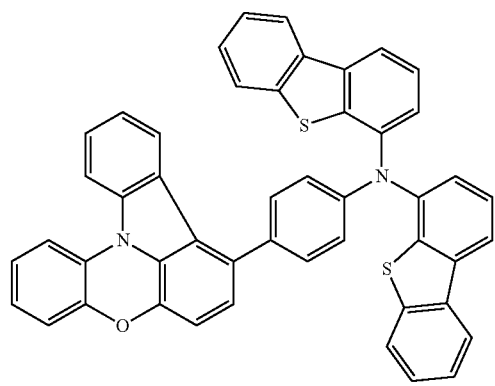
-continued
B27
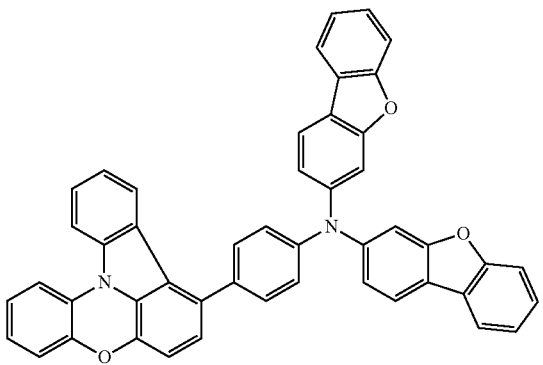
B28
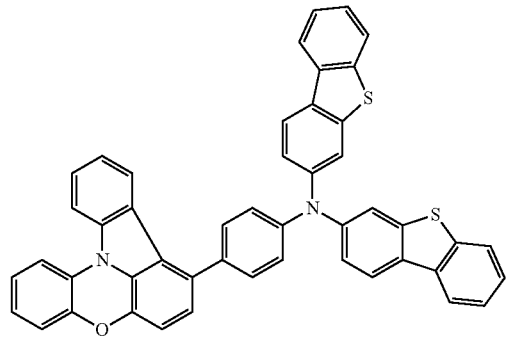
B29
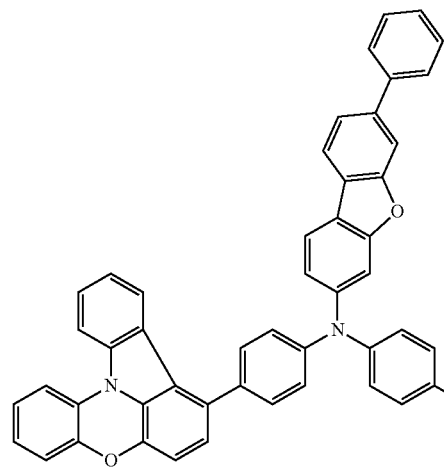
B30
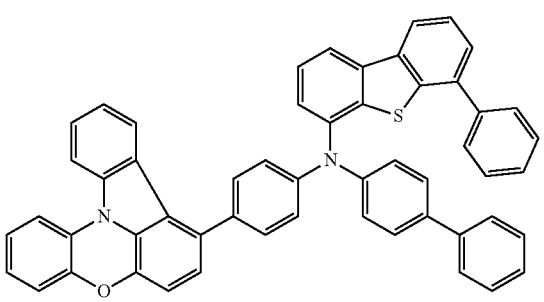

-continued
B31
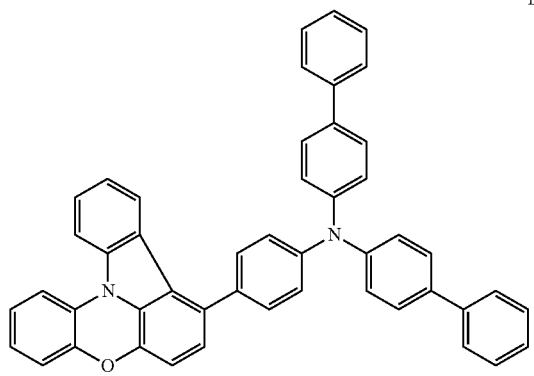
B32
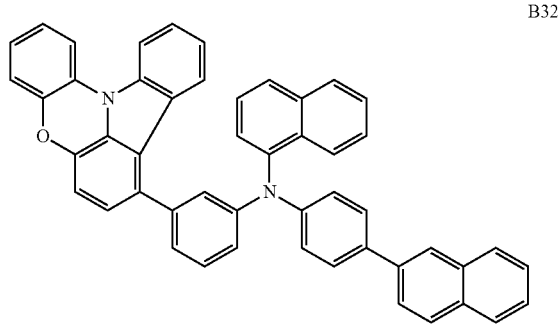
B33
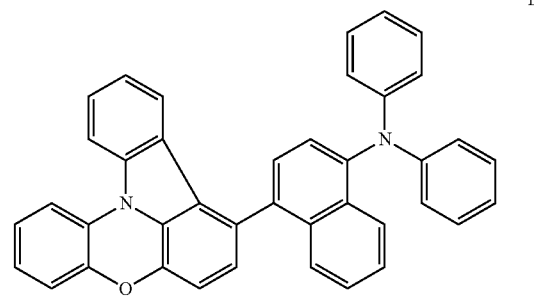
B34
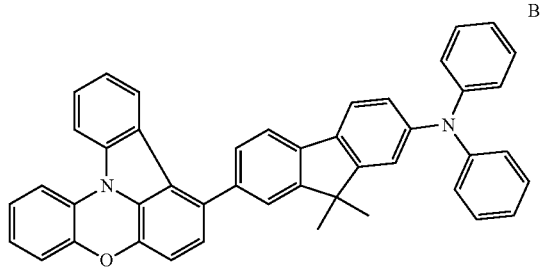
B35
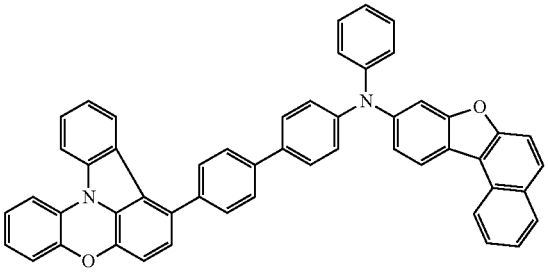
B36
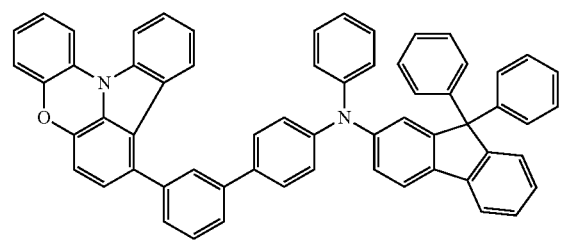
B37
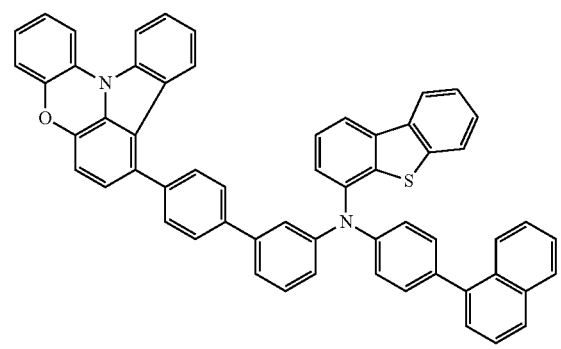
B38
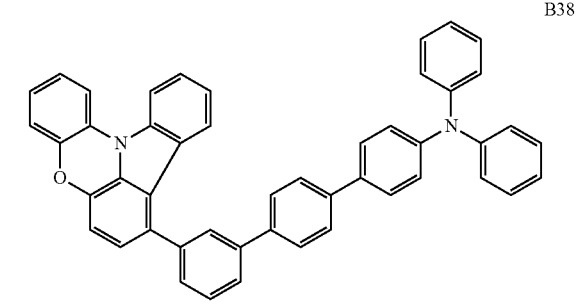
B39
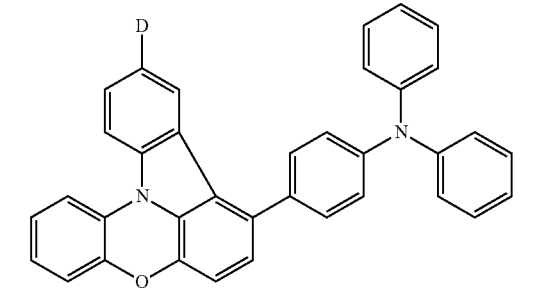
B40
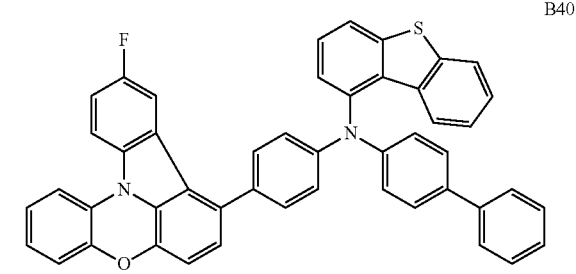

B41
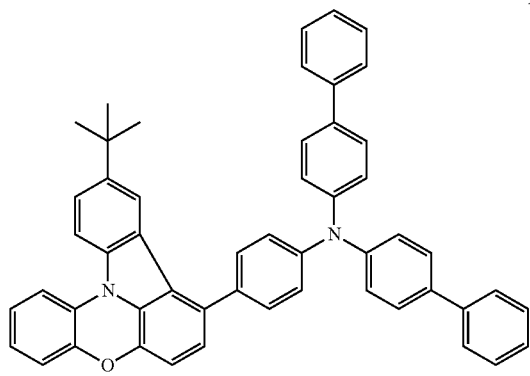
B42
B45
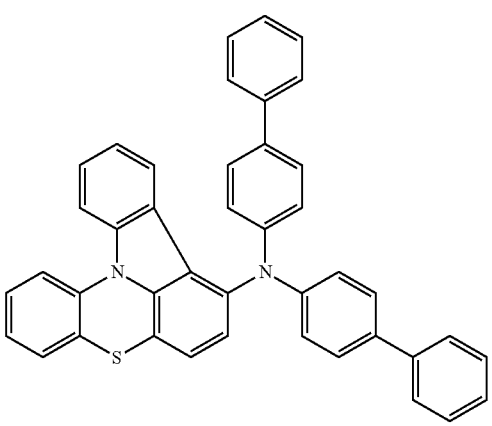
B91
B43
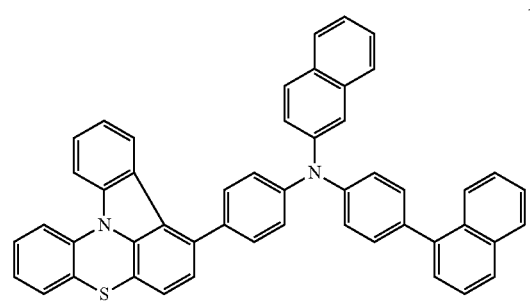
B92
B44
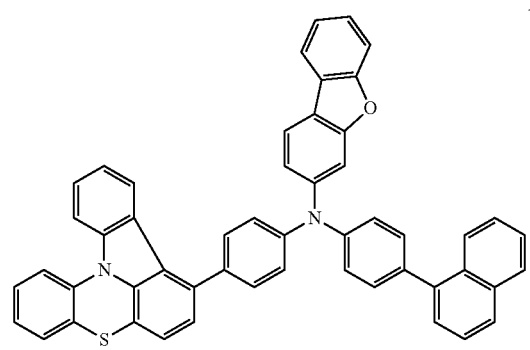
B93
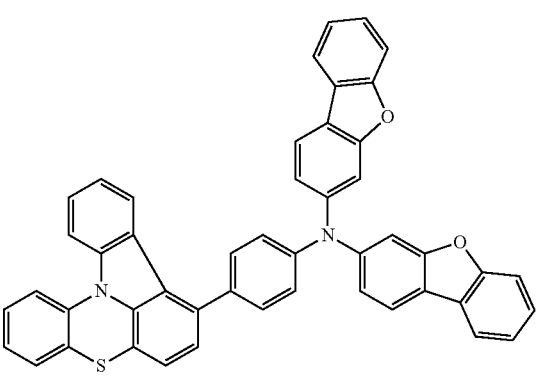

B94
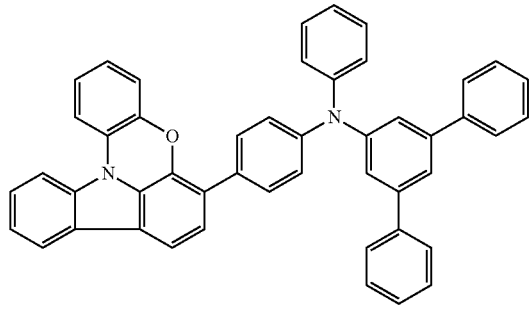
B95
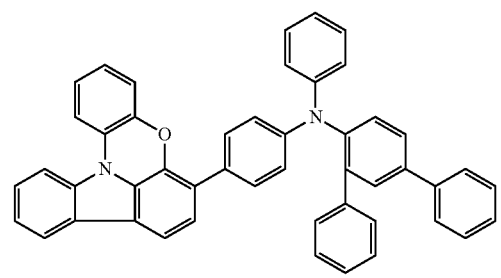
B96
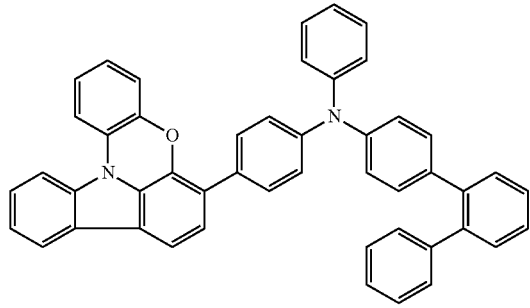
B97
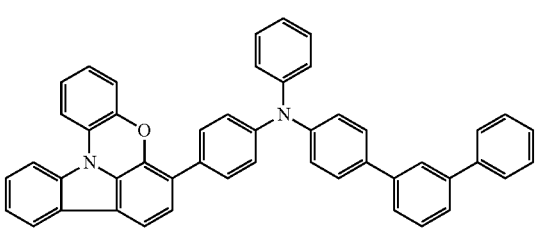
B98
B99
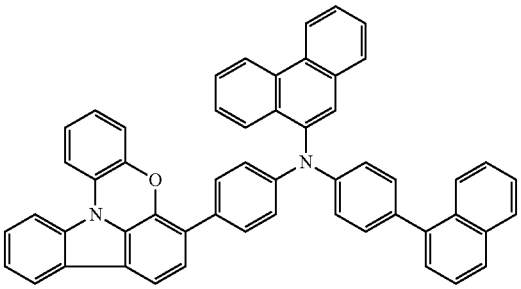
B100
B101
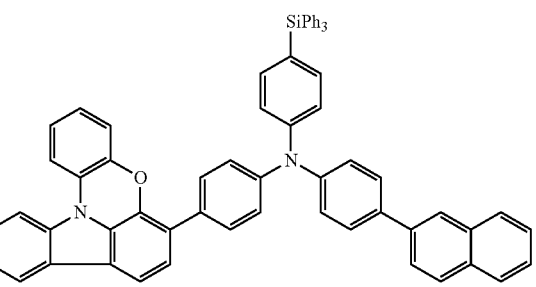
B102
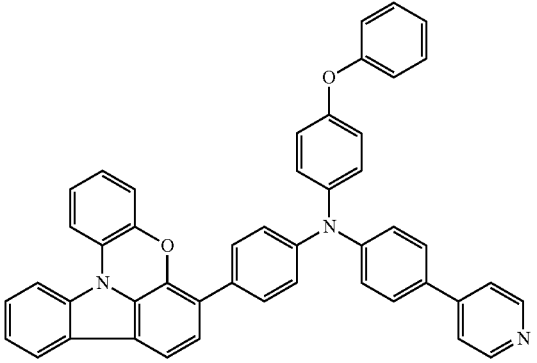

-continued
B103
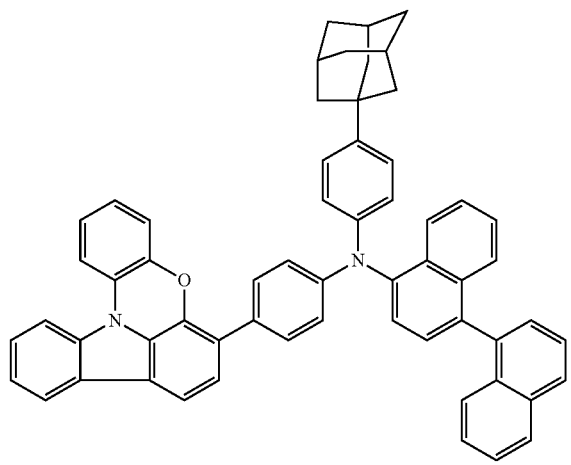
B106
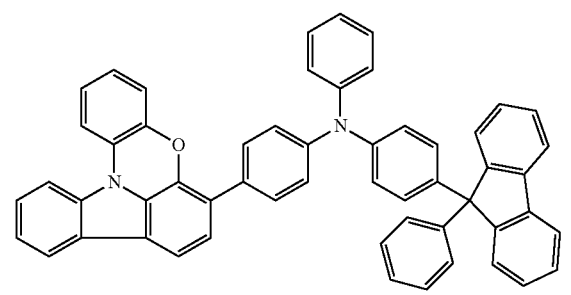
B107
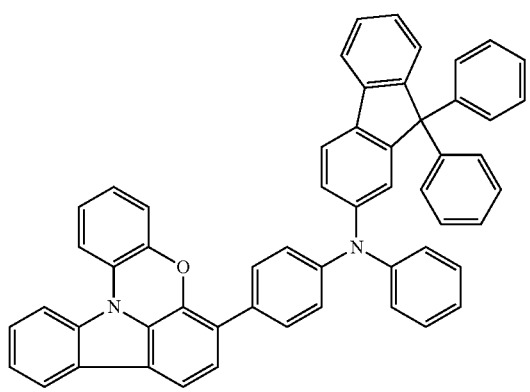
B108
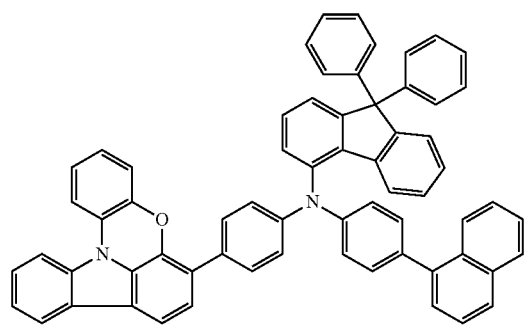
B109
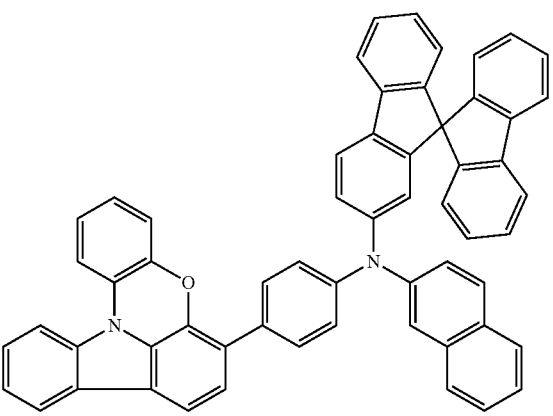
B110
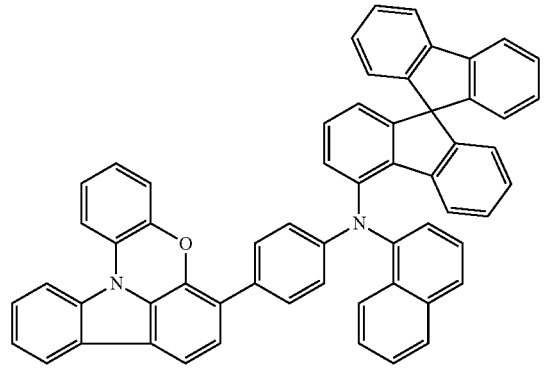
B111
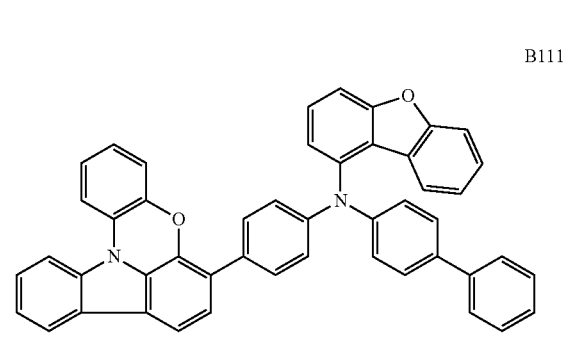
B112
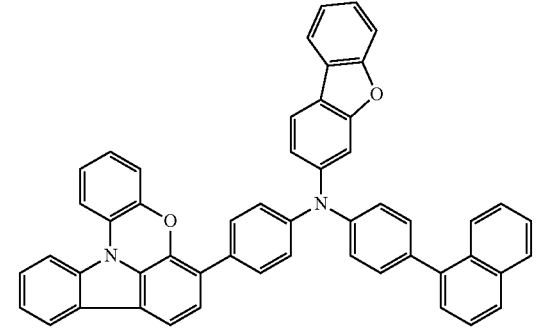

B113
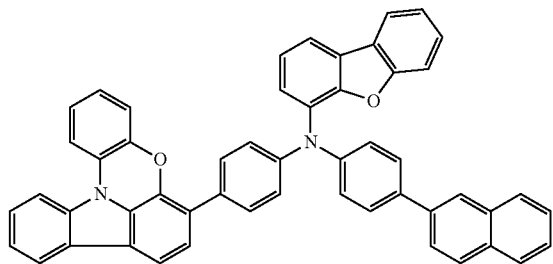
B114
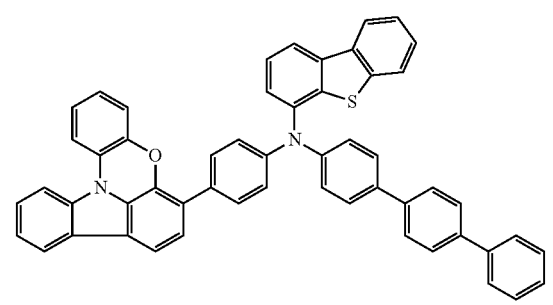
B115
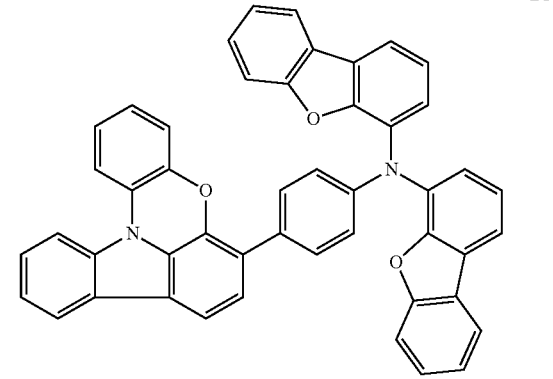
B116
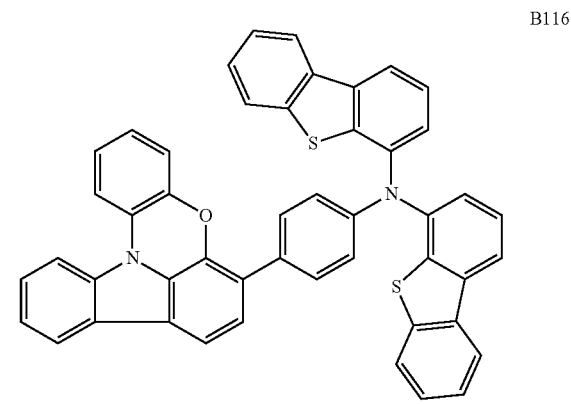
B117
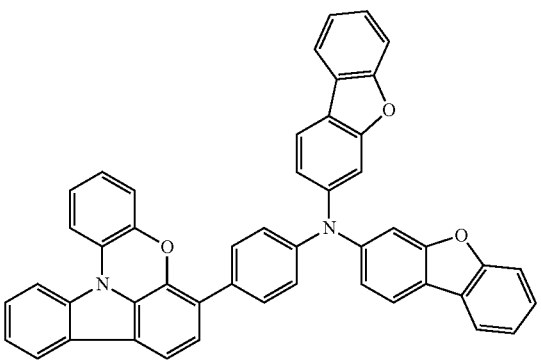
B118
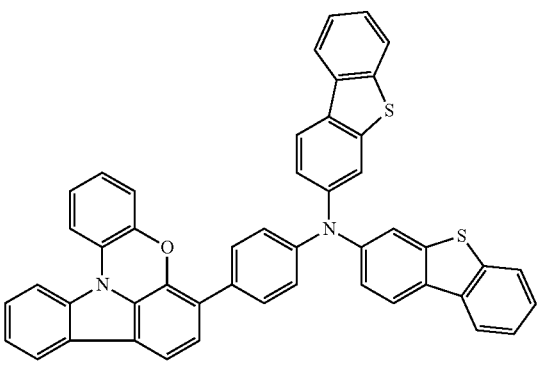
B119
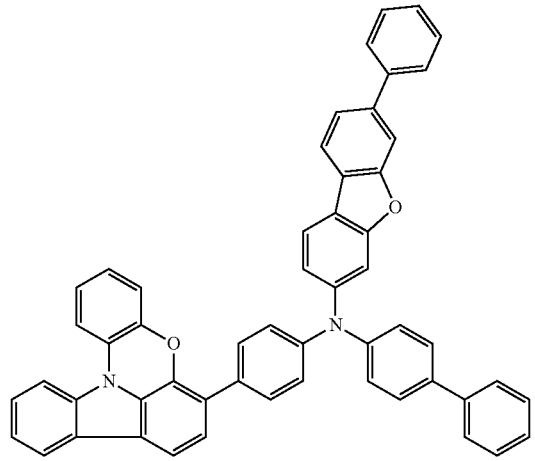
B120
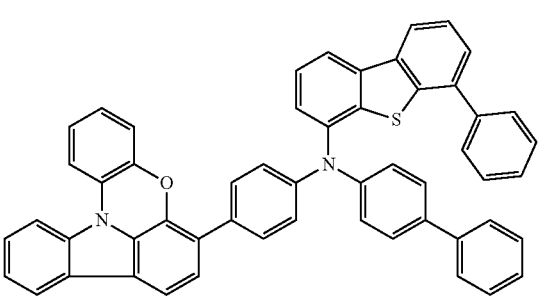

B121
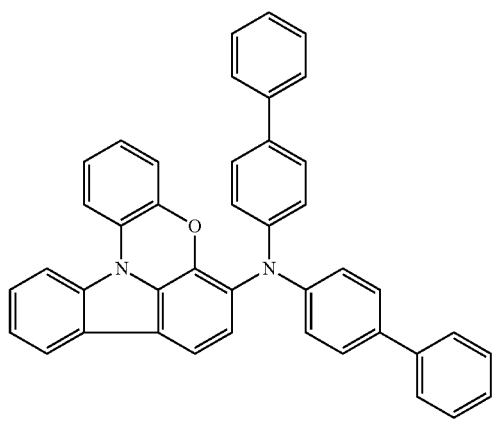
B122
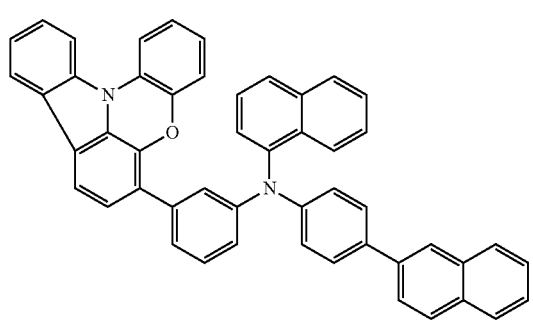
B123
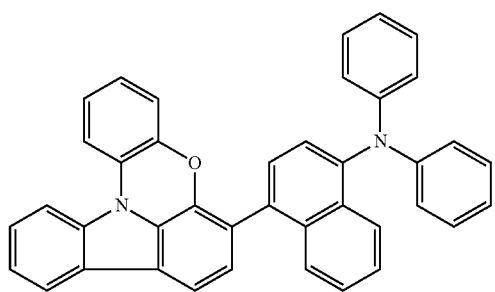
B124
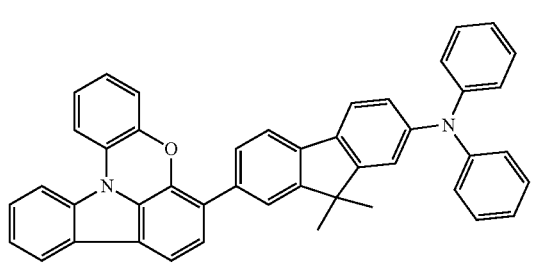
B125
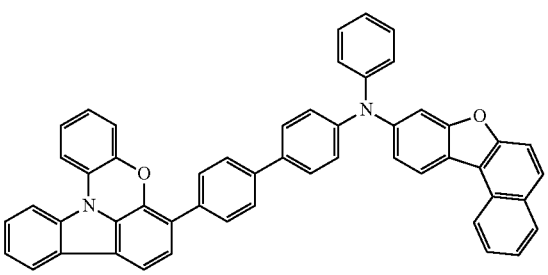
B126
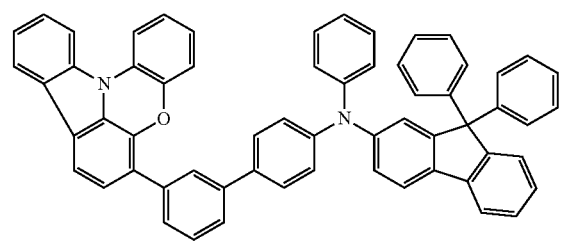
B127
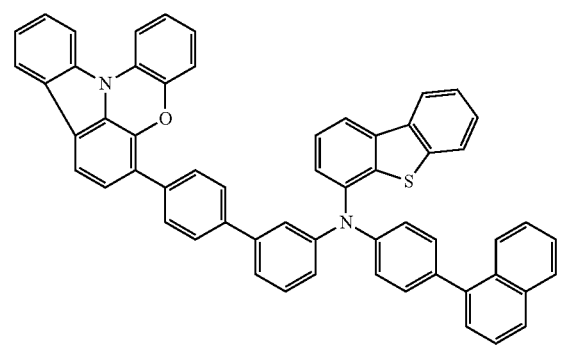
B128
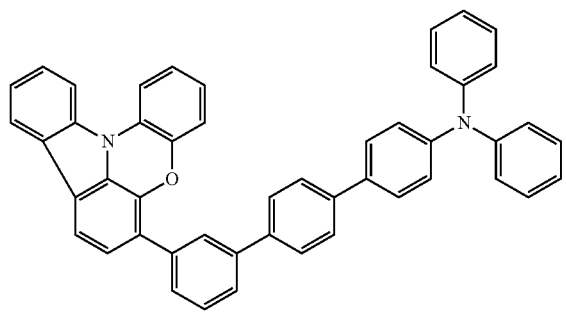
B129
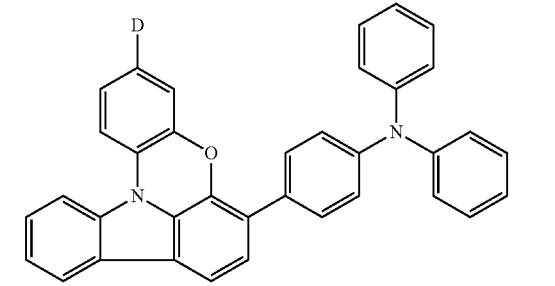
B130
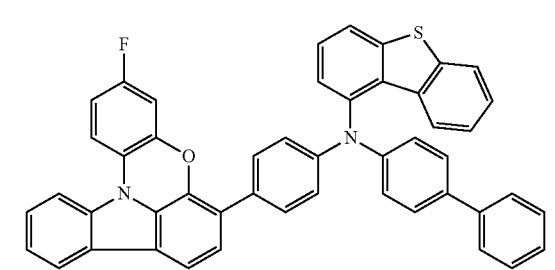

B131
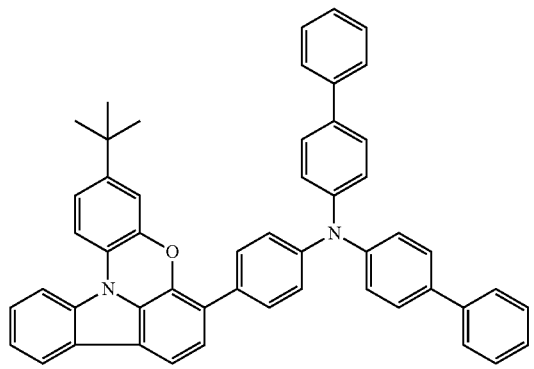
B132
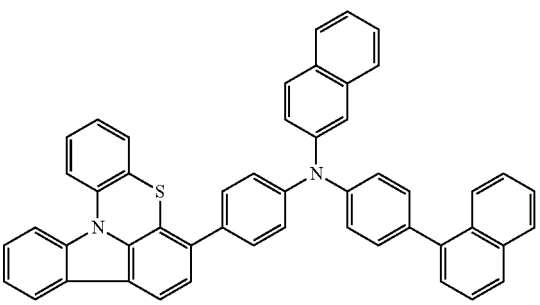
B133
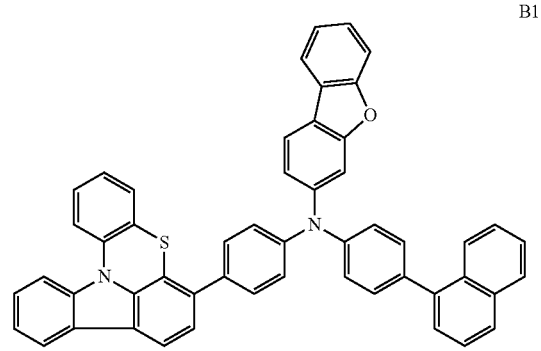
B134
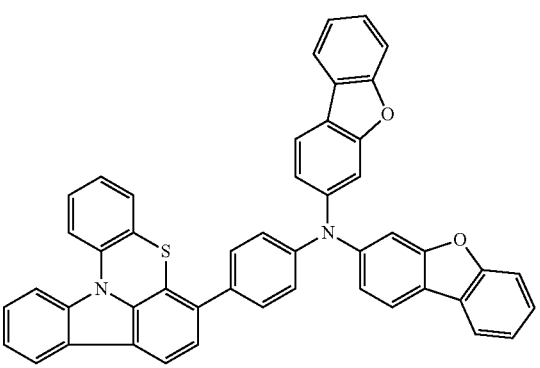
B135
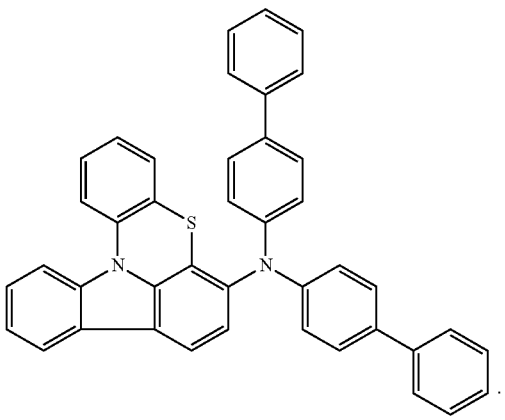
13. The organic electroluminescence device of claim 1, wherein the polycyclic compound of Formula 1 is at least one compound of Compound Group 3:
Compound Group 3
C1
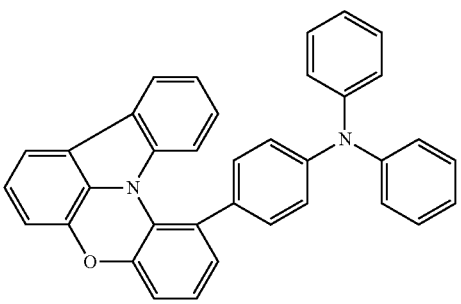
C2
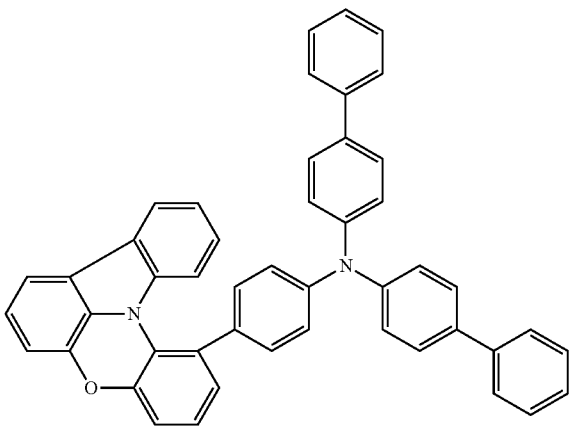

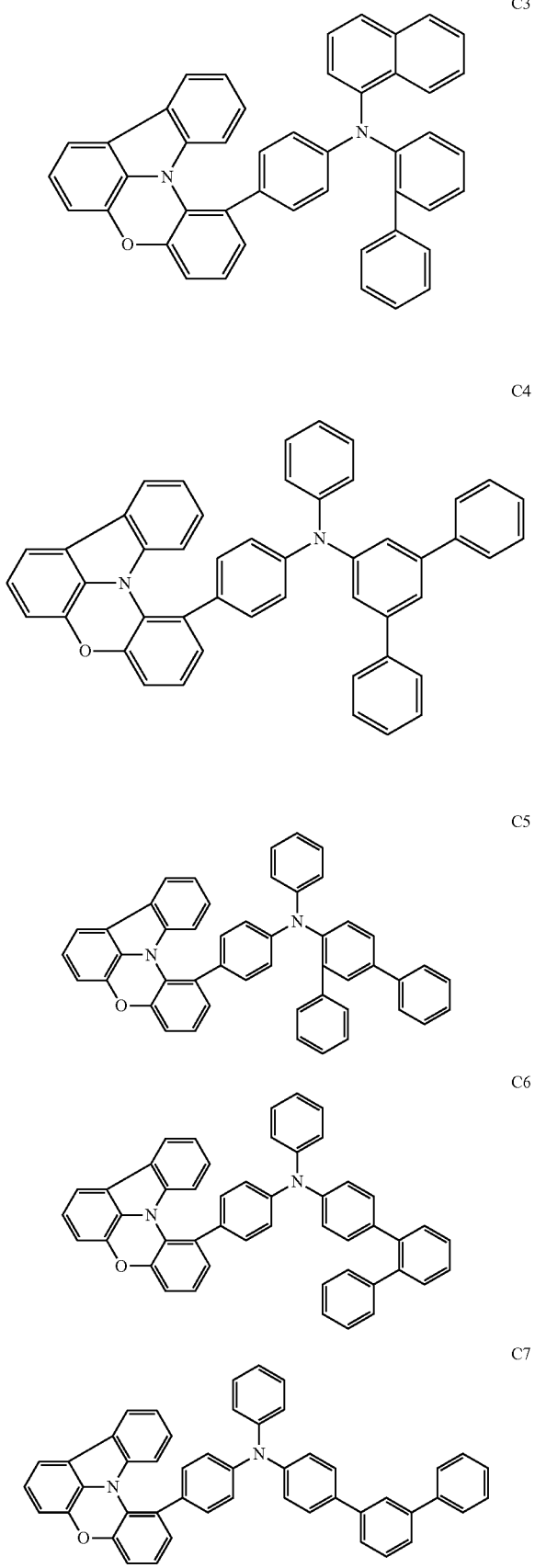
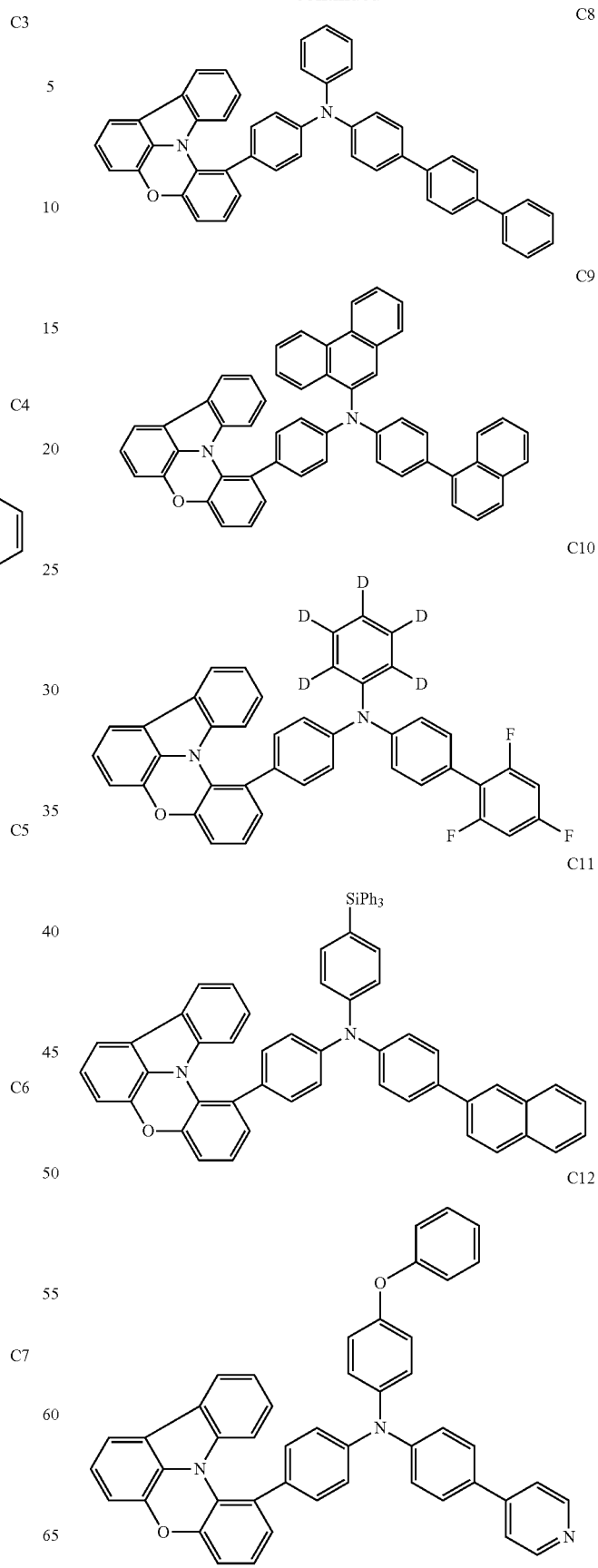

217
-continued
C13
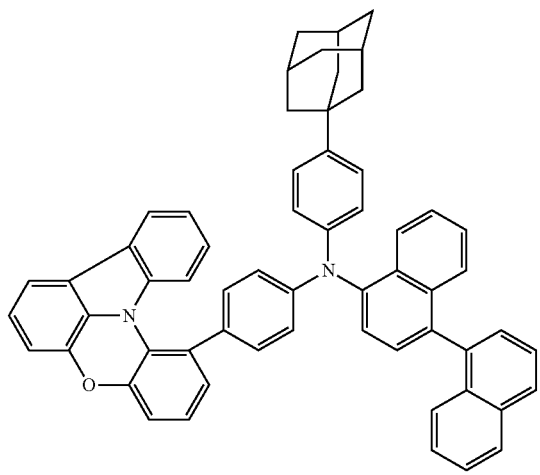
C16
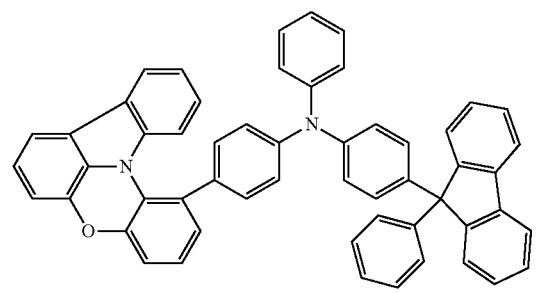
C17
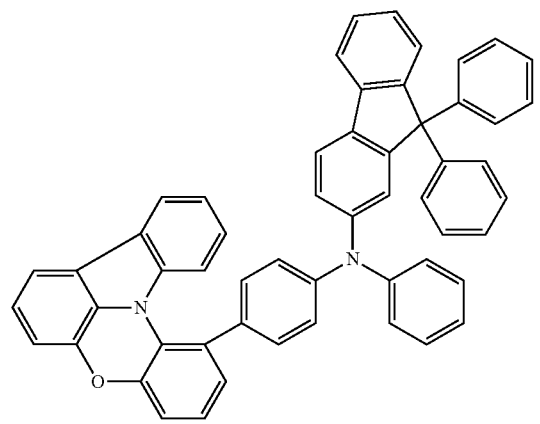
C18
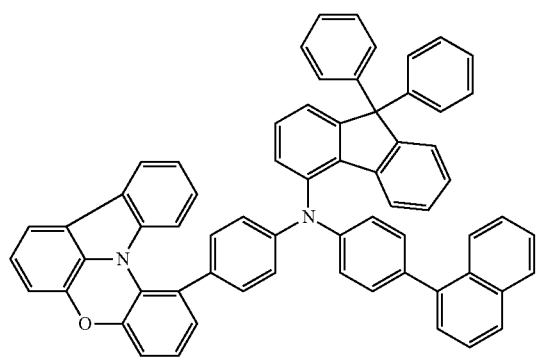
218
-continued
C19
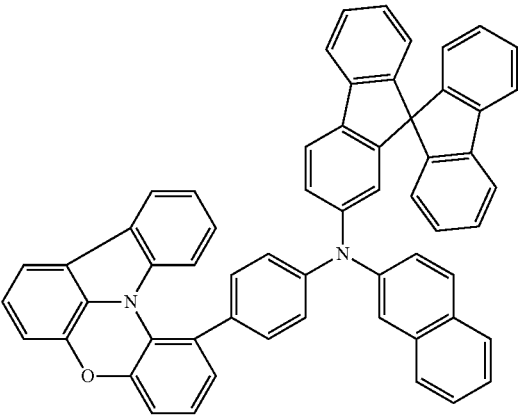
C20
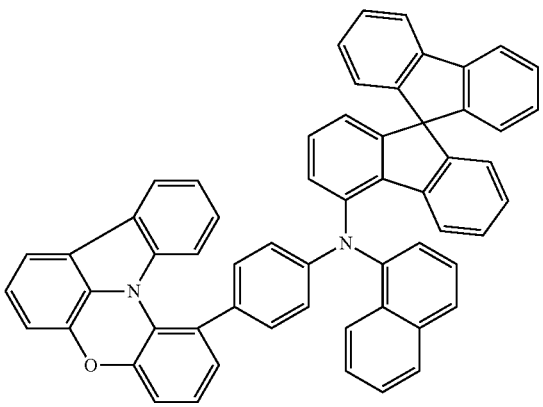
C21
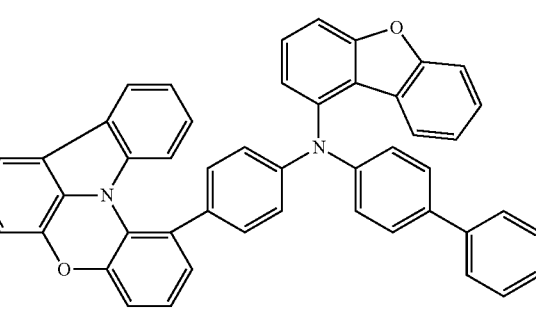
C22
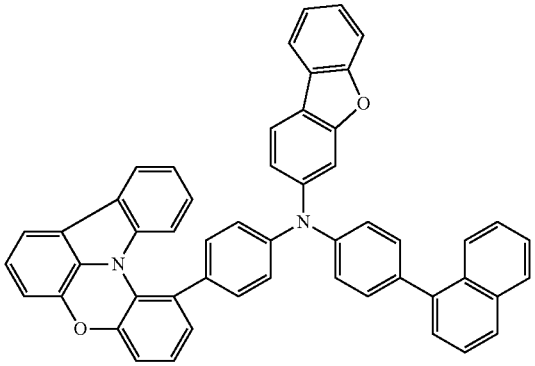

C23
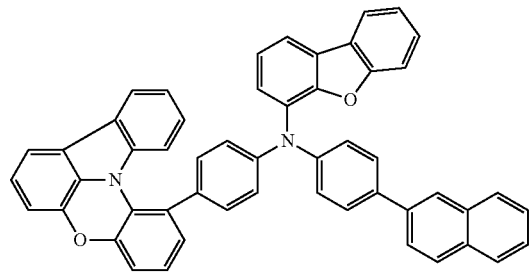
C24
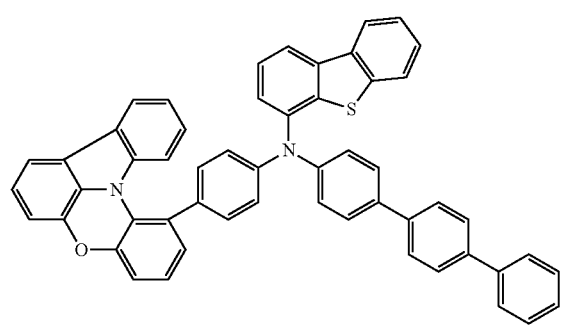
C25
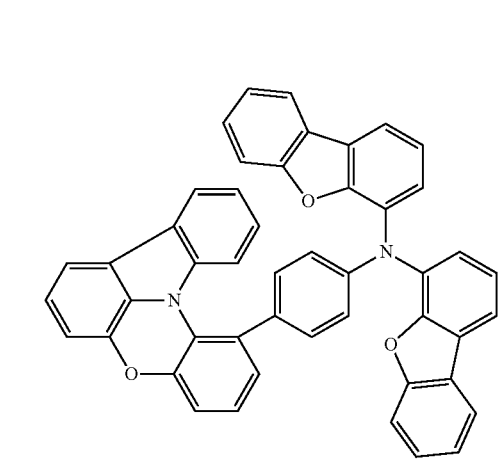
C26
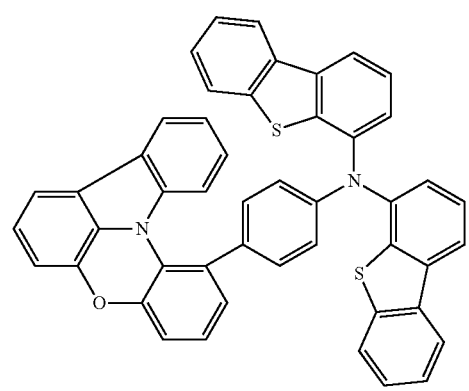
C27
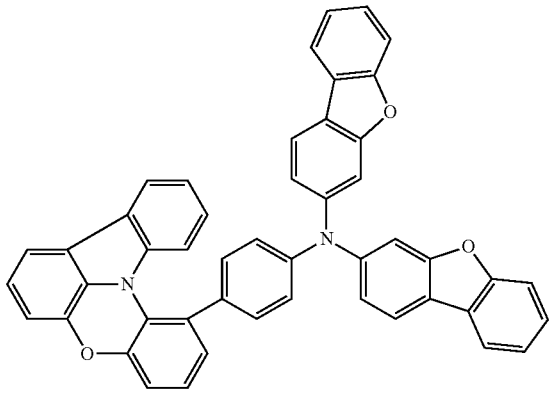
C28
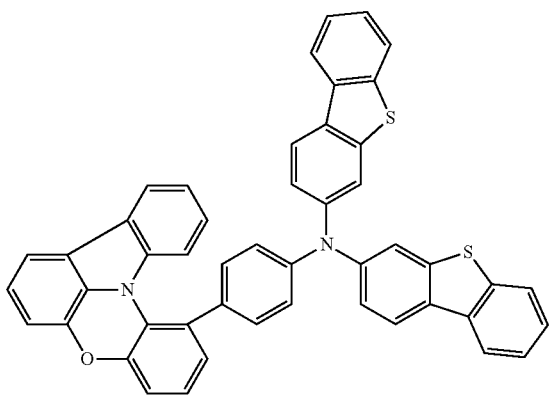
C29
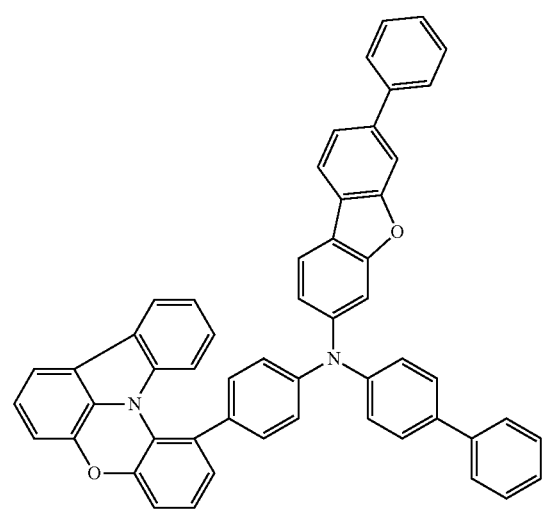

-continued
C30
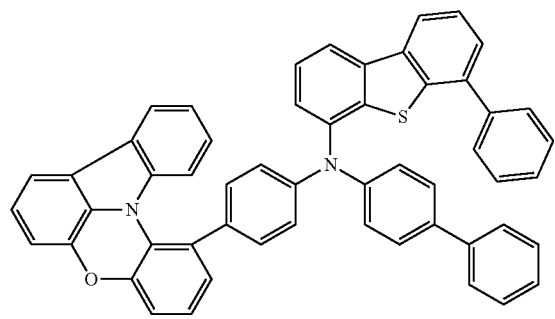
C31
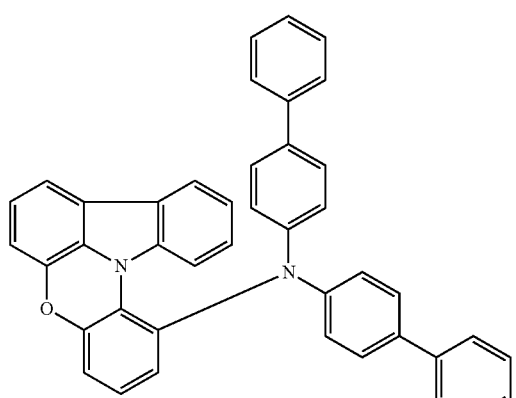
C32
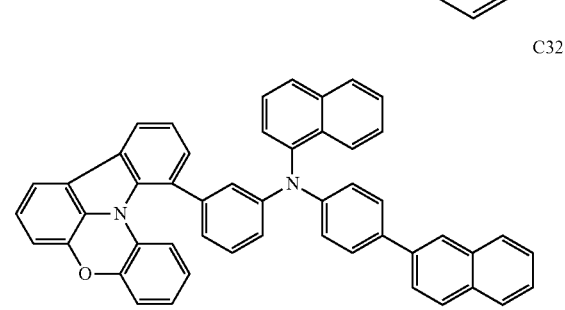
C33
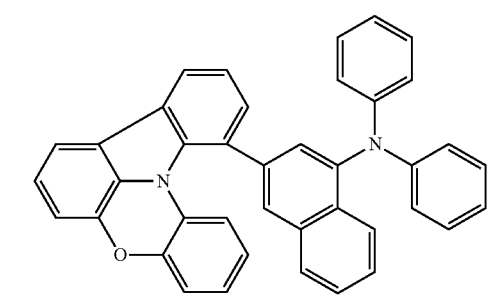
C34
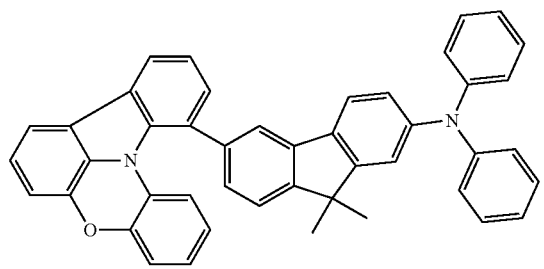
-continued
C35
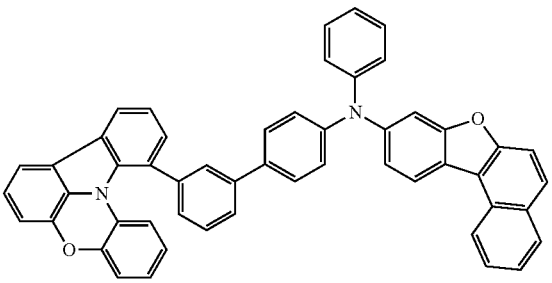
C36
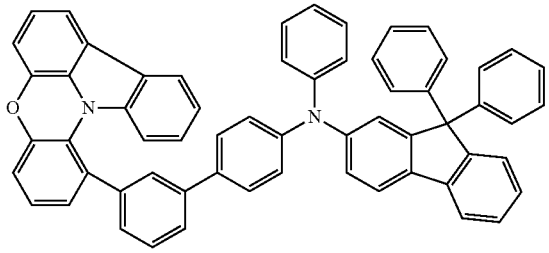
C37
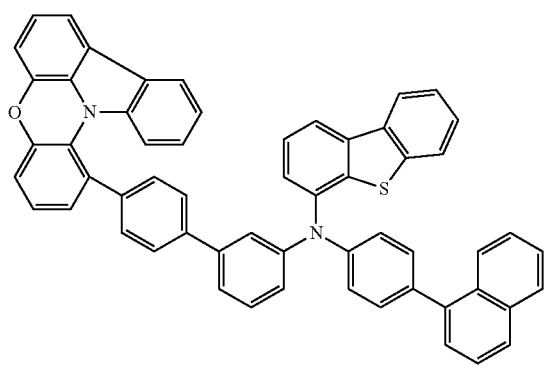
C38
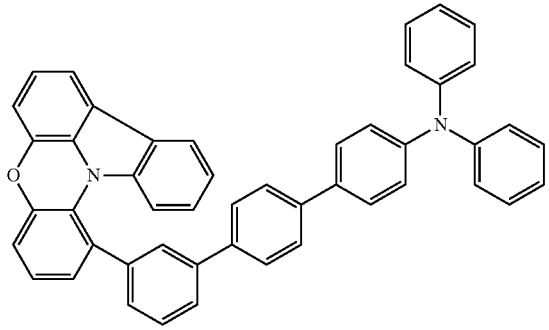
C39
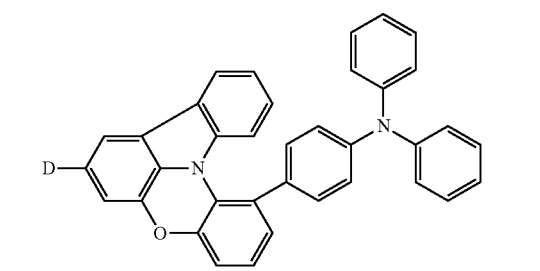

-continued
C40
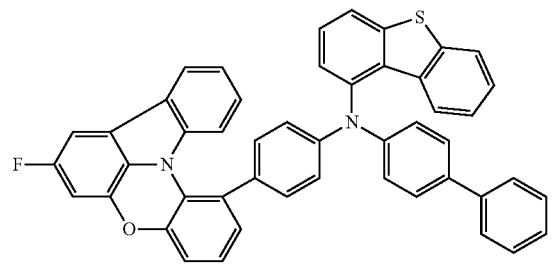
C41
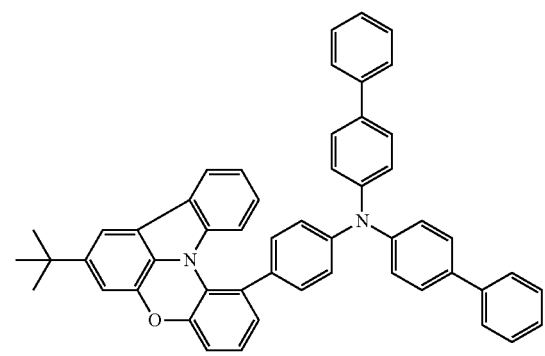
C42
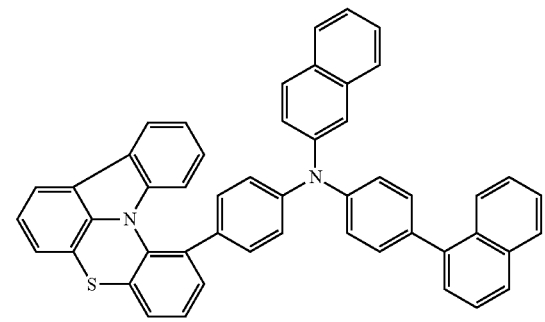
C43
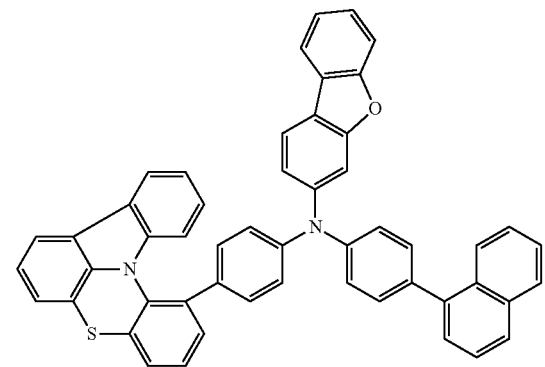
C44
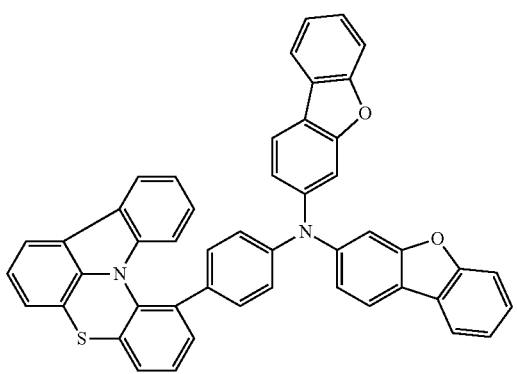
C45
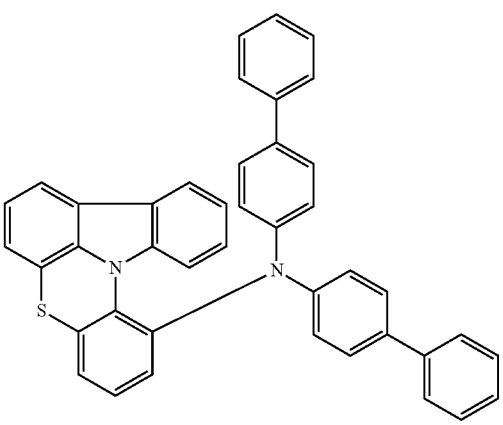
C46
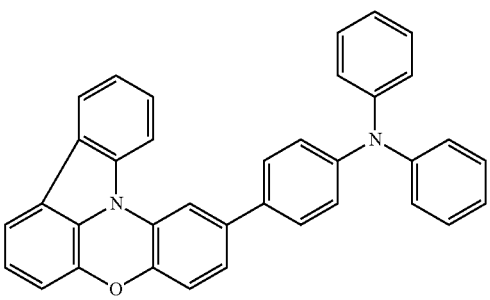
C47
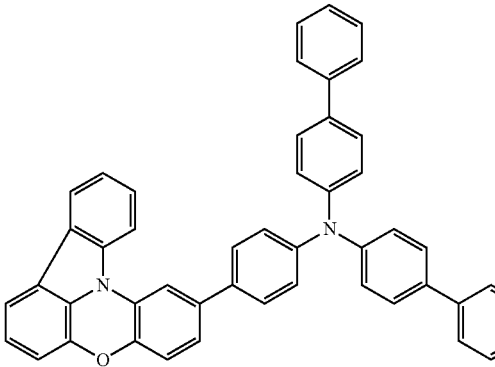

225 226
-continued -continued
C48
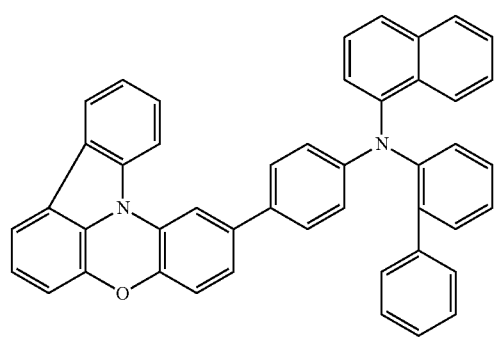
C53
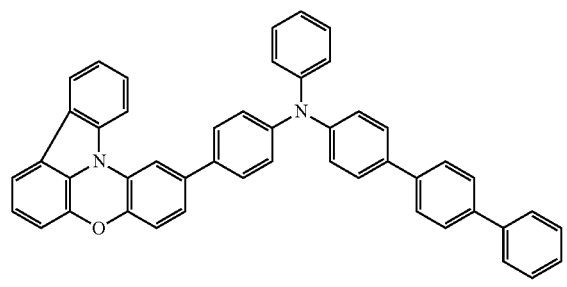
C49
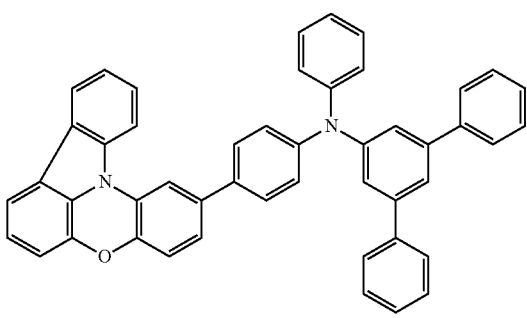
C54
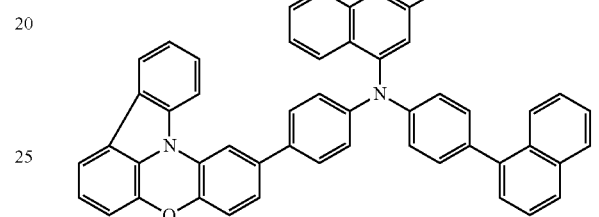
C50
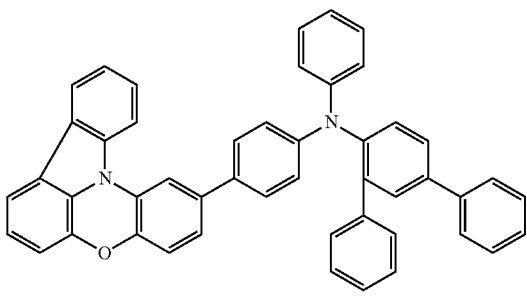
C55
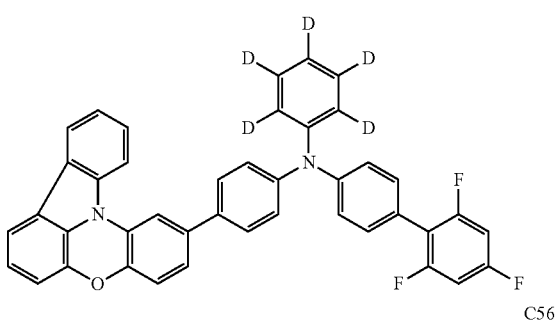
C51
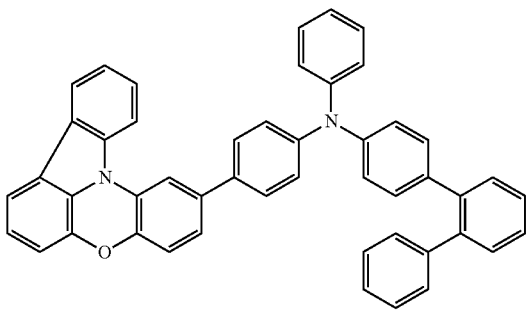
C56
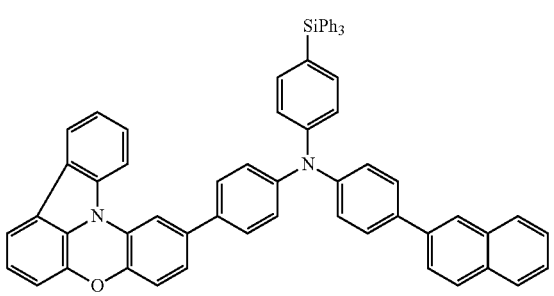
C52
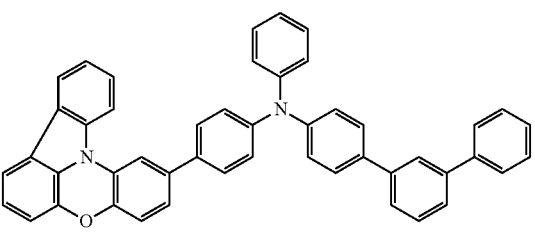
C57
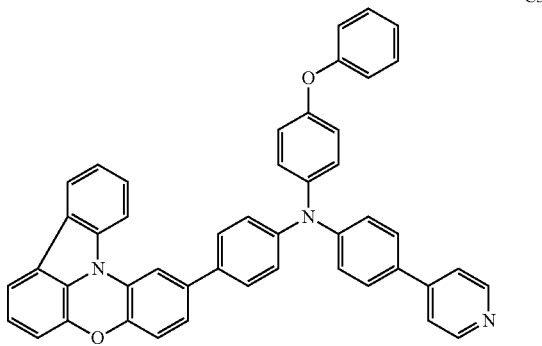

227
-continued
C58
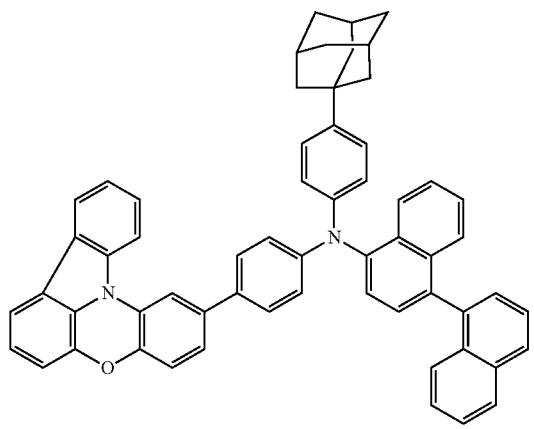
C61
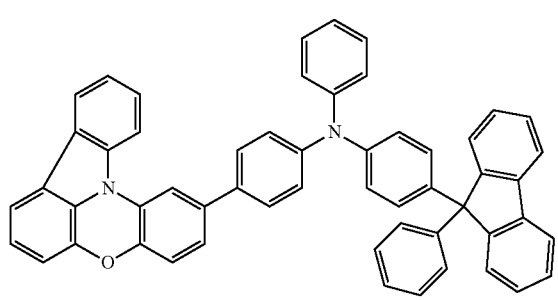
C62
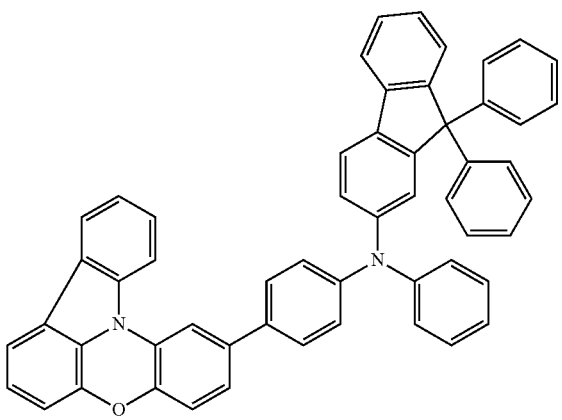
C63
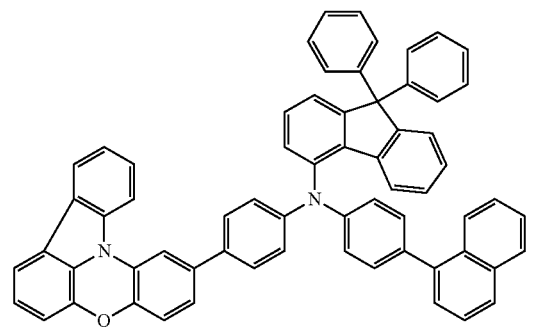
228
-continued
C64
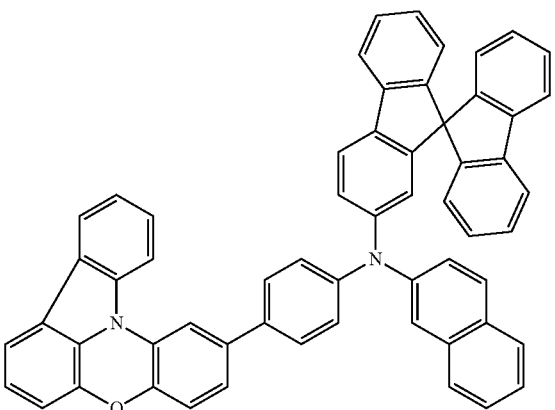
C65
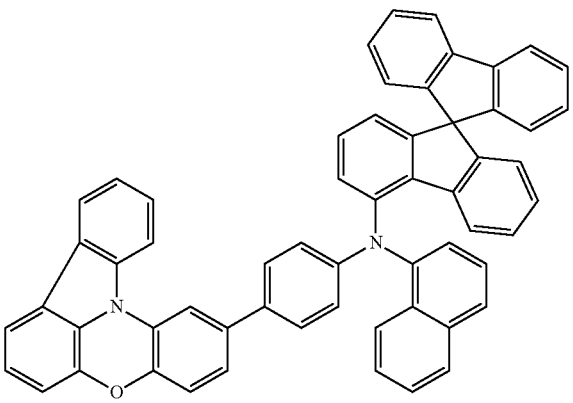
C66
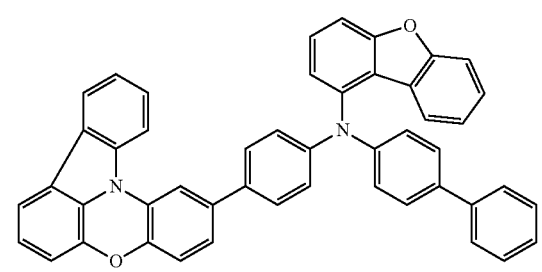
C67
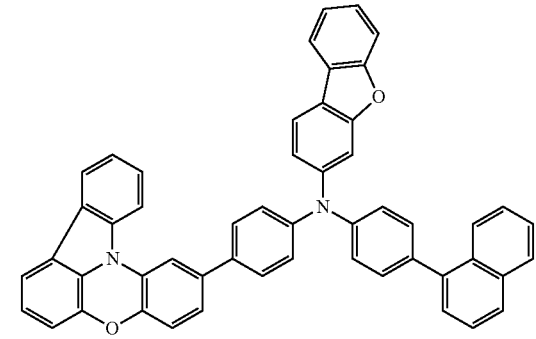

C68
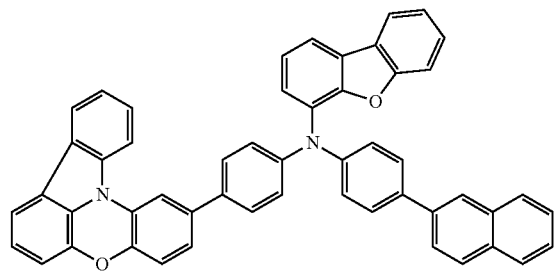
C69
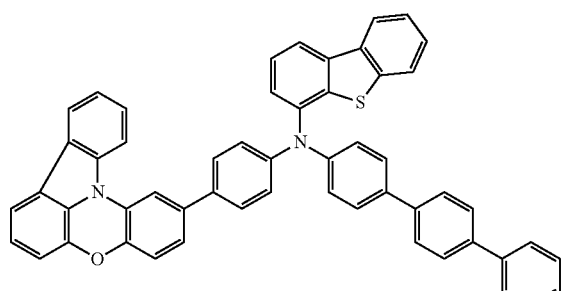
C70
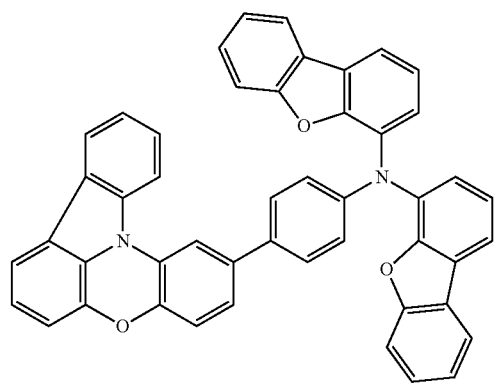
C71
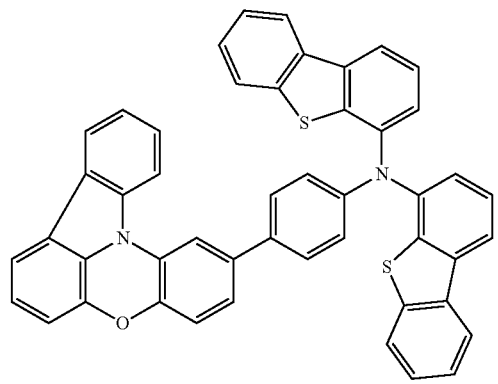
C72
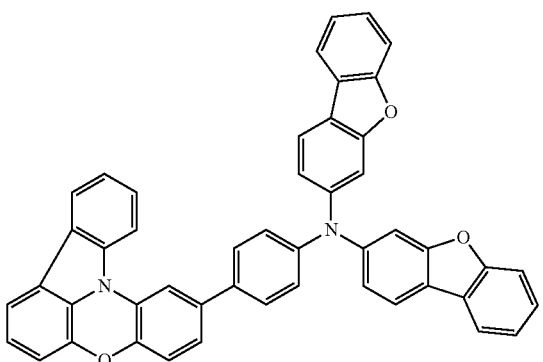
C73
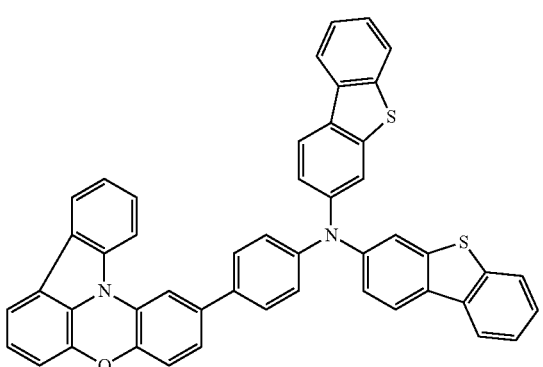
C74
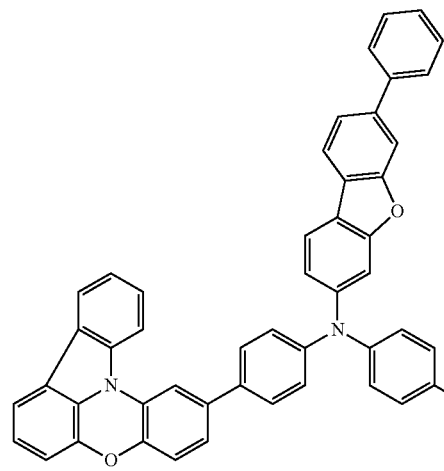
C75
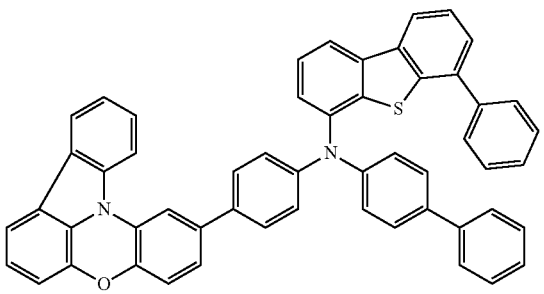

-continued
C76
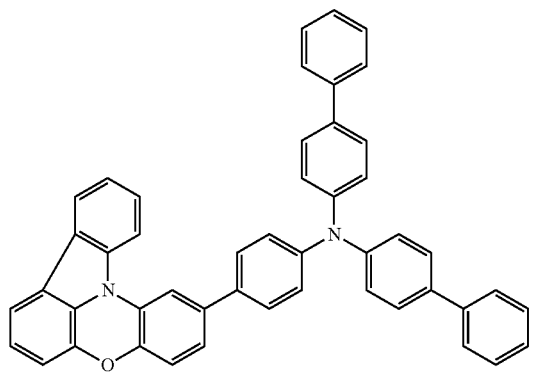
C78
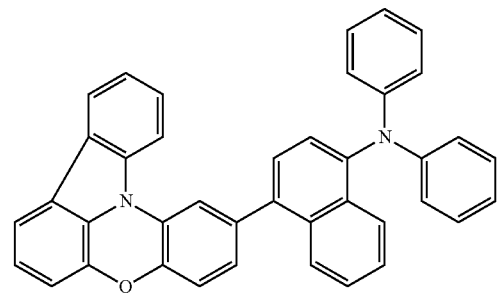
C79
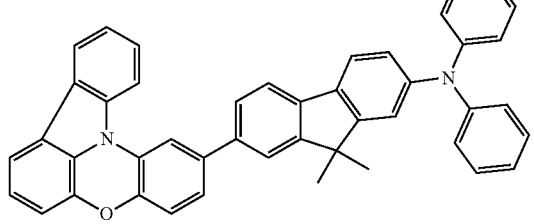
C80
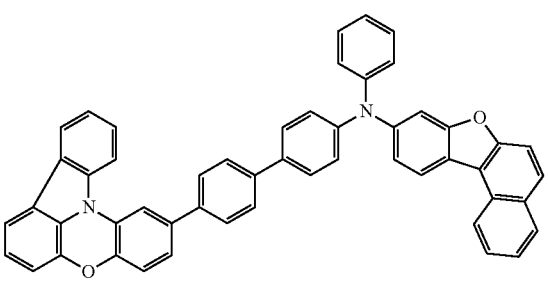
C81
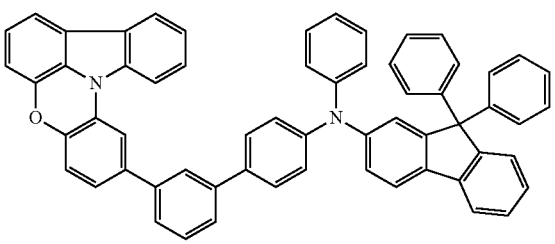
-continued
C82
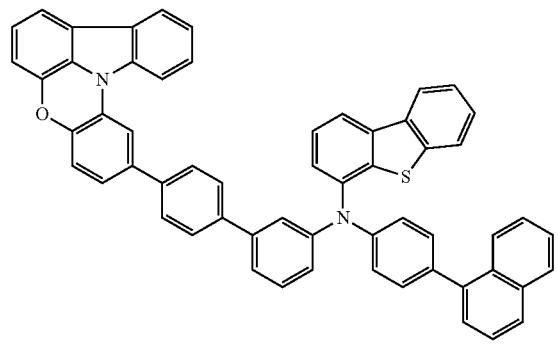
C83
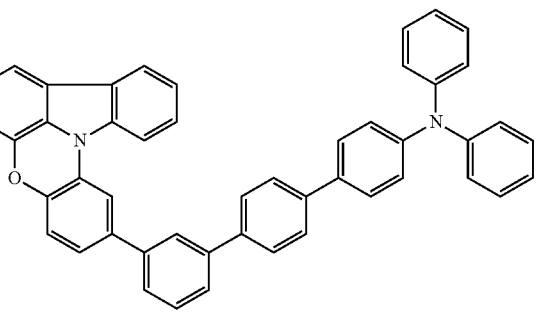
C84
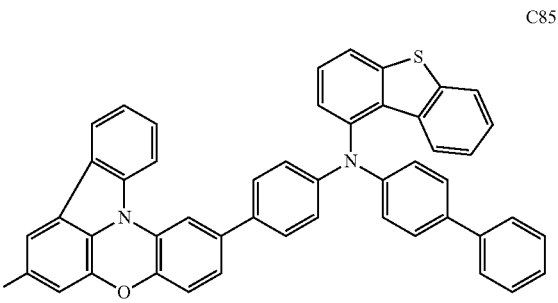
C85
C86
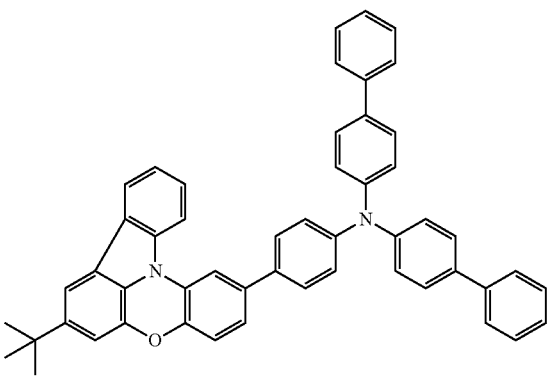

-continued
C87
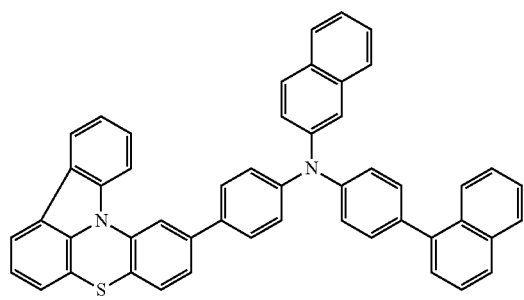
C88
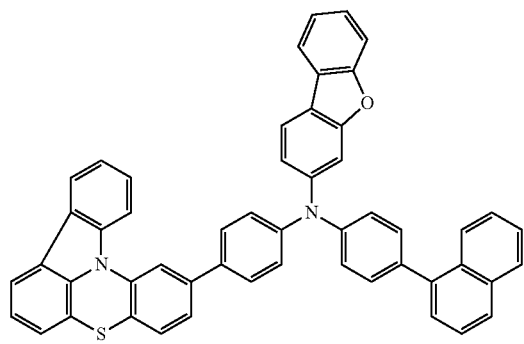
C89
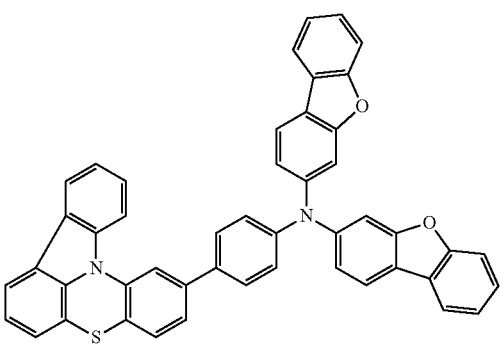
C90
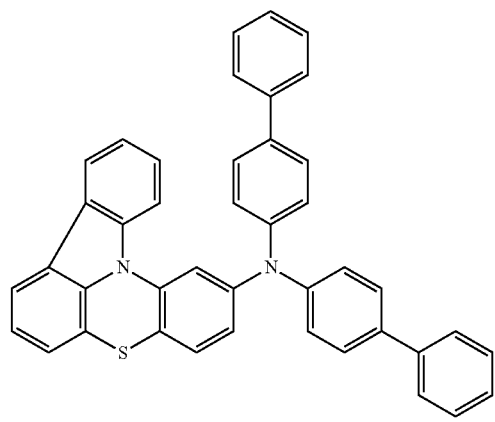
-continued
C136
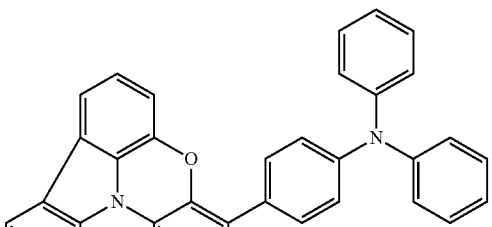
C137
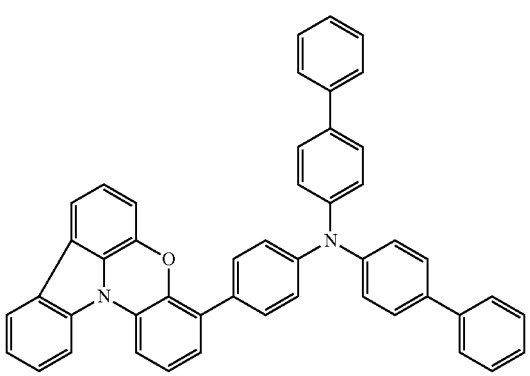
C138
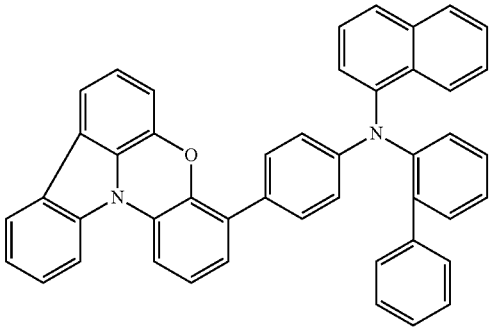
C139
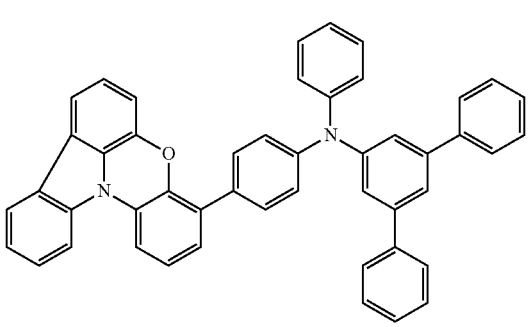

C140
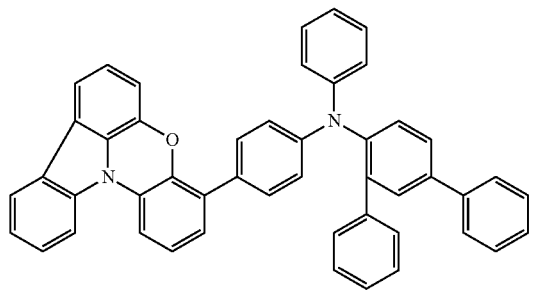
C141
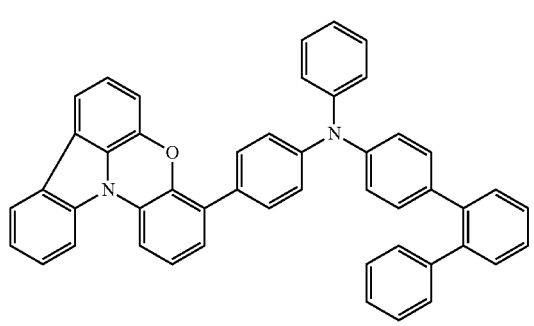
C142
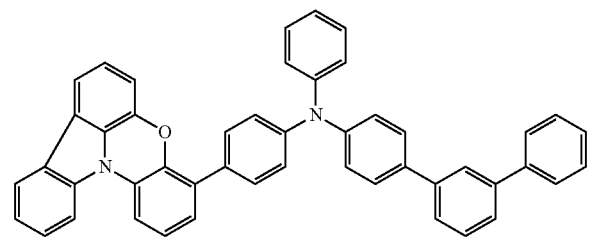
C143
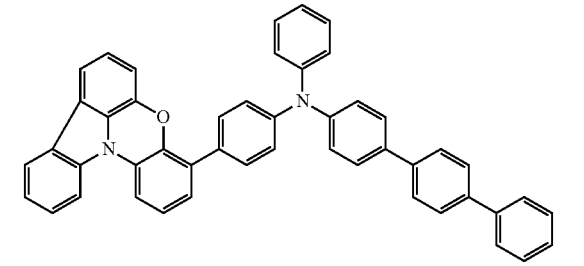
C144
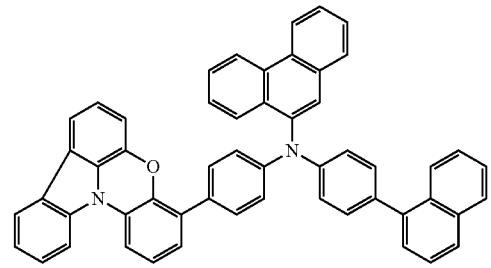
C145
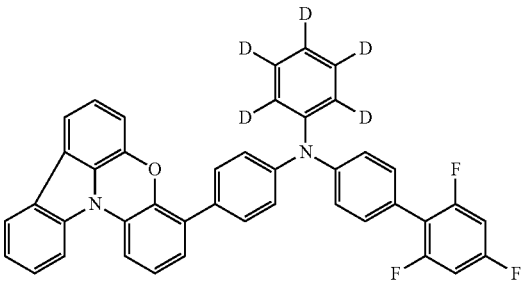
C146
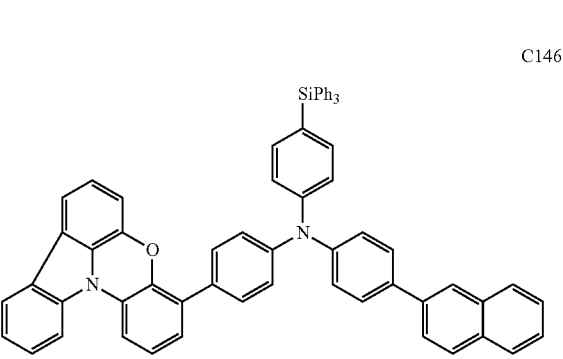
C147
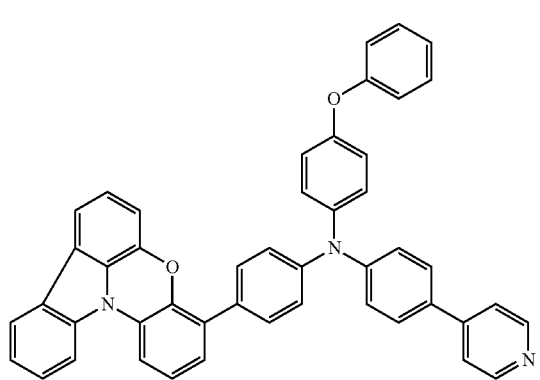
C148
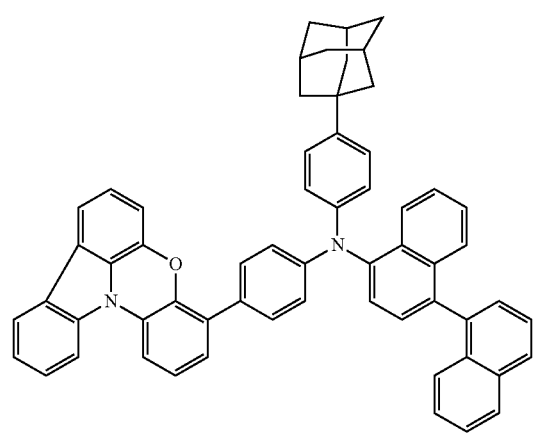

C151
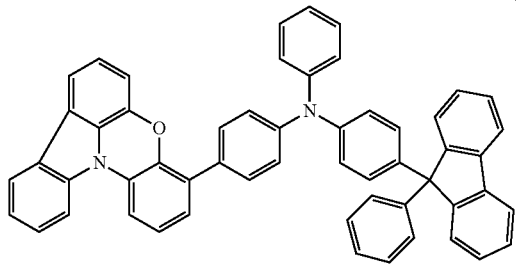
C152
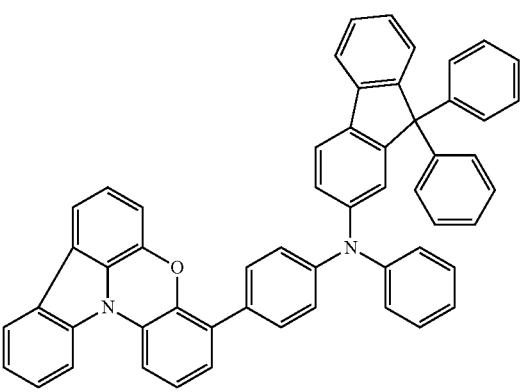
C153
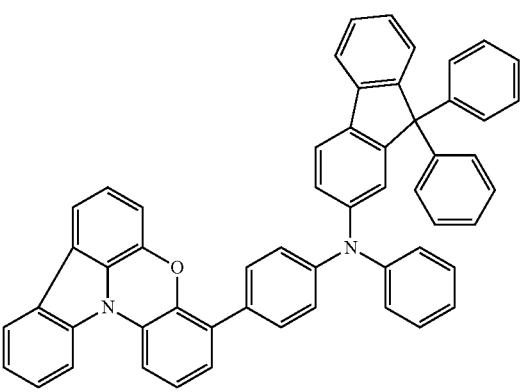
C154
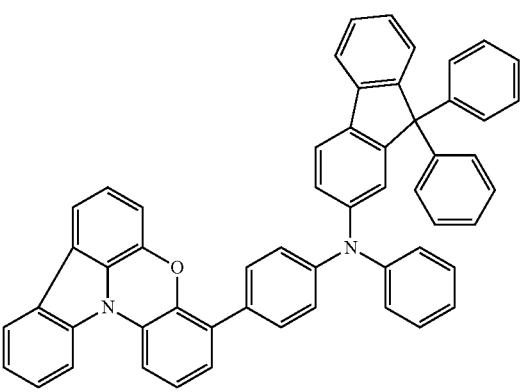
C155
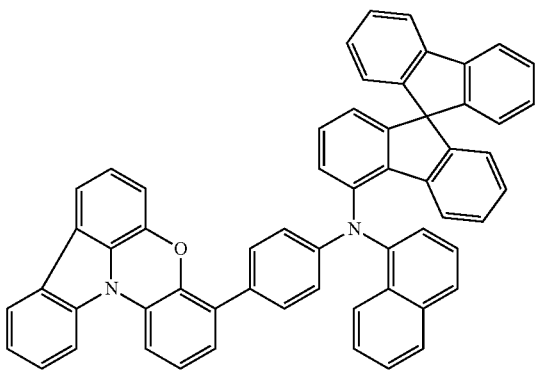
C156
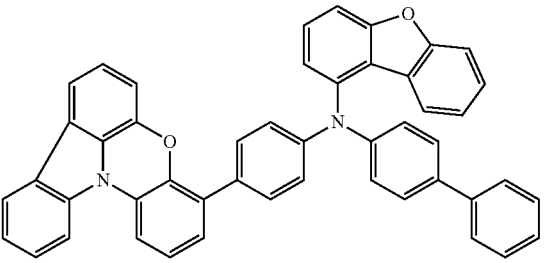
C157
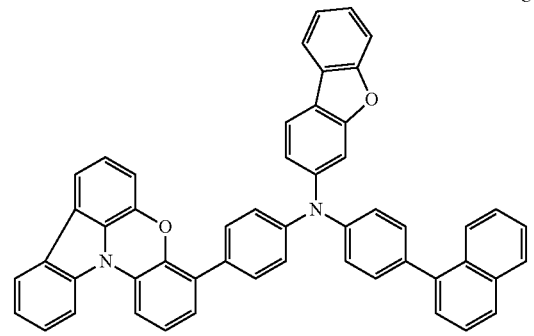
C158
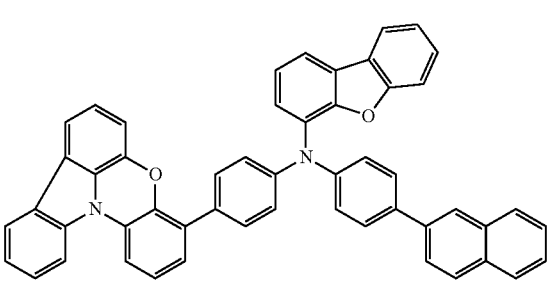
C159
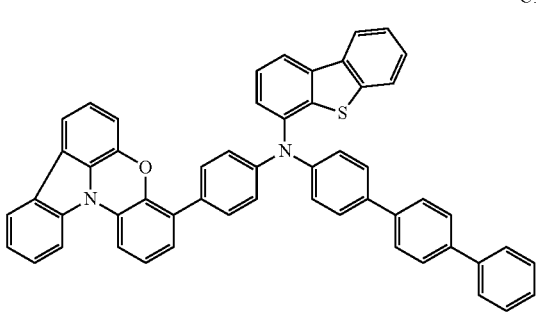

-continued
C160
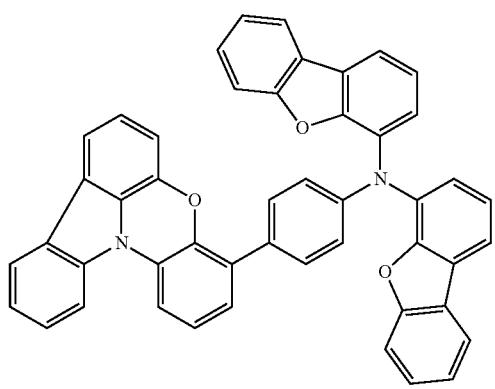
C161
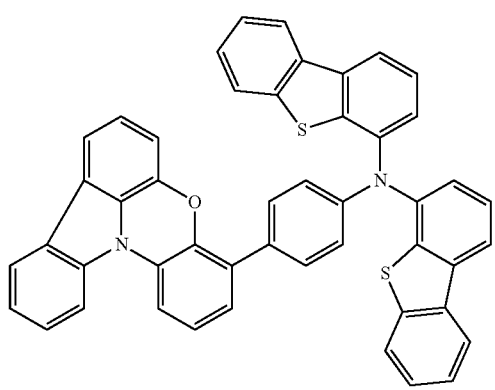
C162
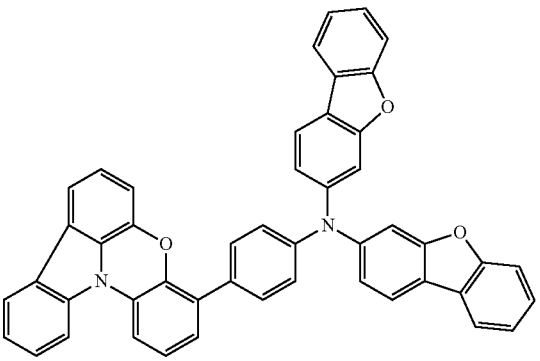
C163
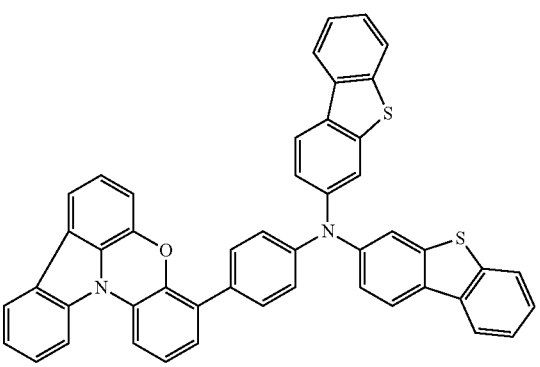
-continued
C164
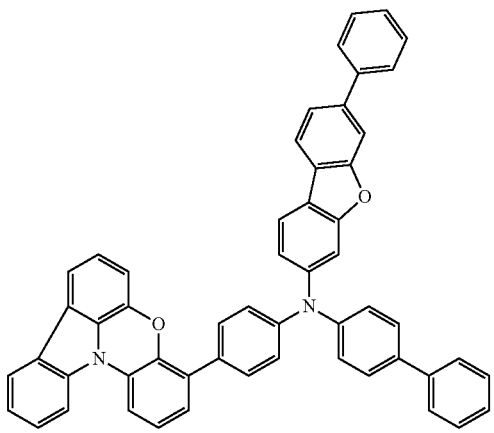
C165
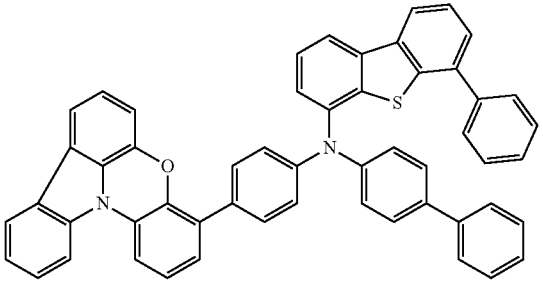
C166
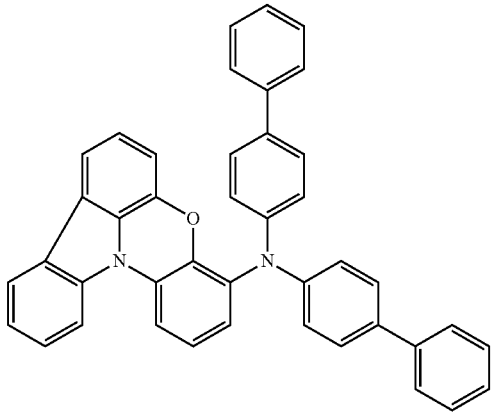
C167

C168
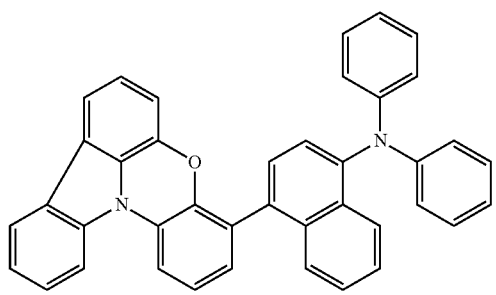
C169
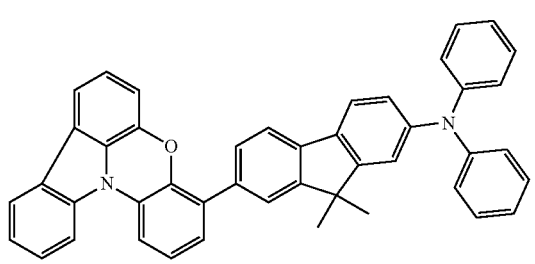
C170
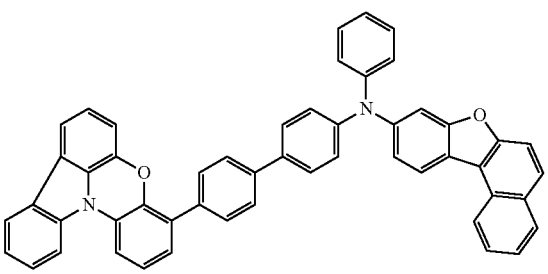
C171
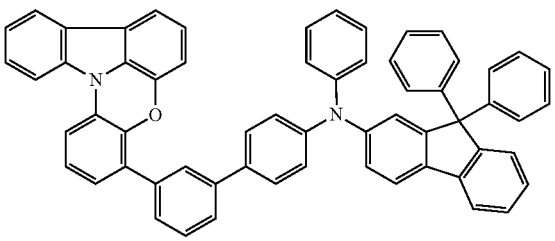
C172
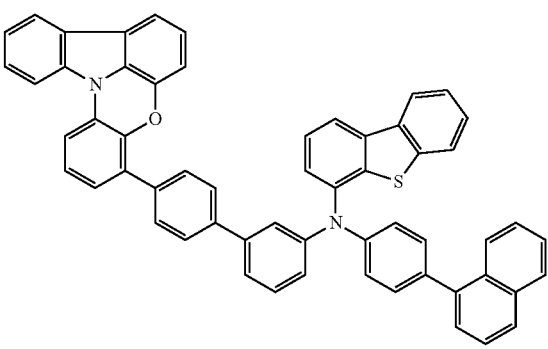
C173
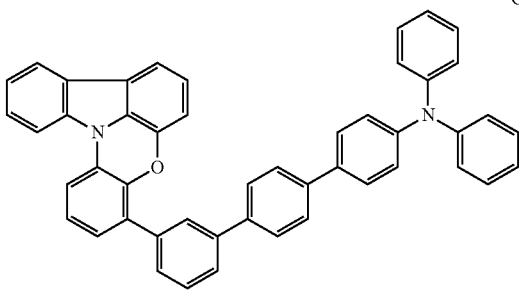
C174
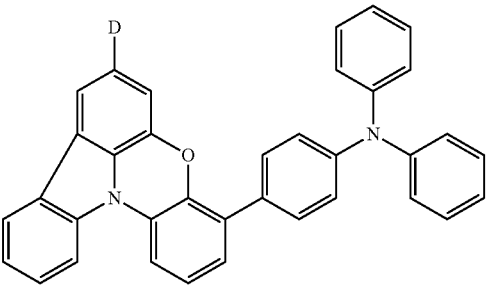
C175
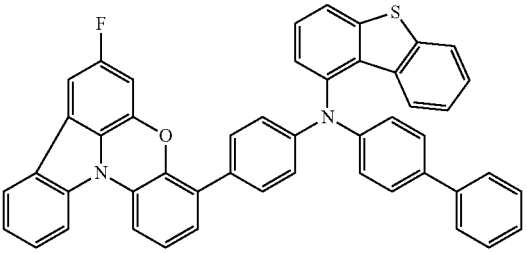
C176
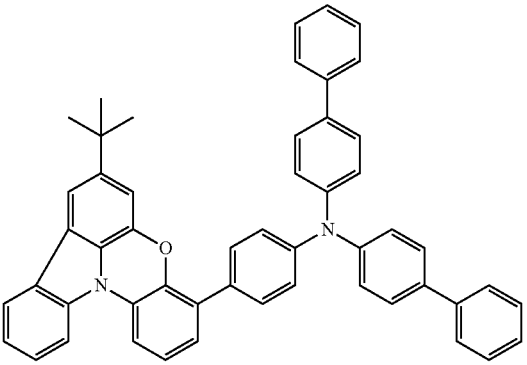
C177
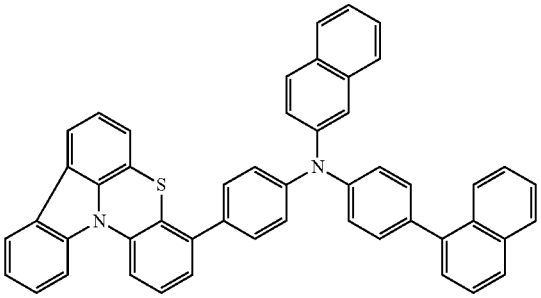

-continued

C178
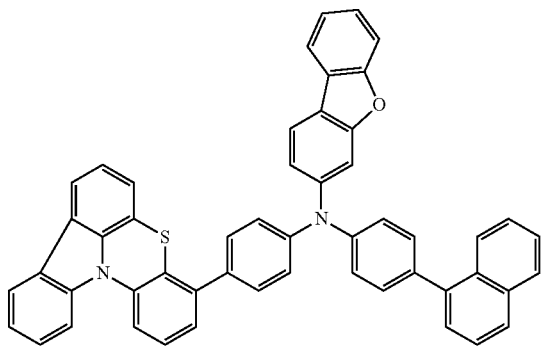

C179
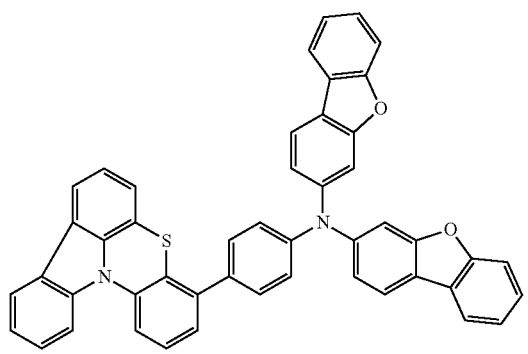

C180
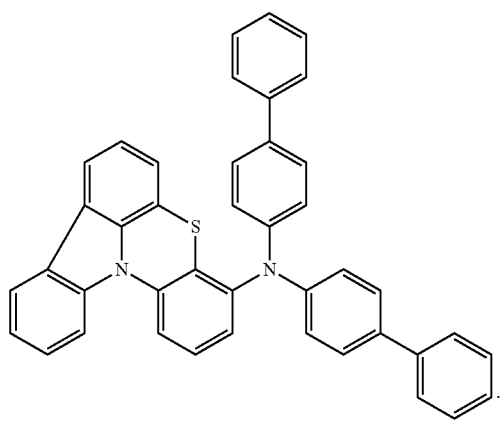

14. A polycyclic compound of the following Formula 1 for an organic electroluminescence device:

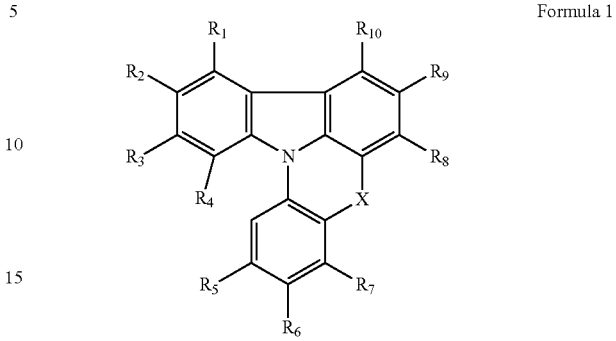

Formula 1 wherein, in Formula 1,
X is O or S;
at least one among $R_1$, $R_3$ to $R_5$, $R_7$, $R_8$, and $R_{10}$ is an amine group of Formula 2:

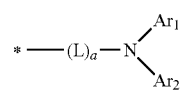

Formula 2 wherein, in Formula 2,
L is a direct linkage, a substituted or unsubstituted arylene group having 6 to 30 ring-forming carbon atoms, or a substituted or unsubstituted heteroarylene group having 2 to 30 ring-forming carbon atoms, provided that L does not include a carbazole group;
$Ar_1$ and $Ar_2$ are each, independently from one another, a substituted or unsubstituted aryl group having 6 to 30 ring-forming carbon atoms, or a substituted or unsubstituted heteroaryl group having 2 to 30 ring-forming carbon atoms, where $Ar_1$ and $Ar_2$ do not bond to each other to form a ring, and
a is 0, 1, 2, 3, or 4, and
the remainder of $R_1$, $R_3$ to $R_5$, $R_7$, $R_8$, and $R_{10}$, which do not include an amine group of Formula 2, are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms,
$R_2$, $R_6$, and Ry are each, independently from one another, a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and
when a is 0, only one of $R_1$, $R_3$ to $R_5$, $R_7$, $R_8$, and $R_{10}$ is an amine group of Formula 2, and
when a is 0, neither $Ar_1$ nor $Ar_2$ are phenyl groups having six ring-forming carbon atoms.
15. The polycyclic compound of claim 14, wherein the compound of Formula 1 is a compound by any one among Formula 3 to Formula 5:

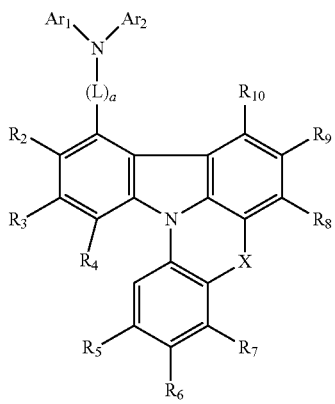

Formula 3

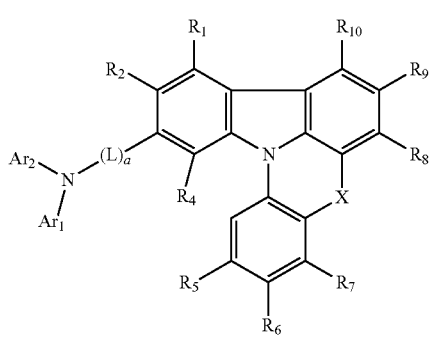

Formula 4

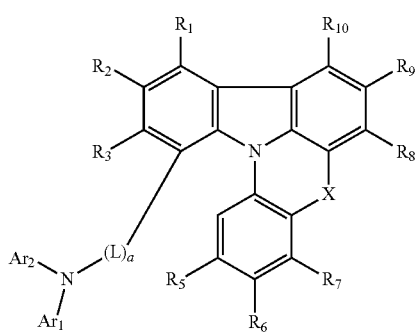

Formula 5 wherein, in Formula 3 to Formula 5, $R_1$ to $R_{10}$ are each, independently from one another, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms; and X, $Ar_1$, $Ar_2$, L, and a have the same meanings as in Formula 1 and Formula 2 of claim 14.

16. The polycyclic compound of claim 14, wherein the compound of Formula 1 is a compound of Formula 6 or Formula 7:

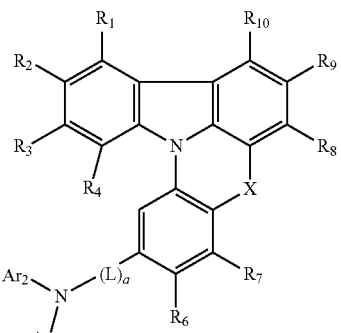

Formula 6

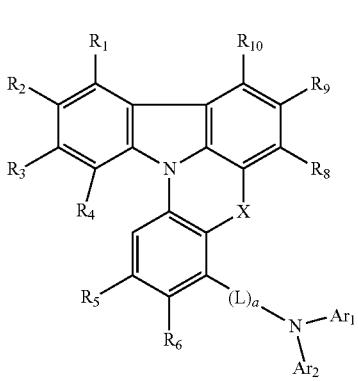

Formula 7 wherein, in Formula 6 and Formula 7, $R_1$ to $R_{10}$ are each, independently from one another, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms; and X, $Ar_1$, $Ar_2$, L, and a have the same meanings as in Formula 1 and Formula 2 of claim 14.

17. The polycyclic compound of claim 14, wherein the compound of Formula 1 is a compound of Formula 8 or Formula 9:

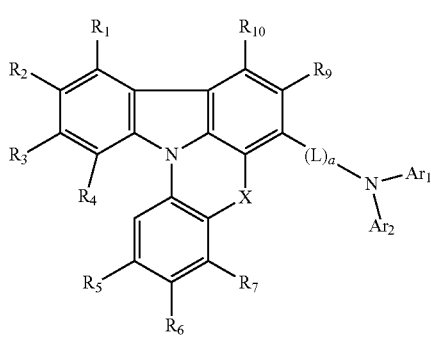

Formula 8

Formula 9

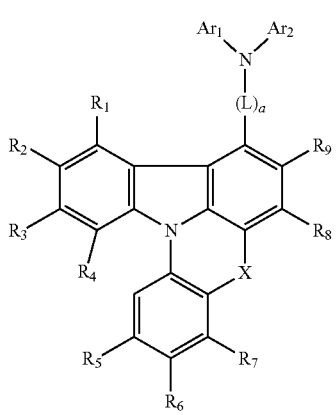

wherein, in Formula 8 and Formula 9, $R_1$ to $R_{10}$ are each, independently from one another, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms; and X, $Ar_1$, $Ar_2$, L, and a have the same meanings as in Formula 1 and Formula 2 of claim 14.

18. The polycyclic compound of claim 14, wherein the polycyclic compound of Formula 1 is a compound of Compound Group 1:

Compound Group 1

A1

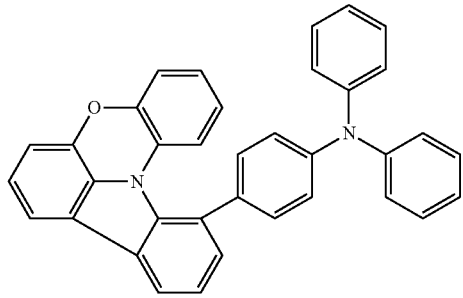

A2

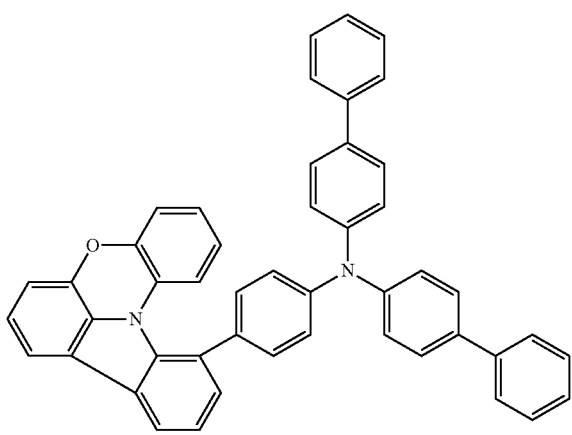

A3

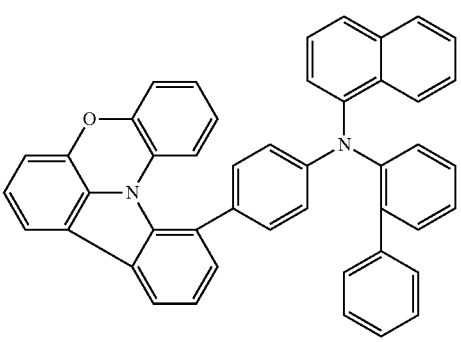

A4

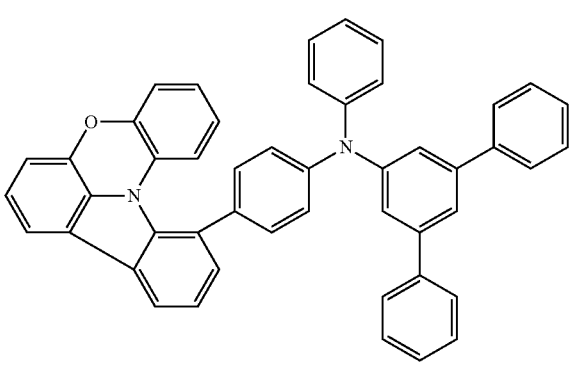

A5

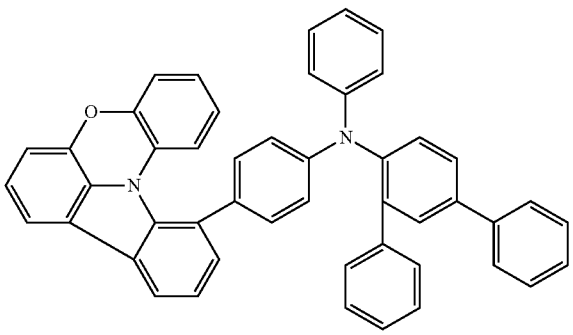

A6

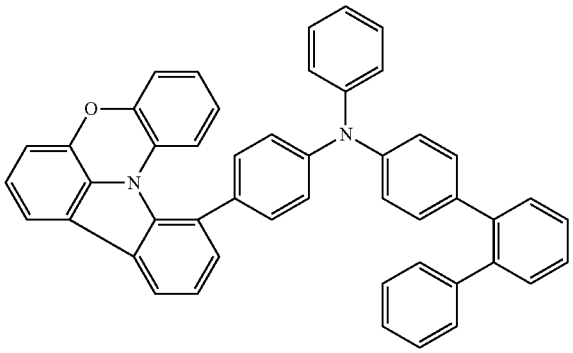

A7
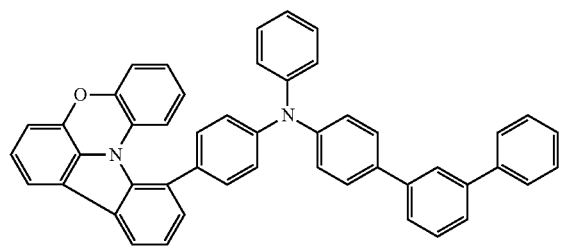
A8
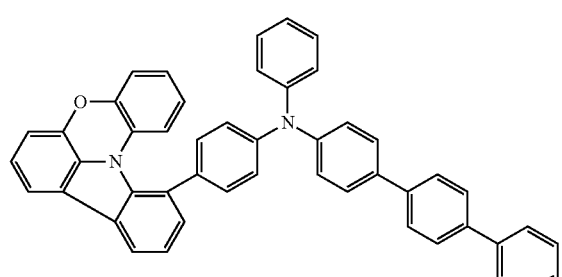
A9
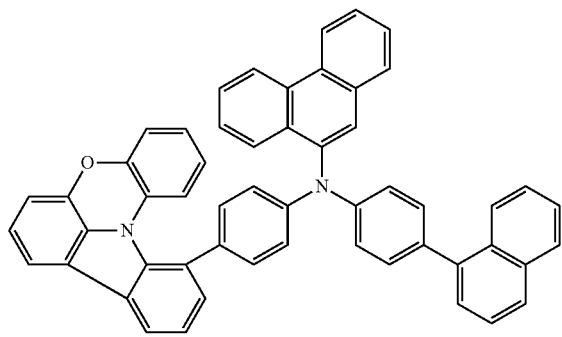
A10
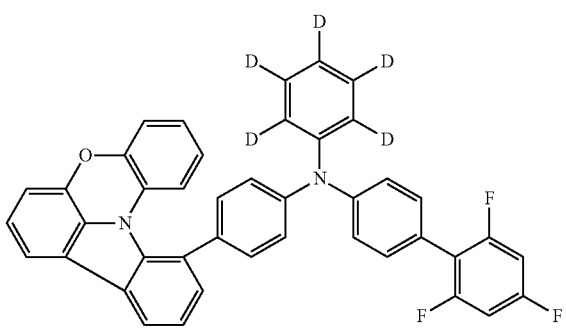
A11
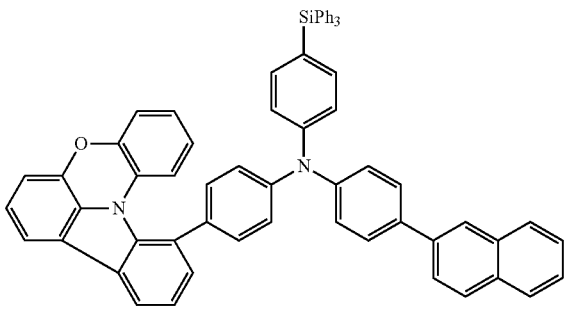
A12
A13
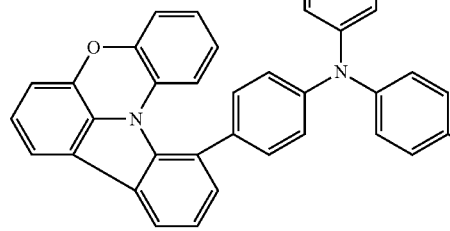
A16
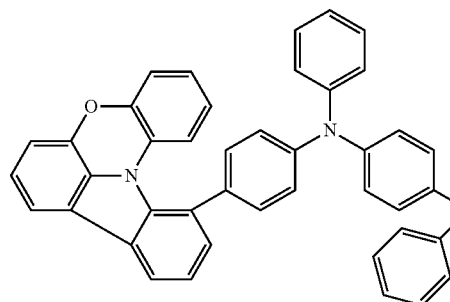

A17
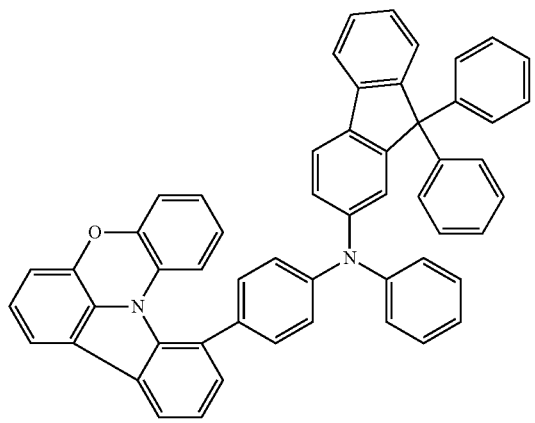
A18
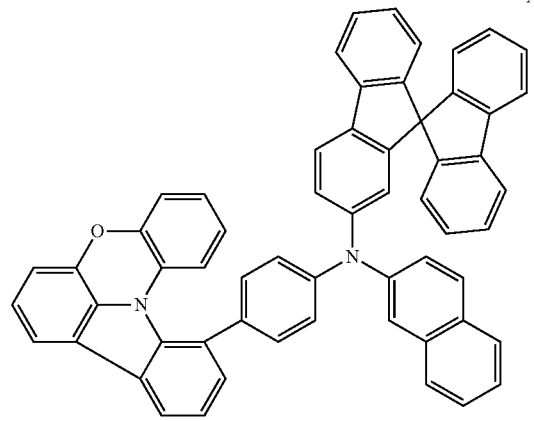
A19
A20
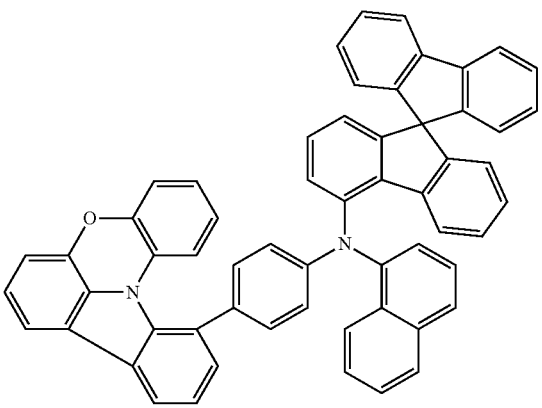
A21
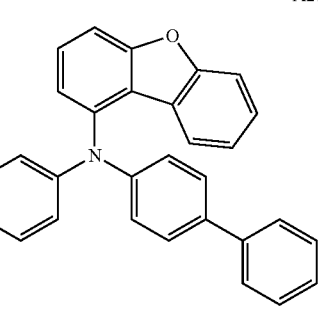
A22
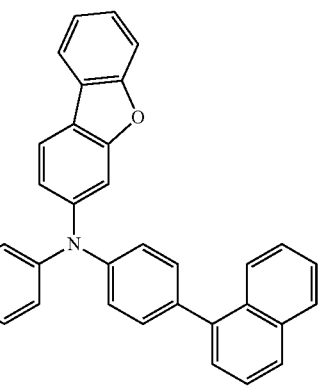
A23
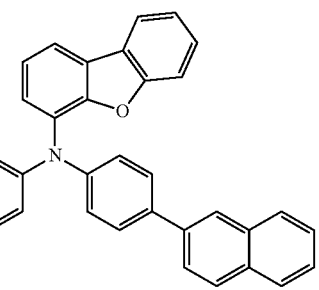

A24
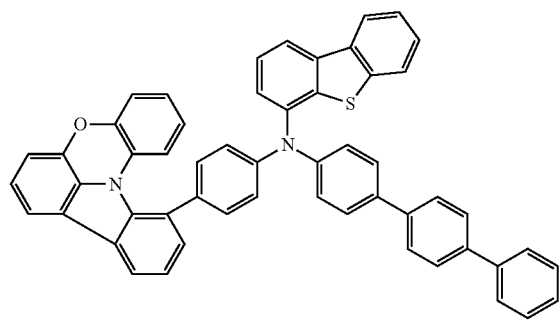
A25
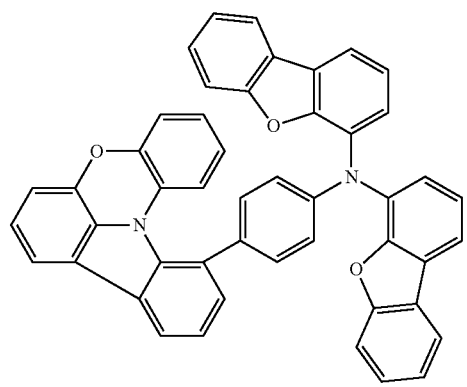
A26
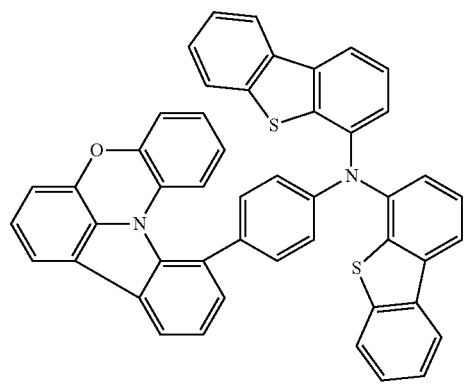
A27
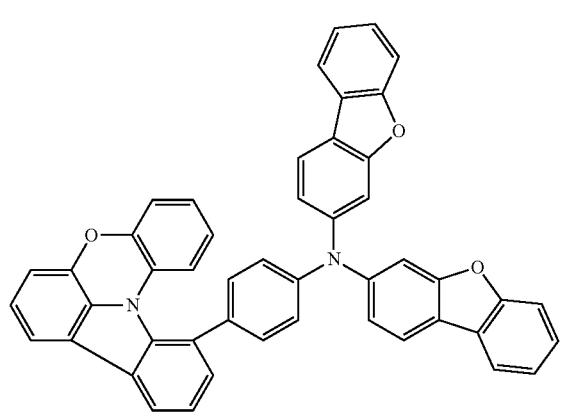
A28
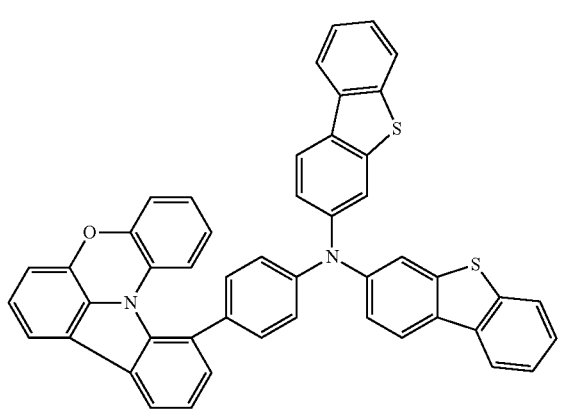
A29
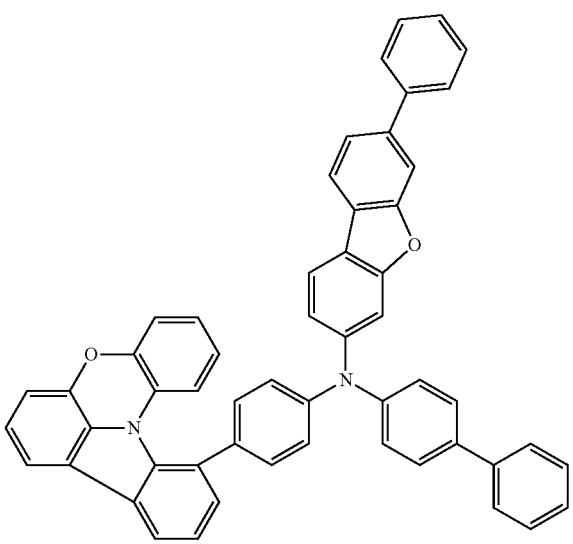
A30
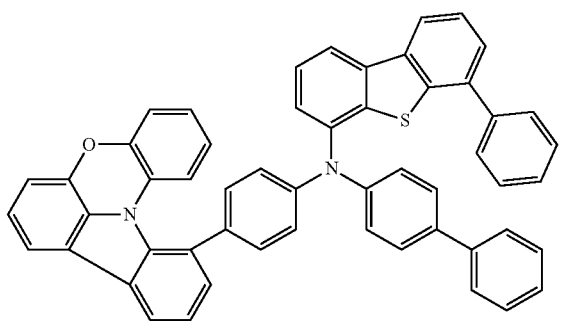

A31
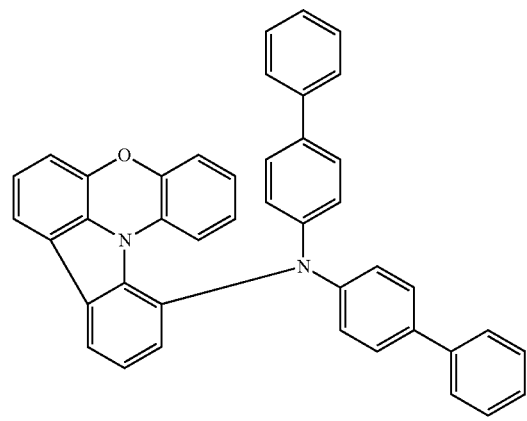
A32
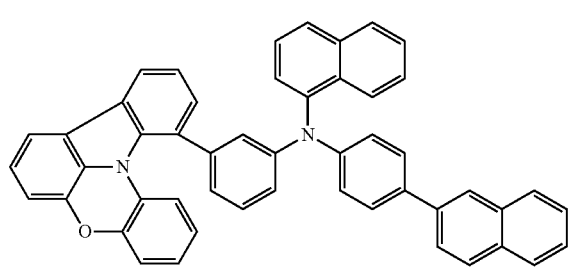
A33
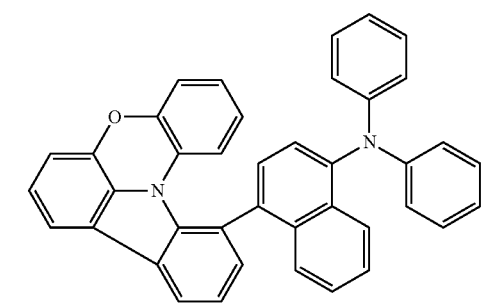
A34
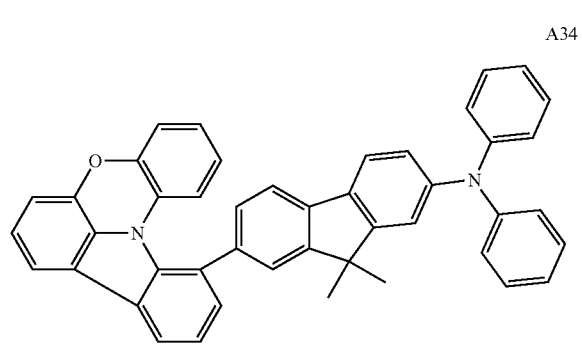
A35
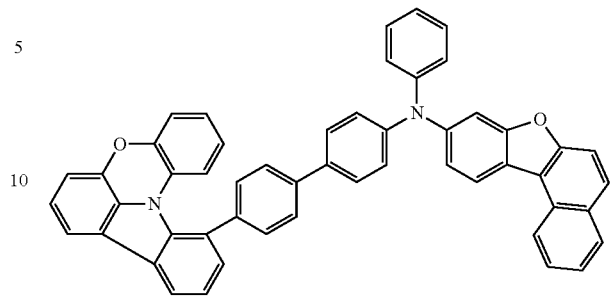
A36
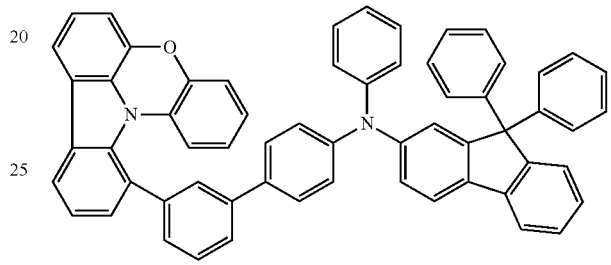
A37
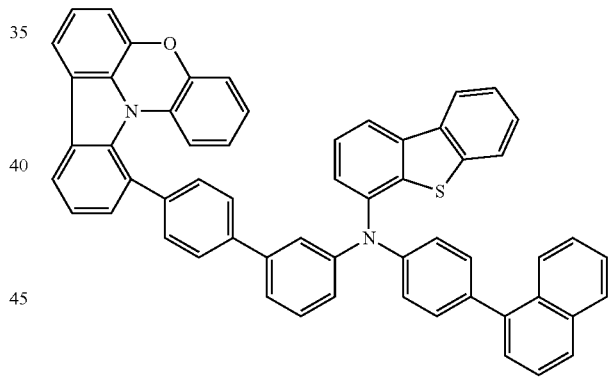
A38
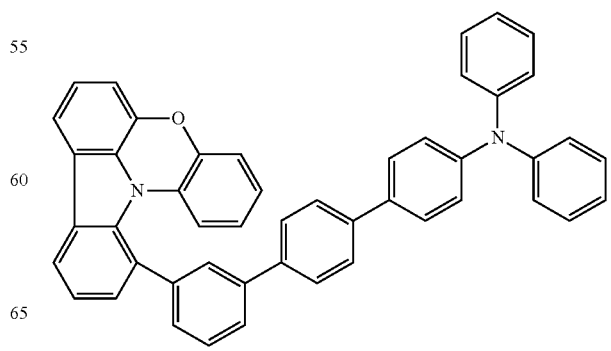

-continued
A39
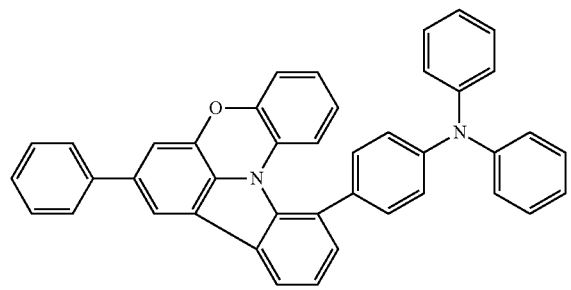
A40
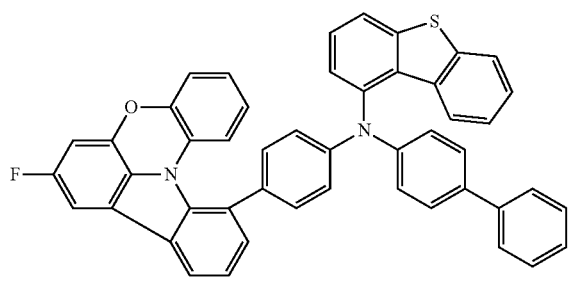
A41
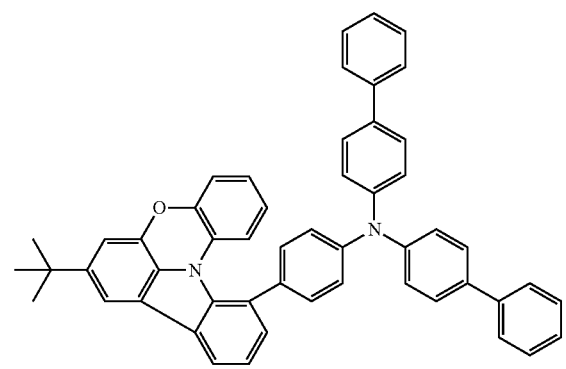
A42
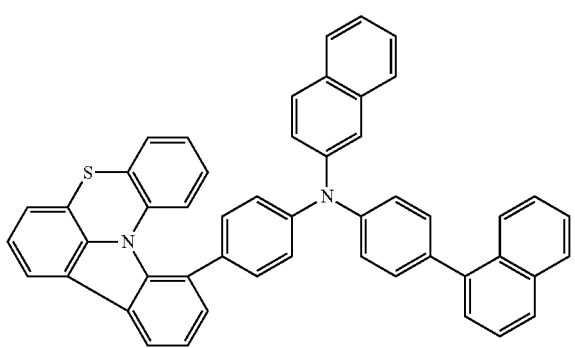
A43
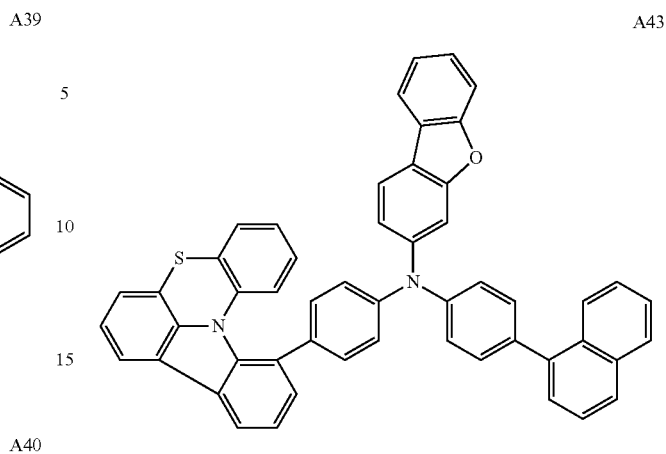
A44
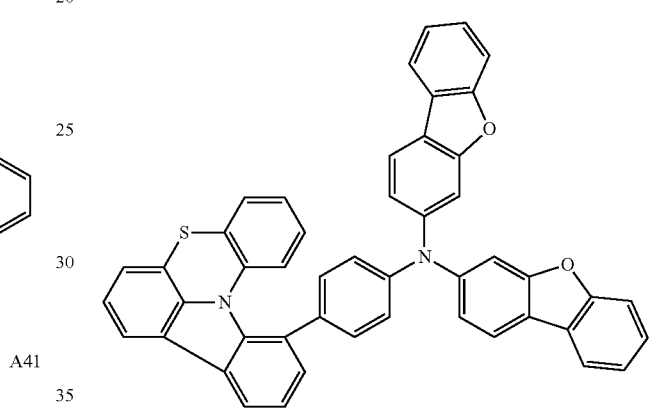
A45
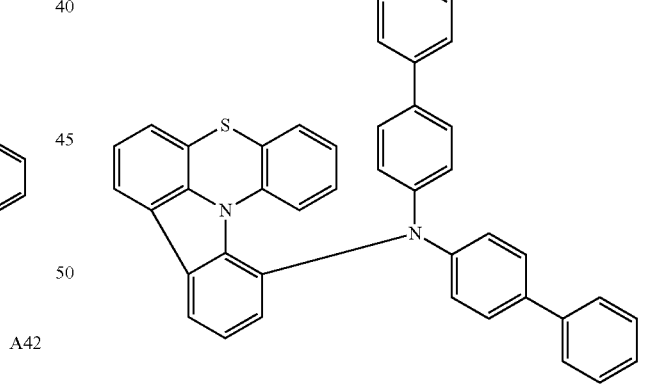
A46
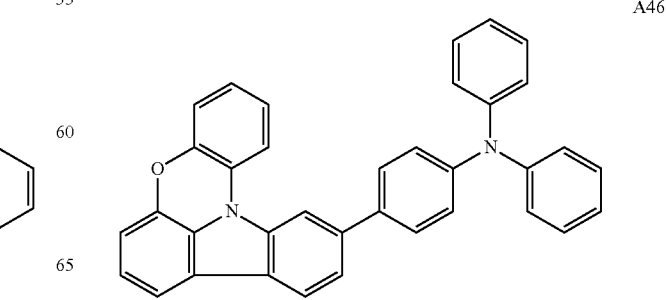

A47
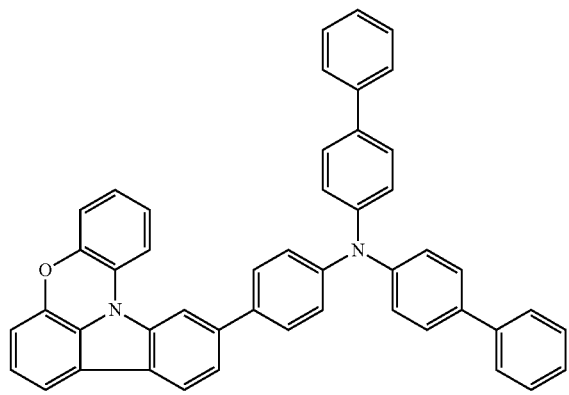
A48
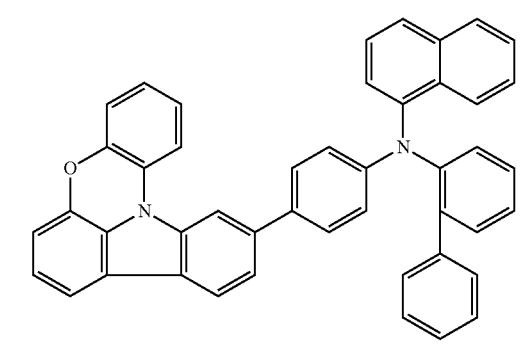
A49
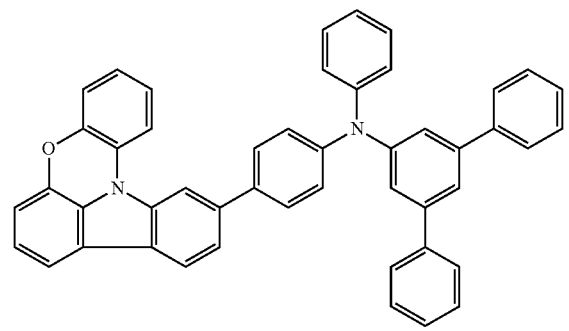
A50
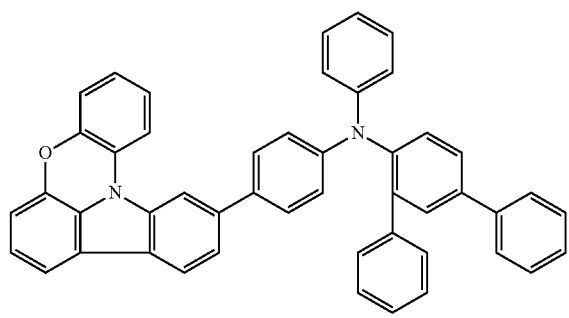
A51
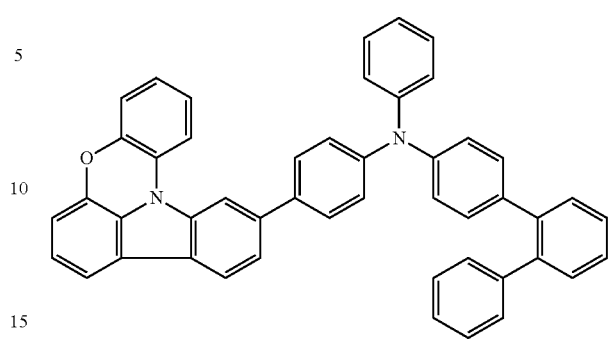
A52
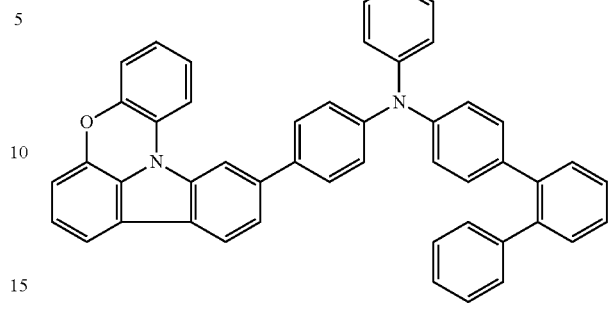
A53
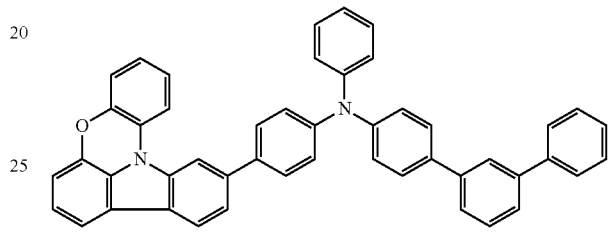
A54
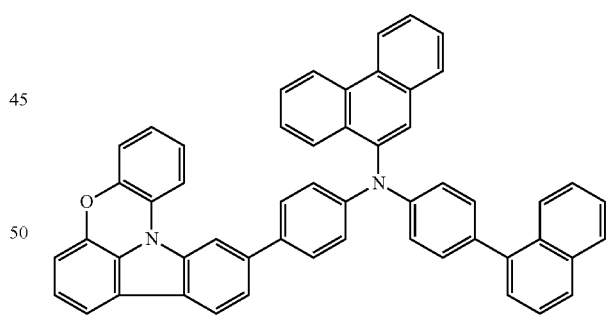
A55
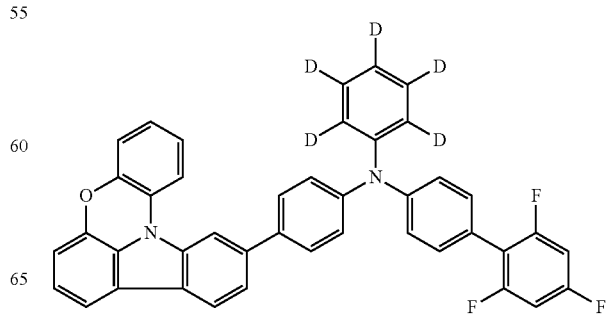

A56
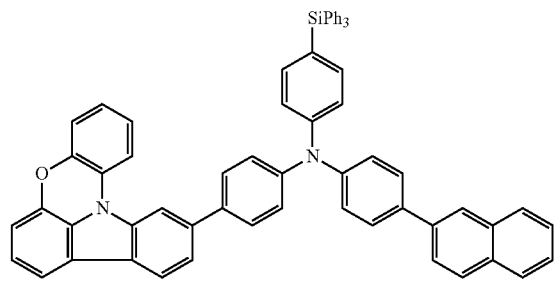
A57
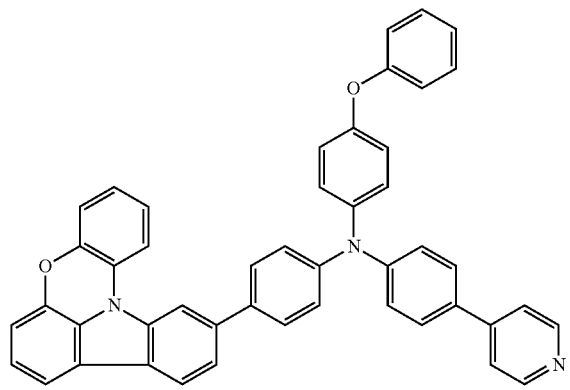
A58
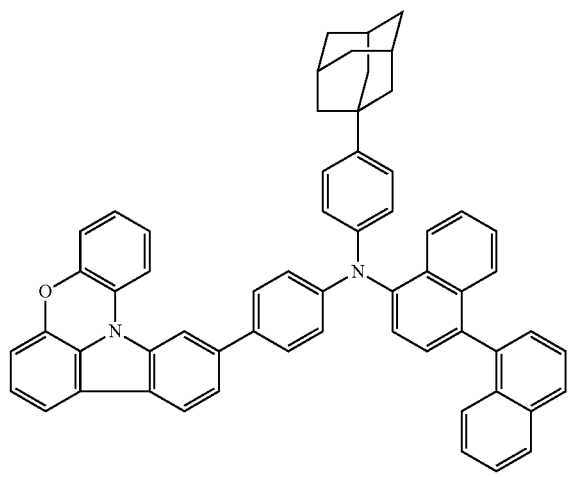
A61
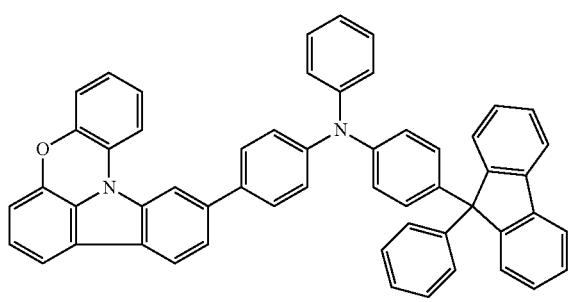
A62
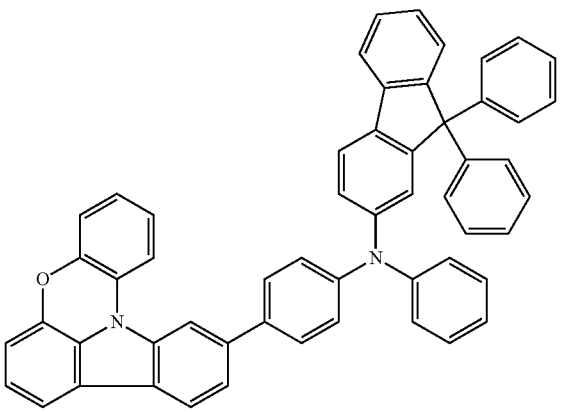
A63
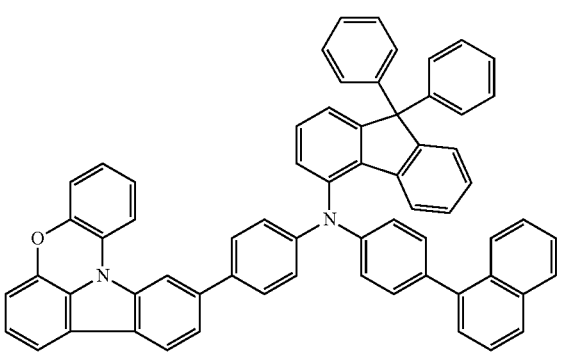
A64
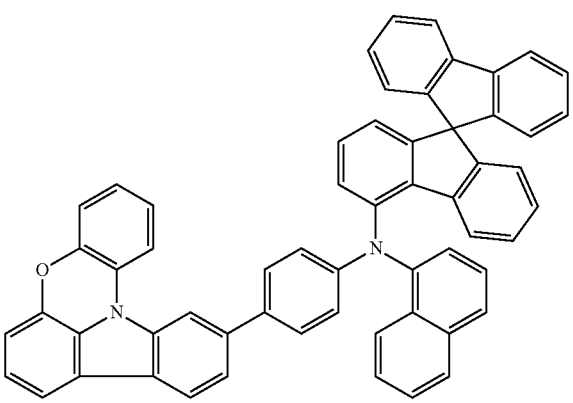
A65

-continued
A66
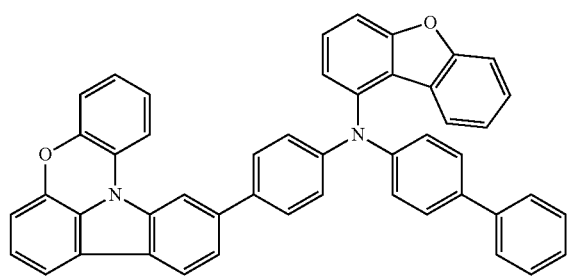
A67
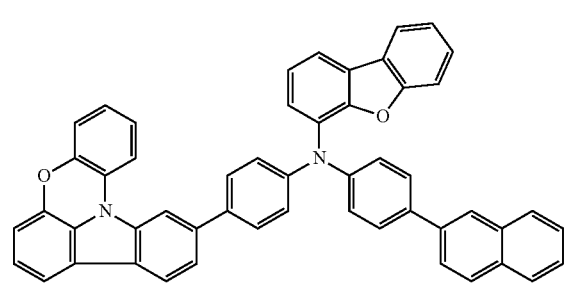
A68
A69
A70
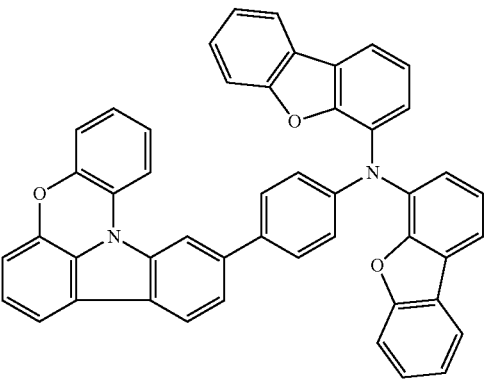
A71
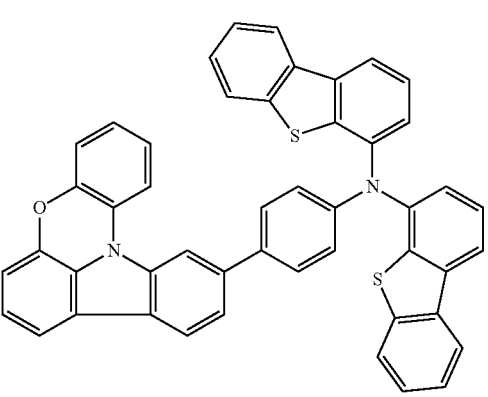
A72
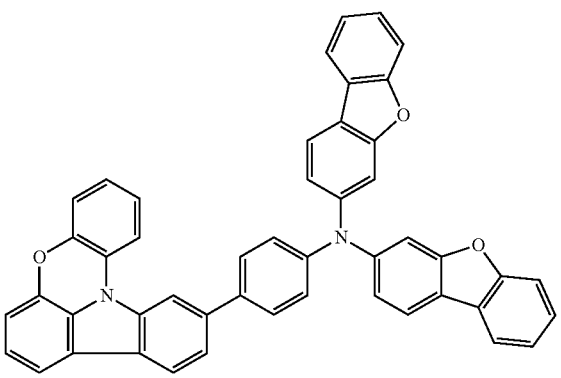
A73
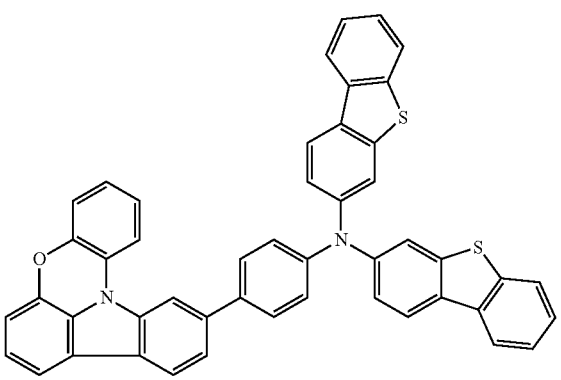

-continued
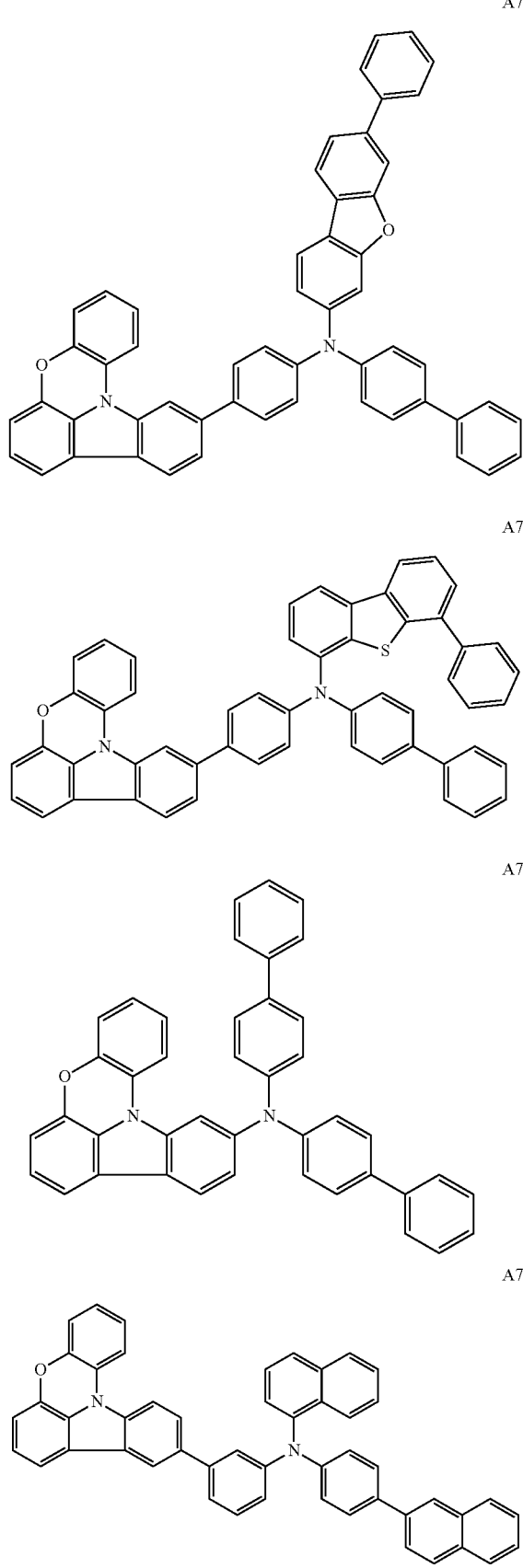
-continued
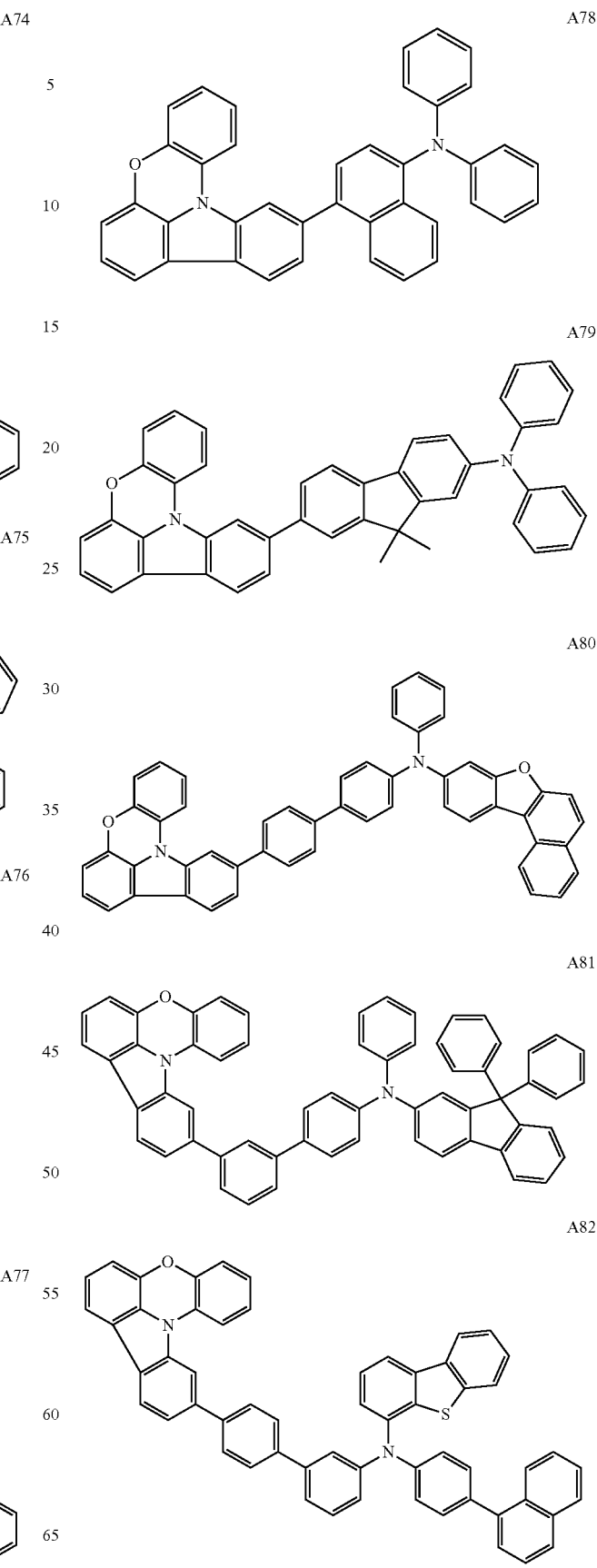

A83
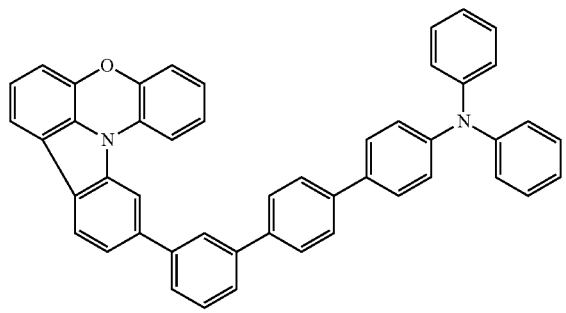
A87
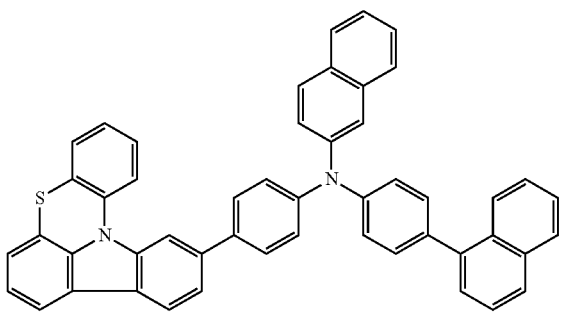
A84
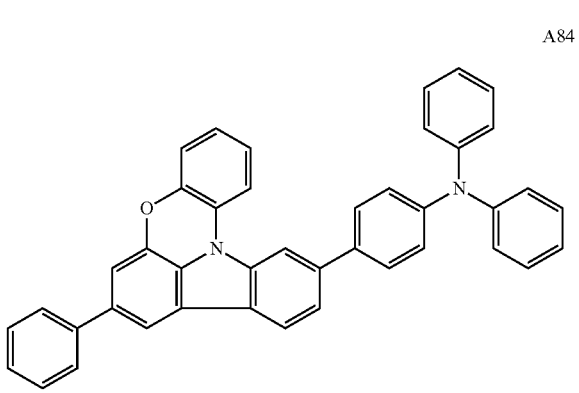
A88
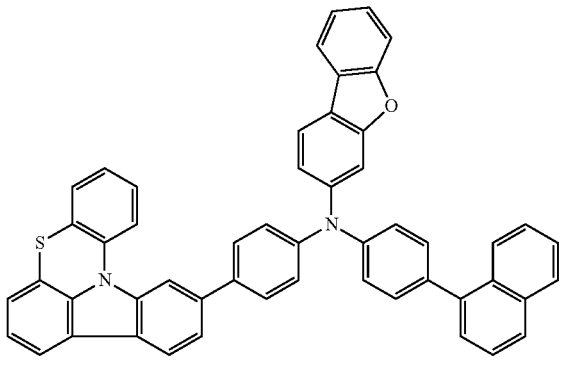
A85
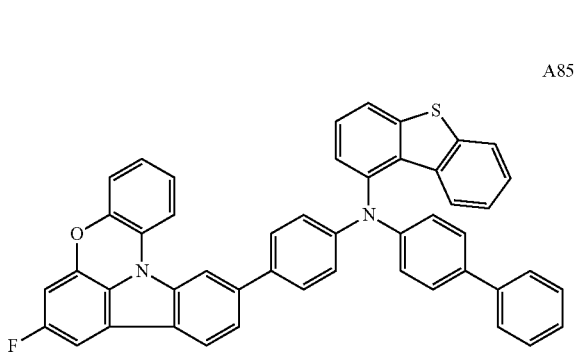
A89
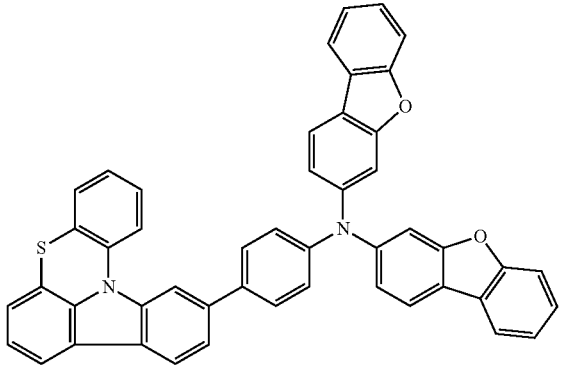
A86
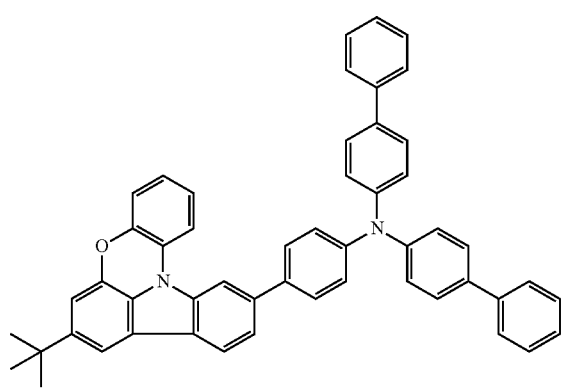
A90
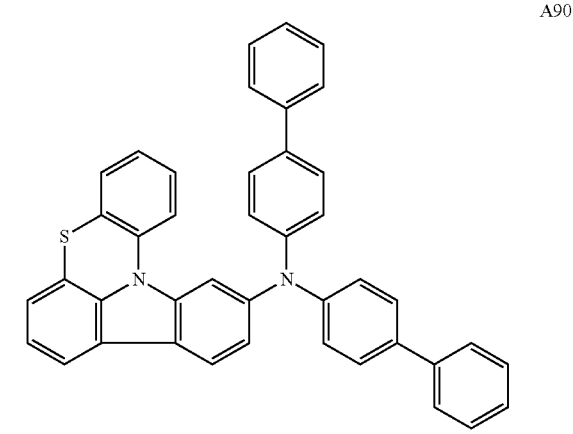

-continued
A136
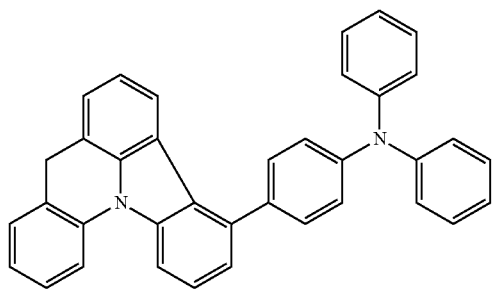
A137
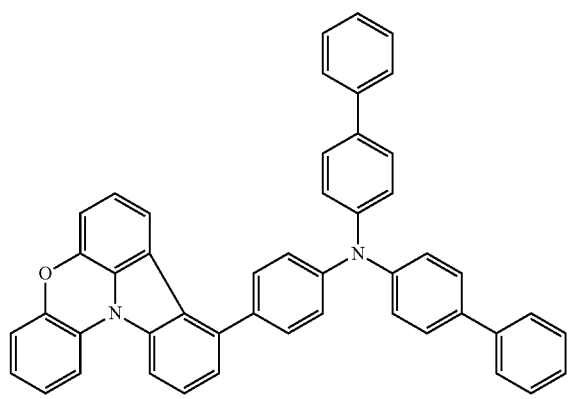
A138
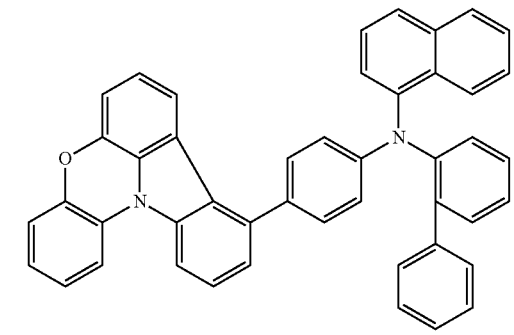
A139
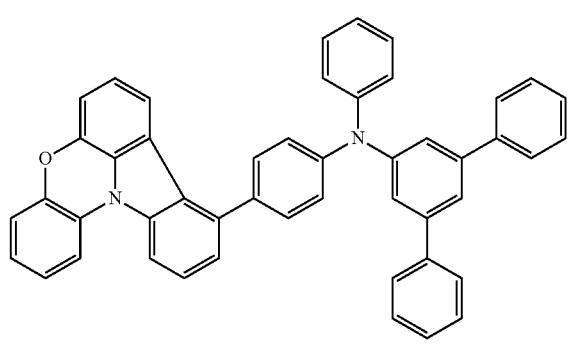
-continued
A140
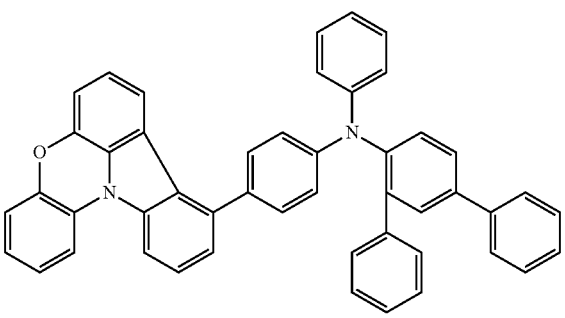
A141
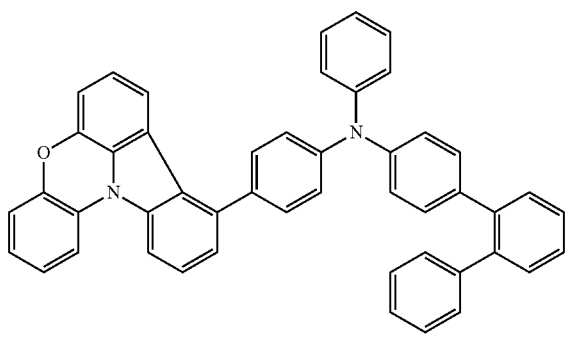
A142
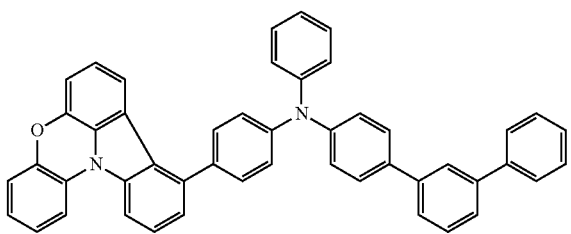
A143
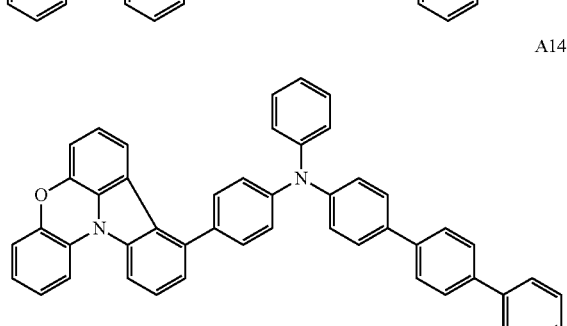
A144
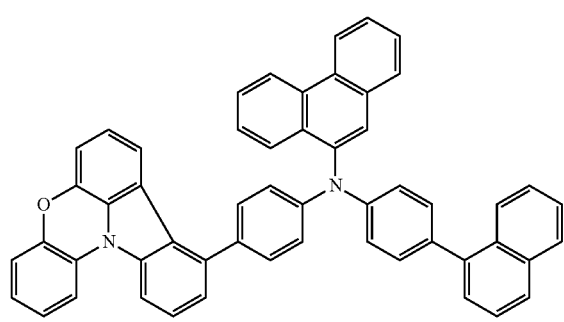

A145 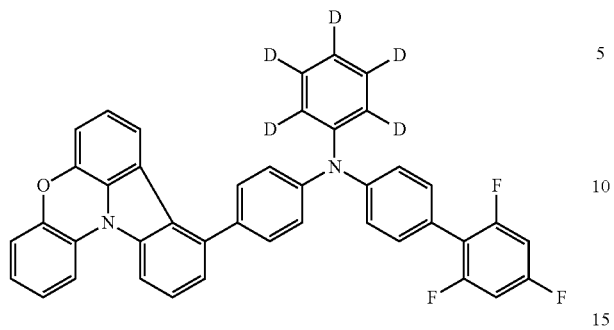
A146 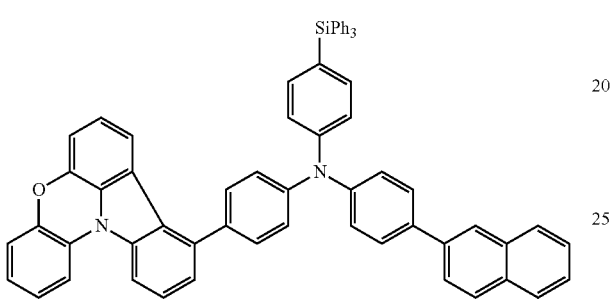
A147 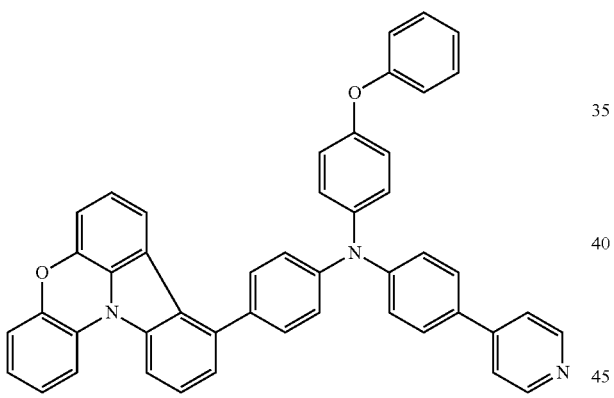
A148 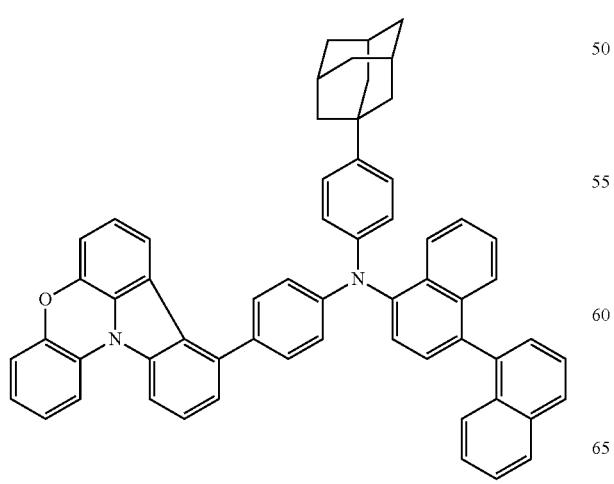
A151 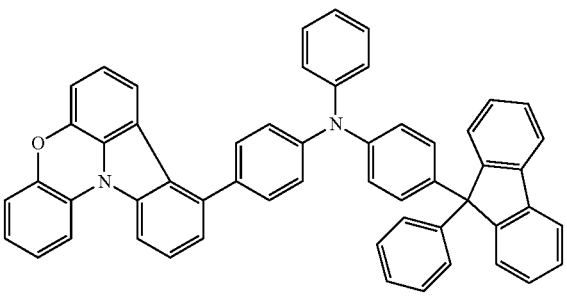
A152 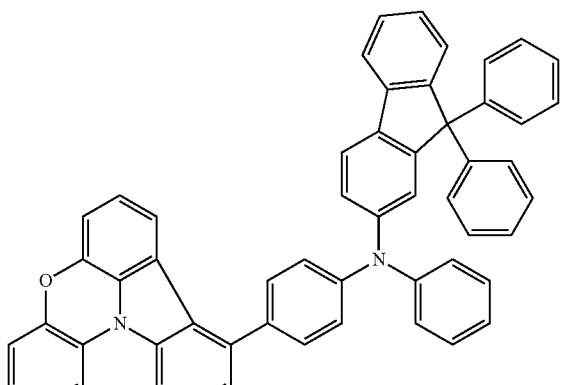
A153 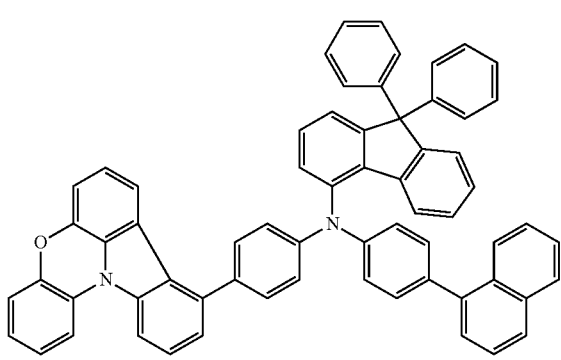
A154 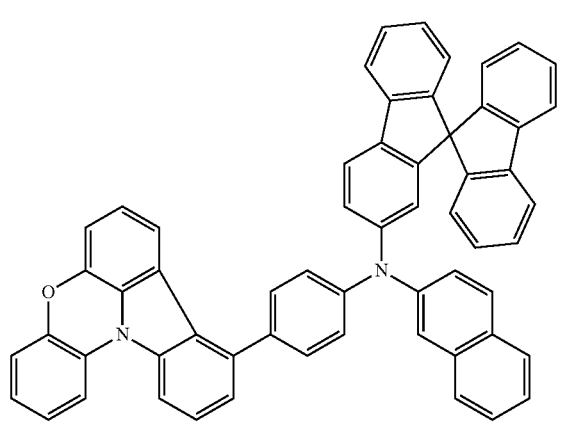

A155
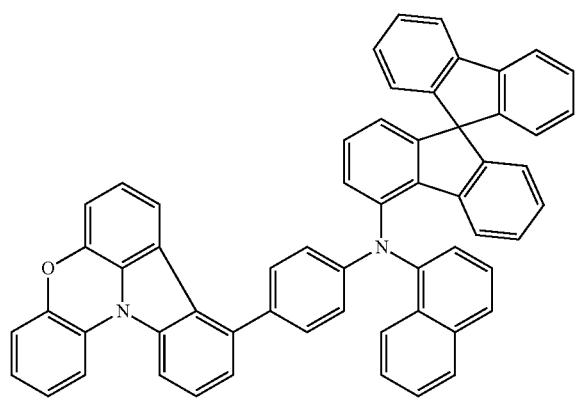
A159
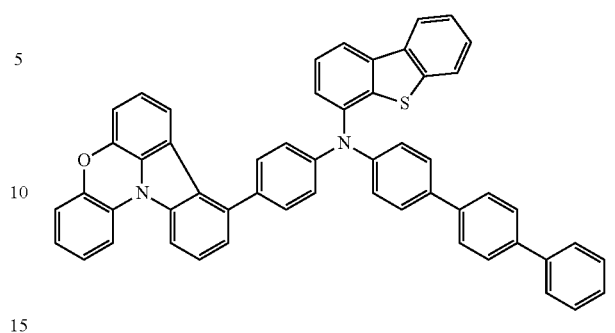
A156
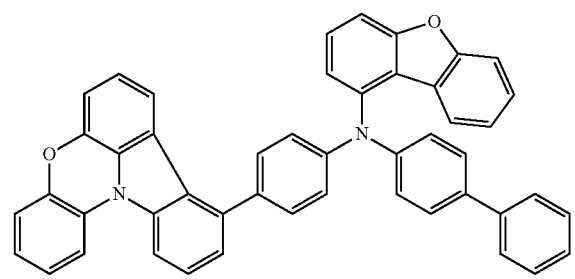
A160
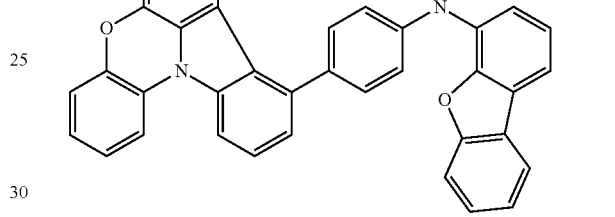
A157
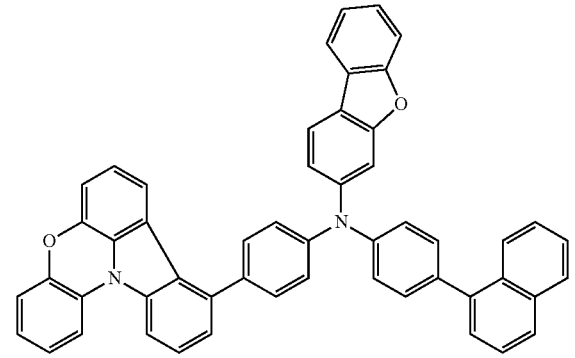
A161
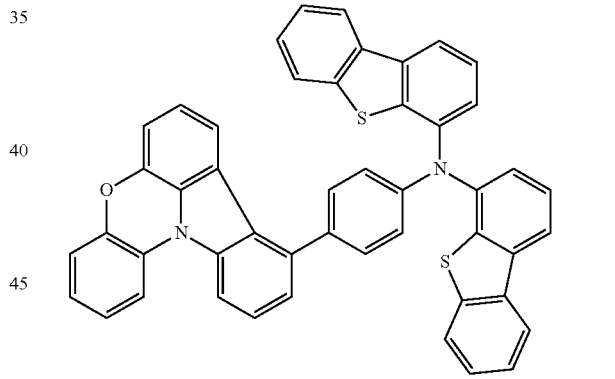
A158
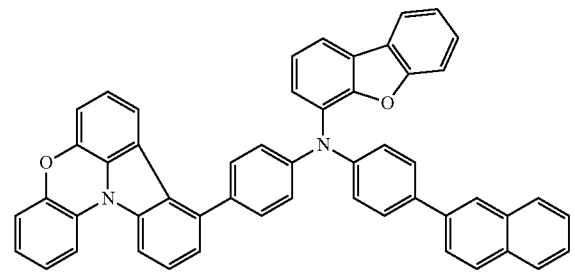
A162
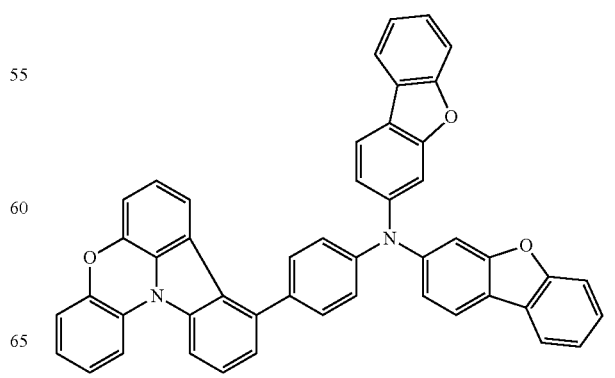

-continued
A163
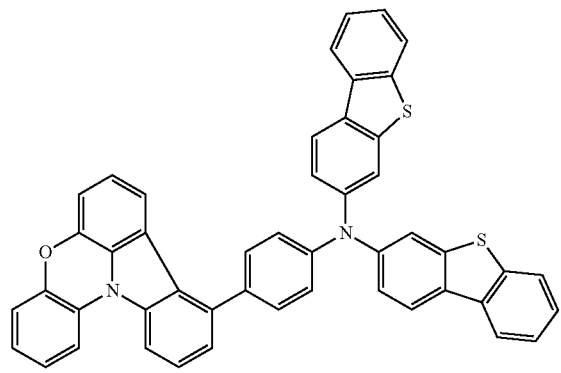
A164
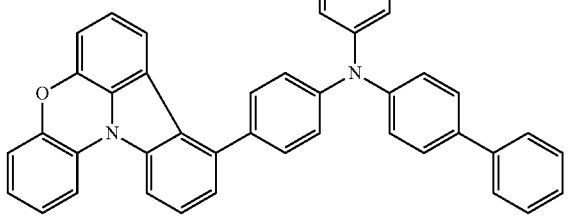
A165
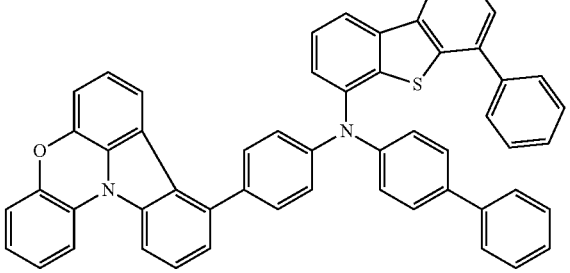
A166
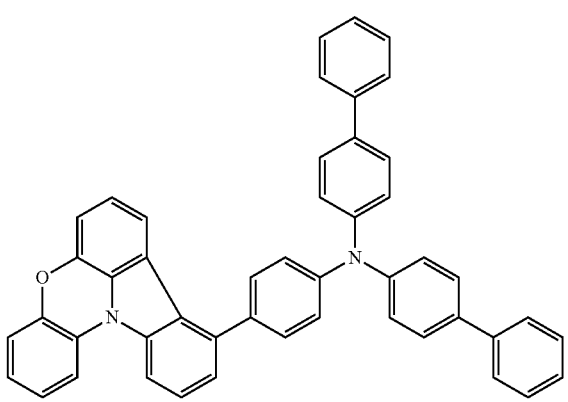
-continued
A167
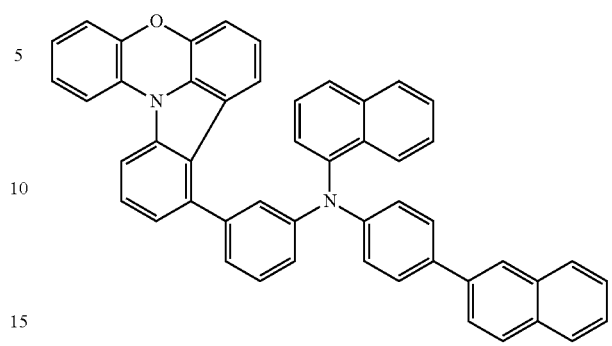
A168
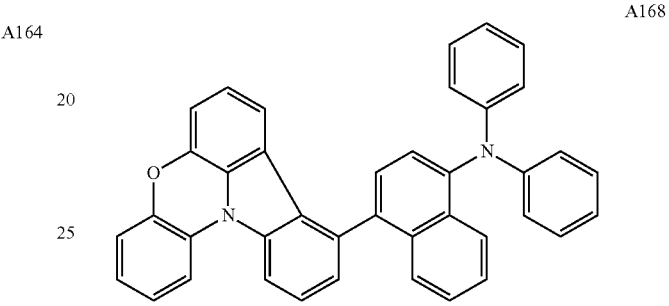
A169
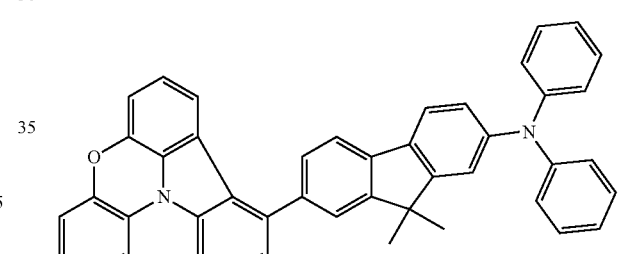
A170
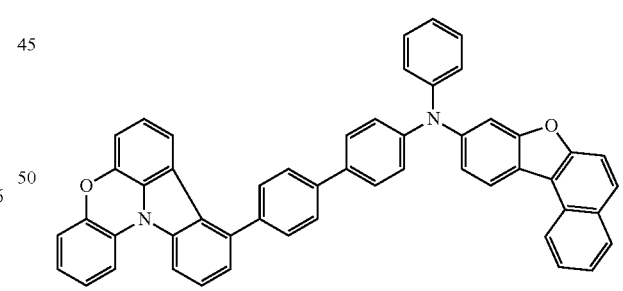
A171
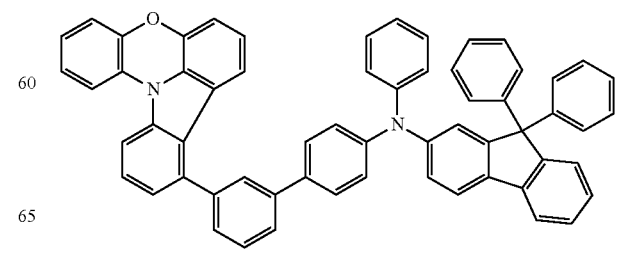

A172
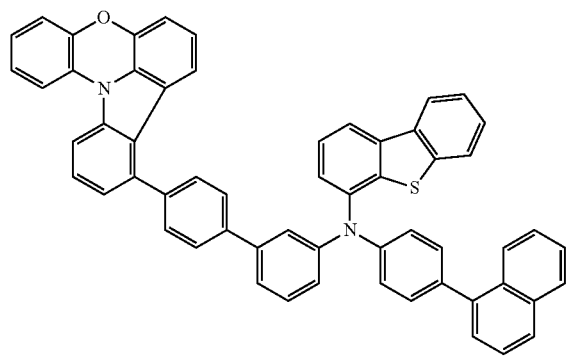
A173
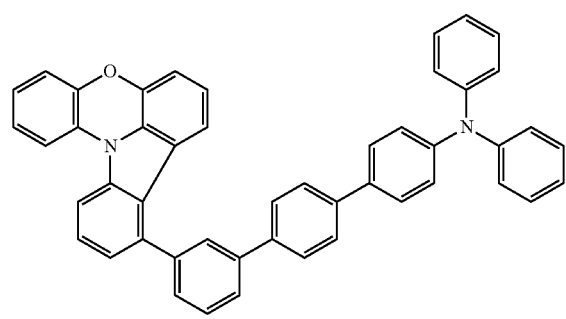
A174
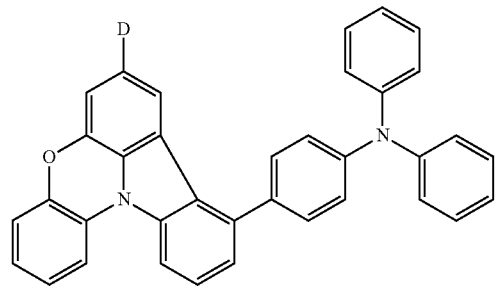
A175
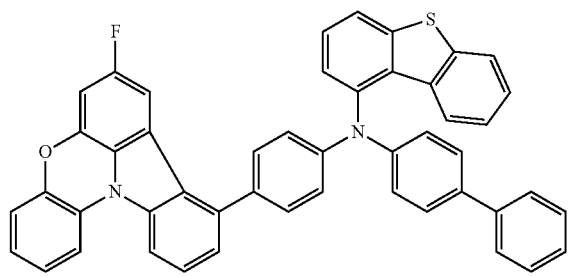
A176
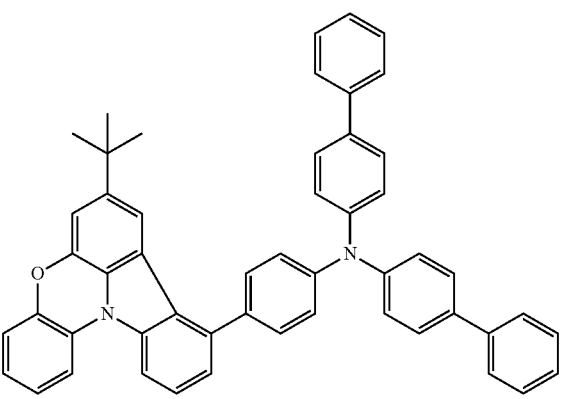
A177
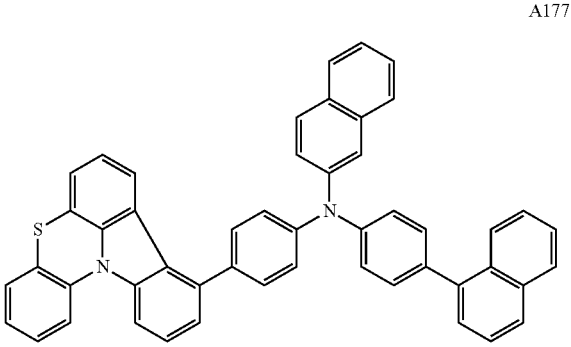
A178
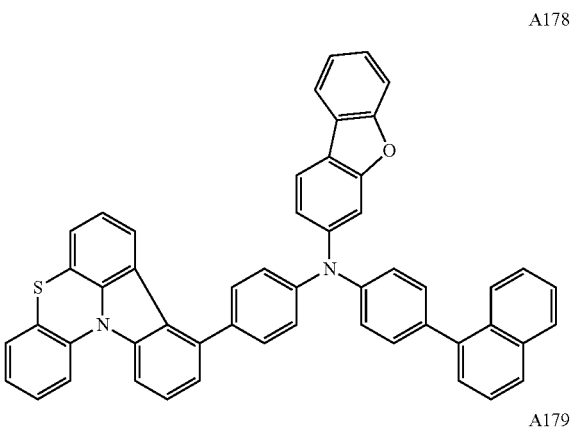
A179
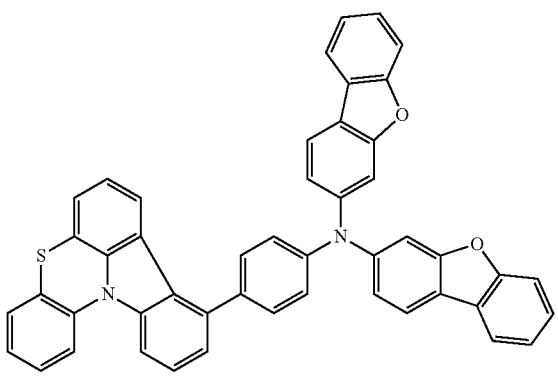

A180
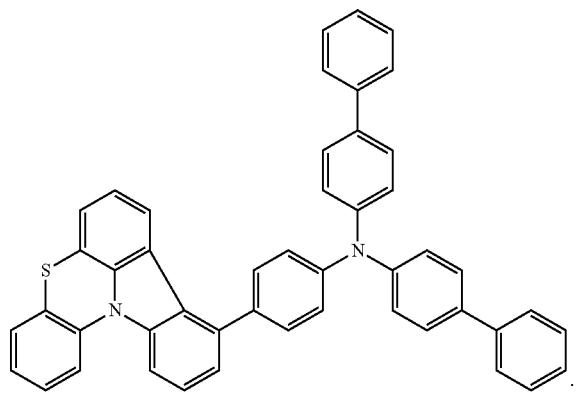
19. The polycyclic compound of claim 14, wherein the polycyclic compound of Formula 1 is a compound of Compound Group 2:
Compound Group 2
B1
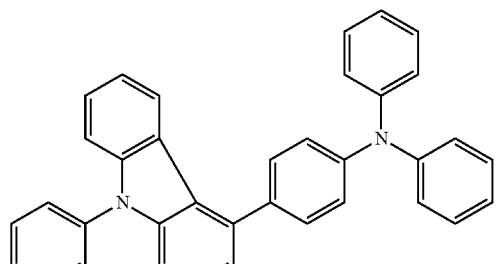
B2
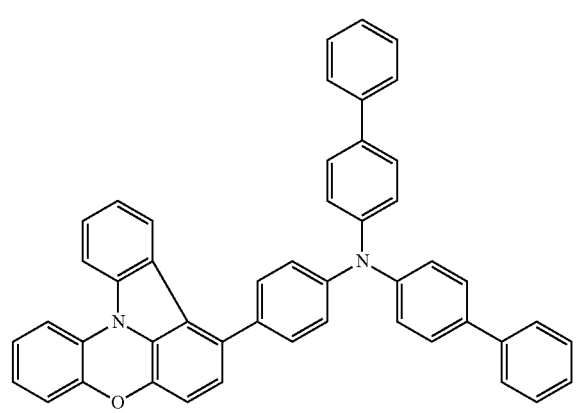
B3
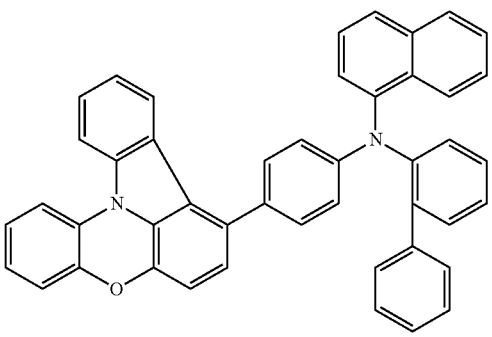
B4
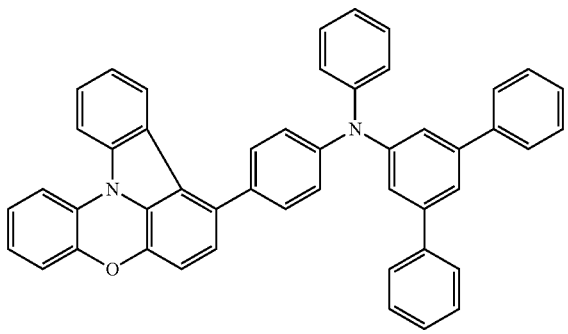
B5
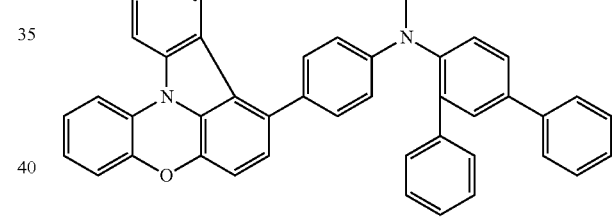
B6
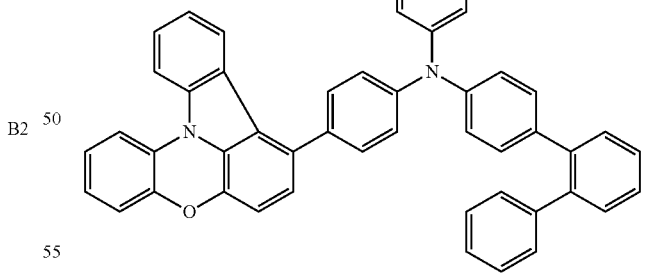
B7
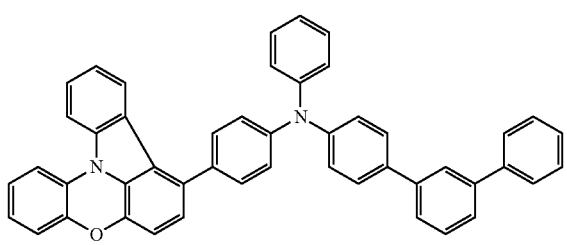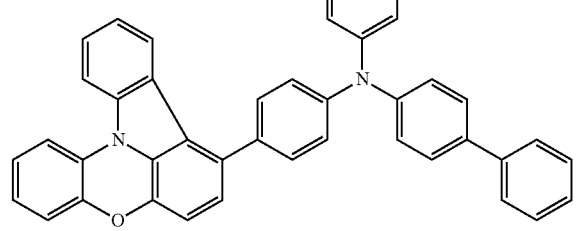

-continued
B8
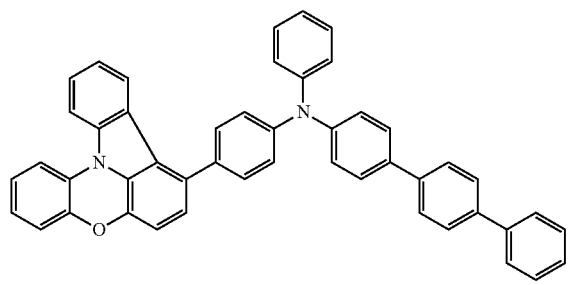
B9
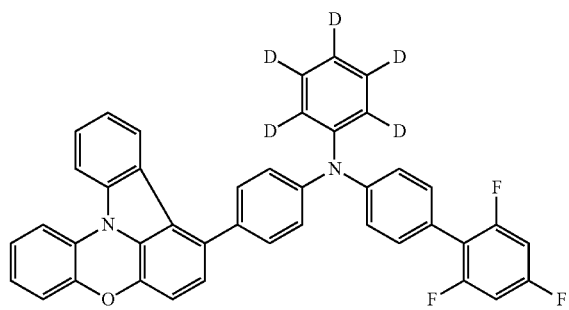
B10
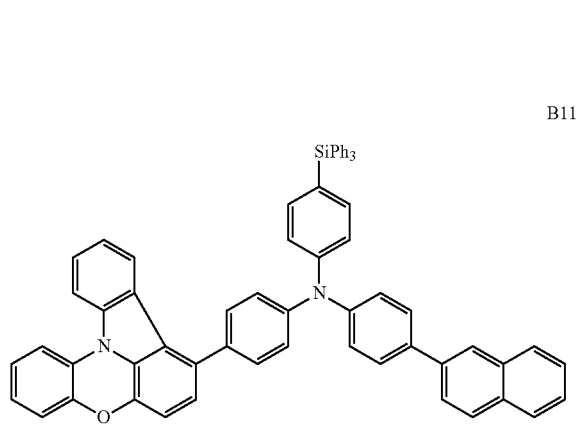
B11
-continued
B12
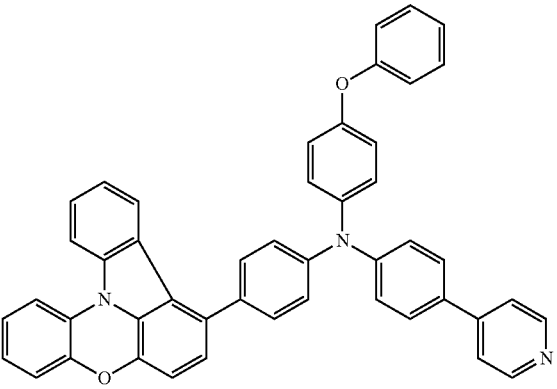
B13
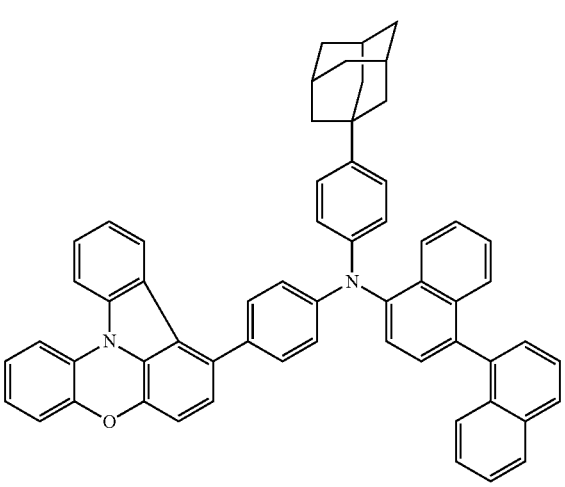
B16
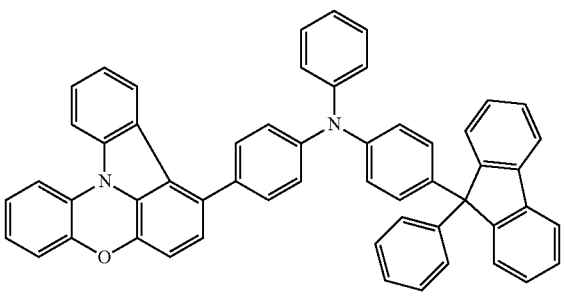
B17
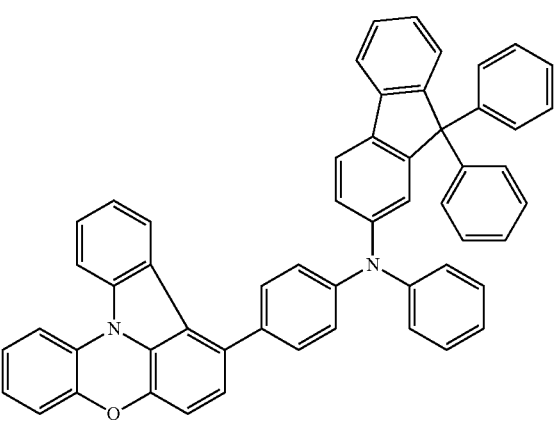

B18
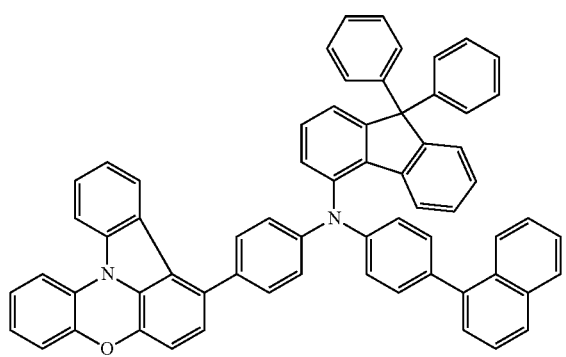
B19
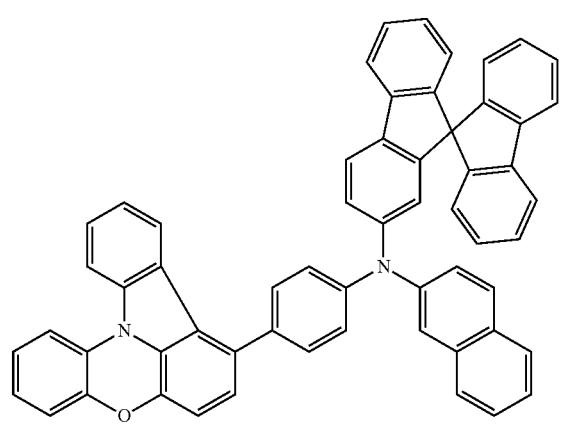
B20
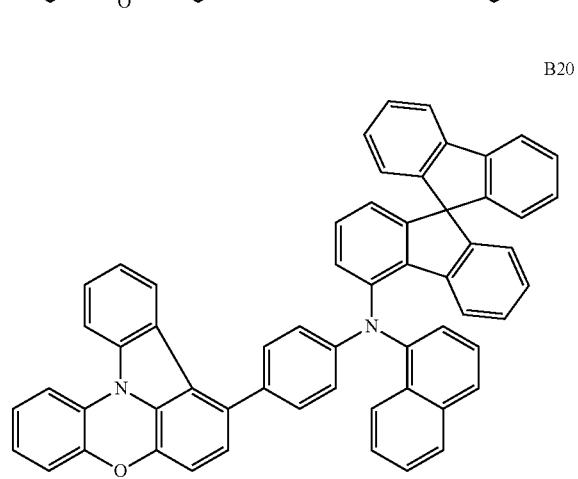
B21
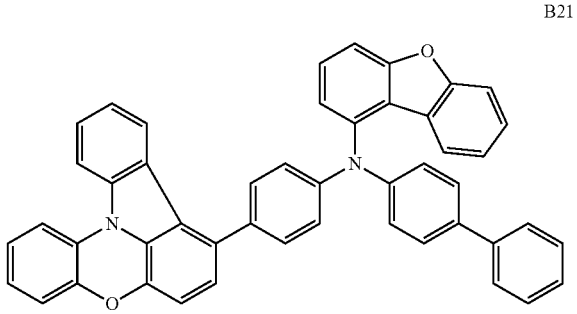
B22
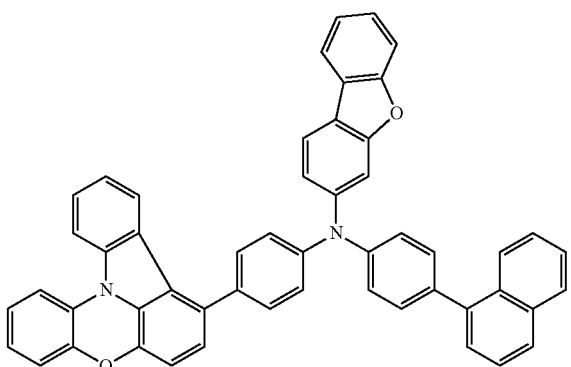
B23
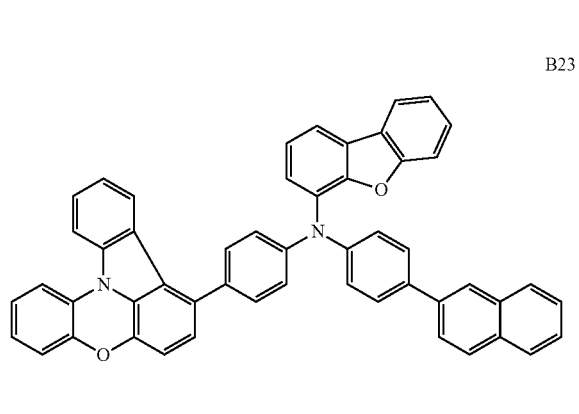
B24
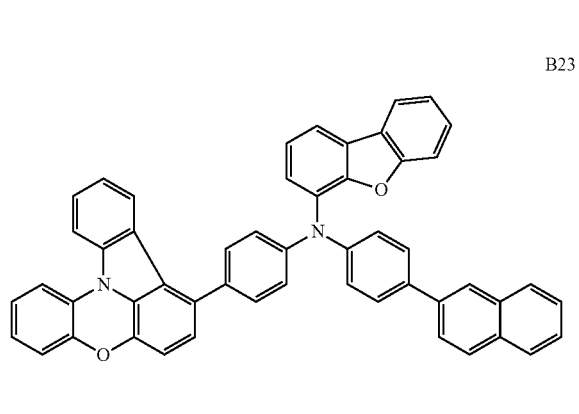
B25
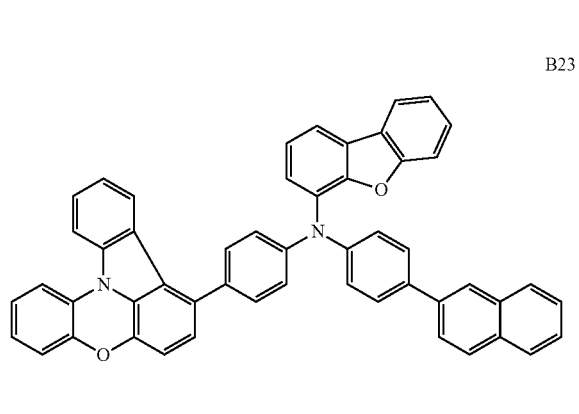

B26
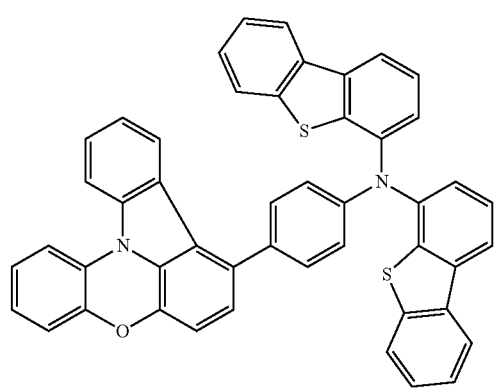
B27
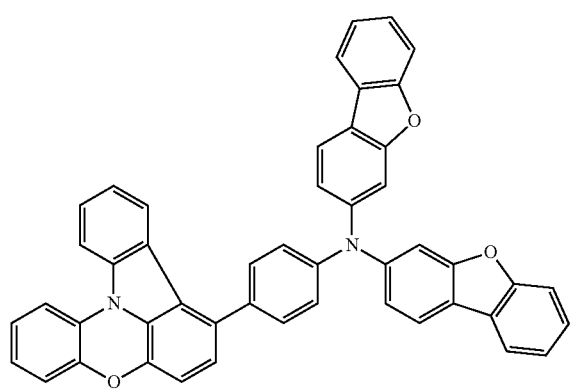
B28
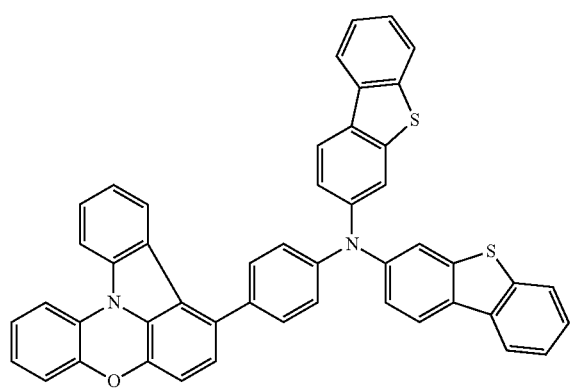
B29
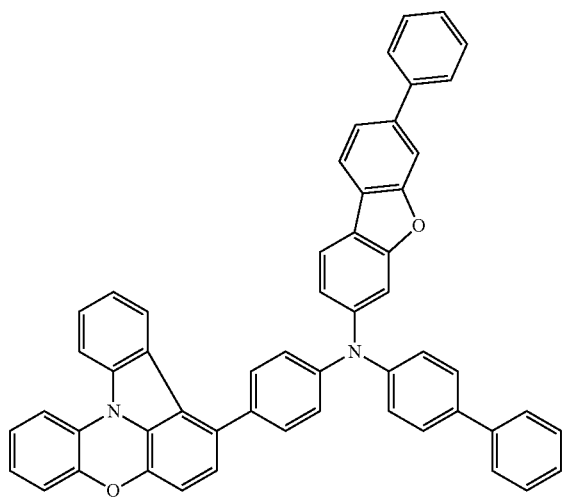
B30
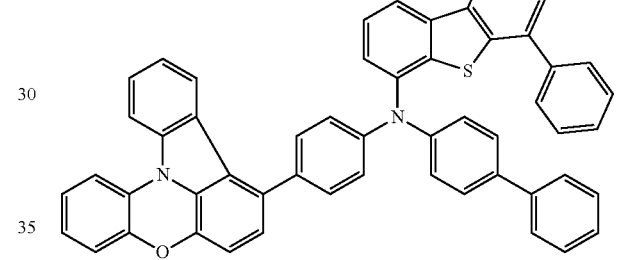
B31
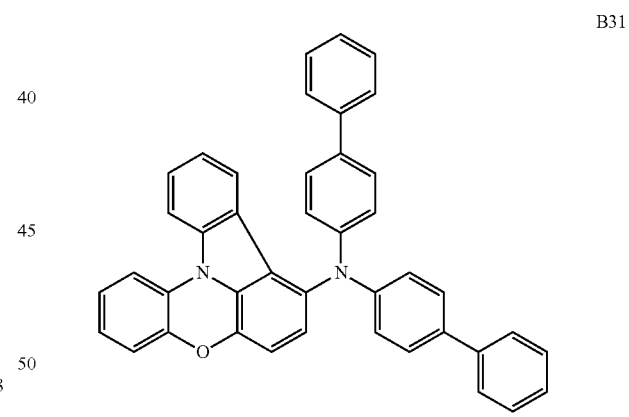
B32
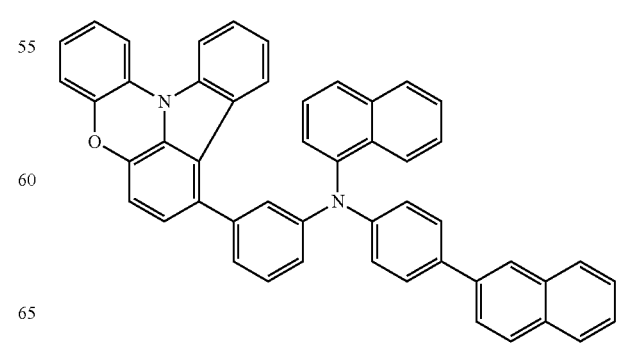

B33
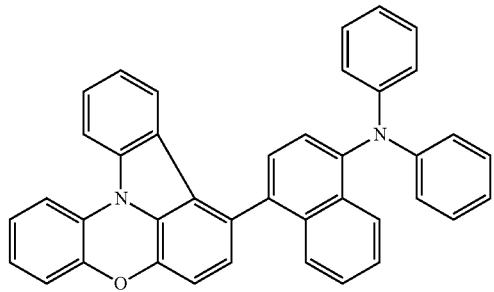
B34
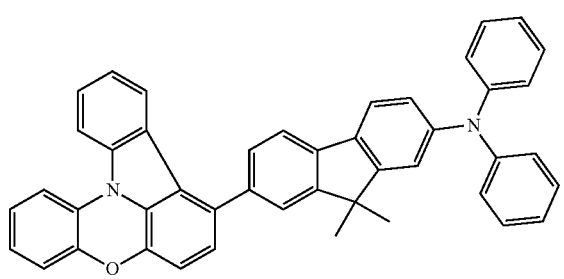
B35
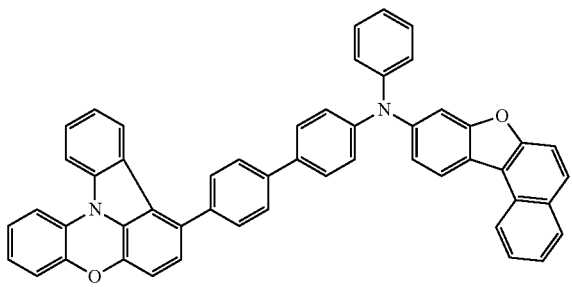
B36
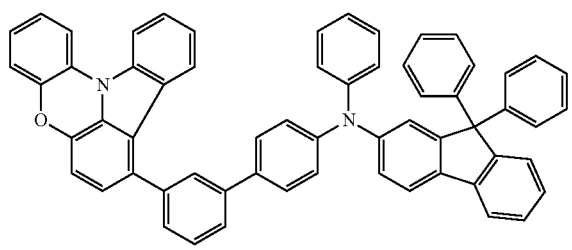
B37
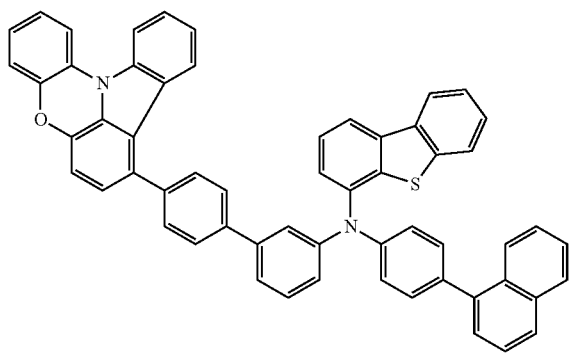
B38
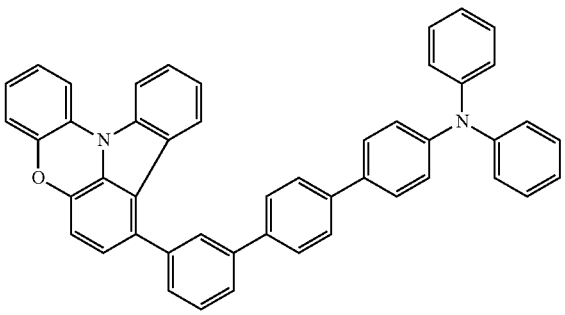
B39
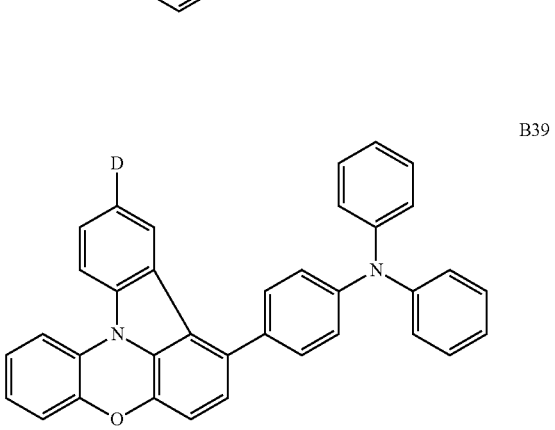
B40
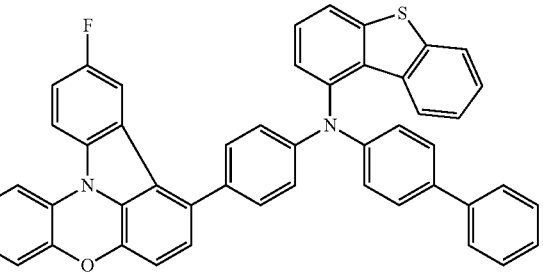
B41
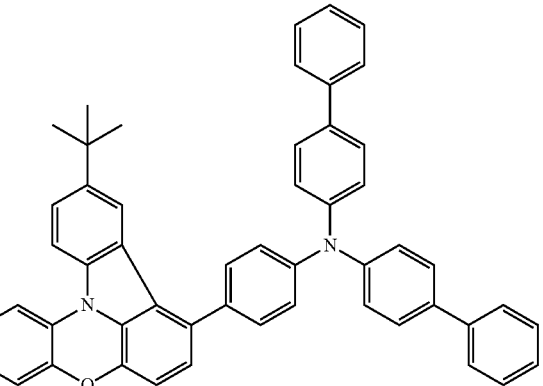

B42
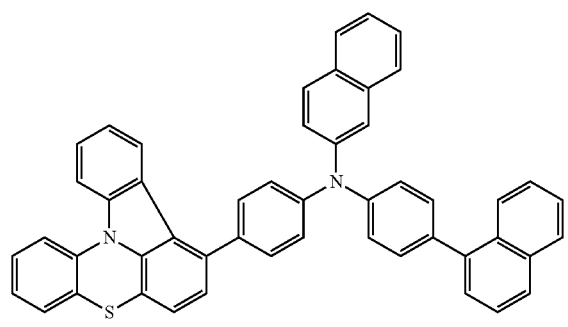
B43
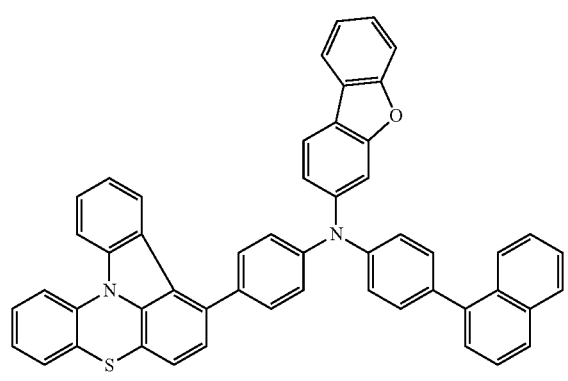
B44
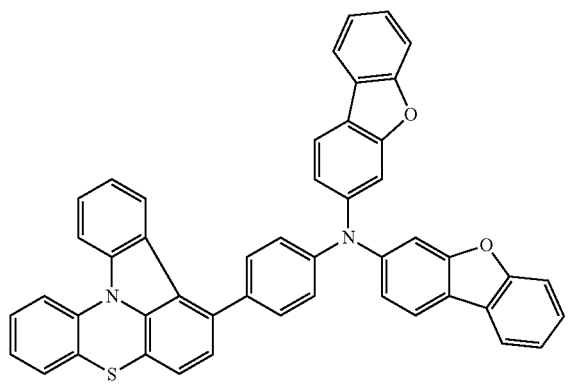
B45
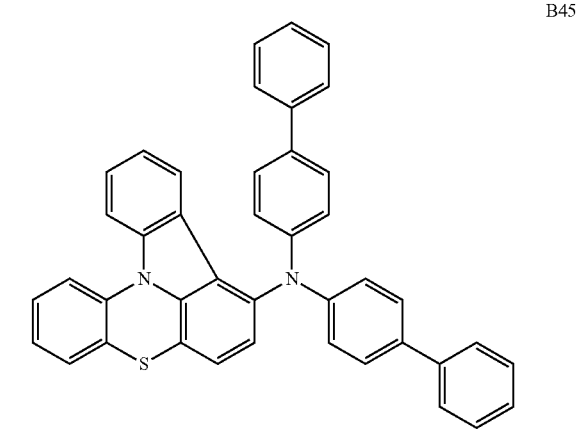
B91
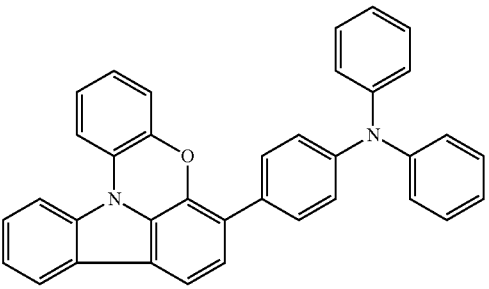
B92
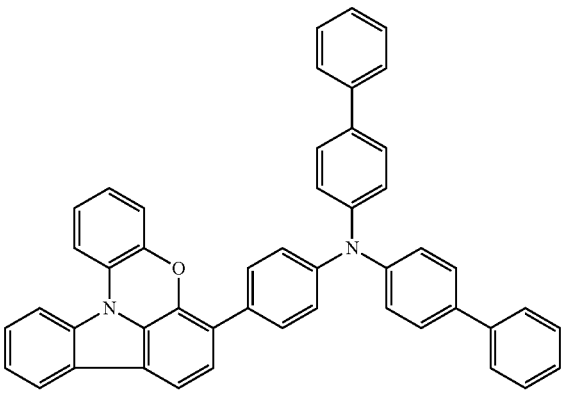
B93
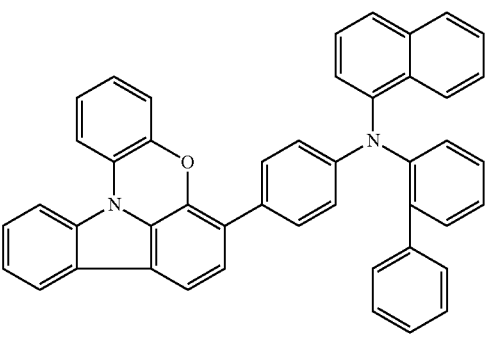
B94
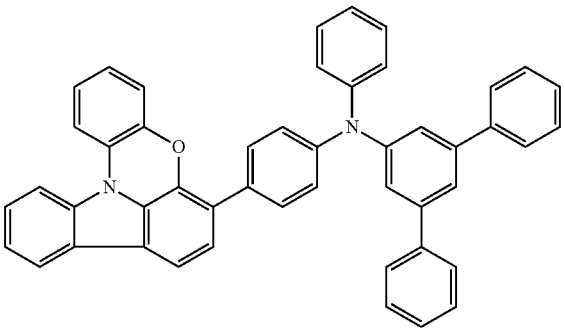

B95
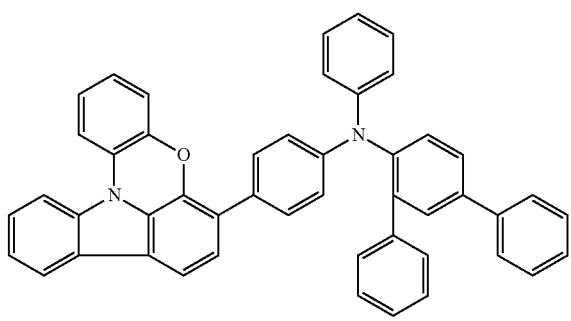
B96
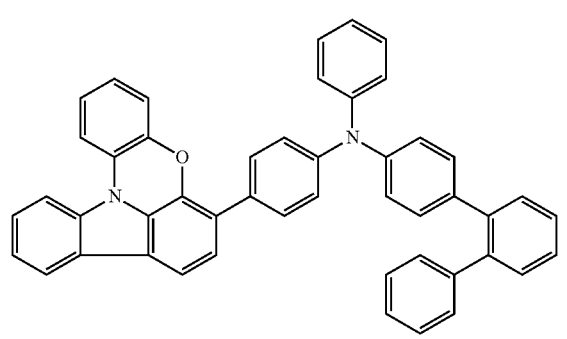
B97
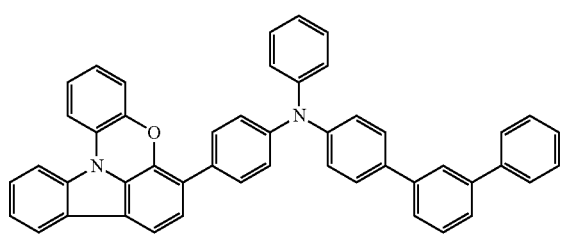
B98
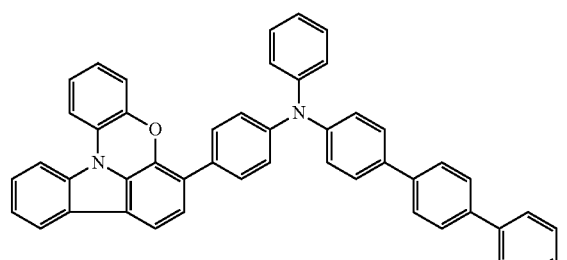
B99
B100
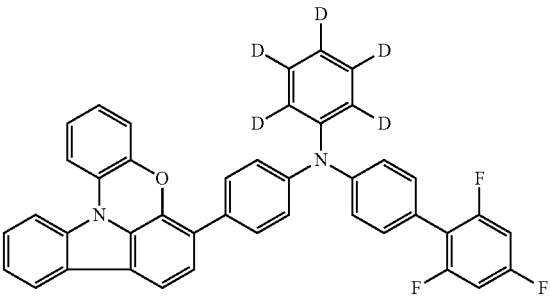
B101
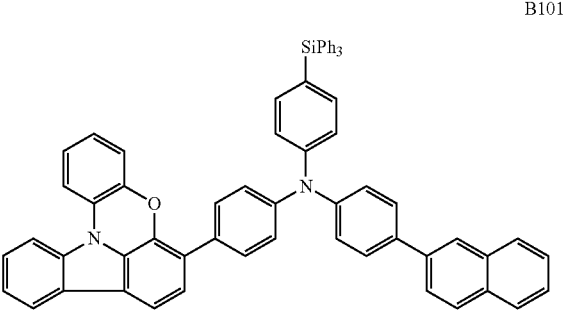
B102
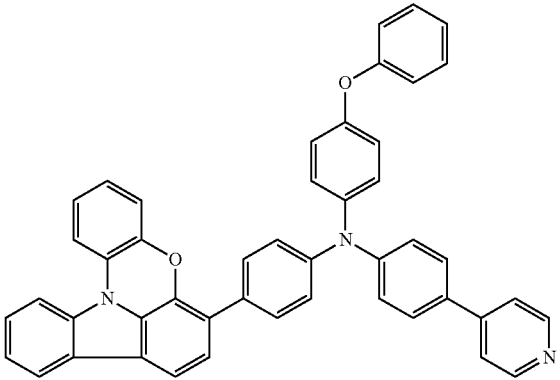
B103
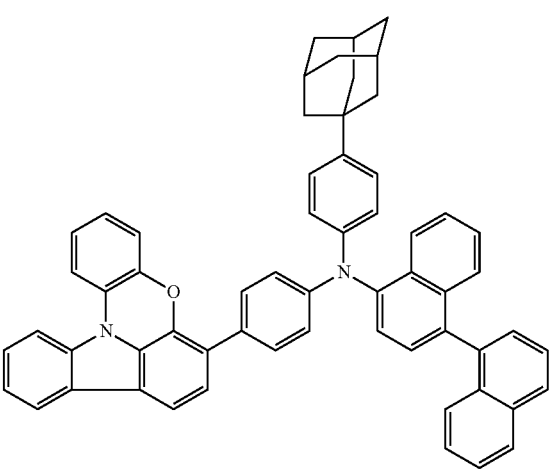

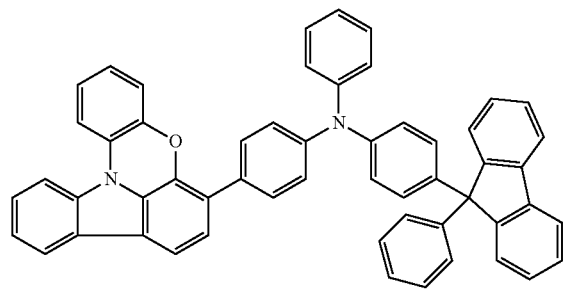
B106
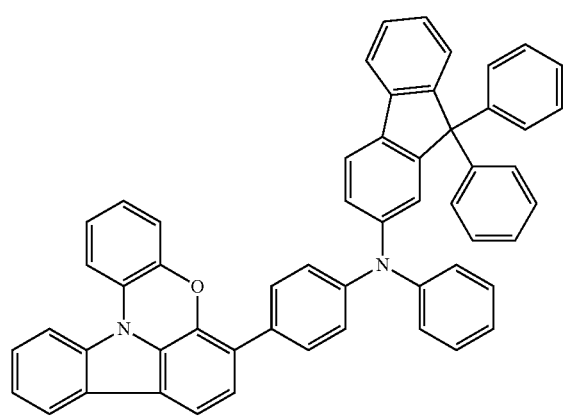
B107
B108
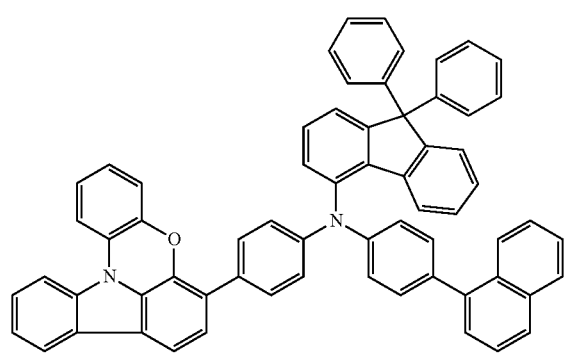
B109
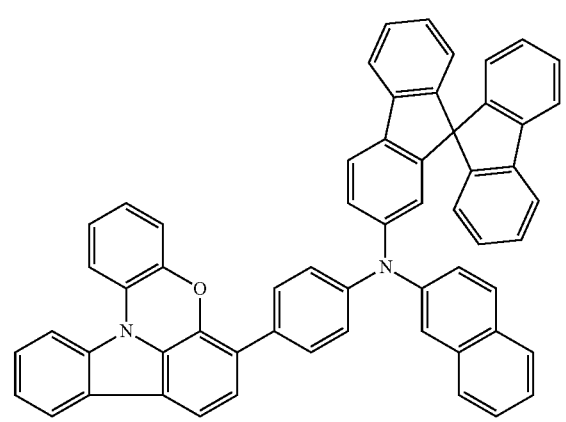
B110
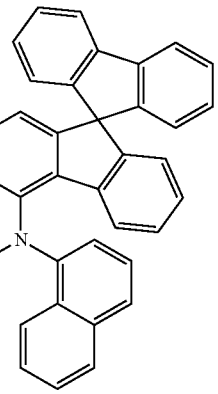
B111
B112
B113

B114
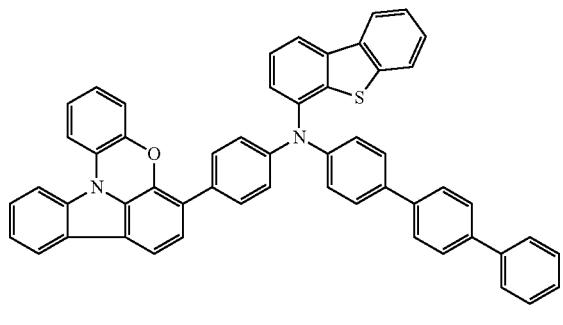
B115
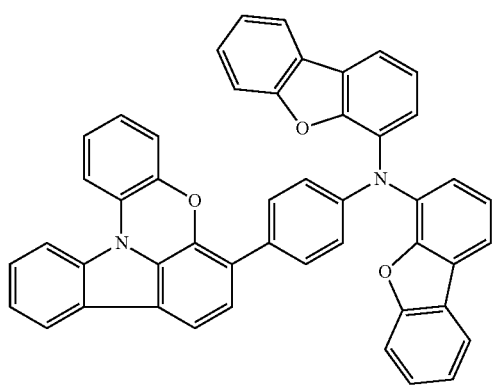
B116
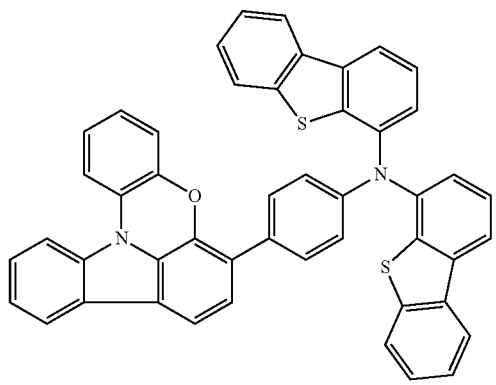
B117
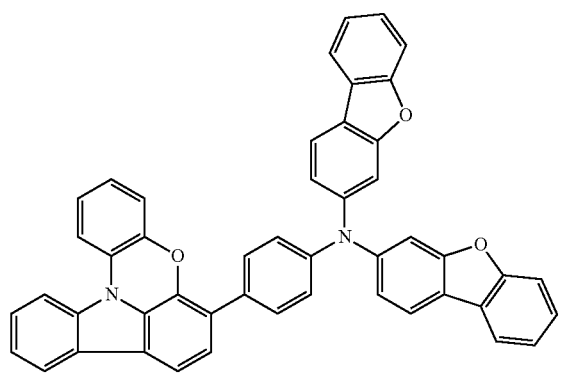
B118
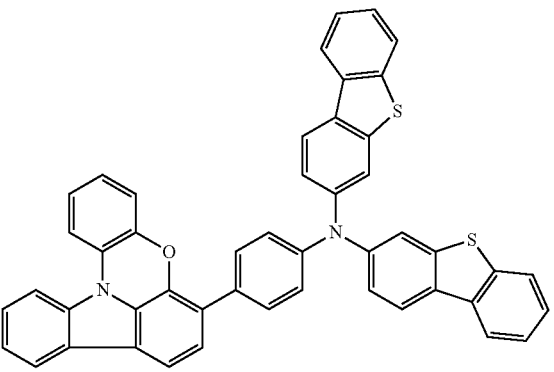
B119
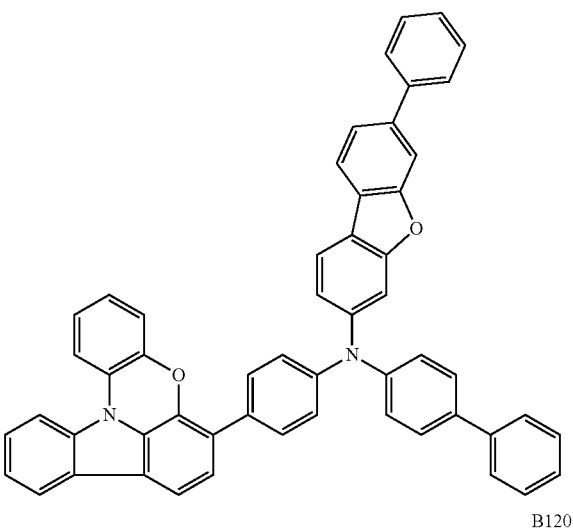
B120
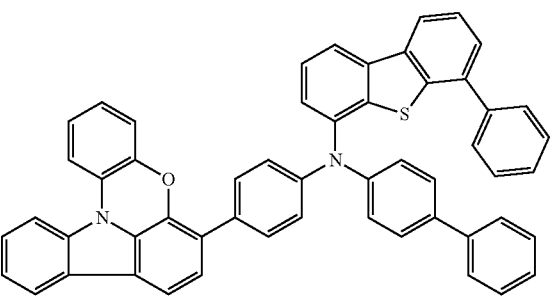
B121
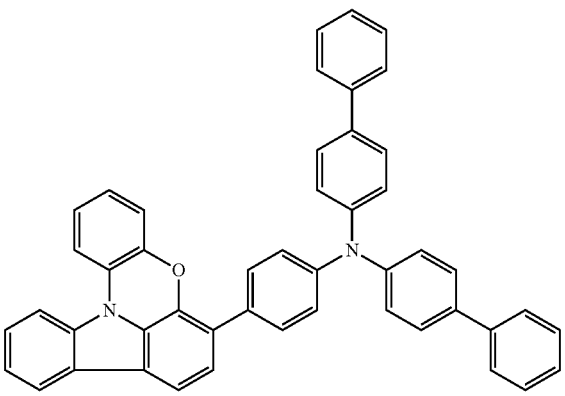

B122
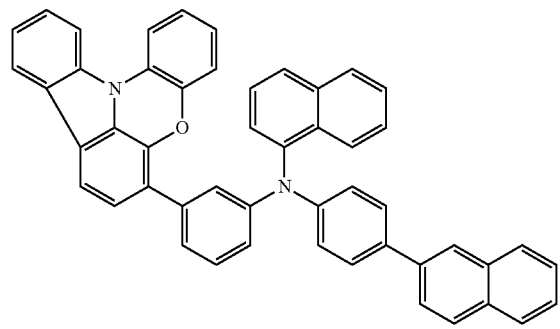
B123
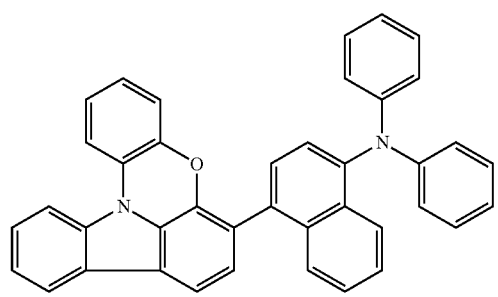
B124
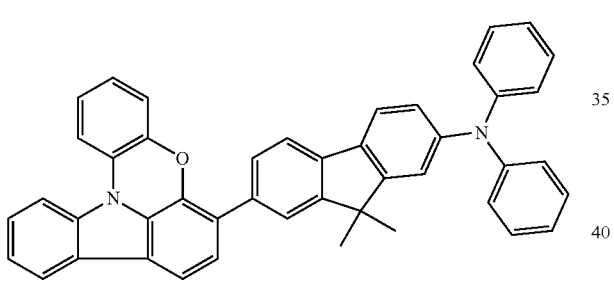
B125
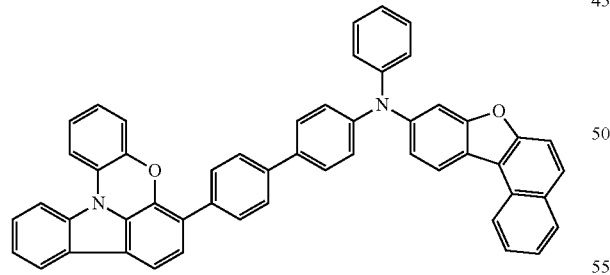
B126
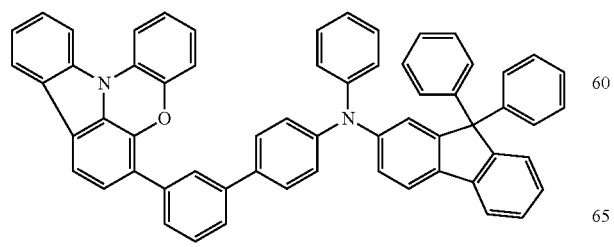
B127
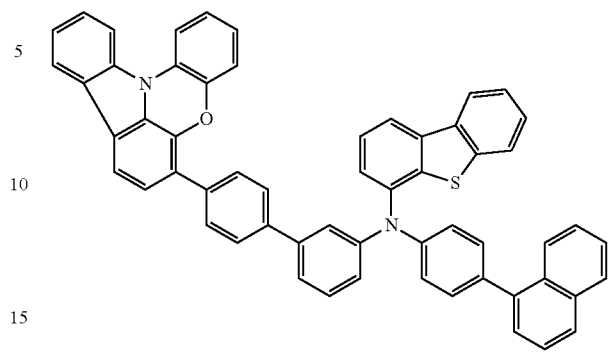
B128
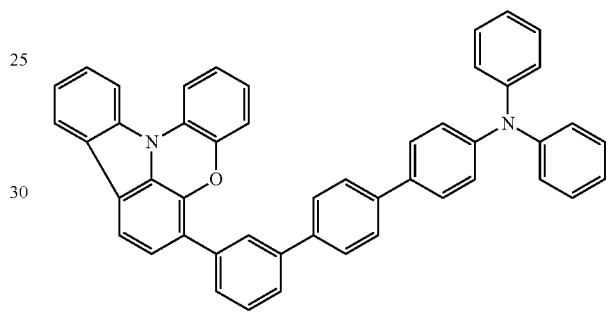
B129
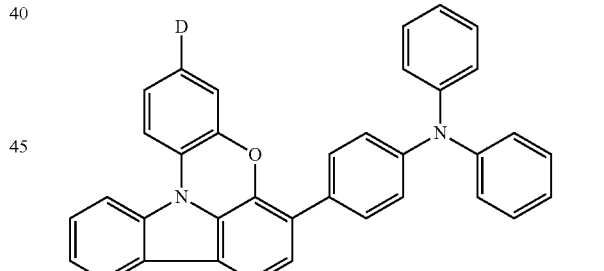
B130
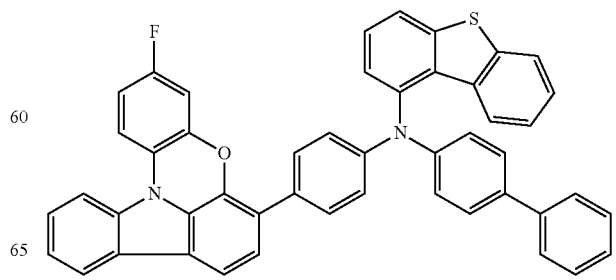

B131
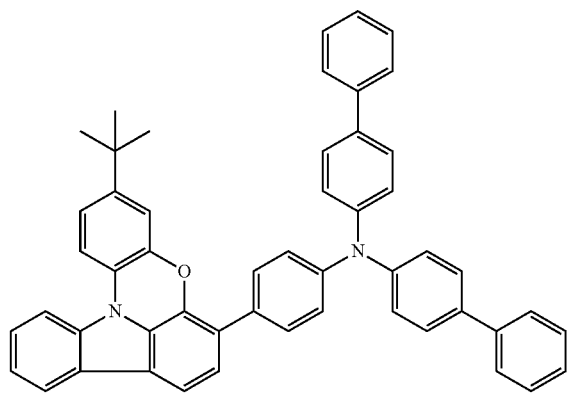
B132
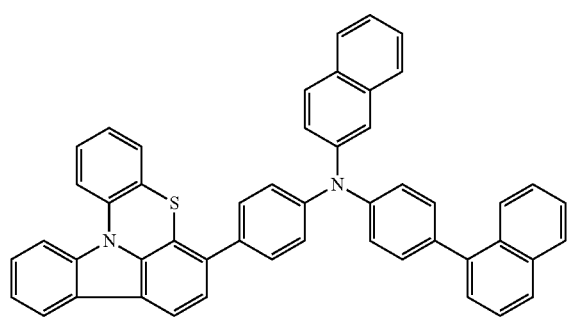
B133
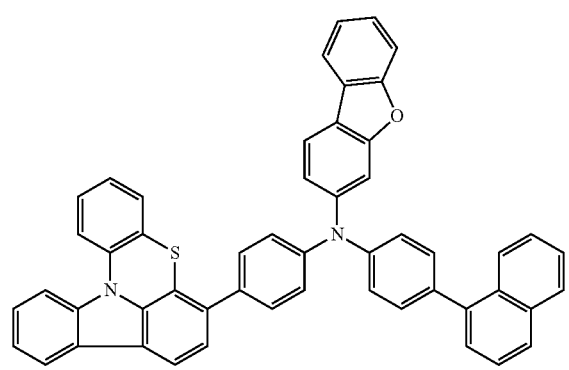
B134
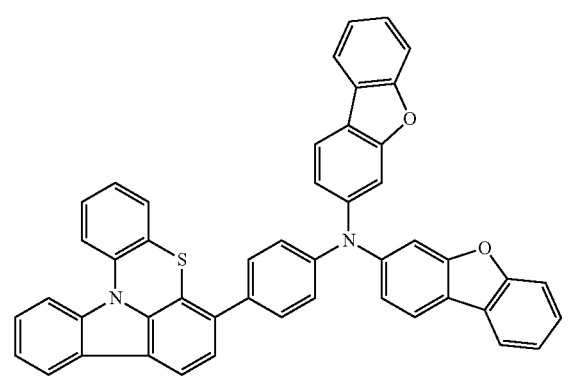
B135
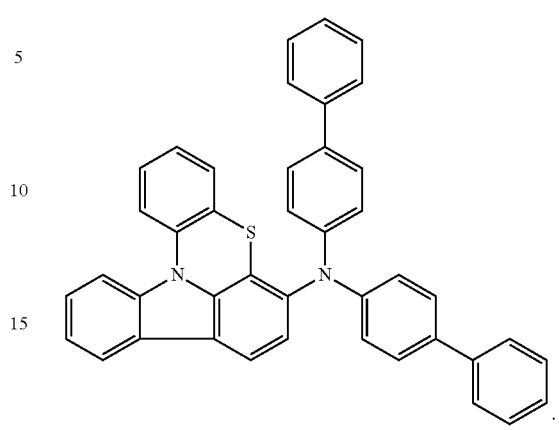
20. The polycyclic compound of claim 14, wherein the polycyclic compound of Formula 1 is a compound of Compound Group 3:
Compound Group 3
C1
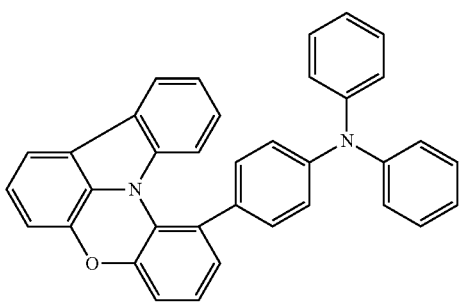
C2

301
-continued
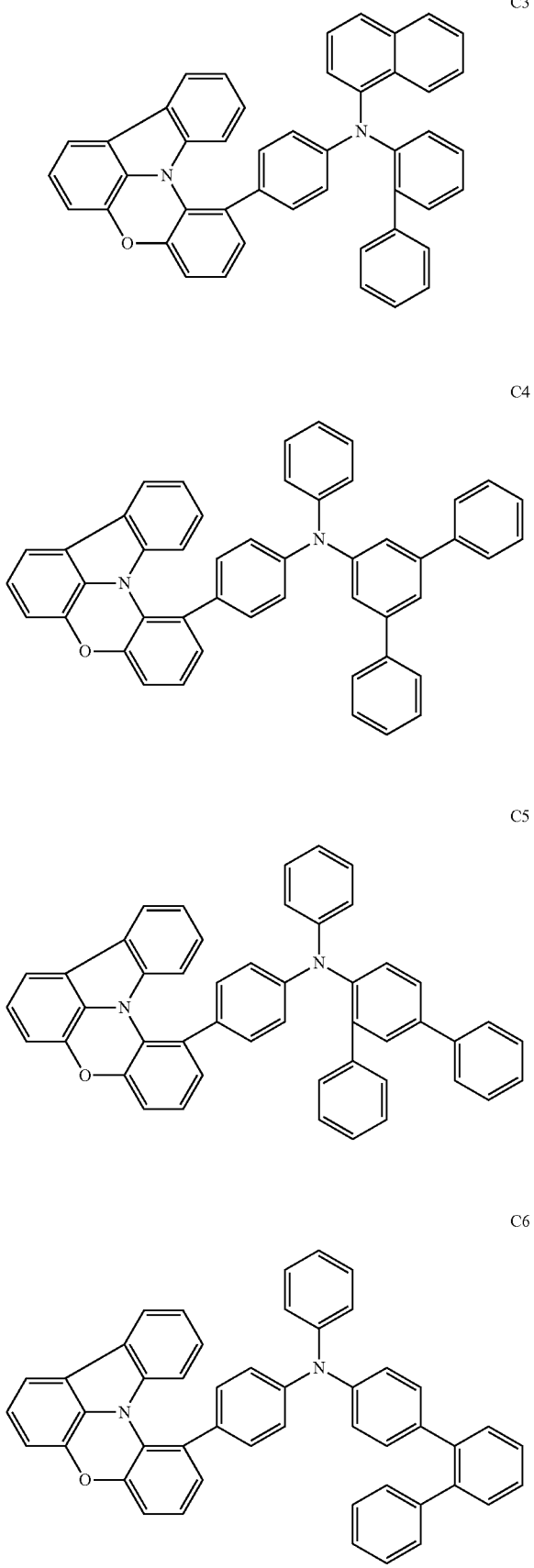
302
-continued
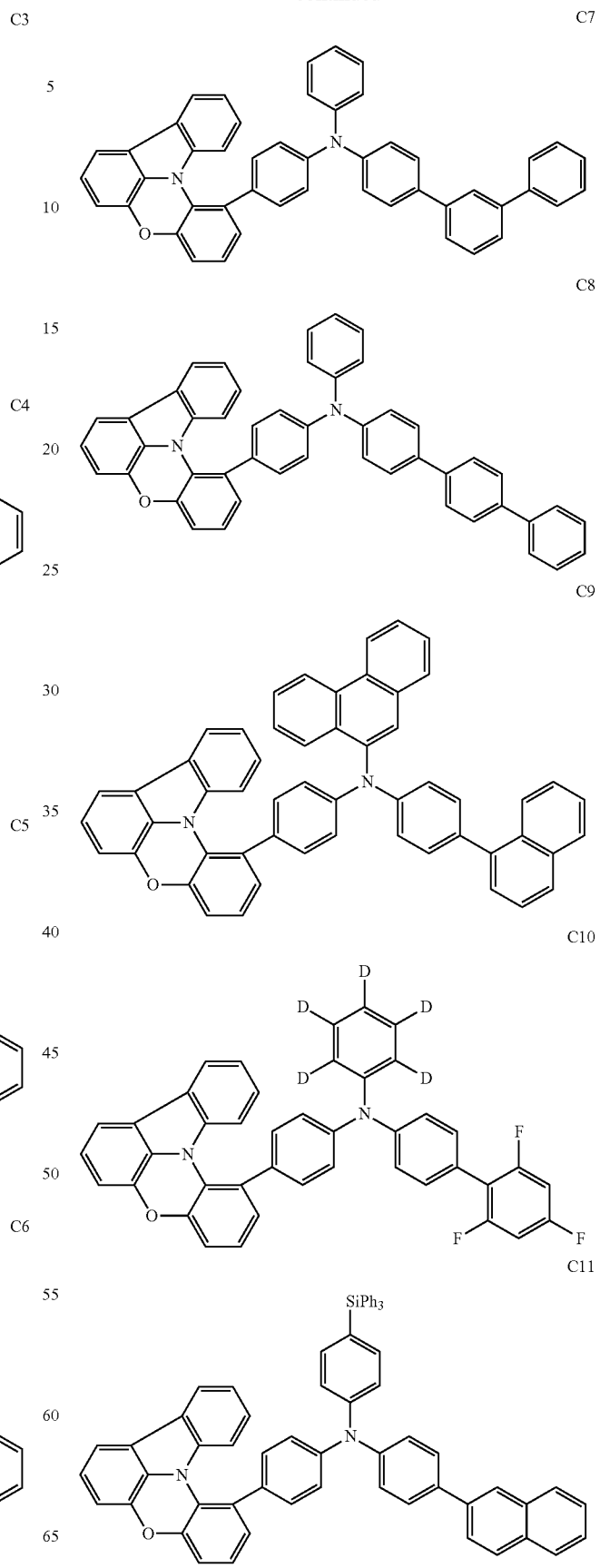

303
-continued
C12
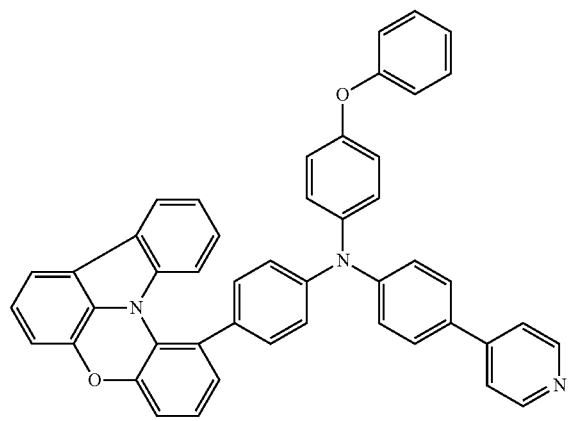
C13
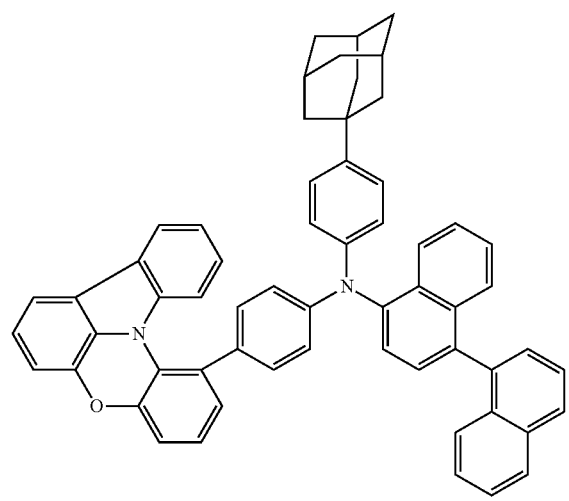
C16
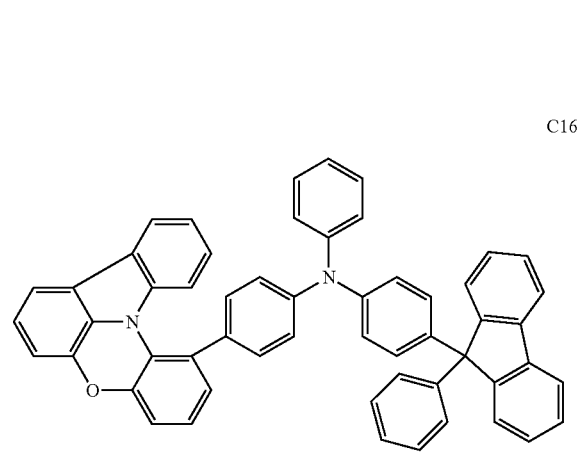
304
-continued
C17
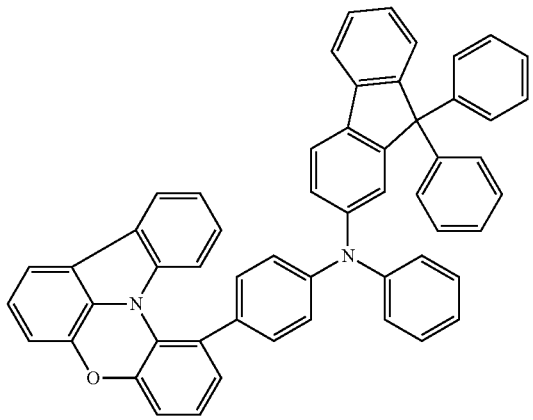
C18
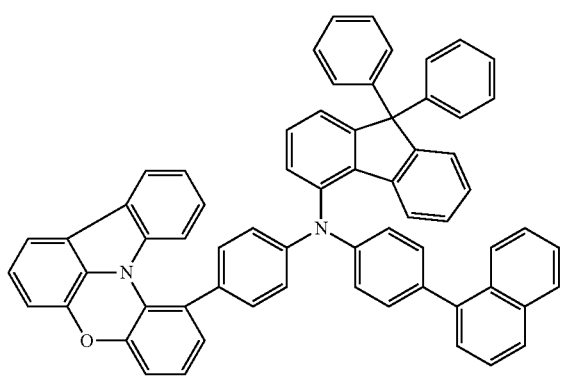
C19
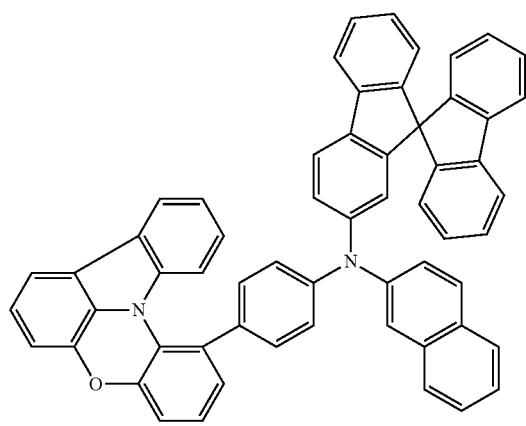

305
-continued
C20
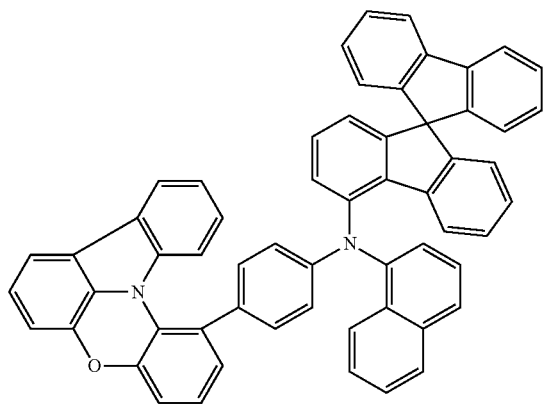
C21
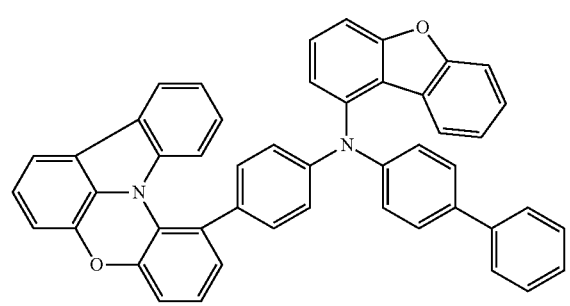
C22
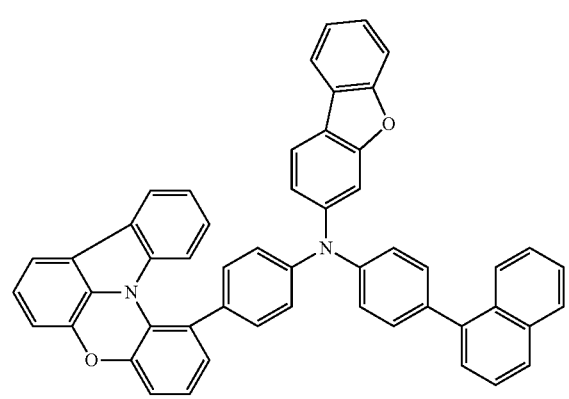
C23
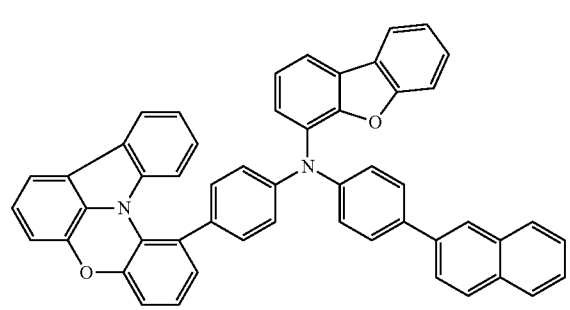
306
-continued
C24
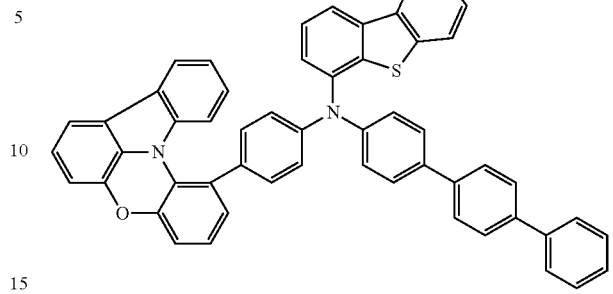
C25
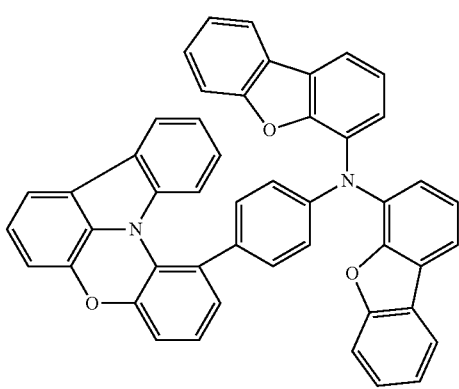
C26
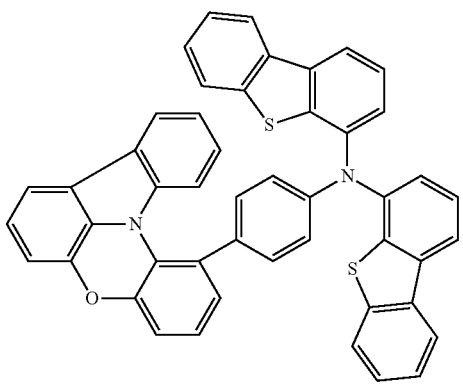
C27
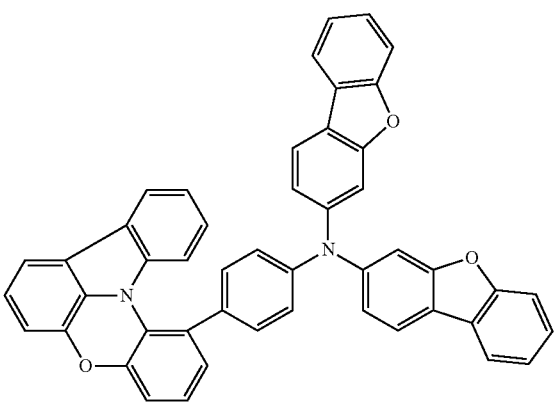

C28
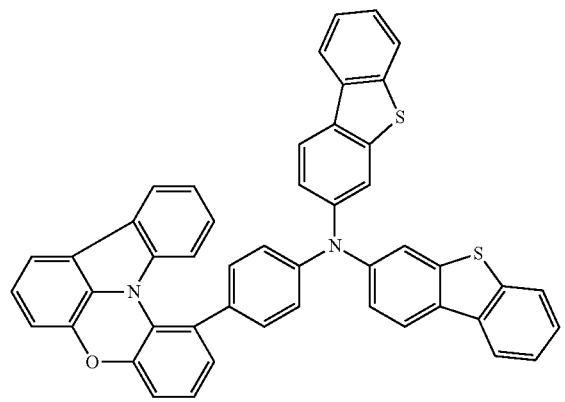
C29
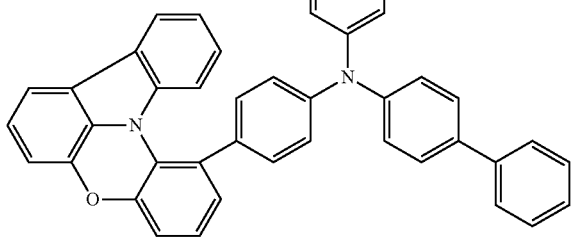
C30
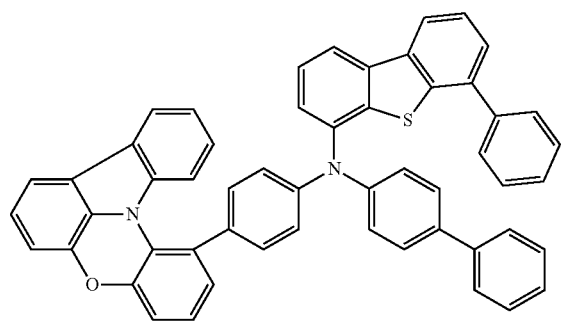
C31
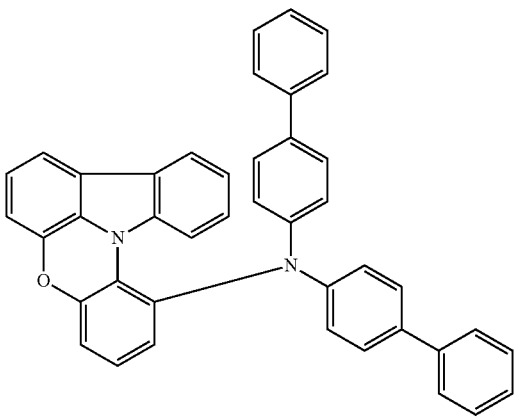
C32
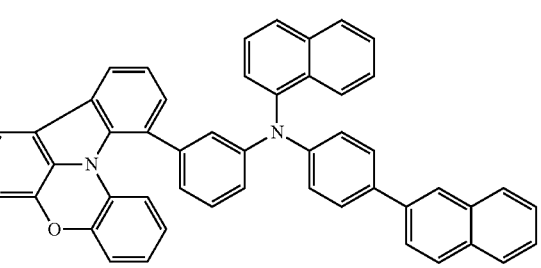
C33
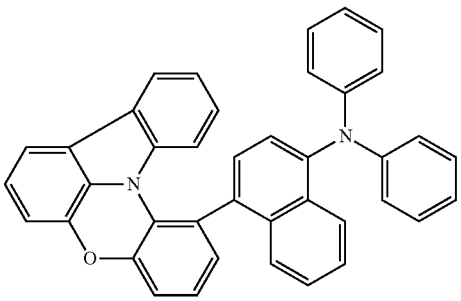
C34
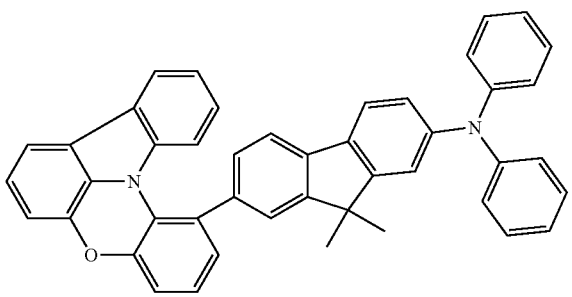

C35
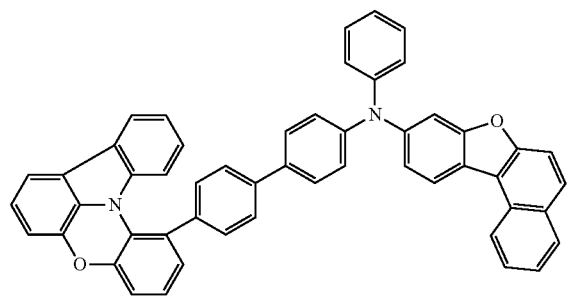
C39
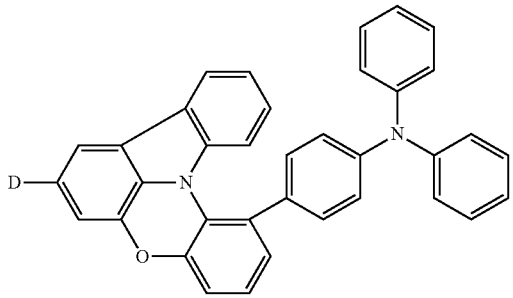
C36
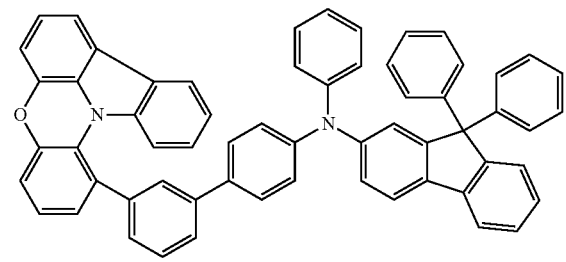
C40
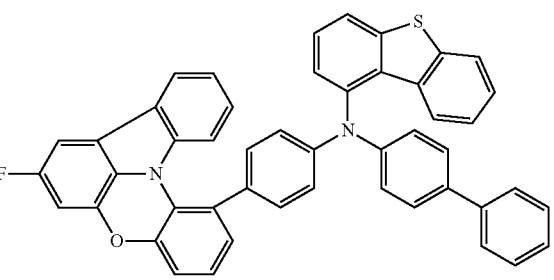
C37
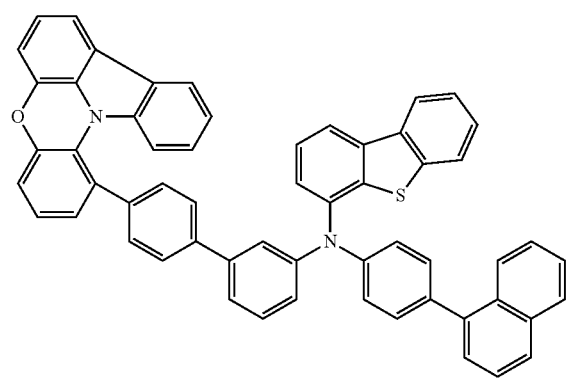
C41
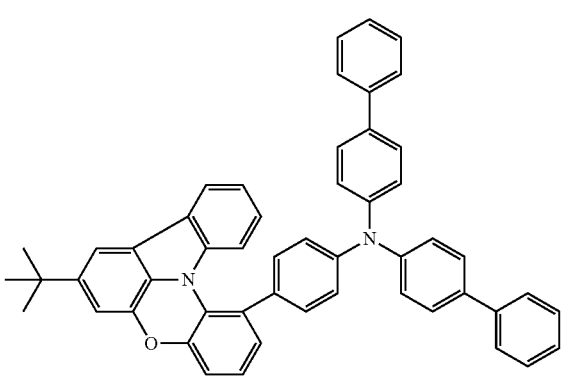
C38
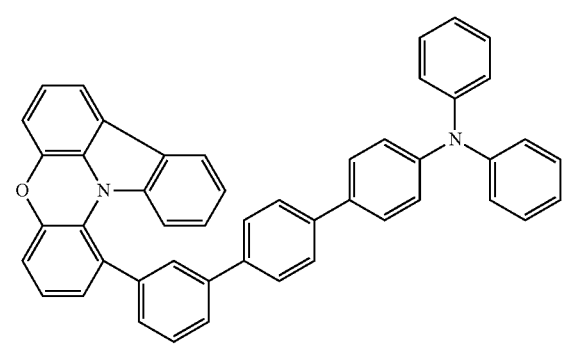
C42
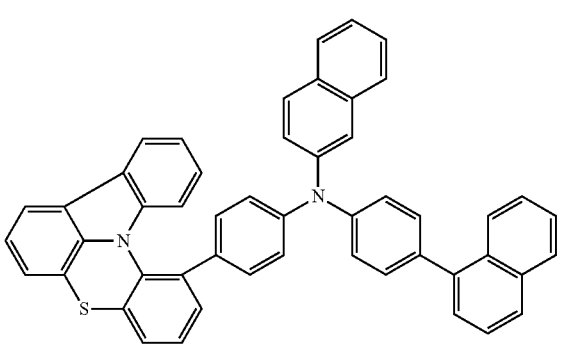

311
-continued
C43
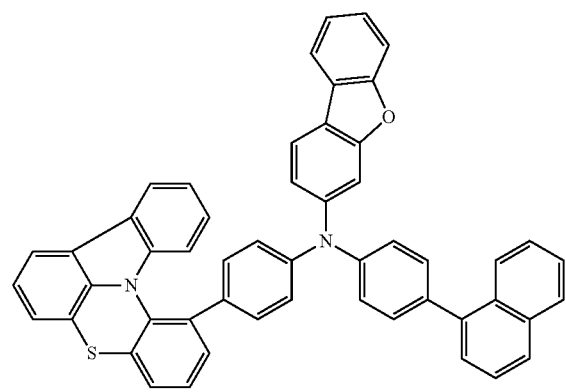
C44
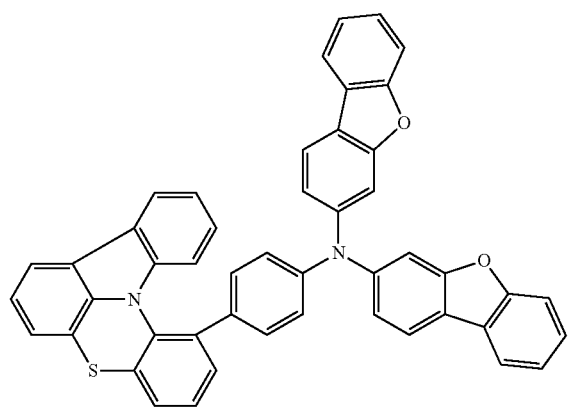
C45
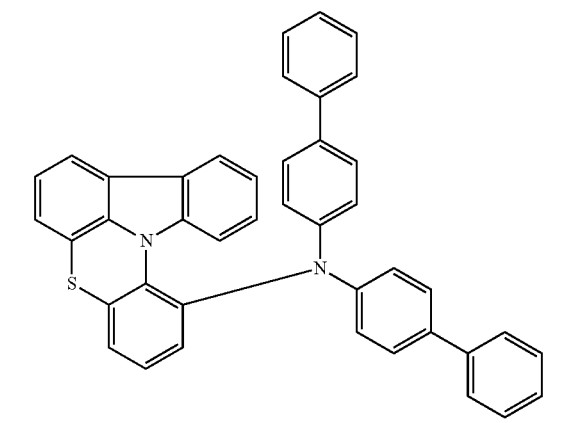
C46
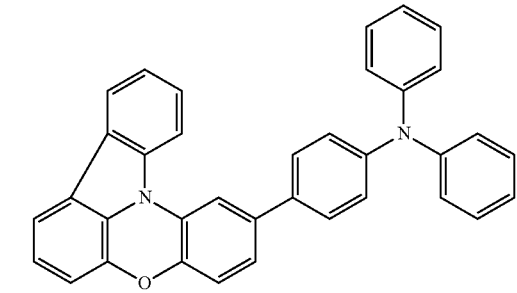
312
-continued
C47
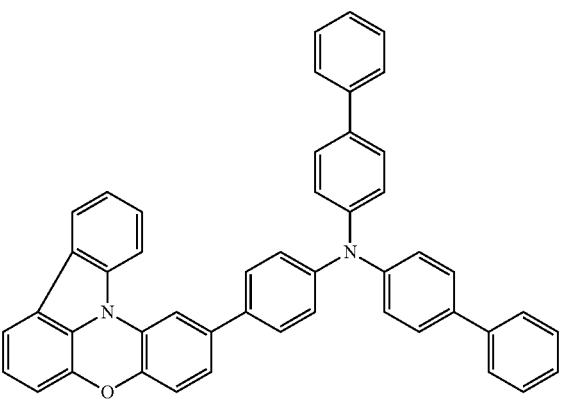
C48
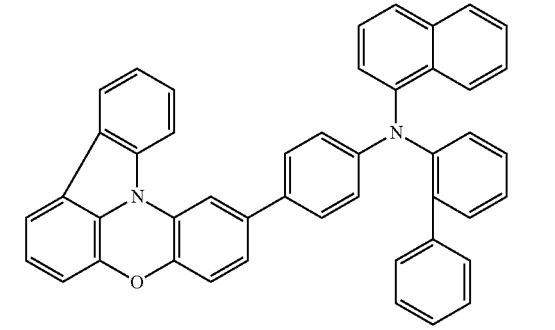
C49
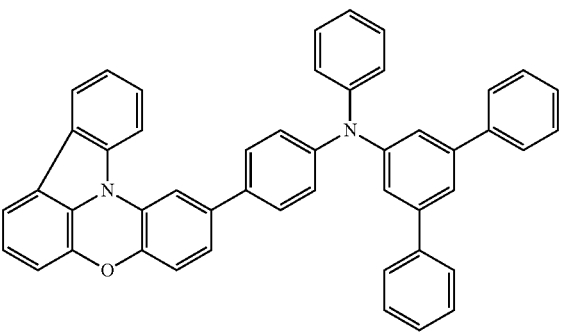
C50
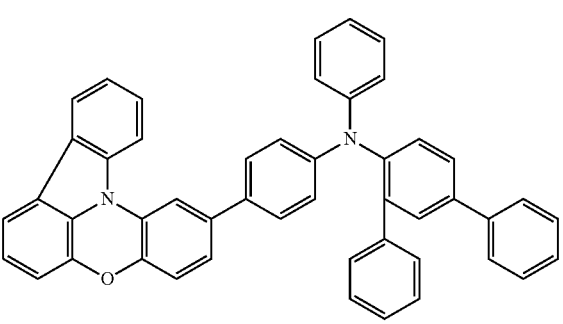

313
-continued
C51
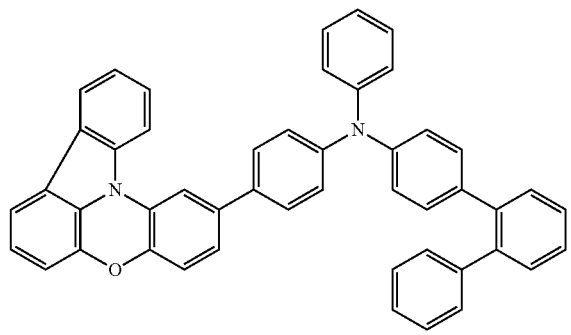
C52
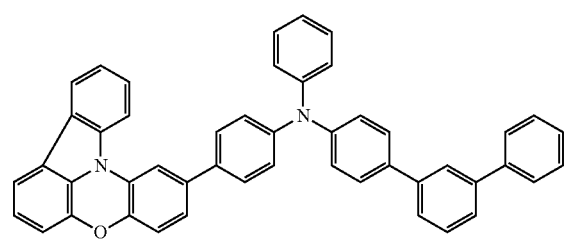
C53
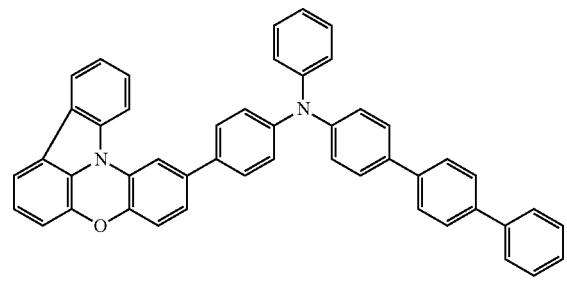
C54
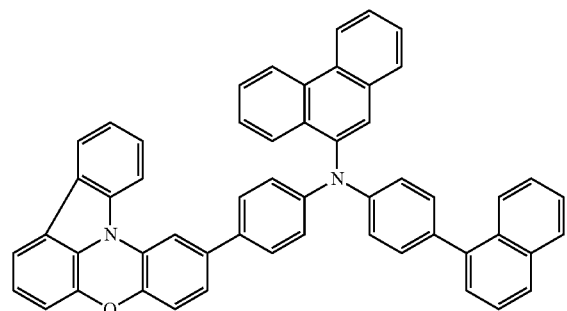
C55
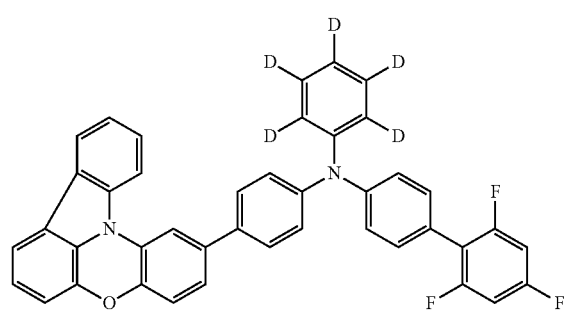
314
-continued
C56
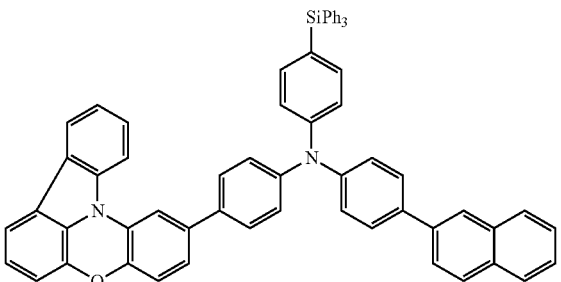
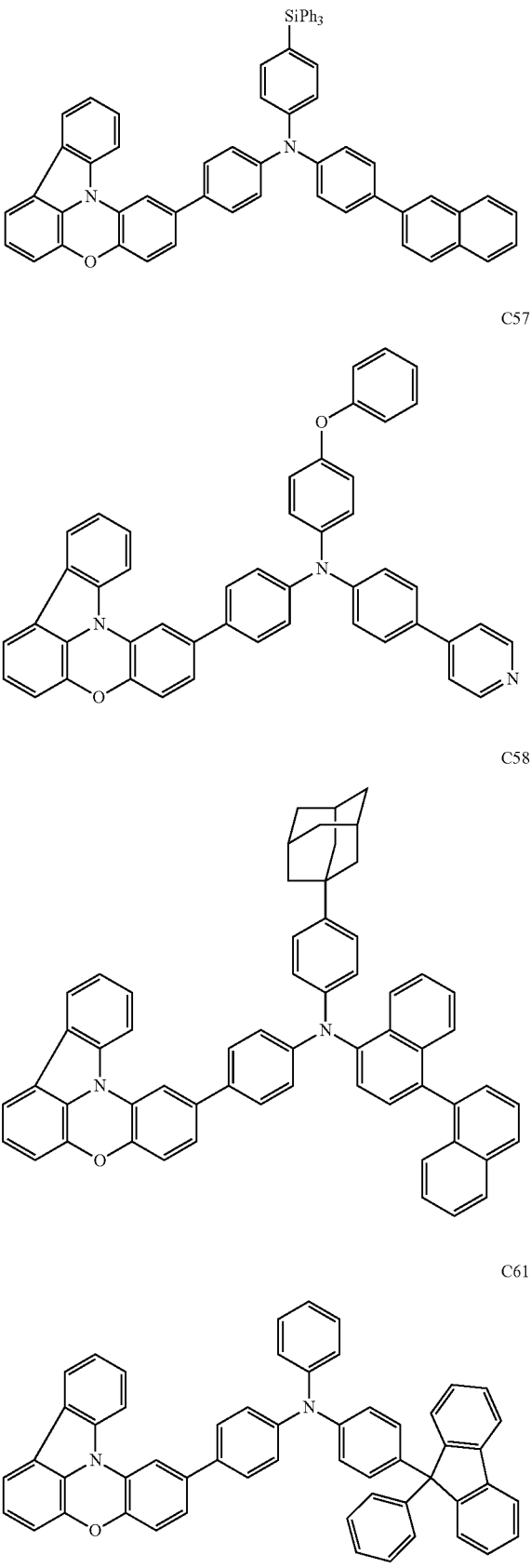

-continued
C62
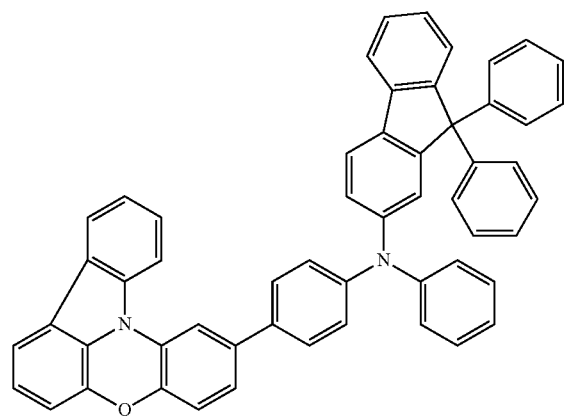
C63
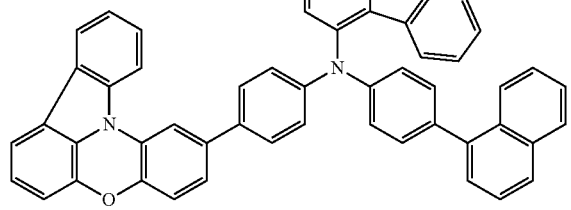
C64
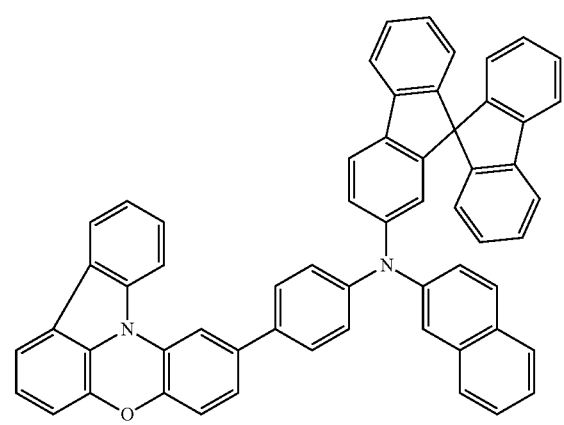
-continued
C65
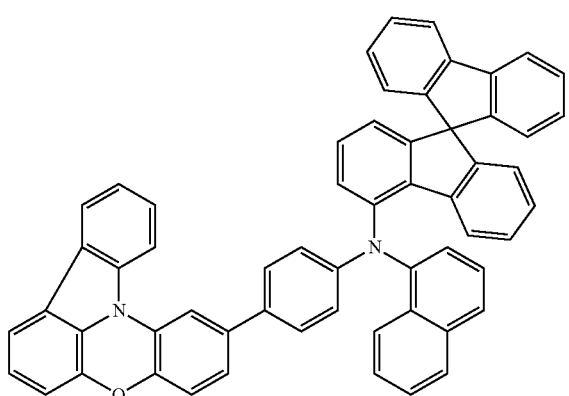
C66
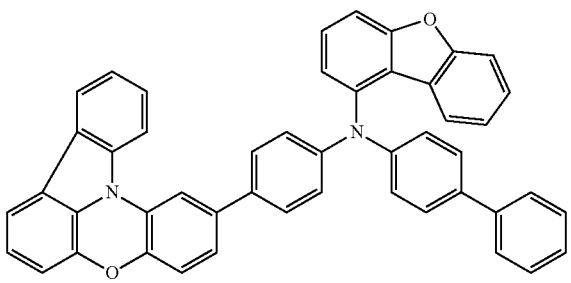
C67
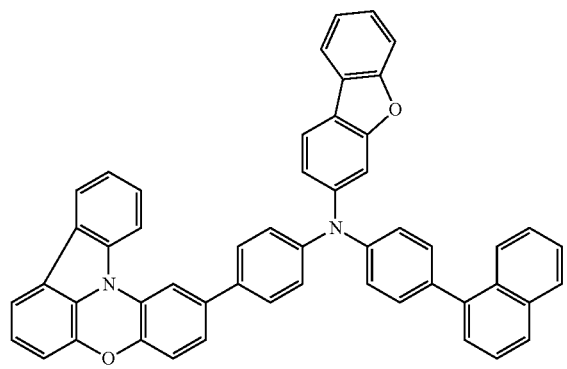
C68
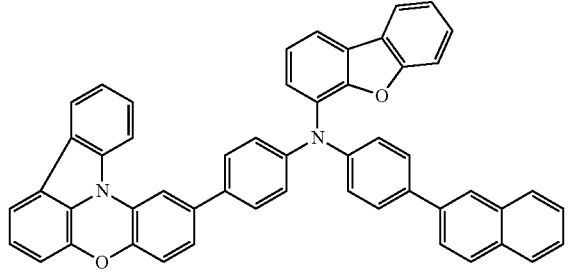

C69
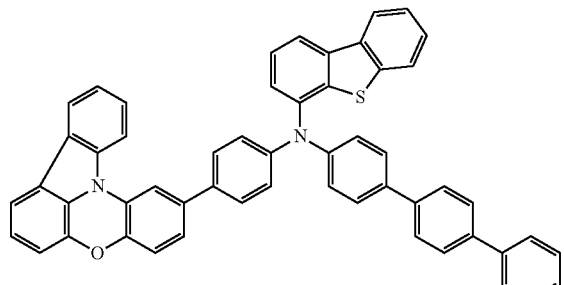
C70
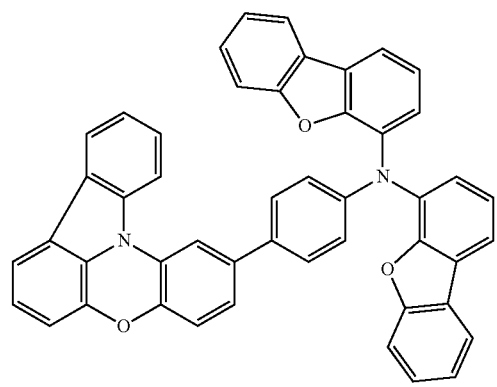
C71
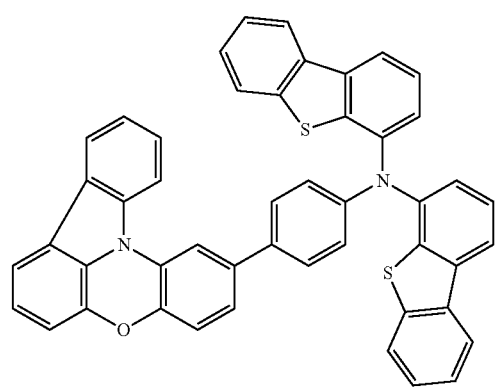
C72
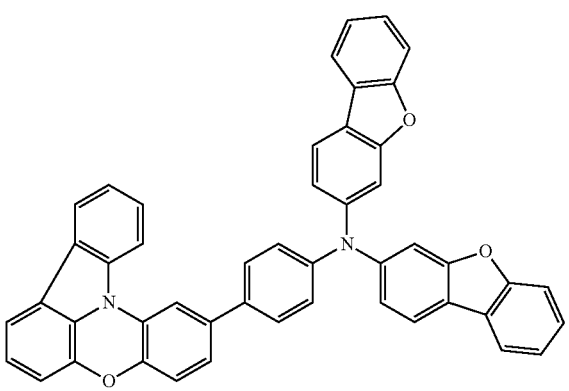
C73
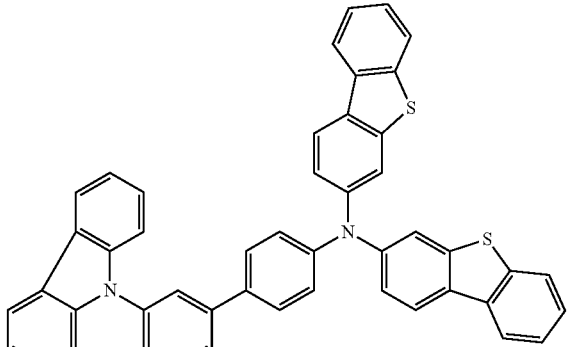
C74
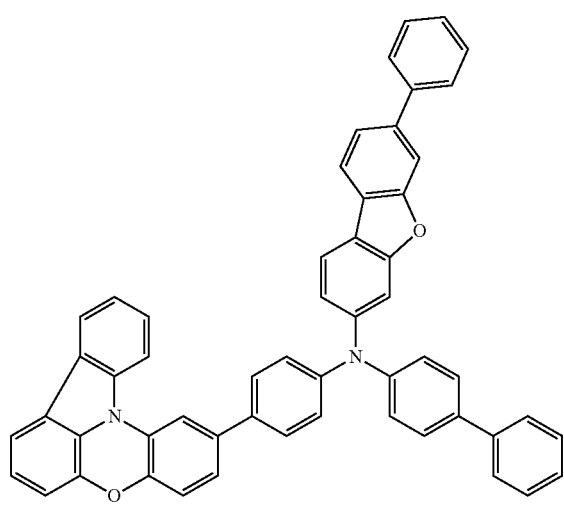
C75
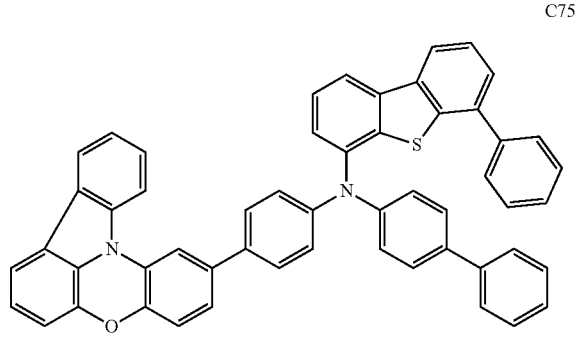

-continued
C76
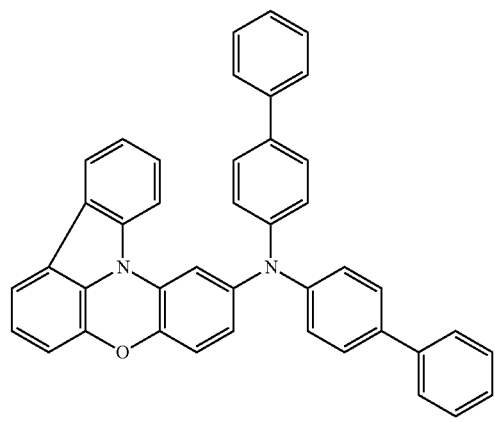
C78
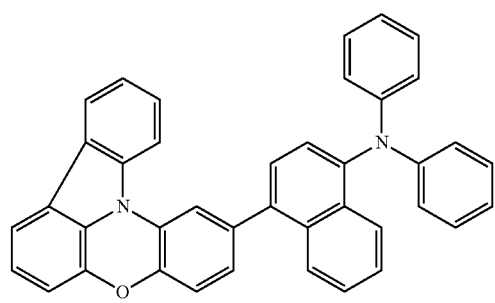
C79
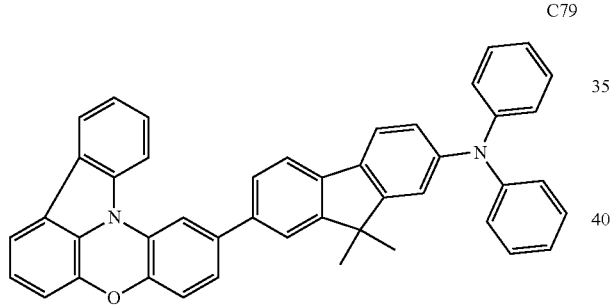
C80
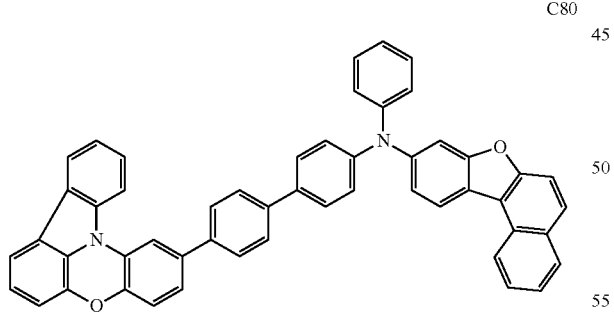
C81
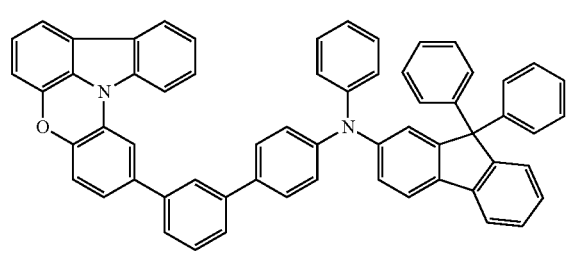
-continued
C82
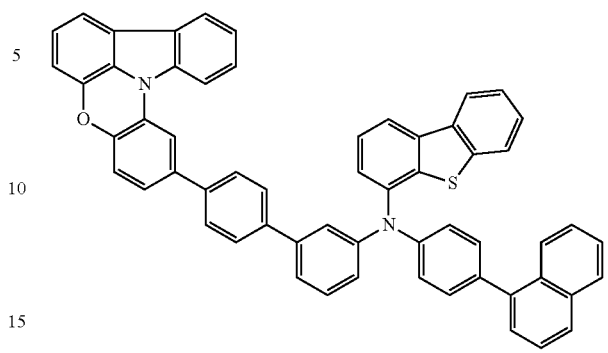
C83
C84
C85

-continued
C86
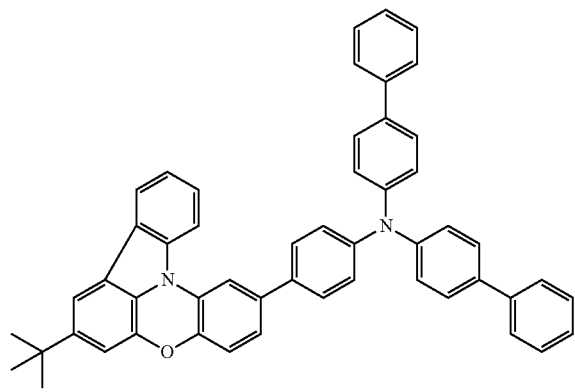
C87
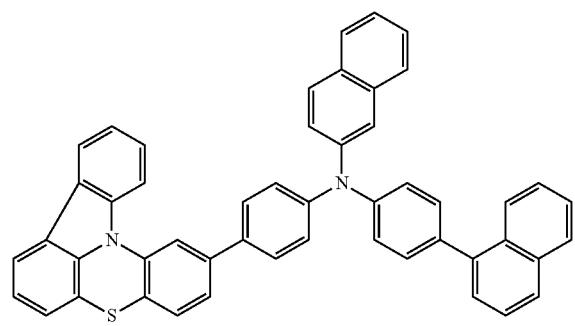
C88
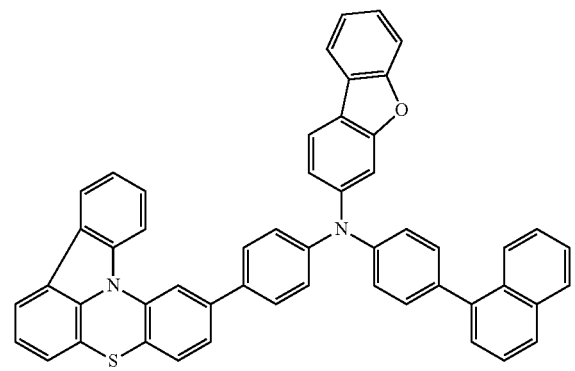
C89
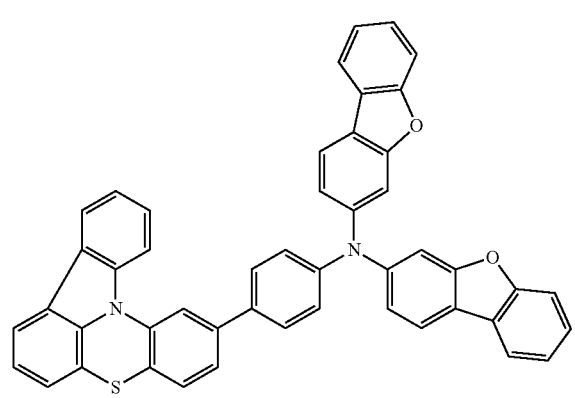
-continued
C90
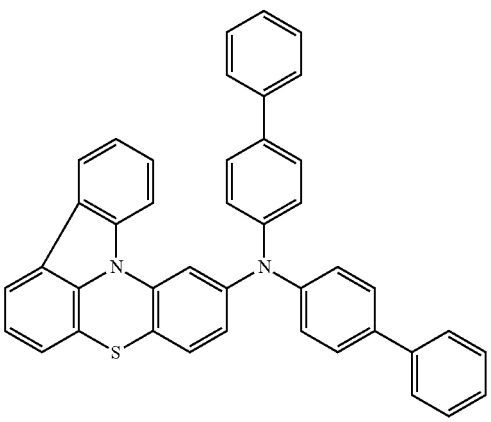
C136
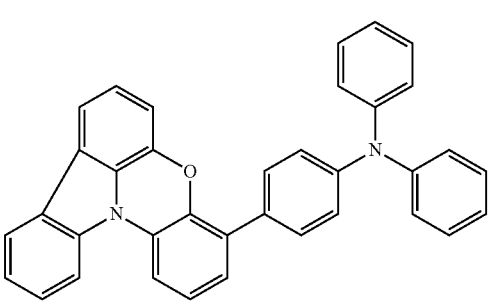
C137
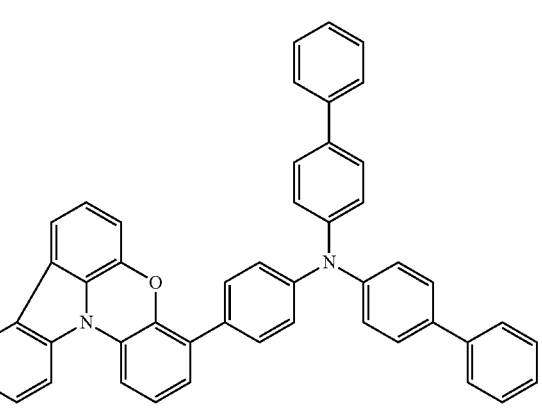
C138
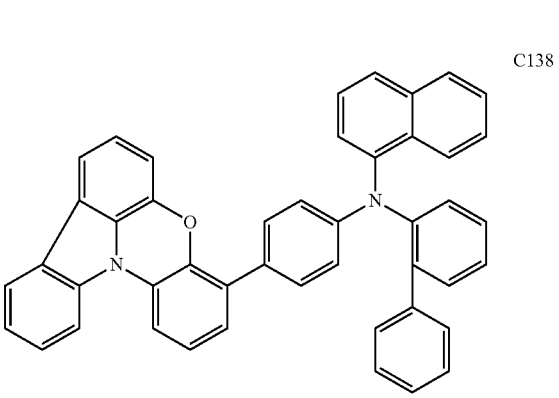

-continued
C139
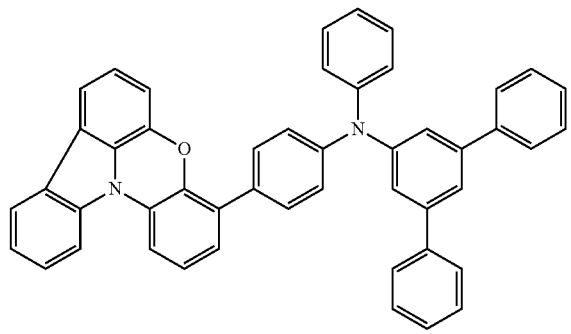
C140
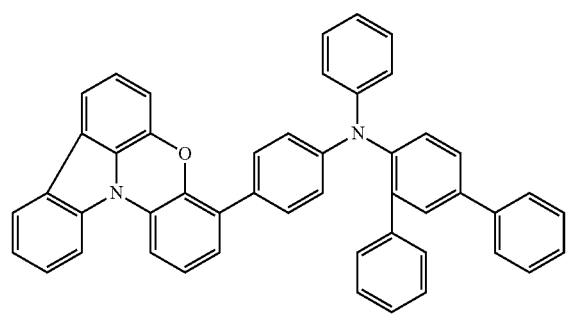
C141
C142
C143
-continued
C144
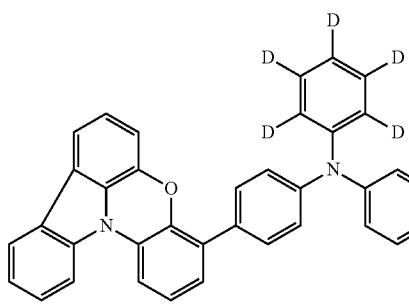
C145
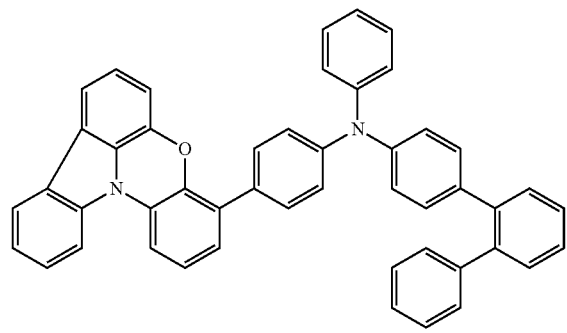
C146
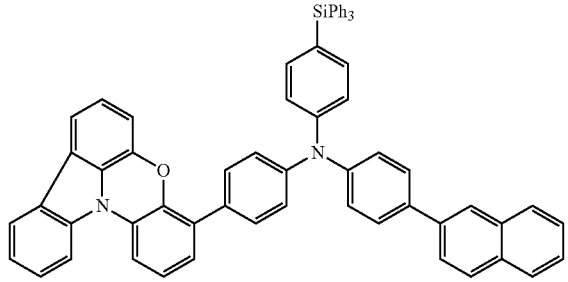
C147
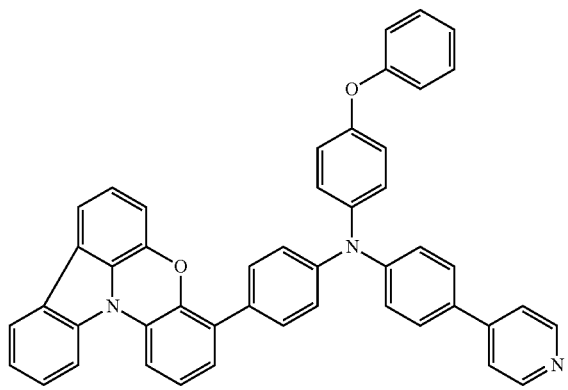

-continued
C148
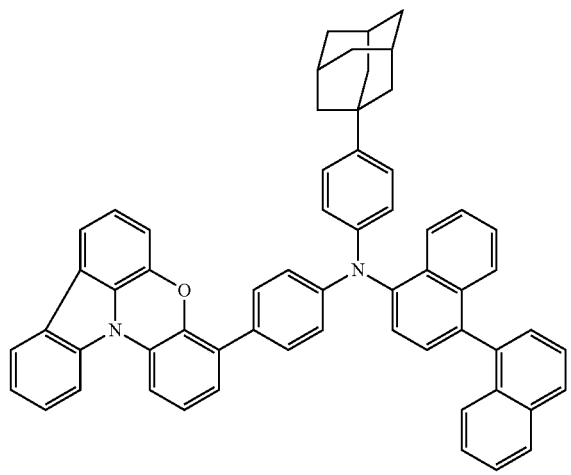
C151
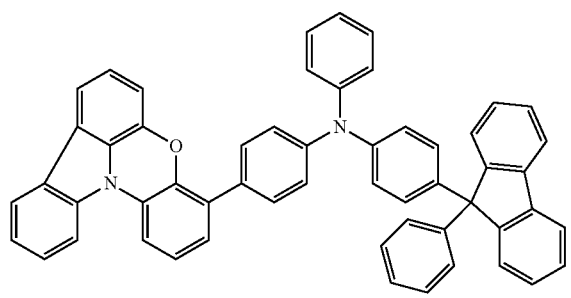
C152
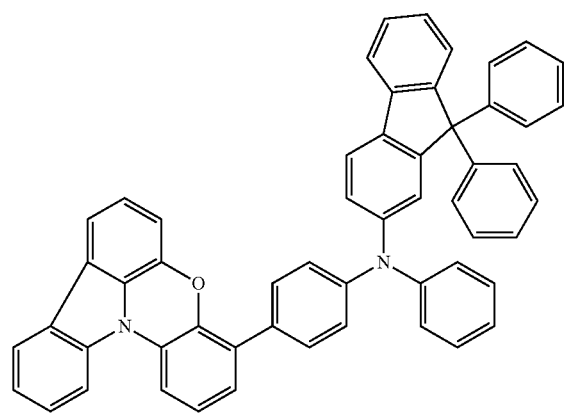
C153
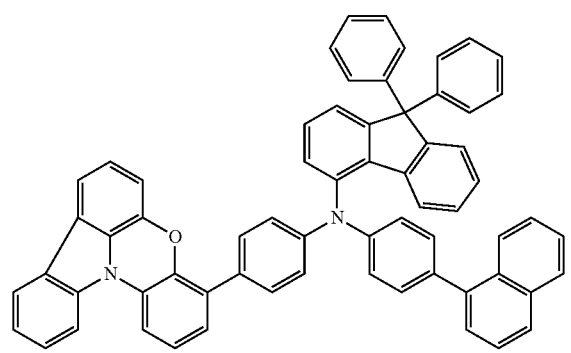
-continued
C154
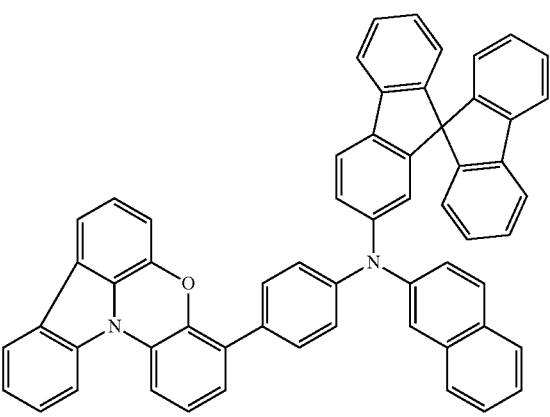
C155
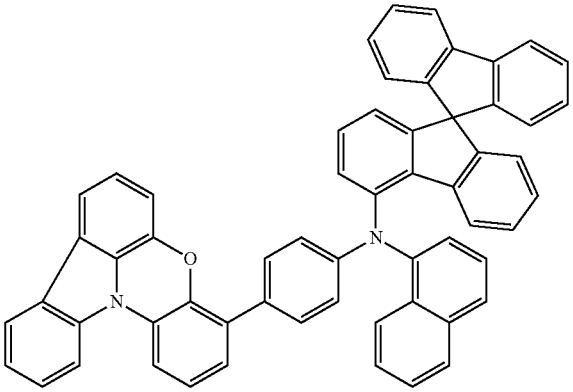
C156
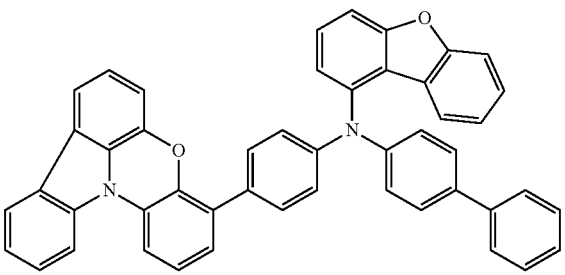
C157
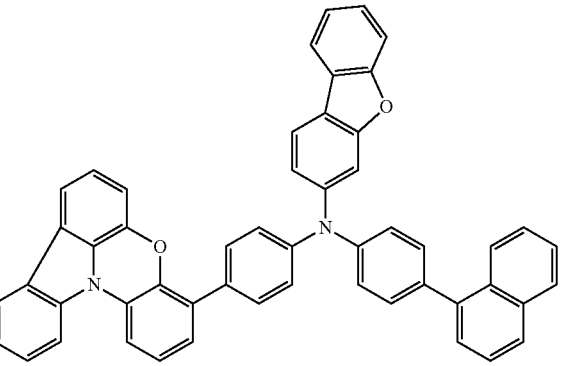

C158
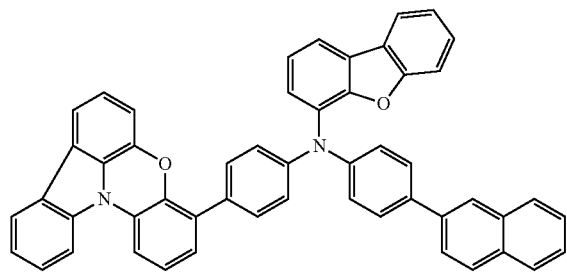
C159
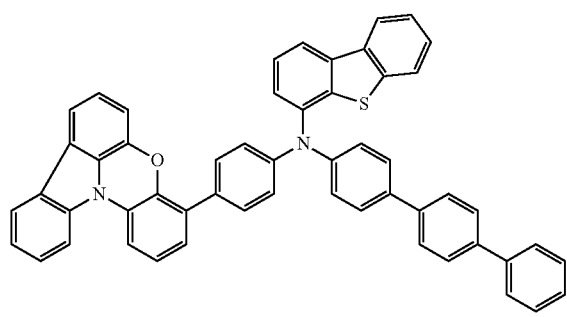
C160
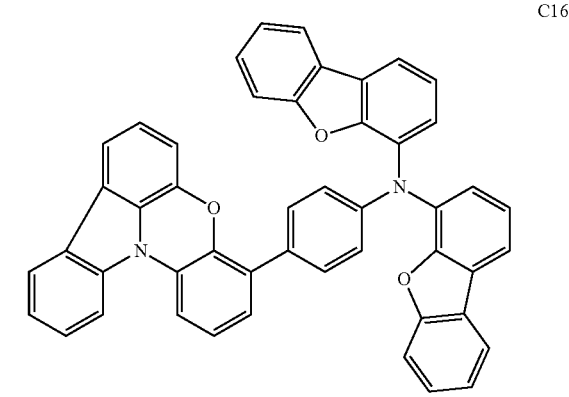
C161
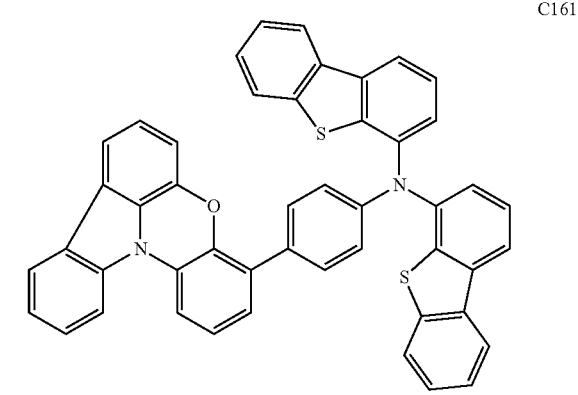
C162
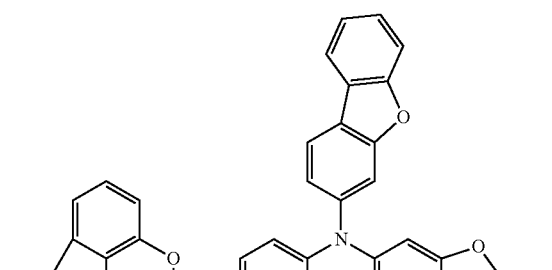
C163
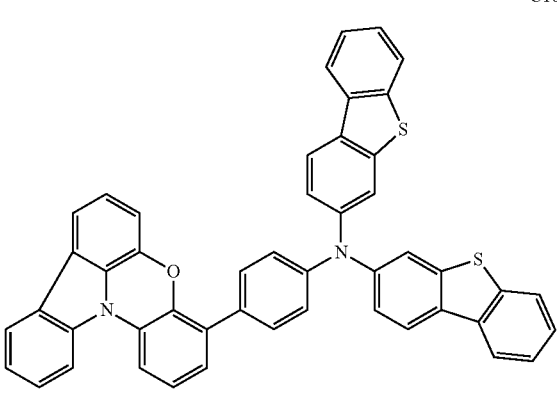
C164
C165
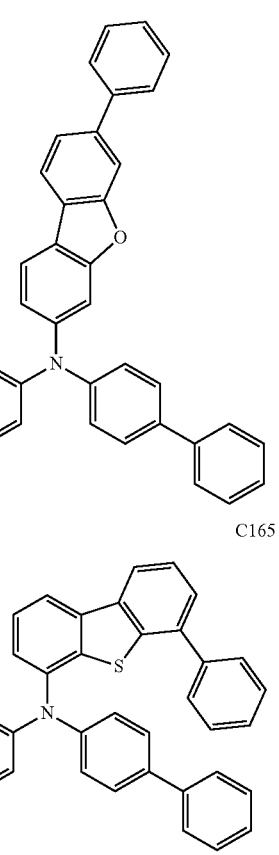

C166
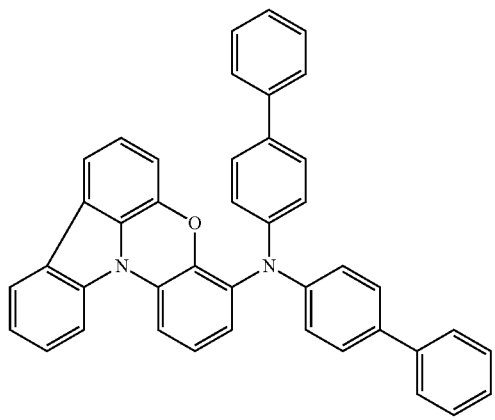
C167
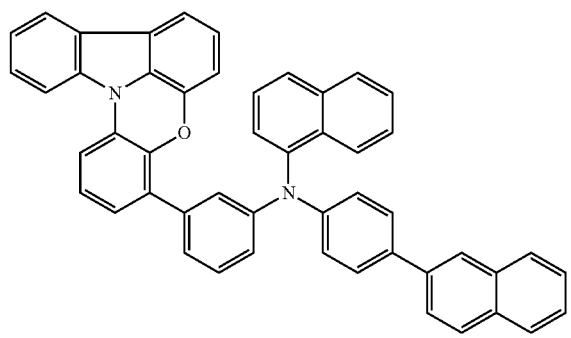
C168
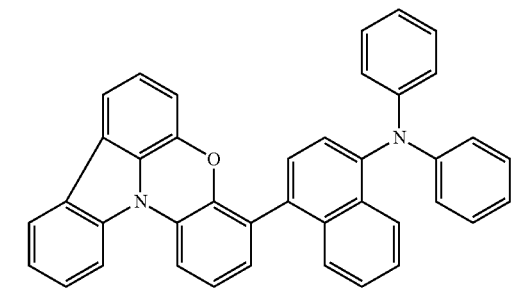
C169
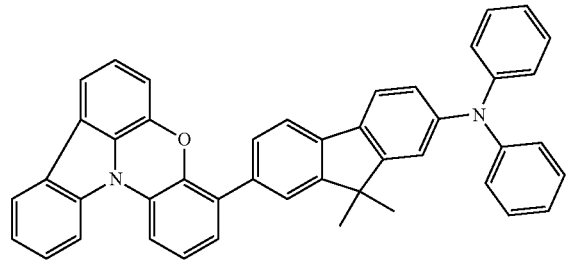
C170
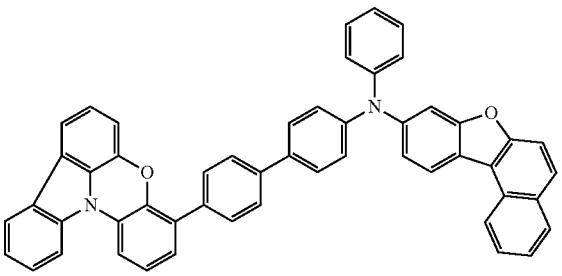
C171
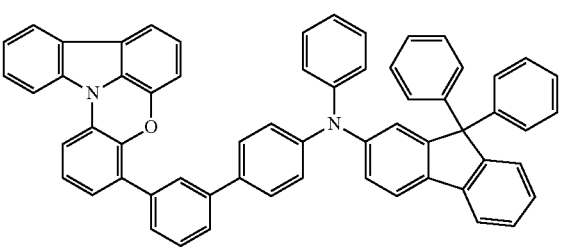
C172
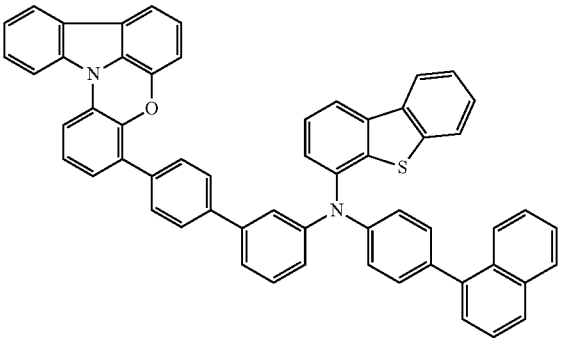
C173
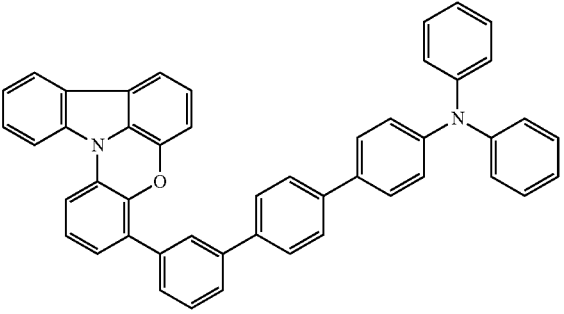
C174
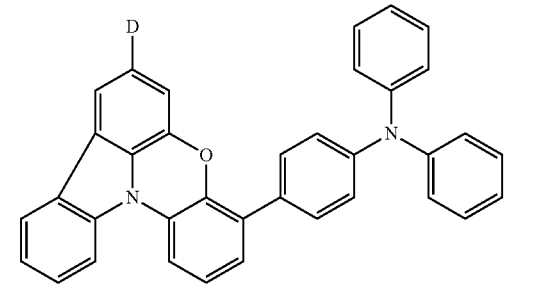

-continued
C175
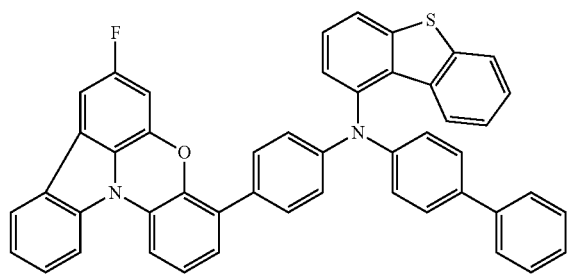
C176
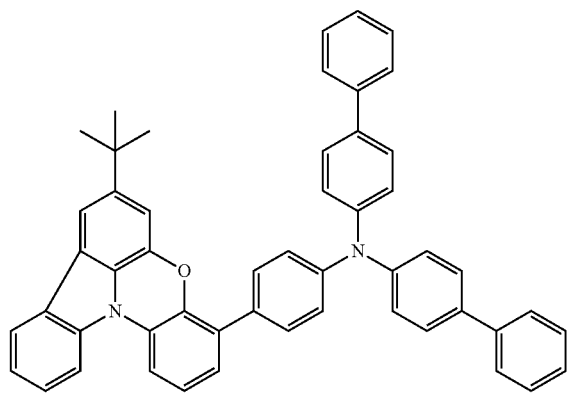
C177
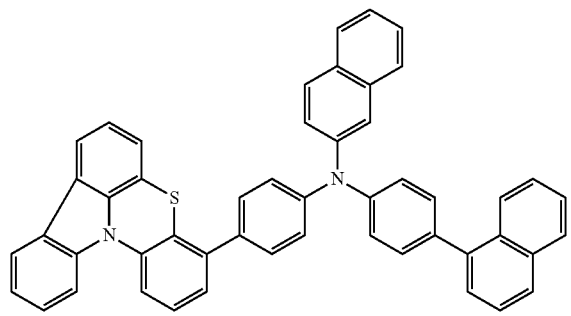
-continued
C178
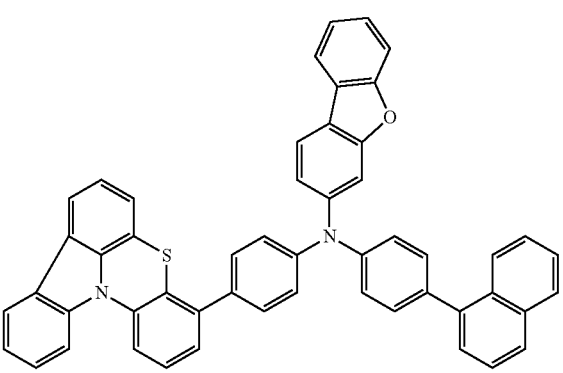
C179
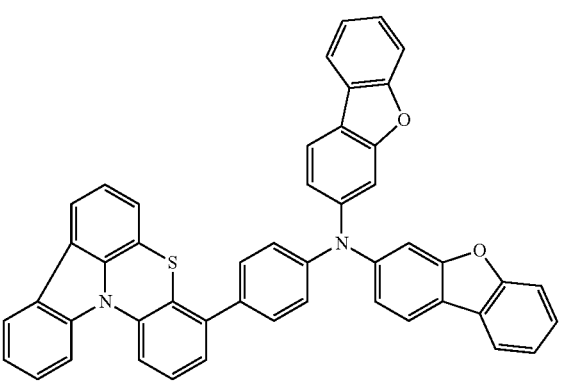
C180
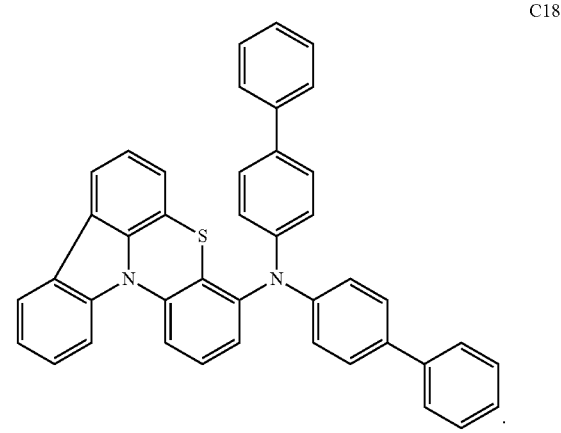
* * * * *